US010443061B2

(12) United States Patent
Koseki et al.

(10) Patent No.: US 10,443,061 B2
(45) Date of Patent: Oct. 15, 2019

(54) HETEROLOGOUS POLYPEPTIDE EXPRESSION CASSETTE

(71) Applicant: Anaeropharma Science, Inc., Tokyo (JP)

(72) Inventors: Koichi Koseki, Tokyo (JP); Takeshi Masaki, Nagano (JP); Koichiro Shioya, Nagano (JP); Hitomi Shimizu, Nagano (JP); Masao Tsukamoto, Nagano (JP); Satoshi Kobayashi, Nagano (JP); Tomio Matsumura, Nagano (JP); Yuko Shimatani, Nagano (JP)

(73) Assignee: Anaeropharma Science, Inc., Tokyo (JP)

( * ) Notice: Subject to any disclaimer, the term of this patent is extended or adjusted under 35 U.S.C. 154(b) by 0 days.

(21) Appl. No.: 15/308,179

(22) PCT Filed: Apr. 17, 2015

(86) PCT No.: PCT/JP2015/002132
§ 371 (c)(1),
(2) Date: Nov. 1, 2016

(87) PCT Pub. No.: WO2015/166640
PCT Pub. Date: Nov. 5, 2015

(65) Prior Publication Data
US 2017/0183667 A1 Jun. 29, 2017

(30) Foreign Application Priority Data
May 1, 2014 (JP) .................................. 2014-094869

(51) Int. Cl.
*C12N 15/74* (2006.01)
*C07K 16/28* (2006.01)
*A61K 35/745* (2015.01)

(52) U.S. Cl.
CPC .......... *C12N 15/746* (2013.01); *A61K 35/745* (2013.01); *C07K 16/2818* (2013.01); *C07K 2317/14* (2013.01); *C07K 2317/622* (2013.01); *C07K 2319/02* (2013.01)

(58) Field of Classification Search
None
See application file for complete search history.

(56) References Cited

U.S. PATENT DOCUMENTS

| 7,229,628 | B1* | 6/2007 | Allison | A61K 39/39 424/154.1 |
| 8,535,939 | B2* | 9/2013 | Shimatani-Shibata | C12N 15/746 435/252.3 |
| 9,730,968 | B2* | 8/2017 | Wada | A61K 35/745 |
| 2003/0086930 | A1* | 5/2003 | Mueller | A61K 39/39541 424/155.1 |
| 2004/0106564 | A1* | 6/2004 | Nilius | A61K 38/57 514/44 R |
| 2004/0126870 | A1 | 7/2004 | Arigoni et al. | |
| 2009/0076250 | A1* | 3/2009 | Honjo | C07K 16/18 530/387.3 |
| 2009/0280091 | A1 | 11/2009 | Hamaji et al. | |
| 2011/0189757 | A1 | 8/2011 | Shimatani-Shibata et al. | |
| 2011/0189758 | A1 | 8/2011 | Shimatani-Shibata et al. | |
| 2011/0190472 | A1 | 8/2011 | Shimatani-Shibata et al. | |
| 2015/0191706 | A1 | 7/2015 | Taira et al. | |

FOREIGN PATENT DOCUMENTS

| EP | 1227152 | 7/2002 |
| JP | 2004-531245 | 10/2004 |
| WO | 2006/109619 | 10/2006 |
| WO | 2010/126073 | 11/2010 |
| WO | 2011/093465 | 8/2011 |
| WO | 2011/093468 | 8/2011 |
| WO | 2014/010758 | 1/2014 |

OTHER PUBLICATIONS

Shkoporov et al in "Production of human basic fibroblast growth factor (FGF-2) in Bifidobacterium breve using a series of novel expression/secretion vectors" (Biotechnol Lett 2008 vol. 30: pp. 1983-1988; published Jun. 25, 2008) (Year: 2008).*
MacConaill et al in Investigation of Protein Export in Bifidobacterium breve UCC2003 Appl Environ Microbiol Dec. 2003 vol. 69 No. 12, pp. 6994-7001). (Year: 2003).*
Chenoll et al in "Safety assessment of strain Bifidobacterium longum CECT 7347, a probiotic able to reduce the toxicity and inflammatory potential of gliadin-derived peptides, based on phenotypic traits, whole genome sequencing and murine trials.", (Year: 2012).*
Schell et al in "The genome sequence of Bifidobacterium longum reflects its adaptation to the human gastrointestinal tract.", Proc. Natl. Acad. Sci. U.S.A. 99:14422-14427(2002). (Year: 2002).*
U.S. Appl. No. 15/529,312, filed May 2017, Koseki et al., A61K35/74, 435/252.300.*
Azuma, "Cancer immunotherapy by blockade of PD-1 immune checkpoint," Journal of clinical and experimental medicine, 2013. vol. 244, No. 9, p. 809-815.

(Continued)

*Primary Examiner* — Catherine S Hibbert
(74) *Attorney, Agent, or Firm* — Occhiuti & Rohlicek LLP

(57) ABSTRACT

An object is to provide a signal peptide that can secrete a heterologous polypeptide with high efficiency outside the bacterial cell in a bacterium of the genus *Bifidobacterium*, an expression cassette that can secrete a heterologous polypeptide with high efficiency outside the bacterial cell, a heterologous polypeptide expression vector, a bacterium of the genus *Bifidobacterium* capable of secreting a heterologous polypeptide. Means for attaining the object is a bacterium of the genus *Bifidobacterium* transformed by a vector having an expression cassette sequentially comprising a promoter DNA functioning in a bacterium of the genus *Bifidobacterium*, a DNA encoding the secretory signal peptide, a DNA encoding a scFv antibody having an antitumor activity, and a terminator DNA functioning in the bacterium of the genus *Bifidobacterium*; and capable of secreting the scFv antibody with high efficiency outside the bacterial cell.

20 Claims, 19 Drawing Sheets
Specification includes a Sequence Listing.

(56) References Cited

OTHER PUBLICATIONS

GenBank Accession No. BAJ72090, Fukuda, S. et al.,Jan. 29, 2011, http://www.ncbi.nln.nih.gov/protein/BAJ72090.1.
GenBank Accession No. ADQ02103, Hao, Y. et al., Jan. 31, 2014, http://www.ncbi.nlm.nih.gov/protein/ADQ02103.1.
GenBank Accession No. EPE38071, Oberg, T.S. et al., Jun. 17, 2013, http://www.ncbi.nlm.nih.gov/protein/EPE38071.1.
GenBank Accession No. EIJ22210, Shkoporov, A. N. et al., May 4, 2012, http://www.ncbi.nln.nih.gov/protein/EIJ22210.1.
GenBank Accession No. E1127286, Shkoporov, A. N. et al., May 4, 2012, http://www.ncbi.nln.nih.gov/protein/EIJ27286.1.
GenBank Accession No. EIJ27376, May 4, 2012, Shkoporov, A. N. et al., http://www.ncbi.nlm.nih.gov/protein/EIJ27376.1.
English Translation of International Preliminary Report on Patentability for corresponding PCT/JP2015/002132 dated Nov. 10, 2016.
Deng, Qiwen, Weiseng Zeng, and Zhijian Yu. "Signal peptide of Arabinosidase enhances secretion of interferon-a2b protein by Bifidobacteria longum." Archives of microbiology 191, No. 9 (2009): 681-686.
Database WPI Week 201006, Thomson Scientific, London, GB; AN 2010-A27213 XP002774854, & CN 101 608 172 A, Dec. 23, 2009, abstract, 2 pages.
Supplementary European Search Report for European Application No. 15785407 dated Oct. 19, 2017, 2 pages.

\* cited by examiner

[Figure 1]
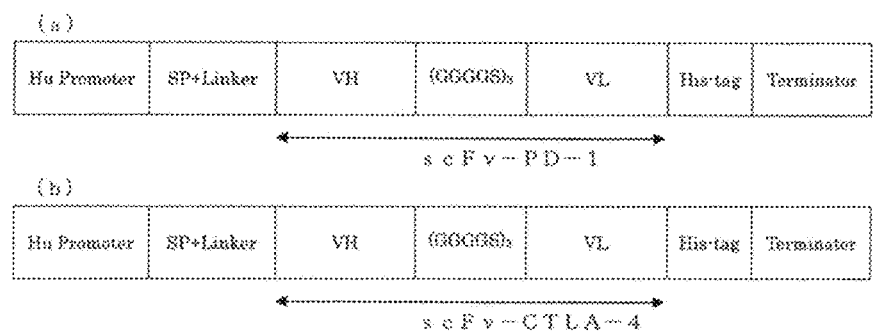
[Figure 2]
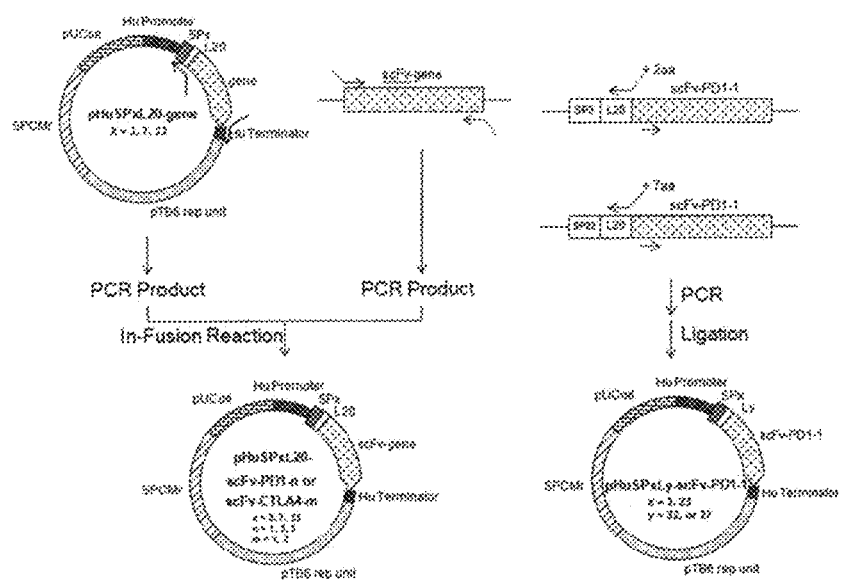

[Figure 3]
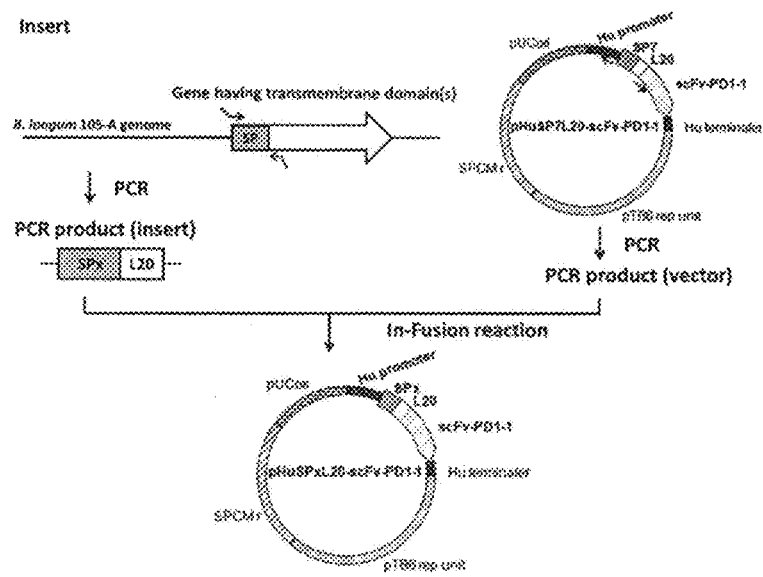
[Figure 4]
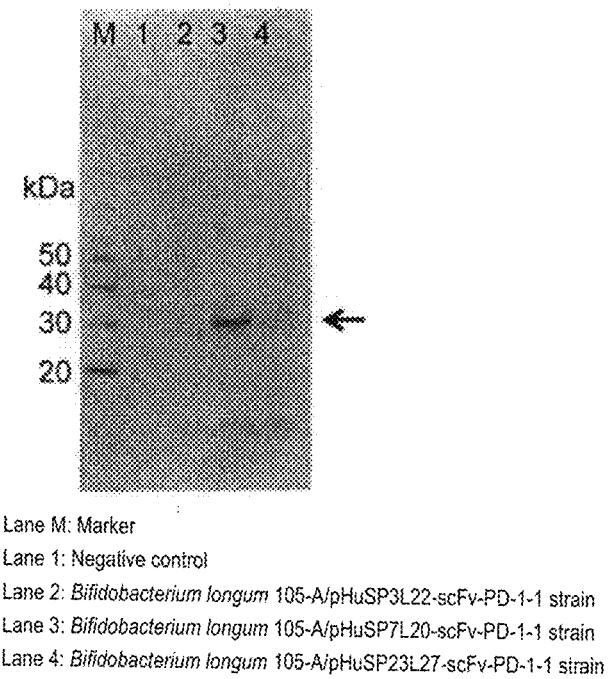
Lane M: Marker
Lane 1: Negative control
Lane 2: *Bifidobacterium longum* 105-A/pHuSP3L22-scFv-PD-1-1 strain
Lane 3: *Bifidobacterium longum* 105-A/pHuSP7L20-scFv-PD-1-1 strain
Lane 4: *Bifidobacterium longum* 105-A/pHuSP23L27-scFv-PD-1-1 strain

[Figure 5]
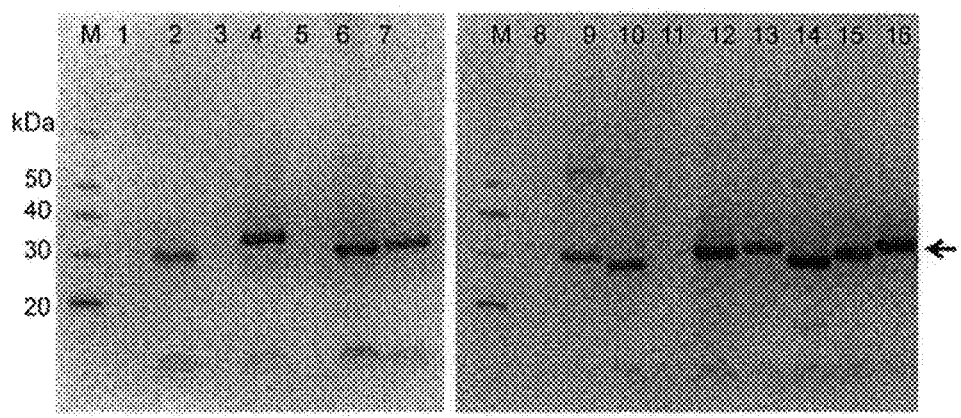
Signal peptide-linker peptide conjugate used in *Bifidobacterium longum* 105-A/pHuSPxL20-scFv-PD-1-1 strain
Lane 1, 8: Negative control (pBEshuttle)
Lane 2: SP7L20
Lane 3: SP42L20
Lane 4: SP45L20
Lane 5: SP48L20
Lane 6: SP50L20
Lane 7: SP52L20
Lane 9: SP55L20
Lane 10: SP58L20
Lane 11: SP62L20
Lane 12: SP64L20
Lane 13: SP66L20
Lane 14: SP67L20
Lane 15: SP68L20
Lane 16: SP69L20

[Figure 6]
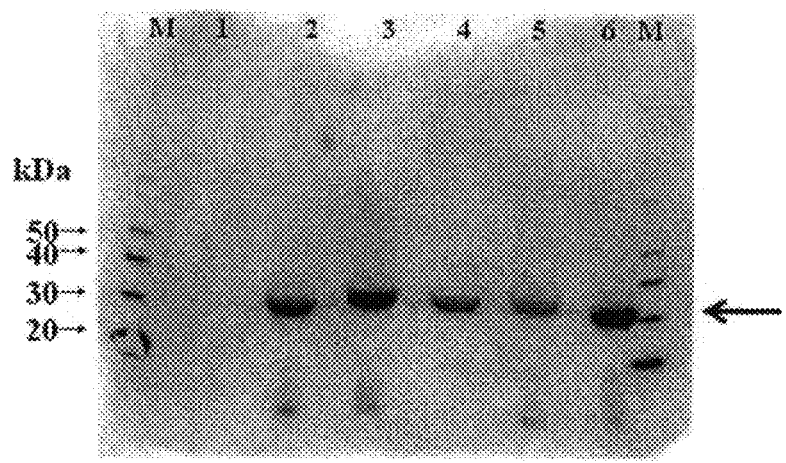
Lane 1: Negative control (pBEshuttle strain)
Lane 2: *Bifidobacterium longum* 105-A/pHuSP7L20-PD-1-1 strain
Lane 3: *Bifidobacterium longum* 105-A/pHuSP7L20-PD-1-2 strain
Lane 4: *Bifidobacterium longum* 105-A/pHuSP7L20-PD-1-3 strain
Lane 5: *Bifidobacterium longum* 105-A/pHuSP7L20-CTLA-4-1 strain
Lane 6: *Bifidobacterium longum* 105-A/pHuSP7L20-CTLA-4-2 strain
M: Molecular-weight Marker
[Figure 7]
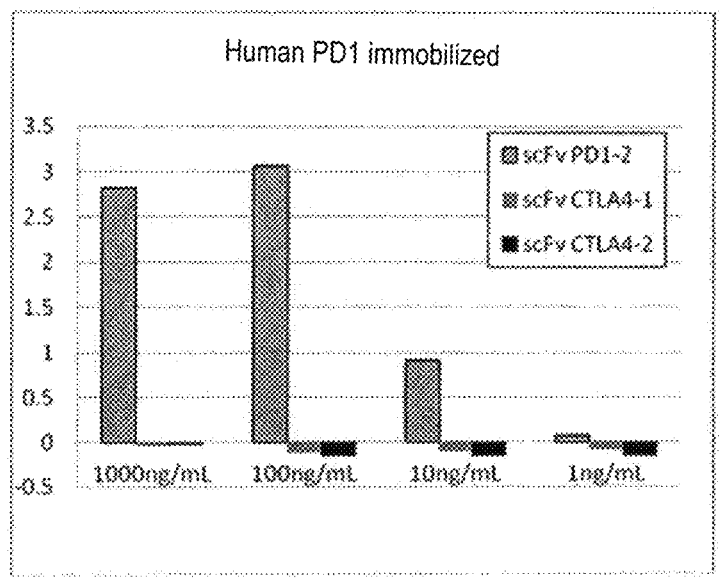

[Figure 8]
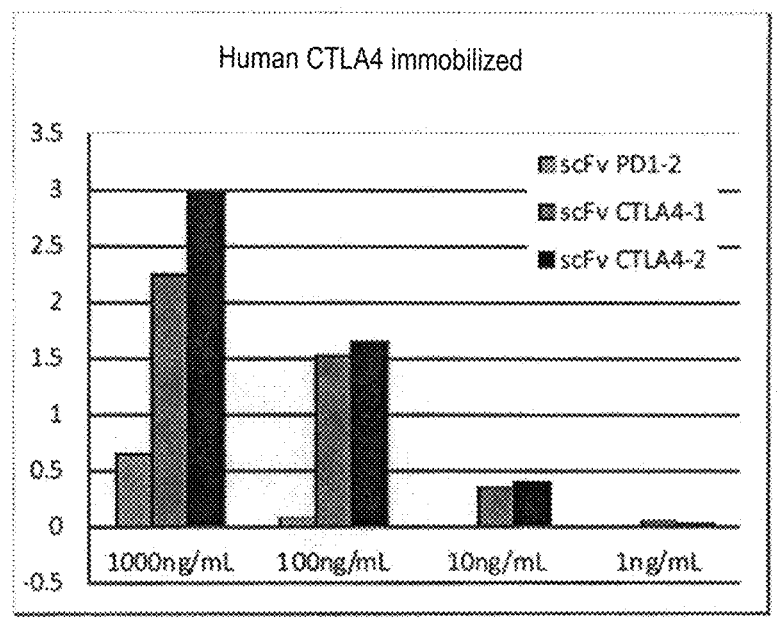
[Figure 9]
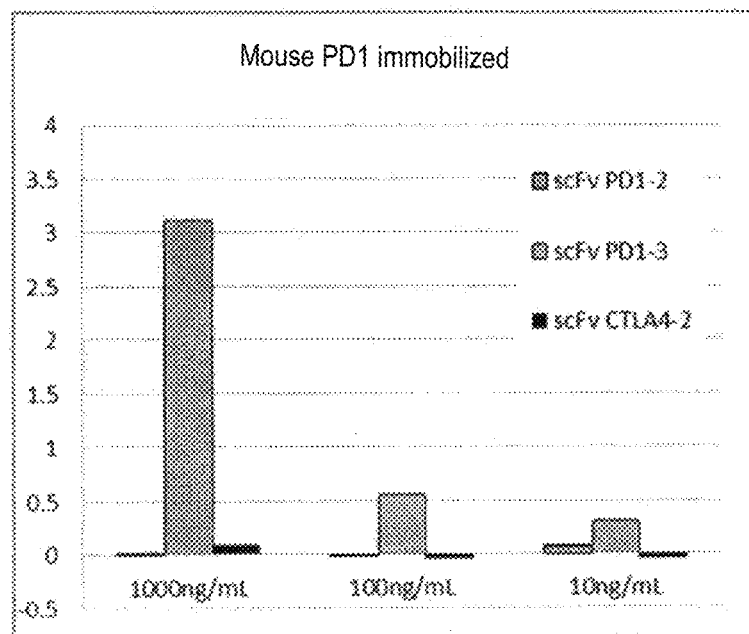

[Figure 10]
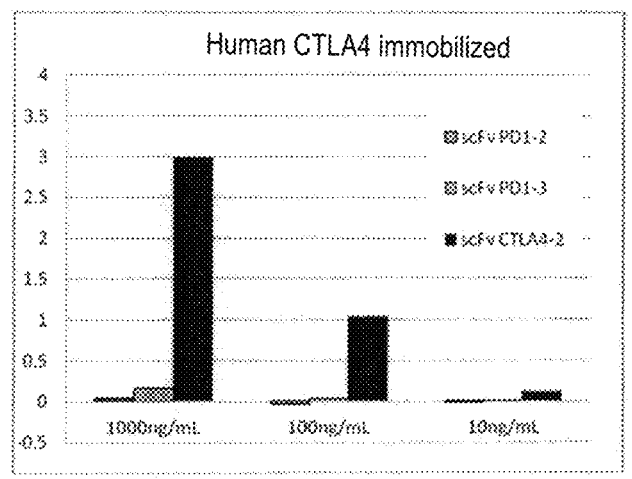
[Figure 11]
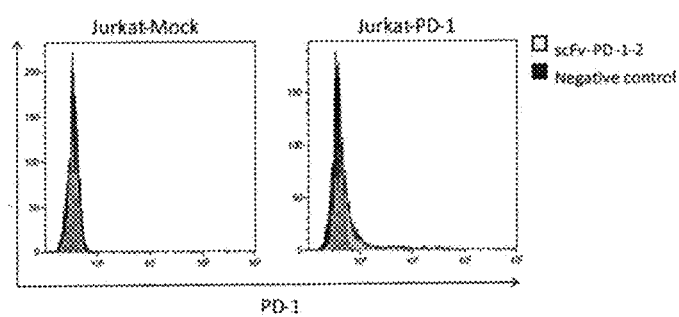

[Figure 12]
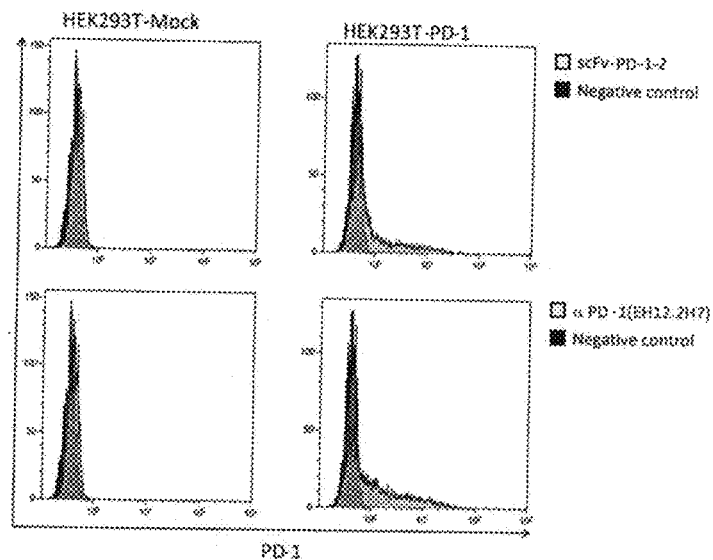
[Figure 13]
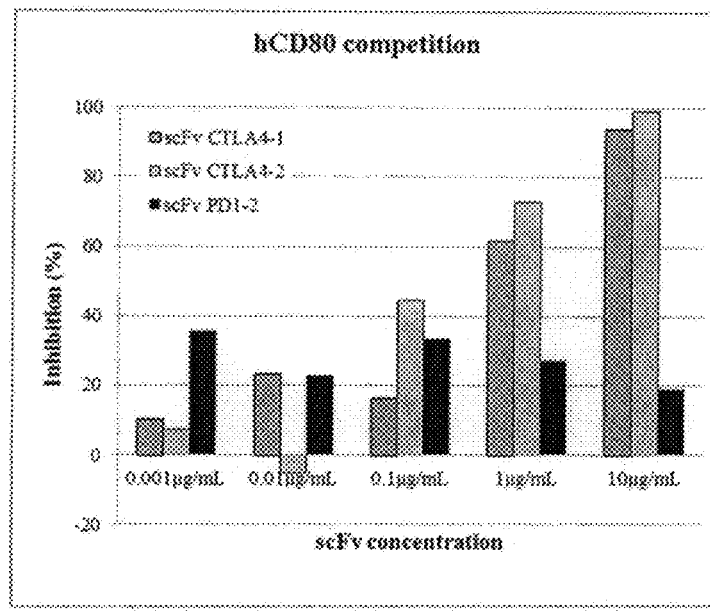

[Figure 14]
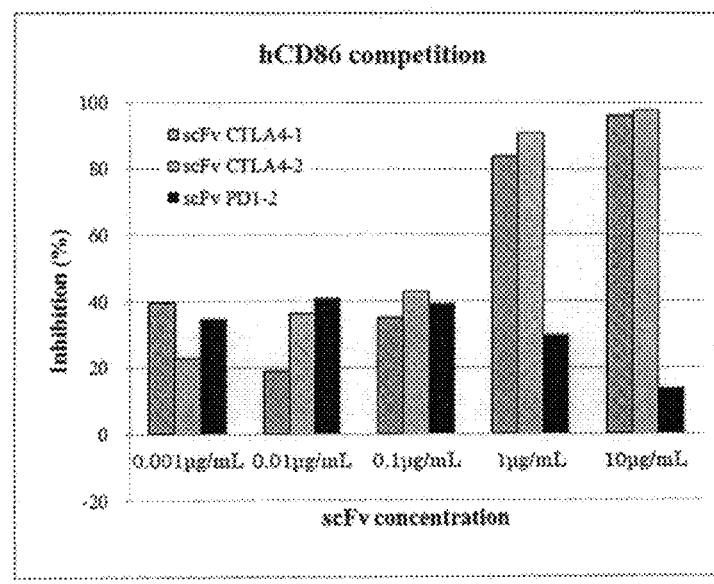
[Figure 15]
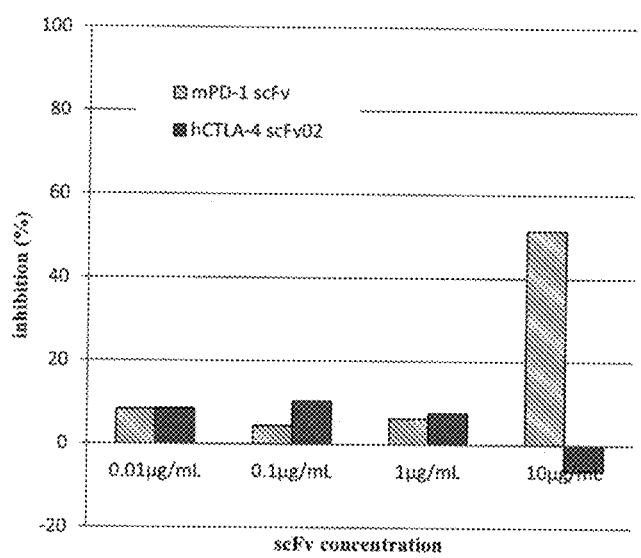

[Figure 16]

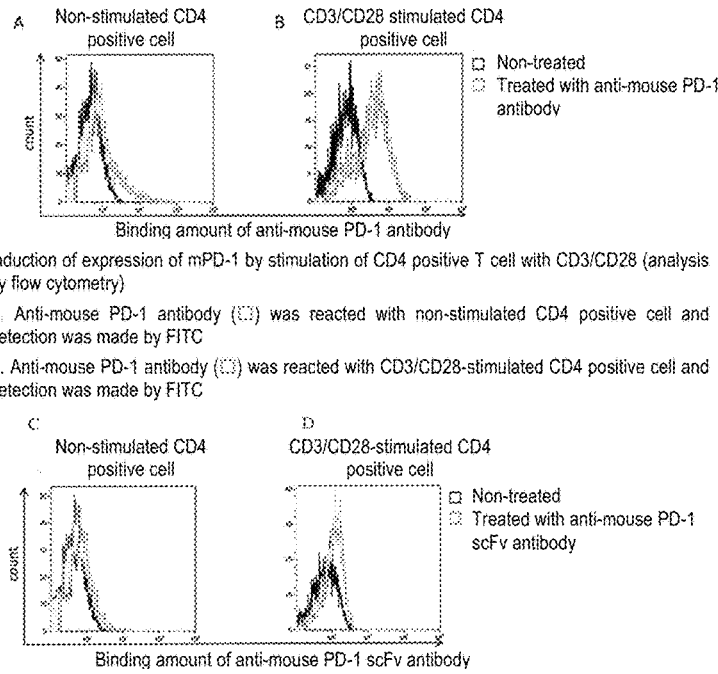

Induction of expression of mPD-1 by stimulation of CD4 positive T cell with CD3/CD28 (analysis by flow cytometry)
A. Anti-mouse PD-1 antibody (☐) was reacted with non-stimulated CD4 positive cell and detection was made by FITC
B. Anti-mouse PD-1 antibody (☐) was reacted with CD3/CD28-stimulated CD4 positive cell and detection was made by FITC

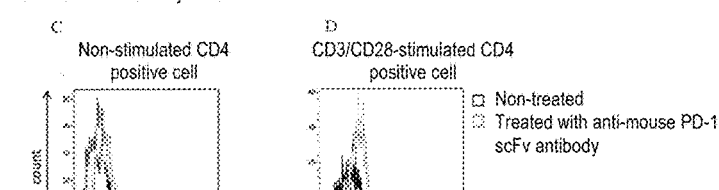

Binding of anti-mouse PD-1 scFv antibody (☐) to CD3 and CD28 stimulated CD4 positive cells (analysis by flow cytometry)
C. Anti-mouse PD-1 scFv antibody (☐) was reacted with non-stimulated CD4 positive cell and Alexa488·anti-His tag antibody was reacted with His thereof and detection was made
D. Anti-mouse PD-1 scFv antibody was reacted with CD3 and CD28 stimulated CD4 positive cell and Alexa488·anti-His tag antibody was reacted with His thereof and detection was made

[Figure 17]

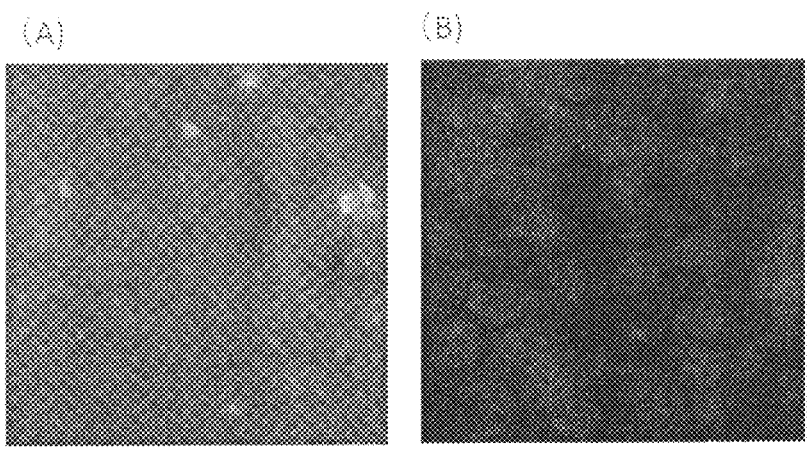

A. Tumor tissue of an anti-mouse PD-1 scFv_ antibody-secreting bacterium of the genus *Bifidobacterium* administered mouse
B. Tumor tissue of not administered mouse

[Figure 18]
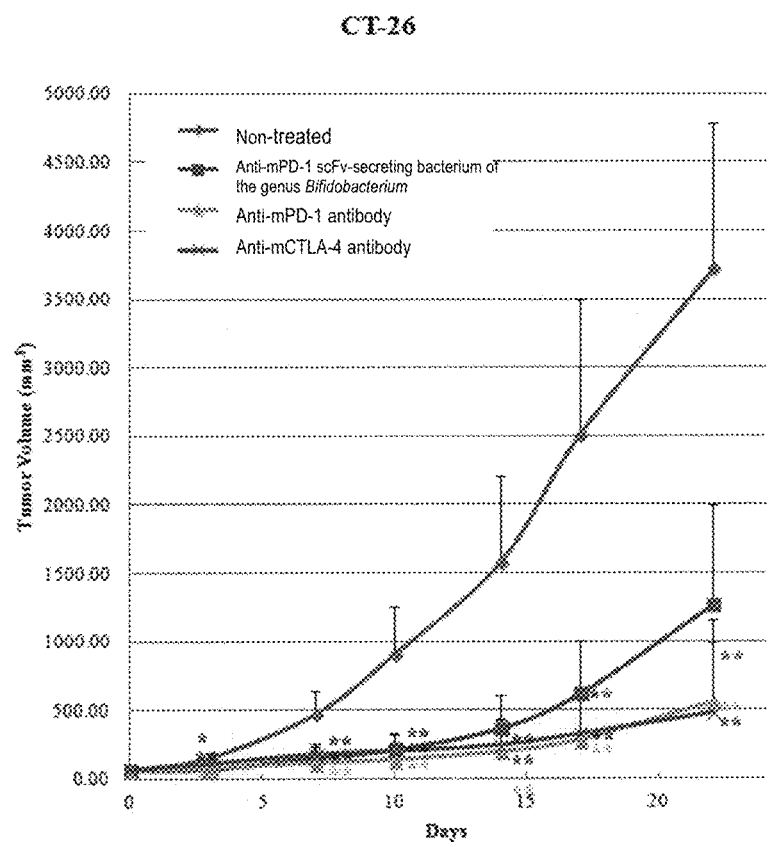
The mean values + S.D. of seven mice.
*: P value < 0.05 (vs Non-treated)
**: P value < 0.01 (vs Non-treated)

[Figure 19]
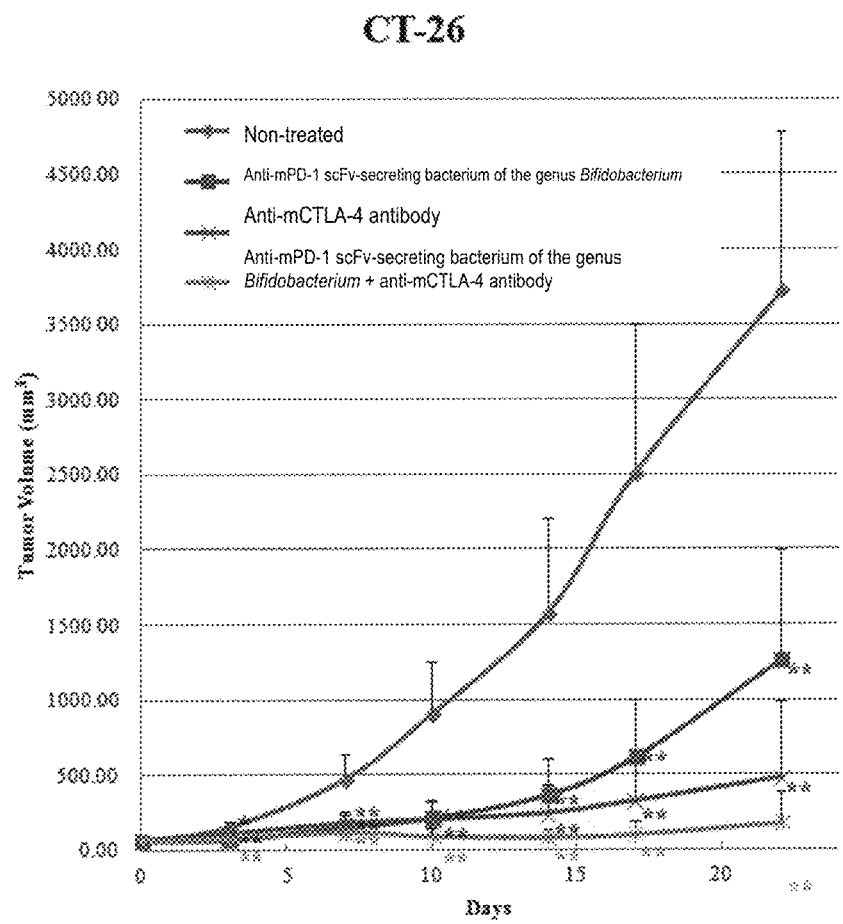
The mean values + S.D. of seven or six mice.
*: P value < 0.05 (vs Non-treated)
**: P value < 0.01 (vs Non-treated)

[Figure 20]
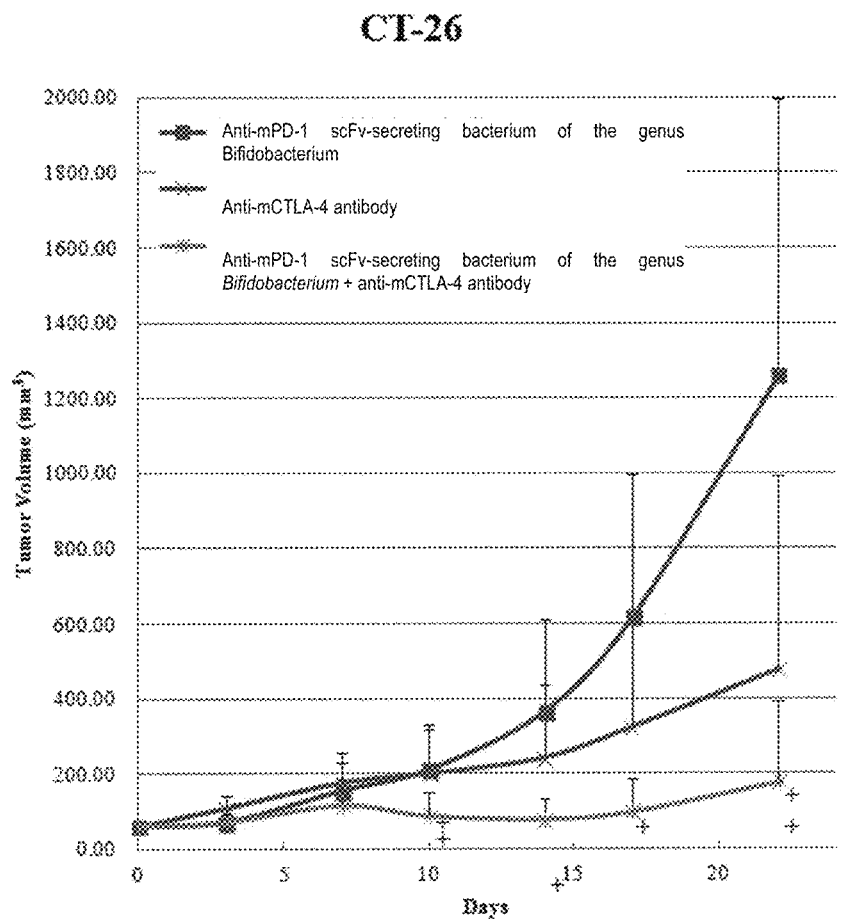
The mean values + S.D. of seven or six animals
+: P value < 0.05 (vs combination treatment)
++: P value < 0.01 (vs combination treatment)

[Figure 21]
*Bifidobacterium longum* 105-A/pHuSP69Ly-hPD-1scFv03 strain
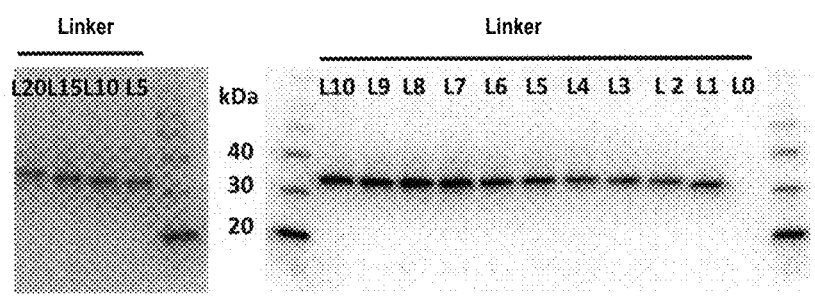
Western analysis of anti-hPD-1 scFv03 antibodies different in linker length secreted in supernatant of bacterium of the genus *Bifidobacterium* culture -
[Figure 22]
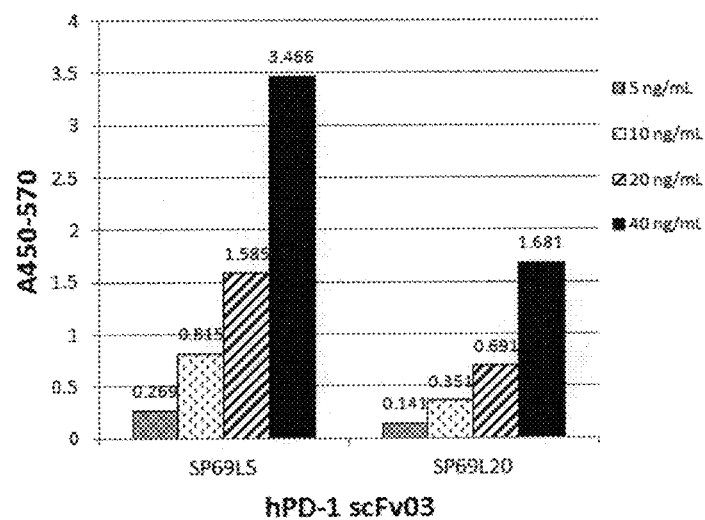

[Figure 23]
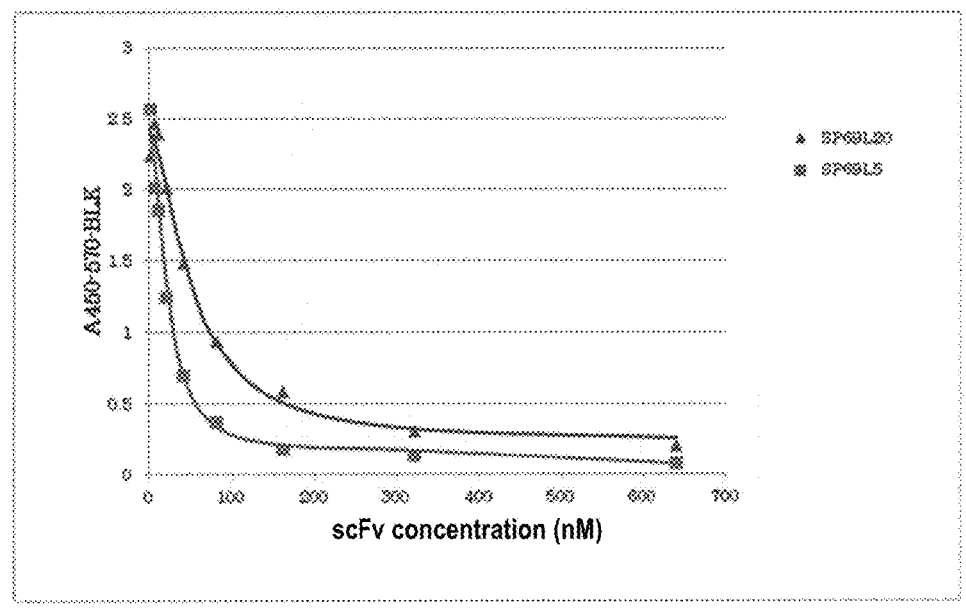

[Figure 24]
(a)
B. longum 105A/pHuSPxL20-hPD-1 scFv03
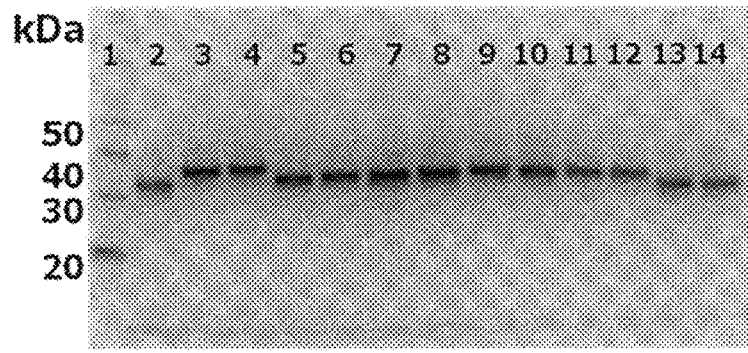
1: Marker
2: SP7
3: SP45 #1
4: SP45 #2
5:
6:
7: SP50 #1
8: SP50 #2
9: SP52 #1
10: SP52 #2
11: SP55 #1
12: SP55 #2
13: SP58 #1
14: SP58 #2
(b)
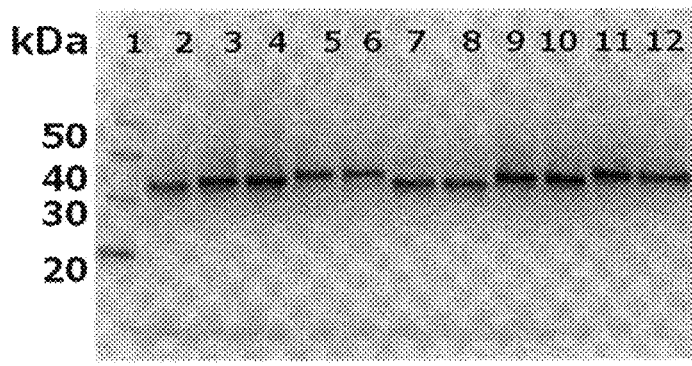
1: Marker
2: SP7
3: SP64 #1
4: SP64 #2
5: SP66 #1
6: SP66 #2
7: SP67 #1
8: SP67 #2
9: SP68 #1
10: SP68 #2
11: SP69 #1
12: SP69 #2

[Figure 25]
(a)
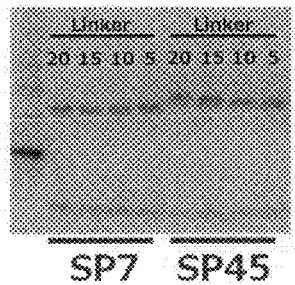
SP7  SP45
(b)
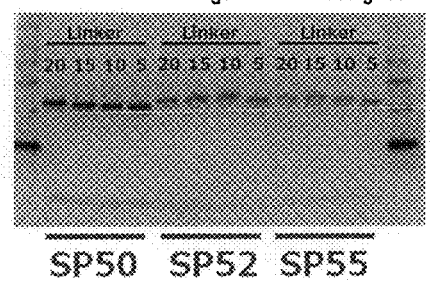
SP50  SP52  SP55
(c)
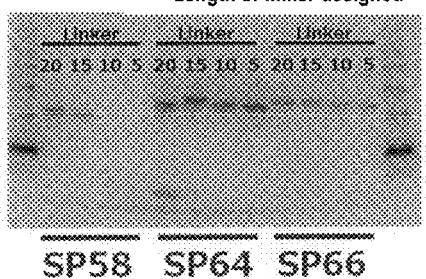
SP58  SP64  SP66
(d)
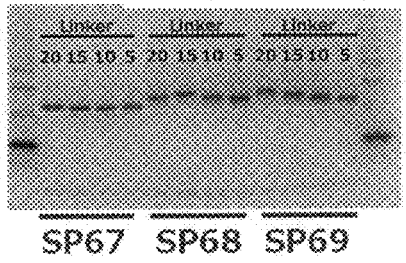
SP67  SP68  SP69

[Figure 26]
(a)
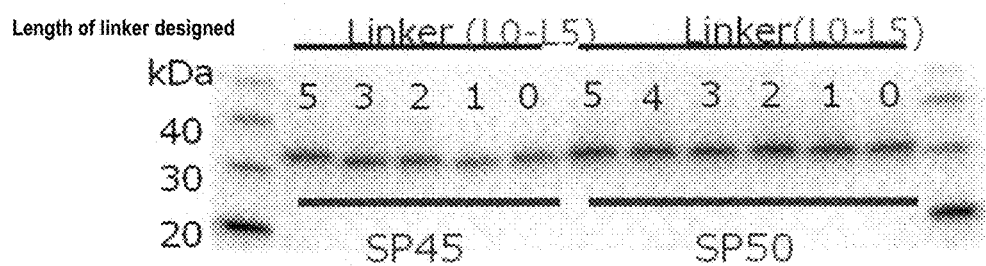
(b)
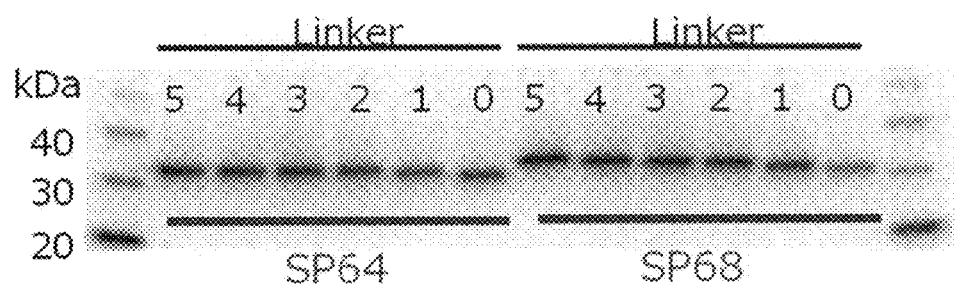
(c)
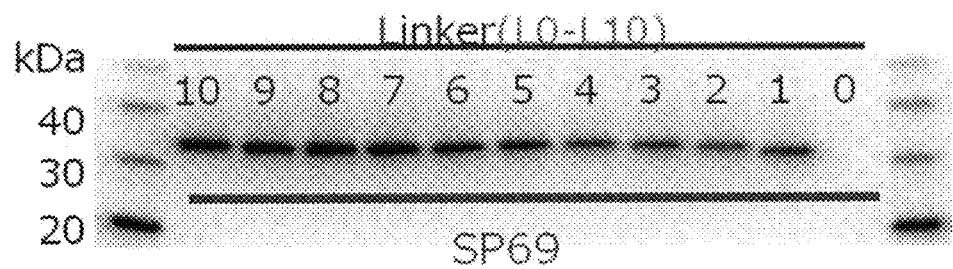

[Figure 27]
*B. longum* 105A/pHuSPxLy-hPD-1 scFV03 (His-tagged)
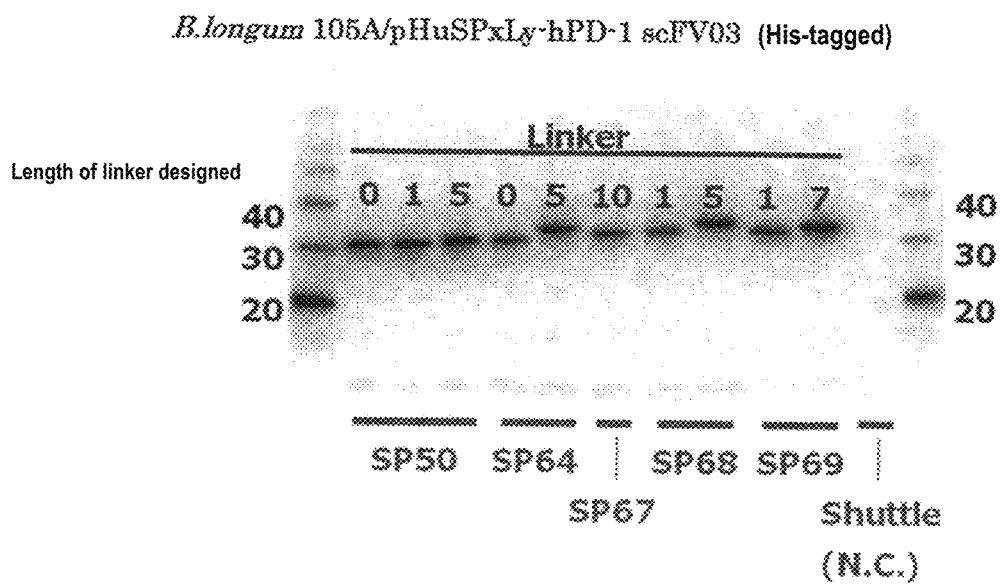
[Figure 28]
Bifidobacterium longum 105-A/pP30SPxL20-hCTLA-4scFv02 strain
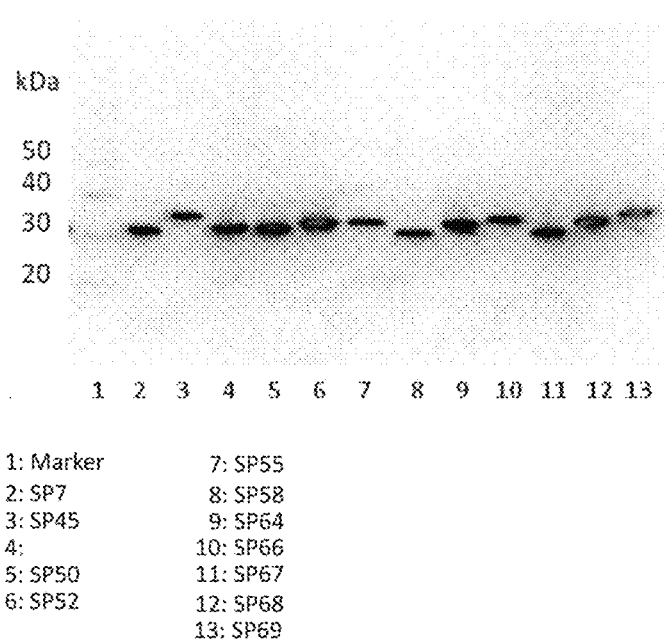
1: Marker
2: SP7
3: SP45
4:
5: SP50
6: SP52
7: SP55
8: SP58
9: SP64
10: SP66
11: SP67
12: SP68
13: SP69

[Figure 29]
*Bifidobacterium longum* 105-A/pP30SPxLy-hCTLA-4scFv02 strain (FLAG-tagged)
(a)
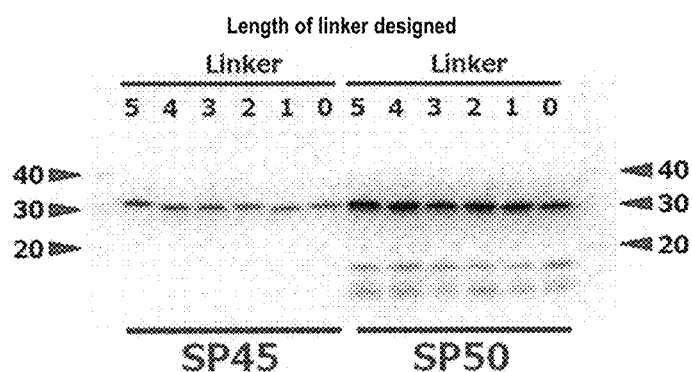
(b)
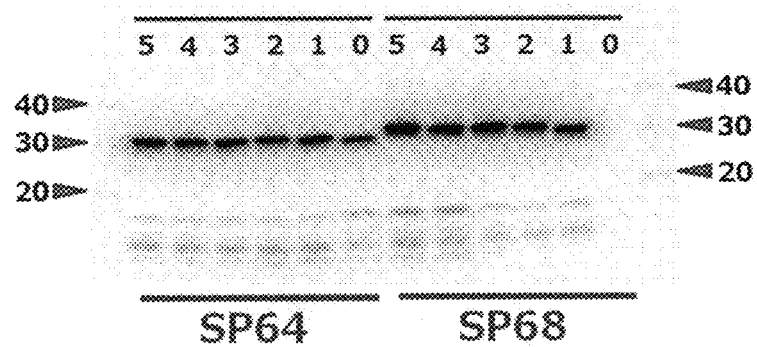
(c)
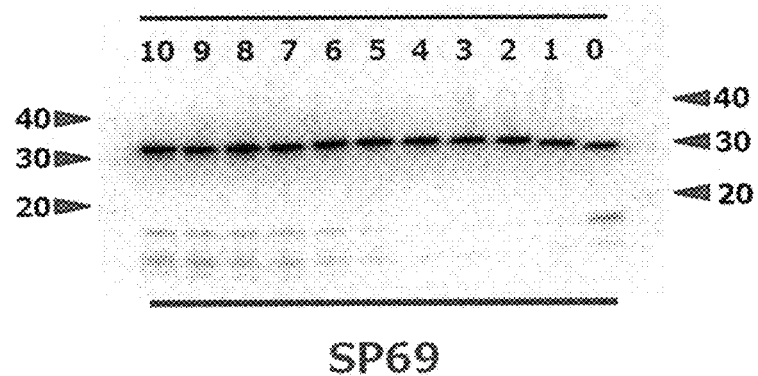

SEQUENCE LISTING

```
<160> NUMBER OF SEQ ID NOS: 142

<210> SEQ ID NO 1
<211> LENGTH: 738
<212> TYPE: DNA
<213> ORGANISM: Homo sapiens
<220> FEATURE:
<221> NAME/KEY: misc_feature
<222> LOCATION: (1)..(1)
<223> OTHER INFORMATION: Inventor: KOSEKI, Koichi; MASAKI, Takeshi;
      SHIOYA, Koichiro; SHIM IZU, Hitomi; TSUKAMOTO, Masao; KOBAYASHI,
      Satoshi; MATSUMURA, Tomio; SHIMATANI, Yuko
<220> FEATURE:
<221> NAME/KEY: CDS
<222> LOCATION: (1)..(738)
<223> OTHER INFORMATION: scFv-PD-1-1

<400> SEQUENCE: 1 atg cag gtc cag ctg gtc cag agc ggc agc gaa ctg aag aag ccg ggc      48
Met Gln Val Gln Leu Val Gln Ser Gly Ser Glu Leu Lys Lys Pro Gly
1               5                   10                  15 gcc tcg gtc aag atc tcg tgc aag gcc tcg ggc tac acc ttc acc aac      96
Ala Ser Val Lys Ile Ser Cys Lys Ala Ser Gly Tyr Thr Phe Thr Asn
            20                  25                  30 tac ggc atg aac tgg gtg cgc cag gcc ccg ggc cag ggc ctg cag tgg     144
Tyr Gly Met Asn Trp Val Arg Gln Ala Pro Gly Gln Gly Leu Gln Trp
        35                  40                  45 atg ggc tgg atc aac acc gac tcc ggc gaa tcc acc tac gcc gag gaa     192
Met Gly Trp Ile Asn Thr Asp Ser Gly Glu Ser Thr Tyr Ala Glu Glu
    50                  55                  60 ttc aag ggc cgc ttc gtg ttc tcc ctg gac acc tcg gtg aac acc gcc     240
Phe Lys Gly Arg Phe Val Phe Ser Leu Asp Thr Ser Val Asn Thr Ala
65                  70                  75                  80 tac ctg cag atc acc tcg ctg acc gcc gaa gac acc ggc atg tac ttc     288
Tyr Leu Gln Ile Thr Ser Leu Thr Ala Glu Asp Thr Gly Met Tyr Phe
                85                  90                  95 tgc gtg cgc gtc ggc tac gat gcc ctg gac tac tgg ggc cag ggc acc     336
Cys Val Arg Val Gly Tyr Asp Ala Leu Asp Tyr Trp Gly Gln Gly Thr
            100                 105                 110 ctg gtc acc gtg tcc agc ggc ggc ggc ggc tcg ggc ggc ggc ggc tcc     384
Leu Val Thr Val Ser Ser Gly Gly Gly Gly Ser Gly Gly Gly Gly Ser
        115                 120                 125 ggc ggc ggc ggc tcc gaa atc gtg ctg acc cag agc ccg tcg tcc ctg     432
Gly Gly Gly Gly Ser Glu Ile Val Leu Thr Gln Ser Pro Ser Ser Leu
    130                 135                 140 agc gcc tcc gtg ggc gac cgc gtg acc atc acc tgc agc gcc cgc tcg     480
Ser Ala Ser Val Gly Asp Arg Val Thr Ile Thr Cys Ser Ala Arg Ser
145                 150                 155                 160
```

-continued

| | |
|---|---|
| tcc gtg agc tac atg cac tgg ttc cag cag aag ccg ggc aag gcc ccg<br>Ser Val Ser Tyr Met His Trp Phe Gln Gln Lys Pro Gly Lys Ala Pro<br>                            165                       170                     175 | 528 |
| aag ctg tgg atc tac cgt acc tcg aac ctg gcc tcc ggc gtg ccg tcc<br>Lys Leu Trp Ile Tyr Arg Thr Ser Asn Leu Ala Ser Gly Val Pro Ser<br>            180                       185                       190 | 576 |
| cgc ttc tcg ggc tcc ggc tcg ggc acc agc tac tgc ctg acc atc aac<br>Arg Phe Ser Gly Ser Gly Ser Gly Thr Ser Tyr Cys Leu Thr Ile Asn<br>                195                       200                     205 | 624 |
| tcc ctg cag ccg gaa gac ttc gcc acc tac tac tgc cag cag cgc tcc<br>Ser Leu Gln Pro Glu Asp Phe Ala Thr Tyr Tyr Cys Gln Gln Arg Ser<br>            210                       215                       220 | 672 |
| tcg ttc ccg ctg acc ttc ggc ggc ggc acc aag ctg gaa atc aag cac<br>Ser Phe Pro Leu Thr Phe Gly Gly Gly Thr Lys Leu Glu Ile Lys His<br>225                       230                       235                     240 | 720 |
| cat cat cac cac cac tga<br>His His His His His<br>               245 | 738 |

<210> SEQ ID NO 2
<211> LENGTH: 750
<212> TYPE: DNA
<213> ORGANISM: Homo sapiens
<220> FEATURE:
<221> NAME/KEY: CDS
<222> LOCATION: (1)..(750)
<223> OTHER INFORMATION: scFv-PD-1-2

<400> SEQUENCE: 2

| | |
|---|---|
| atg cag gtc cag ctg cag gaa tcg ggc ccg ggc ctg gtg aag ccg tcc<br>Met Gln Val Gln Leu Gln Glu Ser Gly Pro Gly Leu Val Lys Pro Ser<br>1                       5                       10                       15 | 48 |
| cag tcg ctg tcg ctg acc tgc acc gtg acc ggc cat agc atc acc agc<br>Gln Ser Leu Ser Leu Thr Cys Thr Val Thr Gly His Ser Ile Thr Ser<br>                20                       25                       30 | 96 |
| gac tac gcc tgg aac tgg ata cgc cag ttc ccg ggc gac aag ctg gaa<br>Asp Tyr Ala Trp Asn Trp Ile Arg Gln Phe Pro Gly Asp Lys Leu Glu<br>                   35                       40                     45 | 144 |
| tgg atg ggc tac atc tcg tac tcc ggc tac acc acc tac aac ccg tcc<br>Trp Met Gly Tyr Ile Ser Tyr Ser Gly Tyr Thr Thr Tyr Asn Pro Ser<br>50                       55                       60 | 192 |
| ctg aag tcg cgc gtg tcc atc acc cgc gac acc agc aag aac cag ttc<br>Leu Lys Ser Arg Val Ser Ile Thr Arg Asp Thr Ser Lys Asn Gln Phe<br>65                       70                       75                     80 | 240 |
| ttc ctg cag ctg aac tcc gtg acc acc gaa gac acc gcc acc tac ttc<br>Phe Leu Gln Leu Asn Ser Val Thr Thr Glu Asp Thr Ala Thr Tyr Phe<br>                     85                       90                     95 | 288 |
| tgc gcc cgc gac ctg gat tac ggc ccg tgg ttc gcc tac tgg ggc cag<br>Cys Ala Arg Asp Leu Asp Tyr Gly Pro Trp Phe Ala Tyr Trp Gly Gln<br>                100                       105                     110 | 336 |
| ggc acc acc gtc acc gtg tcc tcg ggc ggc ggc ggc agc ggc ggc ggc<br>Gly Thr Thr Val Thr Val Ser Ser Gly Gly Gly Gly Ser Gly Gly Gly<br>            115                       120                     125 | 384 |
| ggc tcg ggc ggc ggc ggc tcc gac atc cag atg acc cag tcc ccg gcc<br>Gly Ser Gly Gly Gly Gly Ser Asp Ile Gln Met Thr Gln Ser Pro Ala<br>130                       135                       140 | 432 |
| tcc ctg tcg gcc tcc gtg ggc gaa acc gtg acc ctg acc tgc cgt gcc<br>Ser Leu Ser Ala Ser Val Gly Glu Thr Val Thr Leu Thr Cys Arg Ala<br>145                     150                       155                     160 | 480 |
| tcc gaa aac atc cac aac tac ctg gcc tgg tac cag cag aag cag ggc<br>Ser Glu Asn Ile His Asn Tyr Leu Ala Trp Tyr Gln Gln Lys Gln Gly<br>                   165                       170                     175 | 528 |

| aag tcc ccg cag ctg ctg gtg tac aac gtg aag acc ctg gcc gac ggc | 576 |
| Lys Ser Pro Gln Leu Leu Val Tyr Asn Val Lys Thr Leu Ala Asp Gly | |
| 180 185 190 | |

| gtc ccg tcc cgc ttc tcg ggc tcc ggc tcg ggc acc cag tac tcc ctg | 624 |
| Val Pro Ser Arg Phe Ser Gly Ser Gly Ser Gly Thr Gln Tyr Ser Leu | |
| 195 200 205 | |

| aag atc aac tcc ctg cag ccg gaa gac ttc ggc tcg tac tac tgc cag | 672 |
| Lys Ile Asn Ser Leu Gln Pro Glu Asp Phe Gly Ser Tyr Tyr Cys Gln | |
| 210 215 220 | |

| cac ttc tgg tcg tcc ccg tgg acc ttc ggc ggc ggc acc aag ctg gaa | 720 |
| His Phe Trp Ser Ser Pro Trp Thr Phe Gly Gly Gly Thr Lys Leu Glu | |
| 225 230 235 240 | |

| atc aag cgt cac cac cat cat cat cac tga | 750 |
| Ile Lys Arg His His His His His His | |
| 245 | |

```
<210> SEQ ID NO 3
<211> LENGTH: 762
<212> TYPE: DNA
<213> ORGANISM: Mus musculus
<220> FEATURE:
<221> NAME/KEY: CDS
<222> LOCATION: (1)..(762)
<223> OTHER INFORMATION: scFv-PD-1-3

<400> SEQUENCE: 3
```

| atg gaa gtg cgt ctg ctg gaa tcg ggc ggc ggc ctg gtc aag ccg gag | 48 |
| Met Glu Val Arg Leu Leu Glu Ser Gly Gly Gly Leu Val Lys Pro Glu | |
| 1 5 10 15 | |

| ggc tcg ctg aag ctg tcc tgc gtg gcc tcg ggc ttc acc ttc tcc gac | 96 |
| Gly Ser Leu Lys Leu Ser Cys Val Ala Ser Gly Phe Thr Phe Ser Asp | |
| 20 25 30 | |

| tac ttc atg agc tgg gtg cgc cag gcc ccg ggc aag ggc ctg gaa tgg | 144 |
| Tyr Phe Met Ser Trp Val Arg Gln Ala Pro Gly Lys Gly Leu Glu Trp | |
| 35 40 45 | |

| gtg gcc cat atc tac acc aag tcc tac aac tac gcc acc tac tac tcg | 192 |
| Val Ala His Ile Tyr Thr Lys Ser Tyr Asn Tyr Ala Thr Tyr Tyr Ser | |
| 50 55 60 | |

| ggc tcc gtg aag ggc cgc ttc acc atc tcc cgc gac gat tcg cgt tcc | 240 |
| Gly Ser Val Lys Gly Arg Phe Thr Ile Ser Arg Asp Asp Ser Arg Ser | |
| 65 70 75 80 | |

| atg gtg tac ctg cag atg aac aac ctg cgc acc gaa gat acc gcc acc | 288 |
| Met Val Tyr Leu Gln Met Asn Asn Leu Arg Thr Glu Asp Thr Ala Thr | |
| 85 90 95 | |

| tac tac tgc acc cgc gac ggc tcc ggc tac ccg tcc ctg gat ttc tgg | 336 |
| Tyr Tyr Cys Thr Arg Asp Gly Ser Gly Tyr Pro Ser Leu Asp Phe Trp | |
| 100 105 110 | |

| ggc cag ggc acc cag gtc acc gtg tcc tcg ggc ggc ggc ggc tcc ggc | 384 |
| Gly Gln Gly Thr Gln Val Thr Val Ser Ser Gly Gly Gly Gly Ser Gly | |
| 115 120 125 | |

| ggc ggc ggc agc ggc ggc ggc ggc tcc tac gaa ctg acc cag ccg ccg | 432 |
| Gly Gly Gly Ser Gly Gly Gly Gly Ser Tyr Glu Leu Thr Gln Pro Pro | |
| 130 135 140 | |

| tcc gcc tcc gtc aac gtg ggc gaa acc gtg aag atc acc tgc tcc ggc | 480 |
| Ser Ala Ser Val Asn Val Gly Glu Thr Val Lys Ile Thr Cys Ser Gly | |
| 145 150 155 160 | |

| gac cag ctg ccg aag tac ttc gcc gac tgg ttc cat cag cgc tcc gac | 528 |
| Asp Gln Leu Pro Lys Tyr Phe Ala Asp Trp Phe His Gln Arg Ser Asp | |
| 165 170 175 | |

| cag acc atc ctg cag gtg atc tac gac gat aac aag cgc ccg tcc ggc | 576 |
| Gln Thr Ile Leu Gln Val Ile Tyr Asp Asp Asn Lys Arg Pro Ser Gly | |
| 180 185 190 | |

| | | |
|---|---|---|
| atc ccg gaa cgc atc tcc ggc tcc tcg tcc ggc acc acc gcc acc ctg<br>Ile Pro Glu Arg Ile Ser Gly Ser Ser Ser Gly Thr Thr Ala Thr Leu<br>         195                           200                    205 | 624 |
| acc atc cgt gac gtg cgc gcc gaa gat gaa ggc gac tac tac tgc ttc<br>Thr Ile Arg Asp Val Arg Ala Glu Asp Glu Gly Asp Tyr Tyr Cys Phe<br>210                         215                       220 | 672 |
| agc ggc tac gtg gat tcc gac tcg aag ctg tac gtc ttc ggc tcg ggc<br>Ser Gly Tyr Val Asp Ser Asp Ser Lys Leu Tyr Val Phe Gly Ser Gly<br>225                       230                    235                240 | 720 |
| acc cag ctg acc gtc ctg ggc cat cac cac cat cat cac tga<br>Thr Gln Leu Thr Val Leu Gly His His His His His His<br>                     245                       250 | 762 |

<210> SEQ ID NO 4
<211> LENGTH: 765
<212> TYPE: DNA
<213> ORGANISM: Homo sapiens
<220> FEATURE:
<221> NAME/KEY: CDS
<222> LOCATION: (1)..(765)
<223> OTHER INFORMATION: scFv-CTLA-4-1

<400> SEQUENCE: 4

| | | |
|---|---|---|
| atg cag gtc cag ctg gtc gaa tcg ggc ggc ggc gtc gtc cag ccg ggc<br>Met Gln Val Gln Leu Val Glu Ser Gly Gly Gly Val Val Gln Pro Gly<br>1                   5                      10                   15 | 48 |
| cgt tcc ctg cgt ctg tcg tgc gcc gcc tcg ggc ttc acc ttc tcc agc<br>Arg Ser Leu Arg Leu Ser Cys Ala Ala Ser Gly Phe Thr Phe Ser Ser<br>              20                     25                   30 | 96 |
| tac ggc atg cac tgg gtg cgt cag gcc ccg ggc aag ggc ctg gag tgg<br>Tyr Gly Met His Trp Val Arg Gln Ala Pro Gly Lys Gly Leu Glu Trp<br>         35                       40                    45 | 144 |
| gtg gcc gtc atc tgg tac gac ggc tcc aac aag tac tac gcc gat tcc<br>Val Ala Val Ile Trp Tyr Asp Gly Ser Asn Lys Tyr Tyr Ala Asp Ser<br>    50                      55                    60 | 192 |
| gtc aag ggc cgc ttc acc atc tcg cgt gac aac tcc aag aac acc ctg<br>Val Lys Gly Arg Phe Thr Ile Ser Arg Asp Asn Ser Lys Asn Thr Leu<br>65                    70                     75                   80 | 240 |
| tac ctg cag atg aac tcc ctg cgt gcc gaa gac acc gcc gtg tac tac<br>Tyr Leu Gln Met Asn Ser Leu Arg Ala Glu Asp Thr Ala Val Tyr Tyr<br>              85                     90                   95 | 288 |
| tgc gcc cgc gat ccg cgt ggc gcc acc ctg tac tac tac tac tac ggc<br>Cys Ala Arg Asp Pro Arg Gly Ala Thr Leu Tyr Tyr Tyr Tyr Tyr Gly<br>              100                    105                 110 | 336 |
| atg gat gtc tgg ggc cag ggc acc acc gtg acc gtc tcg tcc ggc ggc<br>Met Asp Val Trp Gly Gln Gly Thr Thr Val Thr Val Ser Ser Gly Gly<br>         115                     120                    125 | 384 |
| ggc ggc tcc ggc ggc ggc ggc agc ggc ggc ggc ggc tcc gac atc cag<br>Gly Gly Ser Gly Gly Gly Gly Ser Gly Gly Gly Gly Ser Asp Ile Gln<br>130                    135                    140 | 432 |
| atg acc cag tcc ccg agc tcg ctg agc gcc tcg gtg ggc gat cgc gtc<br>Met Thr Gln Ser Pro Ser Ser Leu Ser Ala Ser Val Gly Asp Arg Val<br>145                    150                    155                160 | 480 |
| acc atc acc tgc cgt gcc tcc cag agc atc aac tcc tac ctg gac tgg<br>Thr Ile Thr Cys Arg Ala Ser Gln Ser Ile Asn Ser Tyr Leu Asp Trp<br>                  165                   170                 175 | 528 |
| tac cag cag aag ccg ggc aag gcc ccg aag ctg ctg atc tac gcc gcc<br>Tyr Gln Gln Lys Pro Gly Lys Ala Pro Lys Leu Leu Ile Tyr Ala Ala<br>              180                    185                 190 | 576 |
| tcc agc ctg cag agc ggc gtg ccg tcg cgc ttc tcg ggc tcc ggc agc<br>Ser Ser Leu Gln Ser Gly Val Pro Ser Arg Phe Ser Gly Ser Gly Ser<br>         195                     200                    205 | 624 |

```
ggc acc gac ttc acc ctg acc atc tcg tcc ctg cag ccg gag gat ttc    672
Gly Thr Asp Phe Thr Leu Thr Ile Ser Ser Leu Gln Pro Glu Asp Phe
        210                 215                 220 gcc acc tac tac tgc cag cag tac tac tcc acc ccg ttc acc ttc ggc    720
Ala Thr Tyr Tyr Cys Gln Gln Tyr Tyr Ser Thr Pro Phe Thr Phe Gly
225                 230                 235                 240 ccg ggc acc aag gtc gag atc aag cat cat cac cat cat cac tga        765
Pro Gly Thr Lys Val Glu Ile Lys His His His His His His
                245                 250

<210> SEQ ID NO 5
<211> LENGTH: 747
<212> TYPE: DNA
<213> ORGANISM: Homo sapiens
<220> FEATURE:
<221> NAME/KEY: CDS
<222> LOCATION: (1)..(747)
<223> OTHER INFORMATION: scFv-CTLA-4-2

<400> SEQUENCE: 5 atg cag gtc cag ctg gtc gaa tcg ggc ggc ggc gtc gtc cag ccg ggc     48
Met Gln Val Gln Leu Val Glu Ser Gly Gly Gly Val Val Gln Pro Gly
1               5                   10                  15 cgt agc ctg cgt ctg tcg tgc gcc gcc tcg ggc ttc acc ttc tcc agc     96
Arg Ser Leu Arg Leu Ser Cys Ala Ala Ser Gly Phe Thr Phe Ser Ser
            20                  25                  30 tac acc atg cac tgg gtg cgt cag gcc ccg ggc aag ggc ctg gag tgg    144
Tyr Thr Met His Trp Val Arg Gln Ala Pro Gly Lys Gly Leu Glu Trp
        35                  40                  45 gtc acc ttc atc tcc tac gac ggc aac aac aag tac tac gcc gat tcc    192
Val Thr Phe Ile Ser Tyr Asp Gly Asn Asn Lys Tyr Tyr Ala Asp Ser
    50                  55                  60 gtg aag ggc cgc ttc acc atc tcc cgt gac aac agc aag aac acc ctg    240
Val Lys Gly Arg Phe Thr Ile Ser Arg Asp Asn Ser Lys Asn Thr Leu
65                  70                  75                  80 tac ctg cag atg aac tcc ctg cgc gcc gaa gac acc gcc atc tac tac    288
Tyr Leu Gln Met Asn Ser Leu Arg Ala Glu Asp Thr Ala Ile Tyr Tyr
                85                  90                  95 tgc gcc cgt acc ggc tgg ctg ggc ccg ttc gat tac tgg ggc cag ggc    336
Cys Ala Arg Thr Gly Trp Leu Gly Pro Phe Asp Tyr Trp Gly Gln Gly
            100                 105                 110 acc ctg gtg acc gtc tcg tcg ggc ggc ggc ggc tcg ggc ggc ggc ggc    384
Thr Leu Val Thr Val Ser Ser Gly Gly Gly Gly Ser Gly Gly Gly Gly
        115                 120                 125 tcc ggc ggc ggc ggc agc gag atc gtg ctg acc cag tcc ccg ggc acc    432
Ser Gly Gly Gly Gly Ser Glu Ile Val Leu Thr Gln Ser Pro Gly Thr
130                 135                 140 ctg tcg ctg tcc ccg ggc gaa cgc gcc acc ctg tcc tgc cgt gcc agc    480
Leu Ser Leu Ser Pro Gly Glu Arg Ala Thr Leu Ser Cys Arg Ala Ser
145                 150                 155                 160 cag tcg gtc ggc agc tcg tac ctg gcc tgg tac cag cag aag ccg ggc    528
Gln Ser Val Gly Ser Ser Tyr Leu Ala Trp Tyr Gln Gln Lys Pro Gly
                165                 170                 175 cag gcc ccg cgt ctg ctg atc tac ggc gcc ttc tcc cgt gcc acc ggc    576
Gln Ala Pro Arg Leu Leu Ile Tyr Gly Ala Phe Ser Arg Ala Thr Gly
            180                 185                 190 atc ccg gac cgt ttc tcc ggc agc ggc tcg ggc acc gat ttc acc ctg    624
Ile Pro Asp Arg Phe Ser Gly Ser Gly Ser Gly Thr Asp Phe Thr Leu
        195                 200                 205 acc atc tcc cgc ctg gag ccg gaa gat ttc gcc gtc tac tac tgc cag    672
Thr Ile Ser Arg Leu Glu Pro Glu Asp Phe Ala Val Tyr Tyr Cys Gln
    210                 215                 220
```

-continued

```
cag tac ggc tcc agc ccg tgg acc ttc ggc cag ggc acc aag gtg gaa    720
Gln Tyr Gly Ser Ser Pro Trp Thr Phe Gly Gln Gly Thr Lys Val Glu
225                 230                 235                 240 atc aag cat cat cat cat cat cac tga                                747
Ile Lys His His His His His His
                245
```

<210> SEQ ID NO 6
<211> LENGTH: 33
<212> TYPE: PRT
<213> ORGANISM: Bifidobacterium spp.
<220> FEATURE:
<223> OTHER INFORMATION: SP7

<400> SEQUENCE: 6

Met Ala Leu Met Met Ser Val Lys Thr Ile Ile Ser Thr Ser Val Ala
1               5                   10                  15

Ile Ile Ala Thr Gly Ala Met Phe Ala Cys Val Ala Pro Phe Ala Ser
                20                  25                  30

Ala

<210> SEQ ID NO 7
<211> LENGTH: 34
<212> TYPE: PRT
<213> ORGANISM: Bifidobacterium spp.
<220> FEATURE:
<223> OTHER INFORMATION: SP45

<400> SEQUENCE: 7

Met Lys His Leu Ser His Arg Thr Ile Ala Ile Ile Val Ala Leu Leu
1               5                   10                  15

Ser Thr Leu Ser Leu Ala Leu Ala Val Ile Ser Leu Pro His Gln Ala
                20                  25                  30

Tyr Ala

<210> SEQ ID NO 8
<211> LENGTH: 56
<212> TYPE: PRT
<213> ORGANISM: Bifidobacterium spp.
<220> FEATURE:
<223> OTHER INFORMATION: SP50

<400> SEQUENCE: 8

Met Ile Val Ala Tyr Pro His Thr Val Gln Tyr Ala Gly Lys Arg Thr
1               5                   10                  15

Arg Lys Gly Arg Met Met Ile Thr Thr Trp Arg Gln Arg Gly Met Ala
                20                  25                  30

Ile Val Ala Met Leu Thr Gly Leu Ile Ile Met Val Gly Val Val Phe
                35                  40                  45

Gly Ser Ala Asn Thr Ala Tyr Ala
    50                  55

<210> SEQ ID NO 9
<211> LENGTH: 35
<212> TYPE: PRT
<213> ORGANISM: Bifidobacterium spp.
<220> FEATURE:
<223> OTHER INFORMATION: SP52

<400> SEQUENCE: 9

Met Ser Phe His Val Ser Ala Gln Ser Val Arg Ala Val Ala Gly Gly
1               5                   10                  15

```
Leu Val Ala Ala Ala Thr Leu Leu Ser Gly Leu Ala Leu Ala Pro Thr
        20                  25                  30

Ala Met Ala
        35

<210> SEQ ID NO 10
<211> LENGTH: 48
<212> TYPE: PRT
<213> ORGANISM: Bifidobacterium spp.
<220> FEATURE:
<223> OTHER INFORMATION: SP55

<400> SEQUENCE: 10

Met Val Arg Arg Ala Gln Ala Ala Leu Arg Ser Val Glu His Thr Ser
1               5                   10                  15

Val Arg Gln Leu Arg Val Leu Ala Ala Ile Val Phe Leu Phe Ala Met
            20                  25                  30

Val Ile Ala Thr Val Ala Pro Ala Val Thr Ala Pro Met Ala Phe Ala
        35                  40                  45

<210> SEQ ID NO 11
<211> LENGTH: 32
<212> TYPE: PRT
<213> ORGANISM: Bifidobacterium spp.
<220> FEATURE:
<223> OTHER INFORMATION: SP58

<400> SEQUENCE: 11

Met Ala Met Ala Arg Arg Trp Thr Pro Gln Arg Phe Val Thr Leu Arg
1               5                   10                  15

Arg Ile Arg Val Ile Ala Cys Ile Ala Ala Thr Ser Ile Ala Leu Ala
            20                  25                  30

<210> SEQ ID NO 12
<211> LENGTH: 31
<212> TYPE: PRT
<213> ORGANISM: Bifidobacterium spp.
<220> FEATURE:
<223> OTHER INFORMATION: SP64

<400> SEQUENCE: 12

Met Lys Ser Leu Ile Arg Asn Val Ala Ala Gly Val Leu Ala Ala Ala
1               5                   10                  15

Thr Met Leu Gly Ile Ala Gly Leu Gly Ala Thr Thr Ala Ser Ala
            20                  25                  30

<210> SEQ ID NO 13
<211> LENGTH: 26
<212> TYPE: PRT
<213> ORGANISM: Bifidobacterium spp.
<220> FEATURE:
<223> OTHER INFORMATION: SP66

<400> SEQUENCE: 13

Met Lys His Trp Lys Lys Met Ala Ala Ser Leu Ile Ala Ile Ser Thr
1               5                   10                  15

Met Val Ala Val Val Pro Thr Thr Tyr Ala
            20                  25

<210> SEQ ID NO 14
<211> LENGTH: 33
<212> TYPE: PRT
<213> ORGANISM: Bifidobacterium spp.
```

```
<220> FEATURE:
<223> OTHER INFORMATION: SP67

<400> SEQUENCE: 14

Met Lys Ile Asn Asn Lys Gly Lys Gly Ala Leu Ile Ala Ala Ile Thr
1               5                   10                  15

Ala Ala Ala Thr Leu Leu Ser Cys Gly Leu Ala Ala Ala Ser Ala Ser
                20                  25                  30

Ala

<210> SEQ ID NO 15
<211> LENGTH: 43
<212> TYPE: PRT
<213> ORGANISM: Bifidobacterium spp.
<220> FEATURE:
<223> OTHER INFORMATION: SP68

<400> SEQUENCE: 15

Met Val Tyr Asn Ile His Ile Leu Gln Thr Arg Lys Thr Gly Arg Val
1               5                   10                  15

Val Ala Ala Ala Ala Ala Ser Val Leu Cys Cys Met Gly Ala Val Phe
                20                  25                  30

Pro Ala Thr Ile Gly Val Thr Ala Ala Ser Ala
                35                  40

<210> SEQ ID NO 16
<211> LENGTH: 30
<212> TYPE: PRT
<213> ORGANISM: Bifidobacterium spp.
<220> FEATURE:
<223> OTHER INFORMATION: SP69

<400> SEQUENCE: 16

Met Asn Tyr Leu Arg Gln Lys Ile Ser Ala Ser Ala Ile Ala Val Leu
1               5                   10                  15

Ser Thr Cys Gly Leu Ile Leu Ala Pro Met Pro Val Phe Ala
                20                  25                  30

<210> SEQ ID NO 17
<211> LENGTH: 147
<212> TYPE: DNA
<213> ORGANISM: Bifidobacterium spp.
<220> FEATURE:
<221> NAME/KEY: CDS
<222> LOCATION: (1)..(147)
<223> OTHER INFORMATION: SP42L20

<400> SEQUENCE: 17 gtg ccc gtg act acg cgc gta tgg tgt tcg gtc gtt atg gtg cca ttg      48
Val Pro Val Thr Thr Arg Val Trp Cys Ser Val Val Met Val Pro Leu
1               5                   10                  15 gcc agt ttc atg tgc atg gcg caa acc tcg ttc ttc gcc cag aat ttt      96
Ala Ser Phe Met Cys Met Ala Gln Thr Ser Phe Phe Ala Gln Asn Phe
                20                  25                  30 gcg cag gat tcc gca gga tac acg ctg atg gtc ctc tgc acc ttg ctg     144
Ala Gln Asp Ser Ala Gly Tyr Thr Leu Met Val Leu Cys Thr Leu Leu
                35                  40                  45 gca                                                                 147
Ala

<210> SEQ ID NO 18
<211> LENGTH: 138
<212> TYPE: DNA
```

```
<213> ORGANISM: Bifidobacterium spp.
<220> FEATURE:
<221> NAME/KEY: CDS
<222> LOCATION: (1)..(138)
<223> OTHER INFORMATION: SP48L20

<400> SEQUENCE: 18 gtg ctg att ctc atc gtt ctc gcc gta gca atc ggc gtg acc atc ggc    48
Val Leu Ile Leu Ile Val Leu Ala Val Ala Ile Gly Val Thr Ile Gly
1               5                   10                  15 ctg tta ctg ccg cag gtc agc tcc gac gcg gcc aaa atc acc ggt ggc    96
Leu Leu Leu Pro Gln Val Ser Ser Asp Ala Ala Lys Ile Thr Gly Gly
                20                  25                  30 tac gct gcc acc ggt tca gcc gcc gac act ttg aac gcg ctc              138
Tyr Ala Ala Thr Gly Ser Ala Ala Asp Thr Leu Asn Ala Leu
            35                  40                  45

<210> SEQ ID NO 19
<211> LENGTH: 192
<212> TYPE: DNA
<213> ORGANISM: Bifidobacterium spp.
<220> FEATURE:
<221> NAME/KEY: CDS
<222> LOCATION: (1)..(192)
<223> OTHER INFORMATION: SP62L20

<400> SEQUENCE: 19 atg act cgt tcg gac gac gtc gtc aat gag gat ggc cat gac gtc atc    48
Met Thr Arg Ser Asp Asp Val Val Asn Glu Asp Gly His Asp Val Ile
1               5                   10                  15 gcc gca cac act cgc gtt gtc agg ggt atg gct gcg gca ctt gcc gcg    96
Ala Ala His Thr Arg Val Val Arg Gly Met Ala Ala Ala Leu Ala Ala
                20                  25                  30 ata gcc gcc aca gga gcc ggc gtc aca gcc gcg gcc gcc aac gtc atg    144
Ile Ala Ala Thr Gly Ala Gly Val Thr Ala Ala Ala Ala Asn Val Met
            35                  40                  45 ttc acg ttc gcg ctg gac acc aag gcc aaa cgt tcg atg ttc aac atg    192
Phe Thr Phe Ala Leu Asp Thr Lys Ala Lys Arg Ser Met Phe Asn Met
        50                  55                  60

<210> SEQ ID NO 20
<211> LENGTH: 4019
<212> TYPE: DNA
<213> ORGANISM: Artificial Sequence
<220> FEATURE:
<223> OTHER INFORMATION: Linearized vector

<400> SEQUENCE: 20
tgaccttctg ctcgtagcga ttacttcgag cattactgac gacaaagacc ccgaccgaga    60
tggtcggggt cttttttgttg tggtgctgtg acgtgttgtc caaccgtatt attccggact   120
agtcctccag gacctcgtct acgaggcgct gagcgaggaa tggcgcaaaa gggacggcga   180
gatcagcgac ccatgggcca acgacgaggc ggacggatac cagccgccct catacgagcc   240
ggtcaacccc gaacgcagga ctccccagac gccctccgat ggcctgatct gacgtccgaa   300
aaaaggcgct gtgcgcccct tttaaatctt ttataaatct ttttacattc ttttagcccc   360
tccgcagcct tactctccca acgggtttca gccgaaacct acaccaaaag gggagcgaac   420
ctacaccaaa aggggagcga acctacacca aaagggggagc gaacctacac caaaagggga   480
gctatataca cctttttgtta tttaaggtgc aagttgtgct atgctgaggc catgtccaat   540
gagatcgtga agttcagcaa ccagttcaac aacgtcgcgc tgaagaagtt cgacgccgtg   600
cacctggacg tgctcatggc gatcgcctca agggtgaggg agaagggcac ggccacggtg   660
```

```
gagttctcgt tcgaggagct gcgcggcctc atgcgattga ggaagaacct gaccaacaag      720
cagctggccg acaagatcgt gcagacgaac gcgcgcctgc tggcgctgaa ctacatgttc      780
gaggattcgg gcaagatcat ccagttcgcg ctgttcacga agttcgtcac cgacccgcag      840
gaggcgactc tcgcggttgg ggtcaacgag gagttcgcgt tcctgctcaa cgacctgacc      900
agccagttca cgcgcttcga gctggccgag ttcgccgacc tcaagagcaa gtacgccaag      960
gagttctacc gcagggccaa gcagtaccgc agctccggaa tctggaagat cggccgcgac     1020
gagttctgcc gactgcttgg cgttccaccg tcggcaataa cccagacacg atatctgaat     1080
cagaaggttc ttcagccaat tcaggaggag tgtgggcctc tccttggcct gaagatcgag     1140
cgccagtacg tgaaacgcag gctgtcgggc ttcgtgttca cattcgcccg cgagacccct     1200
ccggtgatcg acgccaggcc cgtggaggcg aggaagacgg acggcgacgg caagggccat     1260
tggacgagcg ttgccgggta cggcgaggtg ttcacgacca cggcgttgtt cgacgtgacg     1320
gccgcccggg ctcacttcga cggcaccgtt gaagccgggg agtgccgttt ctgcgcgttt     1380
gacgcgcgca accgcgaaca tcatgcgcgg aacgccggaa ggctgttcta gcggccgtgt     1440
ccgcgcctct ggggcggttg cgcctgccat gggtcgatct gccgctgttc ggcctcacgc     1500
tggtctgtgc gctgcctgat ctccctgagc aggtcggcct tggtcctggg ggcgcttcgc     1560
tcctcgaacg gccgctctc ccccaggtcc tcgggctcgc tcaggtccaa cggctcgtca     1620
ccggacggct cgggccggtt ctctccctgt gccgggttct ccgcctgtgc gcgttgttcg     1680
gccatgcgca gtgcgagggc cttcacctgt tcggggcttg tcgactcgat tttcgttcgt     1740
gaatacatgt tataataact ataactaata acgtaacgtg actggcaaga gatatttta      1800 aaacaatgaa taggtttaca cttactttag ttttatggaa atgaaagatc atatcatata     1860
taatctagaa taaaattaac taaaataatt attatctaga taaaaaattt agaagccaat     1920
gaaatctata aataaactaa attaagttta tttaattaac aactatggat ataaaatagg     1980
tactaatcaa aatagtgagg aggatatatt tgaatacata cgaacaaatt aataaagtga     2040
aaaaaatact tcggaaacat ttaaaaaata accttattgg tacttacatg tttggatcag     2100
gagttgagag tggactaaaa ccaaatagtg atcttgactt tttagtcgtc gtatctgaac     2160
cattgacaga tcaaagtaaa gaaatactta tacaaaaaat tagacctatt tcaaaaaaaa     2220
taggagataa aagcaactta cgatatattg aattaacaat tattattcag caagaaatgg     2280
taccgtggaa tcatcctccc aaacaagaat ttatttatgg agaatggtta caagagcttt     2340
atgaacaaga tacattcct cagaaggaat taaattcaga tttaaccata atgctttacc     2400
aagcaaaacg aaaaaataaa agaatatacg gaaattatga cttagaggaa ttactacctg     2460
atattccatt ttctgatgtg agaagagcca ttatggattc gtcagaggaa ttaatagata     2520
attatcagga tgatgaaacc aactctatat taactttatg ccgtatgatt ttaactatgg     2580
acacgggtaa aatcatacca aaagatattg cgggaaatgc agtggctgaa tcttctccat     2640
tagaacatag ggagagaatt ttgttagcag ttcgtagtta tcttggagag aatattgaat     2700
ggactaatga aaatgtaaat ttaactataa actatttaaa taacagatta aaaaaattat     2760
aaaaaaattg aaaaaatggt ggaaacactt ttttcaattt ttttagatct tgagcaaaag     2820
gccagcaaaa ggccaggaac cgtaaaaagg ccgcgttgct ggcgtttttc cataggctcc     2880
gcccccctga cgagcatcac aaaaatcgac gctcaagtca gaggtggcga aacccgacag     2940
gactataaag ataccaggcg tttccccctg gaagctccct cgtgcgctct cctgttccga     3000
```

```
ccctgccgct taccggatac ctgtccgcct ttctcccttc gggaagcgtg gcgctttctc    3060
atagctcacg ctgtaggtat ctcagttcgg tgtaggtcgt tcgctccaag ctgggctgtg    3120
tgcacgaacc ccccgttcag cccgaccgct gcgccttatc cggtaactat cgtcttgagt    3180
ccaacccggt aagacacgac ttatcgccac tggcagcagc cactggtaac aggattagca    3240
gagcgaggta tgtaggcggt gctacagagt tcttgaagtg gtggcctaac tacggctaca    3300
ctagaagaac agtatttggt atctgcgctc tgctgaagcc agttaccttc ggaaaaagag    3360
ttggtagctc ttgatccggc aaacaaacca ccgctggtag cggtggtttt tttgtttgca    3420
agcagcagat tacgcgcaga aaaaaggat ctcaagaaga tcctttgatc ttttctacgg     3480
atccgtcttc ctgctggcct atgcattggg ttccgcagtg cccactccag gcggtctggg    3540
cggtgtggaa gcggcgctga cattcgcgtt cgtggcggtc ggagtgccgc agggcgtggc    3600
gctttccgcc actttgctgc accgcgtggt gttctactgg ctgcgcattc cgctgggcgc    3660
ggcggccatg aagtggcttg acaagcataa tcttgtctga ttcgtctatt ttcatacccc    3720
cttcggggaa atagatgtga aaaccctat aaaacgcggg ttttcgcaga acatgcgct     3780 agtatcattg atgacaacat ggactaagca aaagtgcttg tccctgacc caagaaggat     3840 gctttatgtt caataagcga cacatcgtcc gtaccattgc ggccaccgcc agcatcctgg    3900
ctctgtcgtt caccgcagcc tgcggttccg gccagtccac cgcatccaat tccaccgatt    3960
cggacgacat cacccagcag acgtacaagc cgggcaagct gacccaggtc cagctggtc    4019
```

<210> SEQ ID NO 21
<211> LENGTH: 4019
<212> TYPE: DNA
<213> ORGANISM: Artificial Sequence
<220> FEATURE:
<223> OTHER INFORMATION: Linearized vector

<400> SEQUENCE: 21

```
tgaccttctg ctcgtagcga ttacttcgag cattactgac gacaaagacc ccgaccgaga      60 tggtcgggt cttttgttg tggtgctgtg acgtgttgtc caaccgtatt attccggact       120
agtcctccag gacctcgtct acgaggcgct gagcgaggaa tggcgcaaaa gggacgcgga     180
gatcagcgac ccatgggcca acgacgaggc ggacggatac cagccgcccct catacgagcc    240 ggtcaacccc gaacgcagga ctccccagac gccctccgat ggcctgatct gacgtccgaa     300
aaaaggcgct gtgcgcccctt tttaaatctt ttataaatct ttttacattc ttttagcccc    360
tccgcagcct tactctccca acgggtttca gccgaaacct acaccaaaag gggagcgaac    420
ctacaccaaa aggggagcga acctacacca aaagggagc gaacctacac caaaagggga     480
gctatataca cctttttgtta tttaaggtgc aagttgtgct atgctgaggc catgtccaat    540
gagatcgtga agttcagcaa ccagttcaac aacgtcgcgc tgaagaagtt cgacgccgtg    600
cacctggacg tgctcatggc gatcgcctca agggtgaggg agaagggcac ggccacggtg    660
gagttctcgt tcgaggagct gcgcggcctc atgcgattga ggaagaacct gaccaacaag    720
cagctggccg acaagatcgt gcagacgaac gcgcgcctgc tggcgctgaa ctacatgttc    780
gaggattcgg gcaagatcat ccagttcgcg ctgttcacga gttcgtcac cgacccgcag     840 gaggcgactc tcgcggttgg ggtcaacgag gagttcgcgt tcctgctcaa cgacctgacc    900
agccagttca cgcgcttcga gctggccgag ttcgccgacc tcaagagcaa gtacgccaag    960
gagttctacc gcagggccaa gcagtaccgc agctccggaa tctggaagat cggccgcgac   1020
gagttctgcc gactgcttgg cgttccaccg tcggcaataa cccagacacg atatctgaat   1080
```

```
cagaaggttc ttcagccaat tcaggaggag tgtgggcctc tccttggcct gaagatcgag    1140
cgccagtacg tgaaacgcag gctgtcgggc ttcgtgttca cattcgcccg cgagacccct    1200
ccggtgatcg acgccaggcc cgtggaggcg aggaagacgg acggcgacgg caagggccat    1260
tggacgagcg ttgccgggta cggcgaggtg ttcacgacca cggcgttgtt cgacgtgacg    1320
gccgcccggg ctcacttcga cggcaccgtt gaagccgggg agtgccgttt ctgcgcgttt    1380
gacgcgcgca accgcgaaca tcatgcgcgg aacgccggaa ggctgttcta gcggccgtgt    1440
ccgcgcctct ggggcggttg cgcctgccat gggtcgatct gccgctgttc ggcctcacgc    1500
tggtctgtgc gctgcctgat ctccctgagc aggtcggcct tggtcctggg ggcgcttcgc    1560
tcctcgaacg gccgctctc ccccaggtcc tcgggctcgc tcaggtccaa cggctcgtca     1620
ccggacggct cgggccggtt ctctcccctgt gccgggttct ccgcctgtgc gcgttgttcg    1680
gccatgcgca gtgcgagggc cttcacctgt tcggggcttg tcgactcgat tttcgttcgt    1740
gaatacatgt tataataact ataactaata acgtaacgtg actggcaaga gatattttta    1800
aaacaatgaa taggtttaca cttactttag ttttatggaa atgaaagatc atatcatata    1860
taatctagaa taaaattaac taaaataatt attatctaga taaaaaattt agaagccaat    1920
gaaatctata aataaactaa attaagttta tttaattaac aactatggat ataaaatagg    1980
tactaatcaa aatagtgagg aggatatatt tgaatacata cgaacaaatt aataaagtga    2040
aaaaaatact tcggaaacat ttaaaaaata accttattgg tacttacatg tttggatcag    2100
gagttgagag tggactaaaa ccaaatagtg atcttgactt tttagtcgtc gtatctgaac    2160
cattgacaga tcaaagtaaa gaaatactta tacaaaaaat tagacctatt tcaaaaaaaa    2220
taggagataa aagcaactta cgatatattg aattaacaat tattattcag caagaaatgg    2280
taccgtggaa tcatcctccc aaacaagaat ttatttatgg agaatggtta caagagcttt    2340
atgaacaagg atacattcct cagaaggaat taaattcaga tttaaccata atgctttacc    2400
aagcaaaacg aaaaaataaa agaatatacg gaaattatga cttagaggaa ttactacctg    2460
atattccatt ttctgatgtg agaagagcca ttatggattc gtcagaggaa ttaatagata    2520
attatcagga tgatgaaacc aactctatat taactttatg ccgtatgatt ttaactatgg    2580
acacgggtaa aatcatacca aaagatattg cgggaaatgc agtggctgaa tcttctccat    2640
tagaacatag ggagagaatt tgttagcag ttcgtagtta tcttggagag atattgaat     2700 ggactaatga aaatgtaaat ttaactataa actatttaaa taacagatta aaaaaattat    2760
aaaaaaattg aaaaaatggt ggaaacactt ttttcaattt ttttagatct tgagcaaaag    2820
gccagcaaaa ggccaggaac cgtaaaaagg ccgcgttgct ggcgtttttc cataggctcc    2880 gccccctga cgagcatcac aaaaatcgac gctcaagtca gaggtggcga acccgacag     2940 gactataaag ataccaggcg tttccccctg gaagctccct cgtgcgctct cctgttccga    3000
ccctgccgct taccggatac ctgtccgcct ttctcccttc gggaagcgtg gcgctttctc    3060
atagctcacg ctgtaggtat ctcagttcgg tgtaggtcgt tcgctccaag ctgggctgtg    3120
tgcacgaacc cccgttcag cccgaccgct gcgccttatc cggtaactat cgtcttgagt     3180
ccaacccggt aagacacgac ttatcgccac tggcagcagc cactggtaac aggattagca    3240
gagcgaggta tgtaggcggt gctacagagt tcttgaagtg gtggcctaac tacggctaca    3300
ctagaagaac agtatttggt atctgcgctc tgctgaagcc agttaccttc ggaaaaagag    3360
ttggtagctc ttgatccggc aaacaaacca ccgctggtag cggtggtttt tttgtttgca    3420
```

```
agcagcagat tacgcgcaga aaaaaaggat ctcaagaaga tcctttgatc ttttctacgg    3480
atccgtcttc ctgctggcct atgcattggg ttccgcagtg cccactccag gcggtctggg    3540
cggtgtggaa gcggcgctga cattcgcgtt cgtggcggtc ggagtgccgc agggcgtggc    3600
gctttccgcc actttgctgc accgcgtggt gttctactgg ctgcgcattc cgctgggcgc    3660
ggcggccatg aagtggcttg acaagcataa tcttgtctga ttcgtctatt ttcatacccc    3720
cttcggggaa atagatgtga aaacccttat aaaacgcggg ttttcgcaga acatgcgct    3780 agtatcattg atgacaacat ggactaagca aaagtgcttg tcccctgacc caagaaggat    3840
gctttatggc gttgatgatg agcgttaaga ctattatttc cacatcagtg gcgattatcg    3900
ccacgggtgc catgtttgcg tgcgtagccc cgtttgcctc tgccgattcc gcgcagacga    3960
gtgctgtggt gtcctcacgt tctttcccga aggcgagttc ggtgcaggtc cagctggtc     4019
```

<210> SEQ ID NO 22
<211> LENGTH: 4019
<212> TYPE: DNA
<213> ORGANISM: Artificial Sequence
<220> FEATURE:
<223> OTHER INFORMATION: Linearized vector

<400> SEQUENCE: 22

```
tgaccttctg ctcgtagcga ttacttcgag cattactgac gacaaagacc ccgaccgaga      60
tggtcggggt cttttgttg tggtgctgtg acgtgttgtc caaccgtatt attccggact     120
agtcctccag gacctcgtct acgaggcgct gagcgaggaa tggcgcaaaa gggacggcga     180
gatcagcgac ccatgggcca acgacgaggc ggacggatac cagccgccct catacgagcc     240
ggtcaacccc gaacgcagga ctccccagac gccctccgat ggcctgatct gacgtccgaa     300
aaaaggcgct gtgcgccctt tttaaatctt ttataaatct ttttacattc ttttagcccc     360
tccgcagcct tactctccca acgggtttca gccgaaacct acaccaaaag gggagcgaac     420
ctacaccaaa aggggagcga acctacacca aaagggagc gaacctacac caaaagggga     480
gctatataca ccttttgtta tttaaggtgc aagttgtgct atgctgaggc catgtccaat     540
gagatcgtga agttcagcaa ccagttcaac aacgtcgcgc tgaagaagtt cgacgccgtg     600
cacctggacg tgctcatggc gatcgcctca agggtgaggg agaagggcac ggccacggtg     660
gagttctcgt tcgaggagct cgcggcctc atgcgattga ggaagaacct gaccaacaag     720
cagctggccg acaagatcgt gcagacgaac gcgcgcctgc tggcgctgaa ctacatgttc     780
gaggattcgg gcaagatcat ccagttcgcg ctgttcacga agttcgtcac cgacccgcag     840
gaggcgactc tcgcggttgg ggtcaacgag gagttcgcgt tcctgctcaa cgacctgacc     900
agccagttca cgcgcttcga gctggccgag ttcgccgacc tcaagagcaa gtacgccaag     960
gagttctacc gcagggccaa gcagtaccgc agctccggaa tctggaagat cggccgcgac    1020
gagttctgcc gactgcttgg cgttccaccg tcggcaataa cccagacacg atatctgaat    1080
cagaaggttc ttcagccaat tcaggaggag tgtgggcctc tccttggcct gaagatcgag    1140
cgccagtacg tgaaacgcag gctgtcgggc ttcgtgttca cattcgcccg cgagacccct    1200
ccggtgatcg acgccaggcc cgtggaggcg aggaagacgg acggcgacgg caagggccat    1260
tggacgagcg ttgccgggta cggcgaggtg ttcacgacca cggcgttgtt cgacgtgacg    1320
gccgccgggg ctcacttcga cggcaccgtt gaagccgggg agtgccgttt ctgcgcgttt    1380
gacgcgcgca accgcgaaca tcatgcgcgg aacgccggaa ggctgttcta gcggccgtgt    1440
ccgcgcctct ggggcggttg cgcctgccat gggtcgatct gccgctgttc ggcctcacgc    1500
```

```
tggtctgtgc gctgcctgat ctccctgagc aggtcggcct tggtcctggg ggcgcttcgc    1560
tcctcgaacg ggccgctctc ccccaggtcc tcgggctcgc tcaggtccaa cggctcgtca    1620
ccggacggct cgggccggtt ctctccctgt gccgggttct ccgcctgtgc gcgttgttcg    1680
gccatgcgca gtgcgagggc cttcacctgt tcggggcttg tcgactcgat tttcgttcgt    1740
gaatacatgt tataataact ataactaata acgtaacgtg actggcaaga gatattttta    1800
aaacaatgaa taggtttaca cttactttag ttttatggaa atgaaagatc atatcatata    1860
taatctagaa taaaattaac taaaataatt attatctaga taaaaaattt agaagccaat    1920
gaaatctata aataaactaa attaagttta tttaattaac aactatggat ataaaatagg    1980
tactaatcaa aatagtgagg aggatatatt tgaatacata cgaacaaatt aataaagtga    2040
aaaaaatact tcggaaacat ttaaaaaata accttattgg tacttacatg tttggatcag    2100
gagttgagag tggactaaaa ccaaatagtg atcttgactt tttagtcgtc gtatctgaac    2160
cattgacaga tcaaagtaaa gaaatactta tacaaaaaat tagacctatt tcaaaaaaaa    2220
taggagataa aagcaactta cgatatattg aattaacaat tattattcag caagaaatgg    2280
taccgtggaa tcatcctccc aaacaagaat ttatttatgg agaatggtta caagagcttt    2340
atgaacaagg atacattcct cagaaggaat taaattcaga tttaaccata atgctttacc    2400
aagcaaaacg aaaaaataaa agaatatacg gaaattatga cttagaggaa ttactacctg    2460
atattccatt ttctgatgtg agaagagcca ttatggattc gtcagaggaa ttaatagata    2520
attatcagga tgatgaaacc aactctatat taactttatg ccgtatgatt ttaactatgg    2580
acacgggtaa aatcatacca aaagatattg cgggaaatgc agtggctgaa tcttctccat    2640
tagaacatag ggagagaatt ttgttagcag ttcgtagtta tcttggagag aatattgaat    2700
ggactaatga aaatgtaaat ttaactataa actatttaaa taacagatta aaaaaattat    2760
aaaaaaattg aaaaaatggt ggaaacactt ttttcaattt ttttagatct tgagcaaaag    2820
gccagcaaaa ggccaggaac cgtaaaaagg ccgcgttgct ggcgttttc cataggctcc    2880 gccccctga cgagcatcac aaaaatcgac gctcaagtca gaggtggcga acccgacag    2940 gactataaag ataccaggcg tttccccctg gaagctccct cgtgcgctct cctgttccga    3000
ccctgccgct taccggatac ctgtccgcct ttctcccttc gggaagcgtg gcgctttctc    3060
atagctcacg ctgtaggtat ctcagttcgg tgtaggtcgt tcgctccaag ctgggctgtg    3120
tgcacgaacc cccgttcag cccgaccgct gcgccttatc cggtaactat cgtcttgagt    3180
ccaacccggt aagacacgac ttatcgccac tggcagcagc cactggtaac aggattagca    3240
gagcgaggta tgtaggcggt gctacagagt tcttgaagtg gtggcctaac tacggctaca    3300
ctagaagaac agtatttggt atctgcgctc tgctgaagcc agttaccttc ggaaaaagag    3360
ttggtagctc ttgatccggc aaacaaacca ccgctggtag cggtggtttt tttgtttgca    3420
agcagcagat tacgcgcaga aaaaaaggat ctcaagaaga tcctttgatc ttttctacgg    3480
atccgtcttc ctgctggcct atgcattggg ttccgcagtg cccactccag gcggtctggg    3540
cggtgtggaa gcggcgctga cattcgcgtt cgtggcggtc ggagtgccgc agggcgtggc    3600
gctttccgcc actttgctgc accgcgtggt gttctactgg ctgcgcattc cgctgggcgc    3660
ggcggccatg aagtggcttg acaagcataa tcttgtctga ttcgtctatt ttcataccc     3720 cttcggggaa atagatgtga aaacccttat aaaacgcggg ttttcgcaga acatgcgct    3780 agtatcattg atgacaacat ggactaagca aaagtgcttg tcccctgacc caagaaggat   3840
```

| gctttatgaa caagcgatgg aacaaactgt gtgtgtccgc cctcgcctgc atggcgttgg | 3900 |
| tcgtgccgtt gaccgcctgt gaaggccaac tgccgacgcc ggctgctgat acctccacca | 3960 |
| aggttgcgcc ggatttgacc gaggcgcagg agaagaagat tcgtcaggtc cagctggtc | 4019 |

```
<210> SEQ ID NO 23
<211> LENGTH: 4019
<212> TYPE: DNA
<213> ORGANISM: Artificial Sequence
<220> FEATURE:
<223> OTHER INFORMATION: Linearized vector

<400> SEQUENCE: 23
```

| tgaccttctg ctcgtagcga ttacttcgag cattactgac gacaaagacc ccgaccgaga | 60 |
| tggtcggggt cttttgttg tggtgctgtg acgtgttgtc caaccgtatt attccggact | 120 |
| agtcctccag gacctcgtct acgaggcgct gagcgaggaa tggcgcaaaa gggacggcga | 180 |
| gatcagcgac ccatgggcca acgacgaggc ggacggatac cagccgccct catacgagcc | 240 |
| ggtcaacccc gaacgcagga ctccccagac gccctccgat ggcctgatct gacgtccgaa | 300 |
| aaaaggcgct gtgcgccctt tttaaatctt ttataaatct ttttacattc ttttagcccc | 360 |
| tccgcagcct tactctccca cgggtttca gccgaaacct acaccaaaag gggagcgaac | 420 |
| ctacaccaaa aggggagcga acctacacca aaagggagc gaacctacac caaaagggga | 480 |
| gctatataca ccttttgtta tttaaggtgc aagttgtgct atgctgaggc catgtccaat | 540 |
| gagatcgtga agttcagcaa ccagttcaac aacgtcgcgc tgaagaagtt cgacgccgtg | 600 |
| cacctggacg tgctcatggc gatcgcctca agggtgaggg agaagggcac ggccacggtg | 660 |
| gagttctcgt tcgaggagct gcgcggcctc atgcgattga ggaagaacct gaccaacaag | 720 |
| cagctggccg acaagatcgt gcagacgaac gcgcgcctgc tggcgctgaa ctacatgttc | 780 |
| gaggattcgg gcaagatcat ccagttcgcg ctgttcacga agttcgtcac cgacccgcag | 840 |
| gaggcgactc tcgcggttgg ggtcaacgag gagttcgcgt tcctgctcaa cgacctgacc | 900 |
| agccagttca cgcgcttcga gctggccgag ttcgccgacc tcaagagcaa gtacgccaag | 960 |
| gagttctacc gcagggccaa gcagtaccgc agctccggaa tctggaagat cggccgcgac | 1020 |
| gagttctgcc gactgcttgg cgttccaccg tcggcaataa cccagacacg atatctgaat | 1080 |
| cagaaggttc ttcagccaat tcaggaggag tgtgggcctc tccttggcct gaagatcgag | 1140 |
| cgccagtacg tgaaacgcag gctgtcgggc ttcgtgttca cattcgcccg cgagacccct | 1200 |
| ccggtgatcg acgccaggcc cgtggaggcg aggaagacgg acggcgacgg caagggccat | 1260 |
| tggacgagcg ttgccgggta cggcgaggtg ttcacgacca cggcgttgtt cgacgtgacg | 1320 |
| gccgccgggg ctcacttcga cggcaccgtt gaagccgggg agtgccgttt ctgcgcgttt | 1380 |
| gacgcgcgca accgcgaaca tcatgcgcgg aacgccgaa ggctgttcta gcggccgtgt | 1440 |
| ccgcgcctct ggggcggttg cgcctgccat gggtcgatct gccgctgttc ggcctcacgc | 1500 |
| tggtctgtgc gctgcctgat ctccctgagc aggtcggcct tggtcctggg ggcgcttcgc | 1560 |
| tcctcgaacg ggccgctctc ccccaggtcc tcgggctcgc tcaggtccaa cggctcgtca | 1620 |
| ccggacggct cgggccggtt ctctcccctgt gccgggttct ccgcctgtgc gcgttgttcg | 1680 |
| gccatgcgca gtgcgagggc cttcacctgt tcggggcttg tcgactcgat tttcgttcgt | 1740 |
| gaatacatgt tataataact ataactaata acgtaacgtg actggcaaga gatattttta | 1800 |
| aaacaatgaa taggtttaca cttactttag ttttatggaa atgaaagatc atatcatata | 1860 |
| taatctagaa taaaattaac taaaataatt attatctaga taaaaaattt agaagccaat | 1920 |

```
gaaatctata aataaactaa attaagttta tttaattaac aactatggat ataaaatagg    1980
tactaatcaa aatagtgagg aggatatatt tgaatacata cgaacaaatt aataaagtga    2040
aaaaaatact tcggaaacat ttaaaaaata accttattgg tacttacatg tttggatcag    2100
gagttgagag tggactaaaa ccaaatagtg atcttgactt tttagtcgtc gtatctgaac    2160
cattgacaga tcaaagtaaa gaaatactta tacaaaaaat tagacctatt tcaaaaaaaa    2220
taggagataa aagcaactta cgatatattg aattaacaat tattattcag caagaaatgg    2280
taccgtggaa tcatcctccc aaacaagaat ttatttatgg agaatggtta caagagcttt    2340
atgaacaagg atacattcct cagaaggaat taaattcaga tttaaccata atgctttacc    2400
aagcaaaacg aaaaaataaa agaatatacg gaaattatga cttagaggaa ttactacctg    2460
atattccatt ttctgatgtg agaagagcca ttatggattc gtcagaggaa ttaatagata    2520
attatcagga tgatgaaacc aactctatat taactttatg ccgtatgatt ttaactatgg    2580
acacgggtaa aatcatacca aaagatattg cgggaaatgc agtggctgaa tcttctccat    2640
tagaacatag ggagagaatt ttgttagcag ttcgtagtta tcttggagag aatattgaat    2700
ggactaatga aaatgtaaat ttaactataa actatttaaa taacagatta aaaaaattat    2760 aaaaaattg aaaaaatggt ggaaacactt ttttcaattt ttttagatct tgagcaaaag    2820
gccagcaaaa ggccaggaac cgtaaaaagg ccgcgttgct ggcgttttte cataggctcc    2880 gcccccctga cgagcatcac aaaaatcgac gctcaagtca gaggtggcga aacccgacag    2940
gactataaag ataccaggcg tttccccctg gaagctccct cgtgcgctct cctgttccga    3000 cctgccgct taccggatac ctgtccgcct ttctccctte gggaagcgtg gcgctttctc    3060
atagctcacg ctgtaggtat ctcagttcgg tgtaggtcgt tcgctccaag ctgggctgtg    3120
tgcacgaacc ccccgttcag cccgaccgct gcgccttatc cggtaactat cgtcttgagt    3180
ccaacccggt aagacacgac ttatcgccac tggcagcagc cactggtaac aggattagca    3240
gagcgaggta tgtaggcggt gctacagagt tcttgaagtg gtggcctaac tacggctaca    3300
ctagaagaac agtatttggt atctgcgctc tgctgaagcc agttaccttc ggaaaaagag    3360
ttggtagctc ttgatccggc aaacaaacca ccgctggtag cggtggtttt tttgtttgca    3420
agcagcagat tacgcgcaga aaaaaaggat ctcaagaaga tcctttgatc ttttctacgg    3480
atccgtcttc ctgctggcct atgcattggg ttccgcagtg cccactccag gcggtctggg    3540
cggtgtggaa gcggcgctga cattcgcgtt cgtggcggtc ggagtgccgc agggcgtggc    3600
gctttccgcc actttgctgc accgcgtggt gttctactgg ctgcgcattc cgctgggcgc    3660
ggcggccatg aagtggcttg acaagcataa tcttgtctga ttcgtctatt ttcatacccc    3720
cttcggggaa atagatgtga aaacccttat aaaacgcggg ttttcgcaga acatgcgct    3780 agtatcattg atgacaacat ggactaagca aaagtgcttg tccctgacc caagaaggat    3840 gctttatggc gttgatgatg agcgttaaga ctattatttc cacatcagtg gcgattatcg    3900
ccacgggtgc catgtttgcg tgcgtagccc cgtttgcctc tgccgattcc gcgcagacga    3960
gtgctgtggt gtcctcacgt tctttcccga aggcgagttc ggtgcaggtc cagctgcag    4019
```

<210> SEQ ID NO 24
<211> LENGTH: 4019
<212> TYPE: DNA
<213> ORGANISM: Artificial Sequence
<220> FEATURE:
<223> OTHER INFORMATION: Linearized vector

<400> SEQUENCE: 24

```
tgaccttctg ctcgtagcga ttacttcgag cattactgac gacaaagacc ccgaccgaga      60
tggtcggggt cttttgttg tggtgctgtg acgtgttgtc caaccgtatt attccggact     120
agtcctccag gacctcgtct acgaggcgct gagcgaggaa tggcgcaaaa gggacggcga     180
gatcagcgac ccatgggcca acgacgaggc ggacggatac cagccgccct catacgagcc     240
ggtcaacccc gaacgcagga ctccccagac gccctccgat ggcctgatct gacgtccgaa     300
aaaaggcgct gtgcgccctt tttaaatctt ttataaatct ttttacattc ttttagcccc     360
tccgcagcct tactctccca acgggtttca gccgaaacct acaccaaaag gggagcgaac     420
ctacaccaaa aggggagcga acctacacca aaggggagc gaacctacac caaaggggga     480
gctatataca ccttttgtta tttaaggtgc aagttgtgct atgctgaggc catgtccaat     540
gagatcgtga agttcagcaa ccagttcaac aacgtcgcgc tgaagaagtt cgacgccgtg     600
cacctggacg tgctcatggc gatcgcctca agggtgaggg agaagggcac ggccacggtg     660
gagttctcgt tcgaggagct cgcgggcctc atgcgattga ggaagaacct gaccaacaag     720
cagctggccg acaagatcgt gcagacgaac gcgcgcctgc tggcgctgaa ctacatgttc     780
gaggattcgg gcaagatcat ccagttcgcg ctgttcacga agttcgtcac cgacccgcag     840
gaggcgactc tcgcggttgg ggtcaacgag gagttcgcgt tcctgctcaa cgacctgacc     900
agccagttca cgcgcttcga gctggccgag ttcgccgacc tcaagagcaa gtacgccaag     960
gagttctacc gcagggccaa gcagtaccgc agctccggaa tctggaagat cggccgcgac    1020
gagttctgcc gactgcttgg cgttccaccg tcggcaataa cccagacacg atatctgaat    1080
cagaaggttc ttcagccaat tcaggaggag tgtgggcctc tccttggcct gaagatcgag    1140
cgccagtacg tgaaacgcag gctgtcgggc ttcgtgttca cattcgcccg cgagacccct    1200
ccggtgatcg acgccaggcc cgtggaggcg aggaagacgg acggcgacgg caagggccat    1260
tggacgagcg ttgccgggta cggcgaggtg ttcacgacca cggcgttgtt cgacgtgacg    1320
gccgcccggg ctcacttcga cggcaccgtt gaagccgggg agtgccgttt ctgcgcgttt    1380
gacgcgcgca accgcgaaca tcatgcgcgg aacgccggaa ggctgttcta gcggccgtgt    1440
ccgcgcctct ggggcggttg cgcctgccat gggtcgatct gccgctgttc ggcctcacgc    1500
tggtctgtgc gctgcctgat ctccctgagc aggtcggcct tggtcctggg ggcgcttcgc    1560
tcctcgaacg ggccgctctc ccccaggtcc tcgggctcgc tcaggtccaa cggctcgtca    1620
ccggacggct cgggccggtt ctctcccctgt gccgggttct ccgcctgtgc gcgttgttcg    1680
gccatgcgca gtgcgagggc cttcacctgt tcggggcttg tcgactcgat tttcgttcgt    1740
gaatacatgt tataataact ataactaata acgtaacgtg actggcaaga gatattttta    1800
aaacaatgaa taggtttaca cttactttag tttatggaa atgaaagatc atatcatata     1860
taatctagaa taaaattaac taaaataatt attatctaga taaaaaattt agaagccaat    1920
gaaatctata aataaactaa attaagttta tttaattaac aactatggat ataaaatagg    1980
tactaatcaa aatagtgagg aggatatatt tgaatacata cgaacaaatt aataaagtga    2040
aaaaaatact tcggaaacat ttaaaaaata accttattgg tacttacatg tttggatcag    2100
gagttgagag tggactaaaa ccaaatagtg atcttgactt tttagtcgtc gtatctgaac    2160
cattgacaga tcaaagtaaa gaaatactta tacaaaaaat tagacctatt tcaaaaaaaa    2220
taggagataa aagcaactta cgatatattg aattaacaat tattattcag caagaaatgg    2280
taccgtggaa tcatcctccc aaacaagaat ttatttatgg agaatggtta caagagcttt    2340
```

```
atgaacaagg atacattcct cagaaggaat taaattcaga tttaaccata atgctttacc    2400
aagcaaaacg aaaaaataaa agaatatacg gaaattatga cttagaggaa ttactacctg    2460
atattccatt ttctgatgtg agaagagcca ttatggattc gtcagaggaa ttaatagata    2520
attatcagga tgatgaaacc aactctatat taactttatg ccgtatgatt ttaactatgg    2580
acacgggtaa aatcatacca aaagatattg cgggaaatgc agtggctgaa tcttctccat    2640
tagaacatag ggagagaatt ttgttagcag ttcgtagtta tcttggagag aatattgaat    2700
ggactaatga aaatgtaaat ttaactataa actatttaaa taacagatta aaaaaattat    2760
aaaaaaattg aaaaaatggt ggaaacactt ttttcaattt ttttagatct tgagcaaaag    2820
gccagcaaaa ggccaggaac cgtaaaaagg ccgcgttgct ggcgtttttc cataggctcc    2880 gccccctga cgagcatcac aaaaatcgac gctcaagtca gaggtggcga acccgacag    2940 gactataaag ataccaggcg tttccccctg gaagctccct cgtgcgctct cctgttccga    3000
ccctgccgct taccggatac ctgtccgcct ttctcccttc gggaagcgtg gcgctttctc    3060
atagctcacg ctgtaggtat ctcagttcgg tgtaggtcgt tcgctccaag ctgggctgtg    3120
tgcacgaacc ccccgttcag cccgaccgct gcgccttatc cggtaactat cgtcttgagt    3180
ccaacccggt aagacacgac ttatcgccac tggcagcagc cactggtaac aggattagca    3240
gagcgaggta tgtaggcggt gctacagagt tcttgaagtg gtggcctaac tacggctaca    3300
ctagaagaac agtatttggt atctgcgctc tgctgaagcc agttaccttc ggaaaaagag    3360
ttggtagctc ttgatccggc aaacaaacca ccgctggtag cggtggtttt tttgtttgca    3420
agcagcagat tacgcgcaga aaaaaggat ctcaagaaga tcctttgatc ttttctacgg    3480
atccgtcttc ctgctggcct atgcattggg ttccgcagtg cccactccag gcggtctggg    3540
cggtgtggaa gcggcgctga cattcgcgtt cgtggcggtc ggagtgccgc agggcgtggc    3600
gctttccgcc actttgctgc accgcgtggt gttctactgg ctgcgcattc cgctgggcgc    3660
ggcggccatg aagtggcttg acaagcataa tcttgtctga ttcgtctatt ttcataccc    3720 cttcggggaa atagatgtga aaacccttat aaaacgcggg ttttcgcaga acatgcgct    3780 agtatcattg atgacaacat ggactaagca aaagtgcttg tccctgacc caagaaggat    3840 gctttatggc gttgatgatg agcgttaaga ctattatttc cacatcagtg gcgattatcg    3900
ccacgggtgc catgtttgcg tgcgtagccc cgtttgcctc tgccgattcc gcgcagacga    3960
gtgctgtggt gtcctcacgt tctttcccga aggcgagttc ggtggaagtg cgtctgctg     4019
```

<210> SEQ ID NO 25
<211> LENGTH: 30
<212> TYPE: PRT
<213> ORGANISM: Bifidobacterium spp.
<220> FEATURE:
<223> OTHER INFORMATION: Linker peptide (SP7)

<400> SEQUENCE: 25

Asp Ser Ala Gln Thr Ser Ala Val Val Ser Ser Arg Ser Phe Pro Lys
1               5                   10                  15

Ala Ser Ser Val Lys Lys Asn Leu Phe Ala Glu Ser Thr Ser
            20                  25                  30

<210> SEQ ID NO 26
<211> LENGTH: 30
<212> TYPE: PRT
<213> ORGANISM: Bifidobacterium spp.
<220> FEATURE:

<223> OTHER INFORMATION: Linker peptide (SP45)

<400> SEQUENCE: 26

Val Asp Gly Thr Asp Gly Thr Ser Gly Thr Asn Ser Thr Ser Gln Gly
1               5                   10                  15

Ser Asp Gly Asp Ser Ala Pro Ile Ala Gly Pro Val Pro Asn
            20                  25                  30

<210> SEQ ID NO 27
<211> LENGTH: 30
<212> TYPE: PRT
<213> ORGANISM: Bifidobacterium spp.
<220> FEATURE:
<223> OTHER INFORMATION: Linker peptide (SP50)

<400> SEQUENCE: 27

Ala Thr Leu Thr Pro Ala Asp Glu Arg Tyr His Val Ala Phe Pro Tyr
1               5                   10                  15

Asn Asp Met Glu Tyr Tyr Val Gly Val Ala Gly Leu Asp Ala
            20                  25                  30

<210> SEQ ID NO 28
<211> LENGTH: 30
<212> TYPE: PRT
<213> ORGANISM: Bifidobacterium spp.
<220> FEATURE:
<223> OTHER INFORMATION: Linker peptide (SP52)

<400> SEQUENCE: 28

Ala Asp Ser Ala Thr Ala Asp Asn Ala Pro Ser Val Ala Gly His Ala
1               5                   10                  15

Tyr Asn Glu Leu Pro Tyr Asn Asn Pro Asp Val Thr Val Thr
            20                  25                  30

<210> SEQ ID NO 29
<211> LENGTH: 30
<212> TYPE: PRT
<213> ORGANISM: Bifidobacterium spp.
<220> FEATURE:
<223> OTHER INFORMATION: Linker peptide (SP55)

<400> SEQUENCE: 29

Asp Ser Ser Thr Ser Ser Ser Ser Ser Ser Ser Ser Ser Ser Val Asp
1               5                   10                  15

Tyr Ala Thr Trp Ala Glu Val Ser Lys Ala Met Asp Lys Gln
            20                  25                  30

<210> SEQ ID NO 30
<211> LENGTH: 30
<212> TYPE: PRT
<213> ORGANISM: Bifidobacterium spp.
<220> FEATURE:
<223> OTHER INFORMATION: Linker peptide (SP58)

<400> SEQUENCE: 30

Gly Ser Phe Ala Phe Thr Ala Arg Lys Ser Val Ala Leu Asn Ile Asn
1               5                   10                  15

Gly Gln Thr Thr Gln Val Thr Thr Tyr Ala Met Thr Ala Thr
            20                  25                  30

<210> SEQ ID NO 31
<211> LENGTH: 30
<212> TYPE: PRT
<213> ORGANISM: Bifidobacterium spp.

```
<220> FEATURE:
<223> OTHER INFORMATION: Linker peptide (SP64)

<400> SEQUENCE: 31

Glu Asp Ala Thr Gly Thr Leu Thr Val Thr Ser Ser Asp Ala Ala Phe
1               5                   10                  15

Asn Gly Lys Lys Val Asn Ala Tyr Gln Met Phe Ser Ala Ser
            20                  25                  30

<210> SEQ ID NO 32
<211> LENGTH: 30
<212> TYPE: PRT
<213> ORGANISM: Bifidobacterium spp.
<220> FEATURE:
<223> OTHER INFORMATION: Linker peptide (SP66)

<400> SEQUENCE: 32

Met Glu Ser Glu Asp Ser Gln Pro Gln Thr Thr Asp Thr Ala Thr Val
1               5                   10                  15

Gln Thr Thr Lys Ala Ala Glu Pro Thr Leu Leu Ala Ser Trp
            20                  25                  30

<210> SEQ ID NO 33
<211> LENGTH: 30
<212> TYPE: PRT
<213> ORGANISM: Bifidobacterium spp.
<220> FEATURE:
<223> OTHER INFORMATION: Linker peptide (SP67)

<400> SEQUENCE: 33

Ala Gly Val Asp Tyr Leu Pro Thr Ile Gly Gln Val Pro Thr Tyr Thr
1               5                   10                  15

Lys Phe Gln Pro Thr Ala Asp Pro Gly Lys Asn Ala Ser Asp
            20                  25                  30

<210> SEQ ID NO 34
<211> LENGTH: 30
<212> TYPE: PRT
<213> ORGANISM: Bifidobacterium spp.
<220> FEATURE:
<223> OTHER INFORMATION: Linker peptide (SP68)

<400> SEQUENCE: 34

Asp Glu Pro Val Glu Leu Val Val Asn Gly Gly Phe Glu Asp Asp Leu
1               5                   10                  15

Asn Gly Trp Lys Ser Gly Thr Val Trp Asn Ser Ser Ala Ser
            20                  25                  30

<210> SEQ ID NO 35
<211> LENGTH: 30
<212> TYPE: PRT
<213> ORGANISM: Bifidobacterium spp.
<220> FEATURE:
<223> OTHER INFORMATION: Linker peptide (SP69)

<400> SEQUENCE: 35

Asp Asp Ser Thr Pro Ser Ser Thr Pro Ser Asp Gly Ser Tyr Thr Thr
1               5                   10                  15

Thr Asp Ser Gly Asp Gly Thr Tyr Ser Ile Pro Met Leu Asn
            20                  25                  30

<210> SEQ ID NO 36
<211> LENGTH: 30
<212> TYPE: DNA
```

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 36
caggtccagc tggtccagag cggcagcgaa                              30

<210> SEQ ID NO 37
<211> LENGTH: 30
<212> TYPE: DNA
<213> ORGANISM: Artificial Sequence
<220> FEATURE:
<223> OTHER INFORMATION: primer

<400> SEQUENCE: 37
caggtccagc tgcaggaatc gggcccgggc                              30

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
gaagtgcgtc tgctggaatc gggcggcggc                              30

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
caggtccagc tggtcgaatc gggcggcggc                              30

<210> SEQ ID NO 40
<211> LENGTH: 36
<212> TYPE: DNA
<213> ORGANISM: Artificial Sequence
<220> FEATURE:
<223> OTHER INFORMATION: primer

<400> SEQUENCE: 40
acgagcagaa ggtcagtggt ggtgatgatg gtgctt                       36

<210> SEQ ID NO 41
<211> LENGTH: 36
<212> TYPE: DNA
<213> ORGANISM: Artificial Sequence
<220> FEATURE:
<223> OTHER INFORMATION: primer

<400> SEQUENCE: 41
gaccagctgg acctgggtca gcttgcccgg cttgta                       36

<210> SEQ ID NO 42
<211> LENGTH: 36
<212> TYPE: DNA
<213> ORGANISM: Artificial Sequence
<220> FEATURE:
<223> OTHER INFORMATION: primer

<400> SEQUENCE: 42
gaccagctgg acctgcaccg aactcgcctt cgggaa                       36

<210> SEQ ID NO 43
<211> LENGTH: 36
<212> TYPE: DNA
<213> ORGANISM: Artificial Sequence
<220> FEATURE:
<223> OTHER INFORMATION: primer

<400> SEQUENCE: 43
gaccagctgg acctgacgaa tcttcttctc ctgcgc                          36

<210> SEQ ID NO 44
<211> LENGTH: 36
<212> TYPE: DNA
<213> ORGANISM: Artificial Sequence
<220> FEATURE:
<223> OTHER INFORMATION: primer

<400> SEQUENCE: 44
acgagcagaa ggtcagtgat gatgatggtg gtgacg                          36

<210> SEQ ID NO 45
<211> LENGTH: 36
<212> TYPE: DNA
<213> ORGANISM: Artificial Sequence
<220> FEATURE:
<223> OTHER INFORMATION: primer

<400> SEQUENCE: 45
ctgcagctgg acctgcaccg aactcgcctt cgggaa                          36

<210> SEQ ID NO 46
<211> LENGTH: 36
<212> TYPE: DNA
<213> ORGANISM: Artificial Sequence
<220> FEATURE:
<223> OTHER INFORMATION: primer

<400> SEQUENCE: 46
acgagcagaa ggtcagtgat gatggtggtg atggcc                          36

<210> SEQ ID NO 47
<211> LENGTH: 36
<212> TYPE: DNA
<213> ORGANISM: Artificial Sequence
<220> FEATURE:
<223> OTHER INFORMATION: primer

<400> SEQUENCE: 47
cagcagacgc acttccaccg aactcgcctt cgggaa                          36

<210> SEQ ID NO 48
<211> LENGTH: 36
<212> TYPE: DNA
<213> ORGANISM: Artificial Sequence
<220> FEATURE:
<223> OTHER INFORMATION: primer

<400> SEQUENCE: 48
acgagcagaa ggtcagtgat gatggtgatg atgctt                          36

<210> SEQ ID NO 49
<211> LENGTH: 36
<212> TYPE: DNA
<213> ORGANISM: Artificial Sequence
<220> FEATURE:

<223> OTHER INFORMATION: primer

<400> SEQUENCE: 49
acgagcagaa ggtcagtgat gatgatgatg atgctt                                    36

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
ggcgatggtc agcttgcccg gcttgtacgt                                           30

<210> SEQ ID NO 51
<211> LENGTH: 42
<212> TYPE: DNA
<213> ORGANISM: Artificial Sequence
<220> FEATURE:
<223> OTHER INFORMATION: primer

<400> SEQUENCE: 51
gatcgtcttg agaatcttca gacgaatctt cttctcctgc gc                             42

<210> SEQ ID NO 52
<211> LENGTH: 24
<212> TYPE: DNA
<213> ORGANISM: Artificial Sequence
<220> FEATURE:
<223> OTHER INFORMATION: primer

<400> SEQUENCE: 52
tgaccttctg ctcgtagcga ttac                                                 24

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
caggtccagc tggtccagag                                                      20

<210> SEQ ID NO 54
<211> LENGTH: 22
<212> TYPE: DNA
<213> ORGANISM: Artificial Sequence
<220> FEATURE:
<223> OTHER INFORMATION: primer

<400> SEQUENCE: 54
aaagcatcct tcttgggtca gg                                                   22

<210> SEQ ID NO 55
<211> LENGTH: 32
<212> TYPE: DNA
<213> ORGANISM: Artificial Sequence
<220> FEATURE:
<223> OTHER INFORMATION: primer

<400> SEQUENCE: 55
caagaaggat gctttgtgcc cgtgactacg cg                                        32

<210> SEQ ID NO 56
<211> LENGTH: 33
<212> TYPE: DNA
<213> ORGANISM: Artificial Sequence
<220> FEATURE:
<223> OTHER INFORMATION: primer

<400> SEQUENCE: 56
gaccagctgg acctgtgcca gcaaggtgca gag          33

<210> SEQ ID NO 57
<211> LENGTH: 35
<212> TYPE: DNA
<213> ORGANISM: Artificial Sequence
<220> FEATURE:
<223> OTHER INFORMATION: primer

<400> SEQUENCE: 57
caagaaggat gctttatgaa gcacctctcc caccg          35

<210> SEQ ID NO 58
<211> LENGTH: 32
<212> TYPE: DNA
<213> ORGANISM: Artificial Sequence
<220> FEATURE:
<223> OTHER INFORMATION: primer

<400> SEQUENCE: 58
gaccagctgg acctgatcgc cgtcgcttcc ct          32

<210> SEQ ID NO 59
<211> LENGTH: 37
<212> TYPE: DNA
<213> ORGANISM: Artificial Sequence
<220> FEATURE:
<223> OTHER INFORMATION: primer

<400> SEQUENCE: 59
caagaaggat gctttgtgct gattctcatc gttctcg          37

<210> SEQ ID NO 60
<211> LENGTH: 34
<212> TYPE: DNA
<213> ORGANISM: Artificial Sequence
<220> FEATURE:
<223> OTHER INFORMATION: primer

<400> SEQUENCE: 60
gaccagctgg acctggagcg cgttcaaagt gtcg          34

<210> SEQ ID NO 61
<211> LENGTH: 33
<212> TYPE: DNA
<213> ORGANISM: Artificial Sequence
<220> FEATURE:
<223> OTHER INFORMATION: primer

<400> SEQUENCE: 61
caagaaggat gctttatgat cgtggcctac ccg          33

<210> SEQ ID NO 62
<211> LENGTH: 39
<212> TYPE: DNA
<213> ORGANISM: Artificial Sequence
<220> FEATURE:
<223> OTHER INFORMATION: primer

```
<400> SEQUENCE: 62
gaccagctgg acctgttcca tatcgttgta tggaaacgc                              39

<210> SEQ ID NO 63
<211> LENGTH: 36
<212> TYPE: DNA
<213> ORGANISM: Artificial Sequence
<220> FEATURE:
<223> OTHER INFORMATION: primer

<400> SEQUENCE: 63
caagaaggat gctttatgag tttccatgta tccgcg                                 36

<210> SEQ ID NO 64
<211> LENGTH: 37
<212> TYPE: DNA
<213> ORGANISM: Artificial Sequence
<220> FEATURE:
<223> OTHER INFORMATION: primer

<400> SEQUENCE: 64
gaccagctgg acctgcagtt cgttatacgc gtgaccg                                37

<210> SEQ ID NO 65
<211> LENGTH: 32
<212> TYPE: DNA
<213> ORGANISM: Artificial Sequence
<220> FEATURE:
<223> OTHER INFORMATION: primer

<400> SEQUENCE: 65
caagaaggat gctttatggt tcgtcgcgcc ca                                     32

<210> SEQ ID NO 66
<211> LENGTH: 34
<212> TYPE: DNA
<213> ORGANISM: Artificial Sequence
<220> FEATURE:
<223> OTHER INFORMATION: primer

<400> SEQUENCE: 66
gaccagctgg acctgccagg tggcgtagtc aacg                                   34

<210> SEQ ID NO 67
<211> LENGTH: 31
<212> TYPE: DNA
<213> ORGANISM: Artificial Sequence
<220> FEATURE:
<223> OTHER INFORMATION: primer

<400> SEQUENCE: 67
caagaaggat gctttatggc aatggcacgg c                                      31

<210> SEQ ID NO 68
<211> LENGTH: 34
<212> TYPE: DNA
<213> ORGANISM: Artificial Sequence
<220> FEATURE:
<223> OTHER INFORMATION: primer

<400> SEQUENCE: 68
gaccagctgg acctgggtgg tttgcccgtt gatg                                   34

<210> SEQ ID NO 69
<211> LENGTH: 35
```

<212> TYPE: DNA
<213> ORGANISM: Artificial Sequence
<220> FEATURE:
<223> OTHER INFORMATION: primer

<400> SEQUENCE: 69
caagaaggat gctttatgac tcgttcggac gacgt                     35

<210> SEQ ID NO 70
<211> LENGTH: 38
<212> TYPE: DNA
<213> ORGANISM: Artificial Sequence
<220> FEATURE:
<223> OTHER INFORMATION: primer

<400> SEQUENCE: 70
gaccagctgg acctgcatgt tgaacatcga acgtttgg                  38

<210> SEQ ID NO 71
<211> LENGTH: 42
<212> TYPE: DNA
<213> ORGANISM: Artificial Sequence
<220> FEATURE:
<223> OTHER INFORMATION: Artificial Sequence

<400> SEQUENCE: 71
caagaaggat gctttatgaa gtcactaatc aggaatgtag cg             42

<210> SEQ ID NO 72
<211> LENGTH: 34
<212> TYPE: DNA
<213> ORGANISM: Artificial Sequence
<220> FEATURE:
<223> OTHER INFORMATION: Artificial Sequence

<400> SEQUENCE: 72
gaccagctgg acctgcttct tgccgttgaa cgcg                      34

<210> SEQ ID NO 73
<211> LENGTH: 38
<212> TYPE: DNA
<213> ORGANISM: Artificial Sequence
<220> FEATURE:
<223> OTHER INFORMATION: primer

<400> SEQUENCE: 73
caagaaggat gctttgtgaa gcattggaag aagatggc                  38

<210> SEQ ID NO 74
<211> LENGTH: 38
<212> TYPE: DNA
<213> ORGANISM: Artificial Sequence
<220> FEATURE:
<223> OTHER INFORMATION: primer

<400> SEQUENCE: 74
gaccagctgg acctgcttag tagtctgcac tgtcgcgg                  38

<210> SEQ ID NO 75
<211> LENGTH: 40
<212> TYPE: DNA
<213> ORGANISM: Artificial Sequence
<220> FEATURE:
<223> OTHER INFORMATION: primer

<400> SEQUENCE: 75

-continued caagaaggat gctttatgaa gataaacaat aagggcaagg          40

<210> SEQ ID NO 76
<211> LENGTH: 37
<212> TYPE: DNA
<213> ORGANISM: Artificial Sequence
<220> FEATURE:
<223> OTHER INFORMATION: primer

<400> SEQUENCE: 76
gaccagctgg acctggggct ggaacttggt gtatgtc               37

<210> SEQ ID NO 77
<211> LENGTH: 44
<212> TYPE: DNA
<213> ORGANISM: Artificial Sequence
<220> FEATURE:
<223> OTHER INFORMATION: primer

<400> SEQUENCE: 77
caagaaggat gctttatggt ttataacatt cacatattgc aaac       44

<210> SEQ ID NO 78
<211> LENGTH: 40
<212> TYPE: DNA
<213> ORGANISM: Artificial Sequence
<220> FEATURE:
<223> OTHER INFORMATION: primer

<400> SEQUENCE: 78
gaccagctgg acctgcttcc aaccattaag atcgtcttcg            40

<210> SEQ ID NO 79
<211> LENGTH: 43
<212> TYPE: DNA
<213> ORGANISM: Artificial Sequence
<220> FEATURE:
<223> OTHER INFORMATION: primer

<400> SEQUENCE: 79
caagaaggat gctttatgaa ttatttacga caaaaaattt cgg        43

<210> SEQ ID NO 80
<211> LENGTH: 38
<212> TYPE: DNA
<213> ORGANISM: Artificial Sequence
<220> FEATURE:
<223> OTHER INFORMATION: primer

<400> SEQUENCE: 80
gaccagctgg acctgaccgc tatcagtcgt ggtgtaac              38

<210> SEQ ID NO 81
<211> LENGTH: 159
<212> TYPE: DNA
<213> ORGANISM: Bifidobacterium spp.
<220> FEATURE:
<221> NAME/KEY: CDS
<222> LOCATION: (1)..(159)
<223> OTHER INFORMATION: SP7L20

<400> SEQUENCE: 81 atg gcg ttg atg atg agc gtt aag act att att tcc aca tca gtg gcg    48
Met Ala Leu Met Met Ser Val Lys Thr Ile Ile Ser Thr Ser Val Ala
1               5                   10                  15 att atc gcc acg ggt gcc atg ttt gcg tgc gta gcc ccg ttt gcc tct    96

```
Ile Ile Ala Thr Gly Ala Met Phe Ala Cys Val Ala Pro Phe Ala Ser
            20                  25                  30 gcc gat tcc gcg cag acg agt gct gtg gtg tcc tca cgt tct ttc ccg    144
Ala Asp Ser Ala Gln Thr Ser Ala Val Val Ser Ser Arg Ser Phe Pro
            35                  40                  45 aag gcg agt tcg gtg                                                159
Lys Ala Ser Ser Val
        50
```

<210> SEQ ID NO 82
<211> LENGTH: 30
<212> TYPE: DNA
<213> ORGANISM: Artificial
<220> FEATURE:
<223> OTHER INFORMATION: Ins-hPD-1scFv03-F1

<400> SEQUENCE: 82
caggtccagc tggtcgaatc gggcggcggc                                   30

<210> SEQ ID NO 83
<211> LENGTH: 36
<212> TYPE: DNA
<213> ORGANISM: Artificial
<220> FEATURE:
<223> OTHER INFORMATION: Ins-hPD-1scFv03-R1

<400> SEQUENCE: 83
acgagcagaa ggtcagtggt ggtgatgatg gtgctt                             36

<210> SEQ ID NO 84
<211> LENGTH: 24
<212> TYPE: DNA
<213> ORGANISM: Artificial
<220> FEATURE:
<223> OTHER INFORMATION: TGA-Hu-Terminator-F

<400> SEQUENCE: 84
tgaccttctg ctcgtagcga ttac                                          24

<210> SEQ ID NO 85
<211> LENGTH: 36
<212> TYPE: DNA
<213> ORGANISM: Artificial
<220> FEATURE:
<223> OTHER INFORMATION: vec-SP7L20-R1

<400> SEQUENCE: 85
gaccagctgg acctgcaccg aactcgcctt cgggaa                             36

<210> SEQ ID NO 86
<211> LENGTH: 729
<212> TYPE: DNA
<213> ORGANISM: Artificial
<220> FEATURE:
<223> OTHER INFORMATION: hPD-1scFv03

<400> SEQUENCE: 86
atgcaggtcc agctggtcga atcgggcggc ggcgtcgtcc agccgggccg ttccctgcgt    60
ctggattgca aggcctcggg catcaccttc tcgaactccg gcatgcactg ggtgcgccag   120
gccccgggca agggcctgga atgggtcgcc gtgatctggt acgatggctc gaagcgctac   180
tacgccgatt ccgtgaaggg ccgcttcacc atctcgcgcg acaactccaa gaacaccctg   240
ttcctgcaga tgaactccct gcgcgccgaa gacaccgccg tgtactactg cgccaccaac   300

```
gatgactact ggggccaggg caccctggtc accgtgtcca gcggcggcgg cggctccggc    360
ggcggcggct cgggcggcgg cggcagcgaa atcgtgctga cccagtcccc ggccaccctg    420
tccctgtccc cgggcgaacg tgccaccctg tcgtgccgcg cctcccagtc ggtgtccagc    480
tacctggcct ggtaccagca gaagccgggc caggccccgc gtctgctgat ctacgacgcc    540
tccaaccgcg ccaccggcat cccggcccgc ttctccggct cgggctccgg caccgacttc    600
accctgacca tctcgtccct ggaaccggag gacttcgccg tctactactg ccagcagtcc    660
tcgaactggc cgcgcacctt cggccagggc accaaggtcg agatcaagca ccatcatcac    720
caccactga                                                           729

<210> SEQ ID NO 87
<211> LENGTH: 4019
<212> TYPE: DNA
<213> ORGANISM: Artificial
<220> FEATURE:
<223> OTHER INFORMATION: Linearized vector fragment

<400> SEQUENCE: 87
tgaccttctg ctcgtagcga ttacttcgag cattactgac gacaaagacc ccgaccgaga     60
tggtcggggt cttttttgttg tggtgctgtg acgtgttgtc caaccgtatt attccggact   120
agtcctccag gacctcgtct acgaggcgct gagcgaggaa tggcgcaaaa gggacggcga    180
gatcagcgac ccatgggcca acgacgaggc ggacggatac cagccgccct catacgagcc    240
ggtcaacccc gaacgcagga ctccccagac gccctccgat ggcctgatct gacgtccgaa    300
aaaaggcgcg tgtcgccctt tttaaatctt ttataaatct ttttacattc ttttagcccc    360
tccgcagcct tactctccca acgggtttca gccgaaacct acaccaaaag gggagcgaac    420
ctacaccaaa aggggagcga acctacacca aaggggagc gaacctacac caaaagggga    480
gctatataca ccttttgtta tttaaggtgc aagttgtgct atgctgaggc catgtccaat    540
gagatcgtga agttcagcaa ccagttcaac aacgtcgcgc tgaagaagtt cgacgccgtg    600
cacctggacg tgctcatggc gatcgcctca agggtgaggg agaagggcac ggccacggtg    660
gagttctcgt tcgaggagct cgcgcggcct catgcgattga ggaagaacct gaccaacaag    720
cagctggccg acaagatcgt gcagacgaac gcgcgcctgc tggcgctgaa ctacatgttc    780
gaggattcgg gcaagatcat ccagttcgcg ctgttcacga agttcgtcac cgacccgcag    840
gaggcgactc tcgcggttgg ggtcaacgag gagttcgcgt tcctgctcaa cgacctgacc    900
agccagttca cgcgcttcga gctggccgag ttcgccgacc tcaagagcaa gtacgccaag    960
gagttctacc gcagggccaa gcagtaccgc agctccggaa tctggaagat cggccgcgac   1020
gagttctgcc gactgcttgg cgttccaccg tcggcaataa cccagacacg atatctgaat   1080
cagaaggttc ttcagccaat tcaggaggag tgtgggcctc tccttggcct gaagatcgag   1140
cgccagtacg tgaaacgcag gctgtcgggc ttcgtgttca cattcgcccg cgagacccct   1200
ccggtgatcg acgccaggcc cgtggaggcg aggaagacgg acggcgacgg caagggccat   1260
tggacgagcg ttgccgggta cggcgaggtg ttcacgacca cggcgttgtt cgacgtgacg   1320
gccgccgggg ctcacttcga cggcaccgtt gaagccgggg agtgccgttt ctgcgcgttt   1380
gacgcgcgca accgcgaaca tcatgcgcgg aacgccggaa ggctgttcta gcggccgtgt   1440
ccgcgcctct ggggcggttg cgcctgccat gggtcgatct gccgctgttc ggcctcacgc   1500
tggtctgtgc gctgcctgat ctccctgagc aggtcggcct tggtcctggg ggcgcttcgc   1560
tcctcgaacg ggccgctctc ccccaggtcc tcgggctcgc tcaggtccaa cggctcgtca   1620
```

```
ccggacggct cgggccggtt ctctccctgt gccgggttct ccgcctgtgc gcgttgttcg    1680
gccatgcgca gtgcgagggc cttcacctgt tcggggcttg tcgactcgat tttcgttcgt    1740
gaatacatgt tataataact ataactaata acgtaacgtg actggcaaga gatattttta    1800
aaacaatgaa taggtttaca cttactttag ttttatggaa atgaaagatc atatcatata    1860
taatctagaa taaaattaac taaaataatt attatctaga taaaaaattt agaagccaat    1920
gaaatctata aataaactaa attaagttta tttaattaac aactatggat ataaaatagg    1980
tactaatcaa aatagtgagg aggatatatt tgaatacata cgaacaaatt aataaagtga    2040
aaaaaatact tcggaaacat ttaaaaaata accttattgg tacttacatg tttggatcag    2100
gagttgagag tggactaaaa ccaaatagtg atcttgactt tttagtcgtc gtatctgaac    2160
cattgacaga tcaaagtaaa gaaatactta tacaaaaaat tagacctatt tcaaaaaaaa    2220
taggagataa aagcaactta cgatatattg aattaacaat tattattcag caagaaatgg    2280
taccgtggaa tcatcctccc aaacaagaat ttatttatgg agaatggtta caagagcttt    2340
atgaacaagg atacattcct cagaaggaat taaattcaga tttaaccata atgctttacc    2400
aagcaaaacg aaaaaataaa agaatatacg gaaattatga cttagaggaa ttactacctg    2460
atattccatt ttctgatgtg agaagagcca ttatggattc gtcagaggaa ttaatagata    2520
attatcagga tgatgaaacc aactctatat aactttatg ccgtatgatt ttaactatgg    2580
acacgggtaa aatcatacca aaagatattg cgggaaatgc agtggctgaa tcttctccat    2640
tagaacatag ggagagaatt ttgttagcag ttcgtagtta tcttggagag aatattgaat    2700
ggactaatga aaatgtaaat ttaactataa actatttaaa taacagatta aaaaaattat    2760
aaaaaaattg aaaaaatggt ggaaacactt ttttcaattt ttttagatct tgagcaaaag    2820
gccagcaaaa ggccaggaac cgtaaaaagg ccgcgttgct ggcgtttttc cataggctcc    2880
gcccccctga cgagcatcac aaaaatcgac gctcaagtca gaggtggcga aacccgacag    2940
gactataaag ataccaggcg tttccccctg gaagctccct cgtgcgctct cctgttccga    3000
ccctgccgct taccggatac ctgtccgcct ttctcccttc gggaagcgtg gcgctttctc    3060
atagctcacg ctgtaggtat ctcagttcgg tgtaggtcgt tcgctccaag ctgggctgtg    3120
tgcacgaacc ccccgttcag cccgaccgct gcgccttatc cggtaactat cgtcttgagt    3180
ccaacccggt aagacacgac ttatcgccac tggcagcagc cactggtaac aggattagca    3240
gagcgaggta tgtaggcggt gctacagagt tcttgaagtg gtggcctaac tacggctaca    3300
ctagaagaac agtatttggt atctgcgctc tgctgaagcc agttaccttc ggaaaaagag    3360
ttggtagctc ttgatccggc aaacaaacca ccgctggtag cggtggtttt tttgtttgca    3420
agcagcagat tacgcgcaga aaaaaggat ctcaagaaga tcctttgatc ttttctacgg    3480
atccgtcttc ctgctggcct atgcattggg ttccgcagtg cccactccag gcggtctggg    3540
cggtgtggaa gcggcgctga cattcgcgtt cgtggcggtc ggagtgccgc agggcgtggc    3600
gctttccgcc actttgctgc accgcgtggt gttctactgg ctgcgcattc cgctgggcgc    3660
ggcggccatg aagtggcttg acaagcataa tcttgtctga ttcgtctatt ttcataccc    3720
cttcggggaa atagatgtga aaacccttat aaaacgcggg ttttcgcaga acatgcgct     3780
agtatcattg atgacaacat ggactaagca aaagtgcttg tcccctgacc caagaaggat    3840
gctttatggc gttgatgatg agcgttaaga ctattatttc cacatcagtg gcgattatcg    3900
ccacgggtgc catgtttgcg tgcgtagccc cgtttgcctc tgccgattcc gcgcagacga    3960
```
gtgctgtggt gtcctcacgt tctttcccga aggcgagttc ggtgcaggtc cagctggtc    4019

<210> SEQ ID NO 88
<211> LENGTH: 4727
<212> TYPE: DNA
<213> ORGANISM: Artificial
<220> FEATURE:
<223> OTHER INFORMATION: pHuSP7L20-hPD-1scFv03

<400> SEQUENCE: 88

```
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaaccctt ataaaacgcg gttttcgca gaaacatgcg      300
ctagtatcat tgatgacaac atggactaag caaaagtgct tgtcccctga cccaagaagg     360
atgctttatg gcgttgatga tgagcgttaa gactattatt tccacatcag tggcgattat     420
cgccacgggt gccatgtttg cgtgcgtagc cccgtttgcc tctgccgatt ccgcgcagac     480
gagtgctgtg gtgtcctcac gttctttccc gaaggcgagt tcggtgcagg tccagctggt     540
cgaatcgggc ggcggcgtcg tccagccggg ccgttccctg cgtctggatt gcaaggcctc     600
gggcatcacc ttctcgaact ccggcatgca ctgggtgcgc caggcccgg gcaagggcct      660
ggaatgggtc gccgtgatct ggtacgatgg ctcgaagcgc tactacgccg attccgtgaa     720
gggccgcttc accatctcgc gcgacaactc caagaacacc ctgttcctgc agatgaactc     780
cctgcgcgcc gaagacaccg ccgtgtacta ctgcgccacc aacgatgact actggggcca     840
gggcaccctg gtcaccgtgt ccagcggcgg cggcggctcc ggcggcggcg gctcgggcgg     900
cggcggcagc gaaatcgtgc tgacccagtc cccggccacc ctgtccctgt cccgggcga     960
acgtgccacc ctgtcgtgcc gcgcctccca gtcggtgtcc agctacctgg cctggtacca    1020
gcagaagccg ggccaggccc gcgtctgct gatctacgac gcctccaacc gcgccaccgg    1080
catcccggcc cgcttctccg gctcgggctc cggcaccgac ttcaccctga ccatctcgtc    1140
cctggaaccg gaggacttcg ccgtctacta ctgccagcag tcctcgaact ggccgcgcac    1200
cttcggccag ggcaccaagg tcgagatcaa gcaccatcat caccaccact gaccttctgc    1260
tcgtagcgat tacttcgagc attactgacg acaaagaccc cgaccgagat ggtcggggtc    1320
ttttttgttgt ggtgctgtga cgtgttgtcc aaccgtatta ttccggacta gtcctccagg    1380
acctcgtcta cgaggcgctg agcgaggaat ggcgcaaaag ggacggcgag atcagcgacc    1440
catgggccaa cgacgaggcg gacggatacc agccgccctc atacgagccg gtcaaccccg    1500
aacgcaggac tccccagacg ccctccgatg gcctgatctg acgtccgaaa aaggcgctg     1560
tgcgcccttt ttaaatcttt tataaatctt tttacattct tttagcccct ccgcagcctt    1620
actctcccaa cgggtttcag ccgaaaccta caccaaaagg ggagcgaacc tacaccaaaa    1680
ggggagcgaa cctacaccaa aaggggagcg aacctacacc aaaagggag ctatatacac     1740
cttttgttat ttaaggtgca agttgtgcta tgctgaggcc atgtccaatg agatcgtgaa    1800
gttcagcaac cagttcaaca acgtcgcgct gaagaagttc gacgccgtgc acctggacgt    1860
gctcatggcg atcgcctcaa gggtgaggga aagggcacg gccacggtgg agttctcgtt     1920
cgaggagctg cgcggcctca tgcgattgag gaagaacctg accaacaagc agctggccga    1980
caagatcgtg cagacgaacg cgcgcctgct ggcgctgaac tacatgttcg aggattcggg    2040
```

```
caagatcatc cagttcgcgc tgttcacgaa gttcgtcacc gacccgcagg aggcgactct    2100
cgcggttggg gtcaacgagg agttcgcgtt cctgctcaac gacctgacca gccagttcac    2160
gcgcttcgag ctggccgagt tcgccgacct caagagcaag tacgccaagg agttctaccg    2220
cagggccaag cagtaccgca gctccggaat ctggaagatc ggccgcgacg agttctgccg    2280
actgcttggc gttccaccgt cggcaataac ccagacacga tatctgaatc agaaggttct    2340
tcagccaatt caggaggagt gtgggcctct ccttggcctg aagatcgagc gccagtacgt    2400
gaaacgcagg ctgtcgggct tcgtgttcac attcgcccgc gagacccctc cggtgatcga    2460
cgccaggccc gtgaggcgga ggaagacgga cggcgacggc aagggccatt ggacgagcgt    2520
tgccgggtac ggcgaggtgt tcacgaccac ggcgttgttc gacgtgacgg ccgcccgggc    2580
tcacttcgac ggcaccgttg aagccgggga gtgccgtttc tgcgcgtttg acgcgcgcaa    2640
ccgcgaacat catgcgcgga acgccggaag gctgttctag cggccgtgtc cgcgcctctg    2700
gggcggttgc gcctgccatg ggtcgatctg ccgctgttcg gcctcacgct ggtctgtgcg    2760
ctgcctgatc tccctgagca ggtcggcctt ggtcctgggg gcgcttcgct cctcgaacgg    2820
gccgctctcc cccaggtcct cgggctcgct caggtccaac ggctcgtcac cggacggctc    2880
gggccggttc tctccctgtg ccgggttctc cgcctgtgcg cgttgttcgg ccatgcgcag    2940
tgcgagggcc ttcacctgtt cggggcttgt cgactcgatt ttcgttcgtg aatacatgtt    3000
ataataacta taactaataa cgtaacgtga ctggcaagag atatttttaa aacaatgaat    3060
aggtttacac ttactttagt tttatggaaa tgaaagatca tatcatatat aatctagaat    3120
aaaattaact aaaataatta ttatctagat aaaaaattta gaagccaatg aaatctataa    3180
ataaactaaa ttaagtttat ttaattaaca actatggata taaaataggt actaatcaaa    3240
atagtgagga ggatatattt gaatacatac gaacaaatta ataaagtgaa aaaaatactt    3300
cggaaacatt taaaaaataa ccttattggt acttacatgt ttggatcagg agttgagagt    3360
ggactaaaac caaatagtga tcttgacttt ttagtcgtcg tatctgaacc attgacagat    3420
caaagtaaag aaatacttat acaaaaaatt agacctattt caaaaaaaat aggagataaa    3480
agcaacttac gatatattga attaacaatt attattcagc aagaaatggt accgtggaat    3540
catcctccca aacaagaatt tatttatgga gaatggttac aagagcttta tgaacaagga    3600
tacattcctc agaaggaatt aaattcagat ttaaccataa tgctttacca agcaaaacga    3660
aaaaataaaa gaatatacgg aaattatgac ttagaggaat tactacctga tattccattt    3720
tctgatgtga gaagagccat tatggattcg tcagaggaat aatagataaa ttatcaggat    3780
gatgaaacca actctatatt aactttatgc cgtatgattt taactatgga cacgggtaaa    3840
atcataccaa aagatattgc gggaaatgca gtggctgaat cttctccatt agaacatagg    3900
gagagaattt tgttagcagt tcgtagttat cttggagaga atattgaatg gactaatgaa    3960
aatgtaaatt taactataaa ctatttaaat aacagattaa aaaaattata aaaaaattga    4020
aaaaatggtg gaaacacttt tttcaatttt tttagatctt gagcaaaagg ccagcaaaag    4080
gccaggaacc gtaaaaaggc cgcgttgctg gcgttttttcc ataggctccg ccccctgac    4140 gagcatcaca aaaatcgacg ctcaagtcag aggtggcgaa acccgacagg actataaaga    4200
taccaggcgt ttccccctgg aagctccctc gtgcgctctc ctgttccgac cctgccgctt    4260
accggatacc tgtccgcctt tctccccttcg ggaagcgtgg cgctttctca tagctcacgc    4320
tgtaggtatc tcagttcggt gtaggtcgtt cgctccaagc tgggctgtgt gcacgaaccc    4380
```

```
cccgttcagc cgaccgctg cgccttatcc ggtaactatc gtcttgagtc caacccggta    4440
agacacgact tatcgccact ggcagcagcc actggtaaca ggattagcag agcgaggtat    4500
gtaggcggtg ctacagagtt cttgaagtgg tggcctaact acggctacac tagaagaaca    4560
gtatttggta tctgcgctct gctgaagcca gttaccttcg gaaaaagagt tggtagctct    4620
tgatccggca acaaaccac cgctggtagc ggtggttttt ttgtttgcaa gcagcagatt    4680
acgcgcagaa aaaaggatc tcaagaagat cctttgatct tttctac                   4727
```

<210> SEQ ID NO 89
<211> LENGTH: 22
<212> TYPE: DNA
<213> ORGANISM: Artificial Sequence
<220> FEATURE:
<223> OTHER INFORMATION: primer

<400> SEQUENCE: 89
aaagcatcct tcttgggtca gg                                              22

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
caggtccagc tggtcgaatc                                                 20

<210> SEQ ID NO 91
<211> LENGTH: 43
<212> TYPE: DNA
<213> ORGANISM: Artificial Sequence
<220> FEATURE:
<223> OTHER INFORMATION: primer

<400> SEQUENCE: 91
caagaaggat gctttatgaa ttatttacga caaaaatttt cgg                       43

<210> SEQ ID NO 92
<211> LENGTH: 38
<212> TYPE: DNA
<213> ORGANISM: Artificial Sequence
<220> FEATURE:
<223> OTHER INFORMATION: primer

<400> SEQUENCE: 92
gaccagctgg acctgaccgc tatcagtcgt ggtgtaac                             38

<210> SEQ ID NO 93
<211> LENGTH: 33
<212> TYPE: DNA
<213> ORGANISM: Artificial Sequence
<220> FEATURE:
<223> OTHER INFORMATION: primer

<400> SEQUENCE: 93
gaccagctgg acctgtggcg ttgaatcatc cgc                                  33

<210> SEQ ID NO 94
<211> LENGTH: 33
<212> TYPE: DNA
<213> ORGANISM: Artificial Sequence
<220> FEATURE:
<223> OTHER INFORMATION: primer

<400> SEQUENCE: 94
gaccagctgg acctgcgatg gcgttgaaga tgg                          33

<210> SEQ ID NO 95
<211> LENGTH: 35
<212> TYPE: DNA
<213> ORGANISM: Artificial Sequence
<220> FEATURE:
<223> OTHER INFORMATION: primer

<400> SEQUENCE: 95
gaccagctgg acctgggtgt aactgccatc cgatg                        35

<210> SEQ ID NO 96
<211> LENGTH: 32
<212> TYPE: DNA
<213> ORGANISM: Artificial Sequence
<220> FEATURE:
<223> OTHER INFORMATION: primer

<400> SEQUENCE: 96
gaccagctgg acctgcgcaa agaccggcat tg                           32

<210> SEQ ID NO 97
<211> LENGTH: 33
<212> TYPE: DNA
<213> ORGANISM: Artificial Sequence
<220> FEATURE:
<223> OTHER INFORMATION: primer

<400> SEQUENCE: 97
gaccagctgg acctgatccg caaagaccgg cat                          33

<210> SEQ ID NO 98
<211> LENGTH: 33
<212> TYPE: DNA
<213> ORGANISM: Artificial Sequence
<220> FEATURE:
<223> OTHER INFORMATION: primer

<400> SEQUENCE: 98
gaccagctgg acctgatcat ccgcaaagac cgg                          33

<210> SEQ ID NO 99
<211> LENGTH: 35
<212> TYPE: DNA
<213> ORGANISM: Artificial Sequence
<220> FEATURE:
<223> OTHER INFORMATION: primer

<400> SEQUENCE: 99
gaccagctgg acctgtgaat catccgcaaa gaccg                        35

<210> SEQ ID NO 100
<211> LENGTH: 36
<212> TYPE: DNA
<213> ORGANISM: Artificial Sequence
<220> FEATURE:
<223> OTHER INFORMATION: primer

<400> SEQUENCE: 100
gaccagctgg acctgcgttg aatcatccgc aaagac                       36

<210> SEQ ID NO 101

```
<211> LENGTH: 35
<212> TYPE: DNA
<213> ORGANISM: Artificial Sequence
<220> FEATURE:
<223> OTHER INFORMATION: primer

<400> SEQUENCE: 101
gaccagctgg acctgagatg gcgttgaatc atccg                           35

<210> SEQ ID NO 102
<211> LENGTH: 37
<212> TYPE: DNA
<213> ORGANISM: Artificial Sequence
<220> FEATURE:
<223> OTHER INFORMATION: primer

<400> SEQUENCE: 102
gaccagctgg acctgtgaag atggcgttga atcatcc                         37

<210> SEQ ID NO 103
<211> LENGTH: 36
<212> TYPE: DNA
<213> ORGANISM: Artificial Sequence
<220> FEATURE:
<223> OTHER INFORMATION: primer

<400> SEQUENCE: 103
gaccagctgg acctgcgttg aagatggcgt tgaatc                          36

<210> SEQ ID NO 104
<211> LENGTH: 32
<212> TYPE: DNA
<213> ORGANISM: Artificial Sequence
<220> FEATURE:
<223> OTHER INFORMATION: primer

<400> SEQUENCE: 104
gaccagctgg acctgtggcg ttgaagatgg cg                              32

<210> SEQ ID NO 105
<211> LENGTH: 63
<212> TYPE: PRT
<213> ORGANISM: Bifidobacterium spp.
<220> FEATURE:
<223> OTHER INFORMATION: SP7L30

<400> SEQUENCE: 105

Met Ala Leu Met Met Ser Val Lys Thr Ile Ile Ser Thr Ser Val Ala
1               5                   10                  15

Ile Ile Ala Thr Gly Ala Met Phe Ala Cys Val Ala Pro Phe Ala Ser
            20                  25                  30

Ala Asp Ser Ala Gln Thr Ser Ala Val Val Ser Ser Arg Ser Phe Pro
        35                  40                  45

Lys Ala Ser Ser Val Lys Lys Asn Leu Phe Ala Glu Ser Thr Ser
    50                  55                  60

<210> SEQ ID NO 106
<211> LENGTH: 64
<212> TYPE: PRT
<213> ORGANISM: Bifidobacterium spp.
<220> FEATURE:
<223> OTHER INFORMATION: SP45L30

<400> SEQUENCE: 106

Met Lys His Leu Ser His Arg Thr Ile Ala Ile Ile Val Ala Leu Leu
```

```
                1               5                  10                 15
Ser Thr Leu Ser Leu Ala Leu Ala Val Ile Ser Leu Pro His Gln Ala
                20                 25                 30

Tyr Ala Val Asp Gly Thr Asp Gly Thr Ser Gly Thr Asn Ser Thr Ser
            35                 40                 45

Gln Gly Ser Asp Gly Asp Ser Ala Pro Ile Ala Gly Pro Val Pro Asn
    50                 55                 60
```

<210> SEQ ID NO 107
<211> LENGTH: 86
<212> TYPE: PRT
<213> ORGANISM: Bifidobacterium spp.
<220> FEATURE:
<223> OTHER INFORMATION: SP50L30

<400> SEQUENCE: 107

```
Met Ile Val Ala Tyr Pro His Thr Val Gln Tyr Ala Gly Lys Arg Thr
1               5                  10                 15

Arg Lys Gly Arg Met Met Ile Thr Thr Trp Arg Gln Arg Gly Met Ala
                20                 25                 30

Ile Val Ala Met Leu Thr Gly Leu Ile Ile Met Val Gly Val Val Phe
            35                 40                 45

Gly Ser Ala Asn Thr Ala Tyr Ala Ala Thr Leu Thr Pro Ala Asp Glu
    50                 55                 60

Arg Tyr His Val Ala Phe Pro Tyr Asn Asp Met Glu Tyr Tyr Val Gly
65                  70                 75                 80

Val Ala Gly Leu Asp Ala
                85
```

<210> SEQ ID NO 108
<211> LENGTH: 65
<212> TYPE: PRT
<213> ORGANISM: Bifidobacterium spp.
<220> FEATURE:
<223> OTHER INFORMATION: SP52L30

<400> SEQUENCE: 108

```
Met Ser Phe His Val Ser Ala Gln Ser Val Arg Ala Val Ala Gly Gly
1               5                  10                 15

Leu Val Ala Ala Ala Thr Leu Leu Ser Gly Leu Ala Leu Ala Pro Thr
                20                 25                 30

Ala Met Ala Ala Asp Ser Ala Thr Ala Asp Asn Ala Pro Ser Val Ala
            35                 40                 45

Gly His Ala Tyr Asn Glu Leu Pro Tyr Asn Asn Pro Asp Val Thr Val
    50                 55                 60

Thr
65
```

<210> SEQ ID NO 109
<211> LENGTH: 78
<212> TYPE: PRT
<213> ORGANISM: Bifidobacterium spp.
<220> FEATURE:
<223> OTHER INFORMATION: SP55L30

<400> SEQUENCE: 109

```
Met Val Arg Arg Ala Gln Ala Ala Leu Arg Ser Val Glu His Thr Ser
1               5                  10                 15

Val Arg Gln Leu Arg Val Leu Ala Ala Ile Val Phe Leu Phe Ala Met
                20                 25                 30
```

Val Ile Ala Thr Val Ala Pro Ala Val Thr Ala Pro Met Ala Phe Ala
            35                  40                  45

Asp Ser Ser Thr Ser Ser Ser Ser Ser Ser Ser Ser Ser Ser Val Asp
 50                  55                  60

Tyr Ala Thr Trp Ala Glu Val Ser Lys Ala Met Asp Lys Gln
 65                  70                  75

<210> SEQ ID NO 110
<211> LENGTH: 62
<212> TYPE: PRT
<213> ORGANISM: Bifidobacterium spp.
<220> FEATURE:
<223> OTHER INFORMATION: SP58L30

<400> SEQUENCE: 110

Met Ala Met Ala Arg Arg Trp Thr Pro Gln Arg Phe Val Thr Leu Arg
 1               5                  10                  15

Arg Ile Arg Val Ile Ala Cys Ile Ala Ala Thr Ser Ile Ala Leu Ala
                20                  25                  30

Gly Ser Phe Ala Phe Thr Ala Arg Lys Ser Val Ala Leu Asn Ile Asn
            35                  40                  45

Gly Gln Thr Thr Gln Val Thr Thr Tyr Ala Met Thr Ala Thr
 50                  55                  60

<210> SEQ ID NO 111
<211> LENGTH: 61
<212> TYPE: PRT
<213> ORGANISM: Bifidobacterium spp.
<220> FEATURE:
<223> OTHER INFORMATION: SP64L30

<400> SEQUENCE: 111

Met Lys Ser Leu Ile Arg Asn Val Ala Ala Gly Val Leu Ala Ala Ala
 1               5                  10                  15

Thr Met Leu Gly Ile Ala Gly Leu Gly Ala Thr Thr Ala Ser Ala Glu
                20                  25                  30

Asp Ala Thr Gly Thr Leu Thr Val Thr Ser Ser Asp Ala Ala Phe Asn
            35                  40                  45

Gly Lys Lys Val Asn Ala Tyr Gln Met Phe Ser Ala Ser
 50                  55                  60

<210> SEQ ID NO 112
<211> LENGTH: 56
<212> TYPE: PRT
<213> ORGANISM: Bifidobacterium spp.
<220> FEATURE:
<223> OTHER INFORMATION: SP66L30

<400> SEQUENCE: 112

Met Lys His Trp Lys Lys Met Ala Ala Ser Leu Ile Ala Ile Ser Thr
 1               5                  10                  15

Met Val Ala Val Val Pro Thr Thr Tyr Ala Met Glu Ser Glu Asp Ser
                20                  25                  30

Gln Pro Gln Thr Thr Asp Thr Ala Thr Val Gln Thr Thr Lys Ala Ala
            35                  40                  45

Glu Pro Thr Leu Leu Ala Ser Trp
 50                  55

<210> SEQ ID NO 113
<211> LENGTH: 63

```
<212> TYPE: PRT
<213> ORGANISM: Bifidobacterium spp.
<220> FEATURE:
<223> OTHER INFORMATION: SP67L30

<400> SEQUENCE: 113

Met Lys Ile Asn Asn Lys Gly Lys Gly Ala Leu Ile Ala Ala Ile Thr
1               5                   10                  15

Ala Ala Ala Thr Leu Leu Ser Cys Gly Leu Ala Ala Ser Ala Ser
            20                  25                  30

Ala Ala Gly Val Asp Tyr Leu Pro Thr Ile Gly Gln Val Pro Thr Tyr
        35                  40                  45

Thr Lys Phe Gln Pro Thr Ala Asp Pro Gly Lys Asn Ala Ser Asp
    50                  55                  60

<210> SEQ ID NO 114
<211> LENGTH: 73
<212> TYPE: PRT
<213> ORGANISM: Bifidobacterium spp.
<220> FEATURE:
<223> OTHER INFORMATION: SP68L30

<400> SEQUENCE: 114

Met Val Tyr Asn Ile His Ile Leu Gln Thr Arg Lys Thr Gly Arg Val
1               5                   10                  15

Val Ala Ala Ala Ala Ser Val Leu Cys Cys Met Gly Ala Val Phe
            20                  25                  30

Pro Ala Thr Ile Gly Val Thr Ala Ala Ser Ala Asp Glu Pro Val Glu
        35                  40                  45

Leu Val Val Asn Gly Gly Phe Glu Asp Asp Leu Asn Gly Trp Lys Ser
    50                  55                  60

Gly Thr Val Trp Asn Ser Ser Ala Ser
65                  70

<210> SEQ ID NO 115
<211> LENGTH: 60
<212> TYPE: PRT
<213> ORGANISM: Bifidobacterium spp.
<220> FEATURE:
<223> OTHER INFORMATION: SP69L30

<400> SEQUENCE: 115

Met Asn Tyr Leu Arg Gln Lys Ile Ser Ala Ser Ala Ile Ala Val Leu
1               5                   10                  15

Ser Thr Cys Gly Leu Ile Leu Ala Pro Met Pro Val Phe Ala Asp Asp
            20                  25                  30

Ser Thr Pro Ser Ser Thr Pro Ser Asp Gly Ser Tyr Thr Thr Thr Asp
        35                  40                  45

Ser Gly Asp Gly Thr Tyr Ser Ile Pro Met Leu Asn
    50                  55                  60

<210> SEQ ID NO 116
<211> LENGTH: 99
<212> TYPE: DNA
<213> ORGANISM: Bifidobacterium spp.
<220> FEATURE:
<221> NAME/KEY: CDS
<222> LOCATION: (1)..(99)
<223> OTHER INFORMATION: SP7

<400> SEQUENCE: 116 atg gcg ttg atg atg agc gtt aag act att att tcc aca tca gtg gcg      48
```

```
Met Ala Leu Met Met Ser Val Lys Thr Ile Ser Thr Ser Val Ala
1               5                   10                  15 att atc gcc acg ggt gcc atg ttt gcg tgc gta gcc ccg ttt gcc tct    96
Ile Ile Ala Thr Gly Ala Met Phe Ala Cys Val Ala Pro Phe Ala Ser
                20                  25                  30 gcc                                                                 99
Ala

<210> SEQ ID NO 117
<211> LENGTH: 102
<212> TYPE: DNA
<213> ORGANISM: Bifidobacterium spp.
<220> FEATURE:
<221> NAME/KEY: CDS
<222> LOCATION: (1)..(102)
<223> OTHER INFORMATION: SP45

<400> SEQUENCE: 117 atg aag cac ctc tcc cac cgc acc atc gcc atc atc gtc gcg ttg ctc    48
Met Lys His Leu Ser His Arg Thr Ile Ala Ile Ile Val Ala Leu Leu
1               5                   10                  15 tcc acg ctg tca ctg gca ctt gcc gtc atc tcc ctt ccg cac cag gcg    96
Ser Thr Leu Ser Leu Ala Leu Ala Val Ile Ser Leu Pro His Gln Ala
                20                  25                  30 tac gca                                                            102
Tyr Ala

<210> SEQ ID NO 118
<211> LENGTH: 168
<212> TYPE: DNA
<213> ORGANISM: Bifidobacterium spp.
<220> FEATURE:
<221> NAME/KEY: CDS
<222> LOCATION: (1)..(168)
<223> OTHER INFORMATION: SP50

<400> SEQUENCE: 118 atg atc gtg gcc tac ccg cac aca gtg cag tat gcg ggg aaa cgt acc    48
Met Ile Val Ala Tyr Pro His Thr Val Gln Tyr Ala Gly Lys Arg Thr
1               5                   10                  15 agg aaa gga cga atg atg ata acg aca tgg cgg caa cgg ggc atg gcc    96
Arg Lys Gly Arg Met Met Ile Thr Thr Trp Arg Gln Arg Gly Met Ala
                20                  25                  30 atc gta gcg atg ctg acc ggt ctg ata ata atg gtg gga gtg gtg ttc   144
Ile Val Ala Met Leu Thr Gly Leu Ile Ile Met Val Gly Val Val Phe
            35                  40                  45 ggc tcg gcg aat acg gcg tat gcc                                    168
Gly Ser Ala Asn Thr Ala Tyr Ala
        50                  55

<210> SEQ ID NO 119
<211> LENGTH: 105
<212> TYPE: DNA
<213> ORGANISM: Bifidobacterium spp.
<220> FEATURE:
<221> NAME/KEY: CDS
<222> LOCATION: (1)..(105)
<223> OTHER INFORMATION: SP52

<400> SEQUENCE: 119 atg agt ttc cat gta tcc gcg caa tcg gtt cgc gcg gtg gcc ggt gga    48
Met Ser Phe His Val Ser Ala Gln Ser Val Arg Ala Val Ala Gly Gly
1               5                   10                  15 ctc gtc gcc gca gcg aca ttg ctg tca ggc ctt gcc ctt gcg ccg acc    96
Leu Val Ala Ala Ala Thr Leu Leu Ser Gly Leu Ala Leu Ala Pro Thr
```

```
                       20                  25                  30 gca atg gcc                                                          105
Ala Met Ala
        35

<210> SEQ ID NO 120
<211> LENGTH: 144
<212> TYPE: DNA
<213> ORGANISM: Bifidobacterium spp.
<220> FEATURE:
<221> NAME/KEY: CDS
<222> LOCATION: (1)..(144)
<223> OTHER INFORMATION: SP55

<400> SEQUENCE: 120 atg gtt cgt cgc gcc cag gct gct ctt cgg tcc gtt gaa cac acc agc    48
Met Val Arg Arg Ala Gln Ala Ala Leu Arg Ser Val Glu His Thr Ser
1               5                   10                  15 gtg agg cag ctg cga gtc ctg gct gcg att gta ttt ctg ttc gcc atg    96
Val Arg Gln Leu Arg Val Leu Ala Ala Ile Val Phe Leu Phe Ala Met
            20                  25                  30 gtc atc gcc act gtg gct cct gca gtc acg gct ccg atg gcc ttc gcc   144
Val Ile Ala Thr Val Ala Pro Ala Val Thr Ala Pro Met Ala Phe Ala
        35                  40                  45

<210> SEQ ID NO 121
<211> LENGTH: 96
<212> TYPE: DNA
<213> ORGANISM: Bifidobacterium spp.
<220> FEATURE:
<221> NAME/KEY: CDS
<222> LOCATION: (1)..(96)
<223> OTHER INFORMATION: SP58

<400> SEQUENCE: 121 atg gca atg gca cgg cgt tgg acc ccg cag cgg ttt gtt aca ctg cgt    48
Met Ala Met Ala Arg Arg Trp Thr Pro Gln Arg Phe Val Thr Leu Arg
1               5                   10                  15 cgc atc cgc gta atc gcc tgt atc gcg gcg acc agt atc gcg ctg gct    96
Arg Ile Arg Val Ile Ala Cys Ile Ala Ala Thr Ser Ile Ala Leu Ala
            20                  25                  30

<210> SEQ ID NO 122
<211> LENGTH: 93
<212> TYPE: DNA
<213> ORGANISM: Bifidobacterium spp.
<220> FEATURE:
<221> NAME/KEY: CDS
<222> LOCATION: (1)..(93)
<223> OTHER INFORMATION: SP64

<400> SEQUENCE: 122 atg aag tca cta atc agg aat gta gcg gcg ggc gtc ctc gca gcc gcc    48
Met Lys Ser Leu Ile Arg Asn Val Ala Ala Gly Val Leu Ala Ala Ala
1               5                   10                  15 acg atg ctc ggc atc gcc ggc ctc ggc gcc acc acc gcc tcc gcg        93
Thr Met Leu Gly Ile Ala Gly Leu Gly Ala Thr Thr Ala Ser Ala
            20                  25                  30

<210> SEQ ID NO 123
<211> LENGTH: 78
<212> TYPE: DNA
<213> ORGANISM: Bifidobacterium spp.
<220> FEATURE:
<221> NAME/KEY: CDS
<222> LOCATION: (1)..(78)
<223> OTHER INFORMATION: SP66
```

```
<400> SEQUENCE: 123 gtg aag cat tgg aag aag atg gca gca tcg ttg att gca ata tca acg    48
Met Lys His Trp Lys Lys Met Ala Ala Ser Leu Ile Ala Ile Ser Thr
1               5                   10                  15 atg gtg gca gta gtt ccg acg acg tat gcc                            78
Met Val Ala Val Val Pro Thr Thr Tyr Ala
            20                  25

<210> SEQ ID NO 124
<211> LENGTH: 99
<212> TYPE: DNA
<213> ORGANISM: Bifidobacterium spp.
<220> FEATURE:
<221> NAME/KEY: CDS
<222> LOCATION: (1)..(99)
<223> OTHER INFORMATION: SP67

<400> SEQUENCE: 124 atg aag ata aac aat aag ggc aag ggc gct ctt atc gcg gca att acc    48
Met Lys Ile Asn Asn Lys Gly Lys Gly Ala Leu Ile Ala Ala Ile Thr
1               5                   10                  15 gcc gcg gca acg cta ttg tca tgc ggg ctg gcc gct gca agt gcc agt    96
Ala Ala Ala Thr Leu Leu Ser Cys Gly Leu Ala Ala Ala Ser Ala Ser
            20                  25                  30 gcg                                                                99
Ala

<210> SEQ ID NO 125
<211> LENGTH: 129
<212> TYPE: DNA
<213> ORGANISM: Bifidobacterium spp.
<220> FEATURE:
<221> NAME/KEY: CDS
<222> LOCATION: (1)..(129)
<223> OTHER INFORMATION: SP68

<400> SEQUENCE: 125 atg gtt tat aac att cac ata ttg caa aca agg aaa acc ggt cgt gtg    48
Met Val Tyr Asn Ile His Ile Leu Gln Thr Arg Lys Thr Gly Arg Val
1               5                   10                  15 gtt gct gct gcg gct gca tcc gtg ctg tgt tgc atg ggg gct gta ttt    96
Val Ala Ala Ala Ala Ala Ser Val Leu Cys Cys Met Gly Ala Val Phe
            20                  25                  30 cca gcg act atc gga gtg act gcg gcg tcg gcc                        129
Pro Ala Thr Ile Gly Val Thr Ala Ala Ser Ala
            35                  40

<210> SEQ ID NO 126
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: SP69

<400> SEQUENCE: 126 atg aat tat tta cga caa aaa att tcg gct agt gct atc gcg gtg ttg    48
Met Asn Tyr Leu Arg Gln Lys Ile Ser Ala Ser Ala Ile Ala Val Leu
1               5                   10                  15 tcg act tgt ggg ttg att ttg gcg cca atg ccg gtc ttt gcg              90
Ser Thr Cys Gly Leu Ile Leu Ala Pro Met Pro Val Phe Ala
            20                  25                  30
```

<210> SEQ ID NO 127
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP7)

<400> SEQUENCE: 127

```
gat tcc gcg cag acg agt gct gtg gtg tcc tca cgt tct ttc ccg aag      48
Asp Ser Ala Gln Thr Ser Ala Val Val Ser Ser Arg Ser Phe Pro Lys
1               5                   10                  15 gcg agt tcg gtg aag aag aat ttg ttc gcc gaa tcc acc tcc              90
Ala Ser Ser Val Lys Lys Asn Leu Phe Ala Glu Ser Thr Ser
            20                  25                  30
```

<210> SEQ ID NO 128
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP45)

<400> SEQUENCE: 128

```
gtc gac ggc aca gac ggc aca agc ggc acg aac agt acg tct cag gga      48
Val Asp Gly Thr Asp Gly Thr Ser Gly Thr Asn Ser Thr Ser Gln Gly
1               5                   10                  15 agc gac ggc gat tcc gcg cca atc gcc ggc ccg gtg ccg aac              90
Ser Asp Gly Asp Ser Ala Pro Ile Ala Gly Pro Val Pro Asn
            20                  25                  30
```

<210> SEQ ID NO 129
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP50)

<400> SEQUENCE: 129

```
gcg acg ttg acg ccc gcc gac gaa aga tat cac gtg gcg ttt cca tac      48
Ala Thr Leu Thr Pro Ala Asp Glu Arg Tyr His Val Ala Phe Pro Tyr
1               5                   10                  15 aac gat atg gaa tat tac gtc ggt gtc gcg ggg ctg gac gct              90
Asn Asp Met Glu Tyr Tyr Val Gly Val Ala Gly Leu Asp Ala
            20                  25                  30
```

<210> SEQ ID NO 130
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP52)

<400> SEQUENCE: 130

```
gcc gat tca gcc acc gct gac aac gcg ccc agc gtt gcc ggt cac gcg      48
Ala Asp Ser Ala Thr Ala Asp Asn Ala Pro Ser Val Ala Gly His Ala
1               5                   10                  15 tat aac gaa ctg ccg tat aac aat cct gat gtc acc gtc acc              90
Tyr Asn Glu Leu Pro Tyr Asn Asn Pro Asp Val Thr Val Thr
            20                  25                  30
```

```
<210> SEQ ID NO 131
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP55)

<400> SEQUENCE: 131 gac agc agc acc agc tcg tcc agt tca tca agc tcg tcc agc gtt gac      48
Asp Ser Ser Thr Ser Ser Ser Ser Ser Ser Ser Ser Ser Ser Val Asp
1               5                   10                  15 tac gcc acc tgg gcc gaa gtc tcc aag gcg atg gac aag cag              90
Tyr Ala Thr Trp Ala Glu Val Ser Lys Ala Met Asp Lys Gln
            20                  25                  30

<210> SEQ ID NO 132
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP58)

<400> SEQUENCE: 132 gga tca ttc gcg ttc acc gcg cgt aaa tcc gtg gcc ctg aac atc aac      48
Gly Ser Phe Ala Phe Thr Ala Arg Lys Ser Val Ala Leu Asn Ile Asn
1               5                   10                  15 ggg caa acc acc caa gtc acc aca tat gcg atg acg gcc acc              90
Gly Gln Thr Thr Gln Val Thr Thr Tyr Ala Met Thr Ala Thr
            20                  25                  30

<210> SEQ ID NO 133
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP64)

<400> SEQUENCE: 133 gaa gat gct acc ggc acg ctg acc gtc acc agc tcg gat gcc gcg ttc      48
Glu Asp Ala Thr Gly Thr Leu Thr Val Thr Ser Ser Asp Ala Ala Phe
1               5                   10                  15 aac ggc aag aag gtg aac gcc tac cag atg ttc tcc gct tcc              90
Asn Gly Lys Lys Val Asn Ala Tyr Gln Met Phe Ser Ala Ser
            20                  25                  30

<210> SEQ ID NO 134
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP66)

<400> SEQUENCE: 134 atg gaa tcg gaa gat tcc caa cca cag aca acc gat acc gcg aca gtg      48
Met Glu Ser Glu Asp Ser Gln Pro Gln Thr Thr Asp Thr Ala Thr Val
1               5                   10                  15 cag act act aag gct gct gaa ccg acg ctg ctc gcc agc tgg              90
Gln Thr Thr Lys Ala Ala Glu Pro Thr Leu Leu Ala Ser Trp
            20                  25                  30
```

<210> SEQ ID NO 135
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP67)

<400> SEQUENCE: 135

```
gca ggt gtg gat tac ctg cct acc atc ggc caa gtg ccg aca tac acc    48
Ala Gly Val Asp Tyr Leu Pro Thr Ile Gly Gln Val Pro Thr Tyr Thr
1               5                   10                  15 aag ttc cag ccc aca gcc gat ccg ggc aag aac gct agc gat            90
Lys Phe Gln Pro Thr Ala Asp Pro Gly Lys Asn Ala Ser Asp
            20                  25                  30
```

<210> SEQ ID NO 136
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP68)

<400> SEQUENCE: 136

```
gat gaa ccc gtc gaa ttg gtc gtc aac ggc gga ttc gaa gac gat ctt    48
Asp Glu Pro Val Glu Leu Val Val Asn Gly Gly Phe Glu Asp Asp Leu
1               5                   10                  15 aat ggt tgg aag tct gga acg gtg tgg aat agc tcc gca tcg            90
Asn Gly Trp Lys Ser Gly Thr Val Trp Asn Ser Ser Ala Ser
            20                  25                  30
```

<210> SEQ ID NO 137
<211> LENGTH: 90
<212> TYPE: DNA
<213> ORGANISM: Bifidobacterium spp.
<220> FEATURE:
<221> NAME/KEY: CDS
<222> LOCATION: (1)..(90)
<223> OTHER INFORMATION: Linker peptide (SP69)

<400> SEQUENCE: 137

```
gat gat tca acg cca tct tca acg cca tcg gat ggc agt tac acc acg    48
Asp Asp Ser Thr Pro Ser Ser Thr Pro Ser Asp Gly Ser Tyr Thr Thr
1               5                   10                  15 act gat agc ggt gat ggc acg tat tcc att ccc atg ttg aac            90
Thr Asp Ser Gly Asp Gly Thr Tyr Ser Ile Pro Met Leu Asn
            20                  25                  30
```

<210> SEQ ID NO 138
<211> LENGTH: 245
<212> TYPE: PRT
<213> ORGANISM: Homo sapiens
<220> FEATURE:
<223> OTHER INFORMATION: scFv-PD-1-1

<400> SEQUENCE: 138

```
Met Gln Val Gln Leu Val Gln Ser Gly Ser Glu Leu Lys Lys Pro Gly
1               5                   10                  15

Ala Ser Val Lys Ile Ser Cys Lys Ala Ser Gly Tyr Thr Phe Thr Asn
            20                  25                  30

Tyr Gly Met Asn Trp Val Arg Gln Ala Pro Gly Gln Gly Leu Gln Trp
        35                  40                  45

Met Gly Trp Ile Asn Thr Asp Ser Gly Glu Ser Thr Tyr Ala Glu Glu
```

```
                50                  55                  60
Phe Lys Gly Arg Phe Val Phe Ser Leu Asp Thr Ser Val Asn Thr Ala
 65                  70                  75                  80

Tyr Leu Gln Ile Thr Ser Leu Thr Ala Glu Asp Thr Gly Met Tyr Phe
                 85                  90                  95

Cys Val Arg Val Gly Tyr Asp Ala Leu Asp Tyr Trp Gly Gln Gly Thr
                100                 105                 110

Leu Val Thr Val Ser Ser Gly Gly Gly Ser Gly Gly Gly Gly Ser
                115                 120                 125

Gly Gly Gly Gly Ser Glu Ile Val Leu Thr Gln Ser Pro Ser Ser Leu
                130                 135                 140

Ser Ala Ser Val Gly Asp Arg Val Thr Ile Thr Cys Ser Ala Arg Ser
145                 150                 155                 160

Ser Val Ser Tyr Met His Trp Phe Gln Gln Lys Pro Gly Lys Ala Pro
                165                 170                 175

Lys Leu Trp Ile Tyr Arg Thr Ser Asn Leu Ala Ser Gly Val Pro Ser
                180                 185                 190

Arg Phe Ser Gly Ser Gly Ser Gly Thr Ser Tyr Cys Leu Thr Ile Asn
                195                 200                 205

Ser Leu Gln Pro Glu Asp Phe Ala Thr Tyr Tyr Cys Gln Gln Arg Ser
                210                 215                 220

Ser Phe Pro Leu Thr Phe Gly Gly Gly Thr Lys Leu Glu Ile Lys His
225                 230                 235                 240

His His His His His
                245

<210> SEQ ID NO 139
<211> LENGTH: 249
<212> TYPE: PRT
<213> ORGANISM: homo sapiens
<220> FEATURE:
<223> OTHER INFORMATION: scFv-PD-1-2

<400> SEQUENCE: 139

Met Gln Val Gln Leu Gln Glu Ser Gly Pro Gly Leu Val Lys Pro Ser
  1               5                  10                  15

Gln Ser Leu Ser Leu Thr Cys Thr Val Thr Gly His Ser Ile Thr Ser
                 20                  25                  30

Asp Tyr Ala Trp Asn Trp Ile Arg Gln Phe Pro Gly Asp Lys Leu Glu
                 35                  40                  45

Trp Met Gly Tyr Ile Ser Tyr Ser Gly Tyr Thr Thr Tyr Asn Pro Ser
 50                  55                  60

Leu Lys Ser Arg Val Ser Ile Thr Arg Asp Thr Ser Lys Asn Gln Phe
 65                  70                  75                  80

Phe Leu Gln Leu Asn Ser Val Thr Thr Glu Asp Thr Ala Thr Tyr Phe
                 85                  90                  95

Cys Ala Arg Asp Leu Asp Tyr Gly Pro Trp Phe Ala Tyr Trp Gly Gln
                100                 105                 110

Gly Thr Thr Val Thr Val Ser Ser Gly Gly Gly Gly Ser Gly Gly Gly
                115                 120                 125

Gly Ser Gly Gly Gly Gly Ser Asp Ile Gln Met Thr Gln Ser Pro Ala
                130                 135                 140

Ser Leu Ser Ala Ser Val Gly Glu Thr Val Thr Leu Thr Cys Arg Ala
145                 150                 155                 160

Ser Glu Asn Ile His Asn Tyr Leu Ala Trp Tyr Gln Gln Lys Gln Gly
```

```
                    165                 170                 175
Lys Ser Pro Gln Leu Leu Val Tyr Asn Val Lys Thr Leu Ala Asp Gly
                180                 185                 190

Val Pro Ser Arg Phe Ser Gly Ser Gly Ser Gly Thr Gln Tyr Ser Leu
                195                 200                 205

Lys Ile Asn Ser Leu Gln Pro Glu Asp Phe Gly Ser Tyr Tyr Cys Gln
                210                 215                 220

His Phe Trp Ser Ser Pro Trp Thr Phe Gly Gly Gly Thr Lys Leu Glu
225                 230                 235                 240

Ile Lys Arg His His His His His His
                245

<210> SEQ ID NO 140
<211> LENGTH: 253
<212> TYPE: PRT
<213> ORGANISM: Mus musculus
<220> FEATURE:
<223> OTHER INFORMATION: scFv-PD-1-3

<400> SEQUENCE: 140

Met Glu Val Arg Leu Leu Glu Ser Gly Gly Gly Leu Val Lys Pro Glu
1               5                   10                  15

Gly Ser Leu Lys Leu Ser Cys Val Ala Ser Gly Phe Thr Phe Ser Asp
                20                  25                  30

Tyr Phe Met Ser Trp Val Arg Gln Ala Pro Gly Lys Gly Leu Glu Trp
                35                  40                  45

Val Ala His Ile Tyr Thr Lys Ser Tyr Asn Tyr Ala Thr Tyr Tyr Ser
            50                  55                  60

Gly Ser Val Lys Gly Arg Phe Thr Ile Ser Arg Asp Asp Ser Arg Ser
65                  70                  75                  80

Met Val Tyr Leu Gln Met Asn Asn Leu Arg Thr Glu Asp Thr Ala Thr
                85                  90                  95

Tyr Tyr Cys Thr Arg Asp Gly Ser Gly Tyr Pro Ser Leu Asp Phe Trp
                100                 105                 110

Gly Gln Gly Thr Gln Val Thr Val Ser Ser Gly Gly Gly Gly Ser Gly
                115                 120                 125

Gly Gly Gly Ser Gly Gly Gly Gly Ser Tyr Glu Leu Thr Gln Pro Pro
                130                 135                 140

Ser Ala Ser Val Asn Val Gly Glu Thr Val Lys Ile Thr Cys Ser Gly
145                 150                 155                 160

Asp Gln Leu Pro Lys Tyr Phe Ala Asp Trp Phe His Gln Arg Ser Asp
                165                 170                 175

Gln Thr Ile Leu Gln Val Ile Tyr Asp Asp Asn Lys Arg Pro Ser Gly
                180                 185                 190

Ile Pro Glu Arg Ile Ser Gly Ser Ser Ser Gly Thr Thr Ala Thr Leu
                195                 200                 205

Thr Ile Arg Asp Val Arg Ala Glu Asp Glu Gly Asp Tyr Tyr Cys Phe
            210                 215                 220

Ser Gly Tyr Val Asp Ser Asp Ser Lys Leu Tyr Val Phe Gly Ser Gly
225                 230                 235                 240

Thr Gln Leu Thr Val Leu Gly His His His His His
                245                 250

<210> SEQ ID NO 141
<211> LENGTH: 254
<212> TYPE: PRT
```

```
<213> ORGANISM: Homo sapiens
<220> FEATURE:
<223> OTHER INFORMATION: scFv-CTLA-4-1

<400> SEQUENCE: 141

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser Ser
            20                  25                  30

Tyr Gly Met His Trp Val Arg Gln Ala Pro Gly Lys Gly Leu Glu Trp
        35                  40                  45

Val Ala Val Ile Trp Tyr Asp Gly Ser Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Pro Arg Gly Ala Thr Leu Tyr Tyr Tyr Tyr Gly
            100                 105                 110

Met Asp Val Trp Gly Gln Gly Thr Thr Val Thr Val Ser Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Asn Ser Tyr Leu Asp Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Tyr Tyr Ser Thr Pro Phe Thr Phe Gly
225                 230                 235                 240

Pro Gly Thr Lys Val Glu Ile Lys His His His His His His
                245                 250

<210> SEQ ID NO 142
<211> LENGTH: 248
<212> TYPE: PRT
<213> ORGANISM: Homo sapiens
<220> FEATURE:
<223> OTHER INFORMATION: scFv-CTLA-4-2

<400> SEQUENCE: 142

Met Gln Val Gln Leu Val Glu Ser Gly Gly Gly Val Val Gln Pro Gly
1               5                   10                  15

Arg Ser Leu Arg Leu Ser Cys Ala Ala Ser Gly Phe Thr Phe Ser Ser
            20                  25                  30

Tyr Thr Met His Trp Val Arg Gln Ala Pro Gly Lys Gly Leu Glu Trp
        35                  40                  45

Val Thr Phe Ile Ser Tyr Asp Gly Asn Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80
```

-continued

```
Tyr Leu Gln Met Asn Ser Leu Arg Ala Glu Asp Thr Ala Ile Tyr Tyr
                85                  90                  95

Cys Ala Arg Thr Gly Trp Leu Gly Pro Phe Asp Tyr Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Gly Ser Glu Ile Val Leu Thr Gln Ser Pro Gly Thr
130                 135                 140

Leu Ser Leu Ser Pro Gly Glu Arg Ala Thr Leu Ser Cys Arg Ala Ser
145             150                 155                 160

Gln Ser Val Gly Ser Ser Tyr Leu Ala Trp Tyr Gln Gln Lys Pro Gly
                165                 170                 175

Gln Ala Pro Arg Leu Leu Ile Tyr Gly Ala Phe Ser Arg Ala Thr Gly
            180                 185                 190

Ile Pro Asp Arg Phe Ser Gly Ser Gly Ser Gly Thr Asp Phe Thr Leu
            195                 200                 205

Thr Ile Ser Arg Leu Glu Pro Glu Asp Phe Ala Val Tyr Tyr Cys Gln
    210                 215                 220

Gln Tyr Gly Ser Ser Pro Trp Thr Phe Gly Gln Gly Thr Lys Val Glu
225                 230                 235                 240

Ile Lys His His His His His His
                245
```

US 10,443,061 B2

HETEROLOGOUS POLYPEPTIDE EXPRESSION CASSETTE

CROSS REFERENCE TO RELATED APPLICATIONS

This application is a National Phase under 35 USC 371 of International Application No. PCT/JP2015/002132 filed on Apr. 17, 2015, which claims priority to Japanese Application No. 2014-094869 filed May 1, 2014, the contents of which are hereby incorporated by reference in their entirety.

TECHNICAL FIELD

The present invention relates to an expression cassette comprising a promoter DNA, a DNA encoding a secretory signal peptide, a DNA encoding a linker peptide, a DNA encoding a heterologous polypeptide and a terminator DNA sequentially in this order and expressed in a bacterium of the genus Bifidobacterium. The present invention also relates to a vector comprising the expression cassette, a bacterium of the genus Bifidobacterium transformed with the vector and a pharmaceutical composition comprising the bacterium.

SEQUENCE LISTING

The present application contains a Sequence Listing that has been submitted in ASCII format via EFS-Web and is hereby incorporated by reference into the present specification in its entirety. The .txt file was created on Jan. 20, 2017; is named 5F001-002_SL.txt; and is 113 KB in size.

BACKGROUND ART

Recently, for treating diseases such as cancer, therapies using a gene transport carrier have been increasingly developed. For example, an anaerobic enteric bacterium, if it is systemically administered, is accumulated in a hypoxic solid tumor. Using this property, a transformed microorganism which can express a gene encoding a protein having an anti-tumor activity or a protein having an activity to convert a precursor of an anti-tumor agent into the anti-tumor agent at a target site of disease (see, for example, Patent Document 1) has been proposed.

Also, an expression cassette, which comprises a promoter, a DNA encoding a signal sequence, a DNA encoding a polypeptide or a cloning site for inserting the DNA (see, for example, Patent Document 2); and a recombinant obligatory anaerobic gram-positive bacterium, which comprises a nucleic acid encoding a fusion protein comprising a signal peptide, a single-chain antibody and one or more heterologous polypeptides and which can express the nucleic acid therein (see, for example, Patent Document 3) have been proposed.

However, signal peptides proposed in the above documents are found in membrane proteins and secretory proteins. In the context, a signal peptide having better secretion efficiency is desirably identified.

PRIOR ART DOCUMENTS

Patent Documents

Patent Document 1: International Publication No. WO2006/109619
Patent Document 2: International Publication No. WO2010/126073
Patent Document 3: International Publication No. WO2014/010758

SUMMARY OF INVENTION

Object to be Solved by the Invention

An object of the present invention is to provide, in producing a heterologous polypeptide by a bacterium of the genus Bifidobacterium, a signal peptide which enables to secrete the heterologous polypeptide with high efficiency outside the bacterial cell; a heterologous polypeptide expression cassette, which enables to secrete the heterologous polypeptide outside the bacterial cell with high efficiency by using such a signal peptide; a heterologous polypeptide expression vector having the expression cassette integrated therein; and a bacterium of the genus Bifidobacterium, which is transformed with the heterologous polypeptide expression vector and can secrete the heterologous polypeptide.

Means to Solve the Object

The present inventors have already developed an anti-cancer therapy using a bacterium of the genus Bifidobacterium, which is transformed with a vector prepared by integrating a gene for cytosine deaminase, i.e., an enzyme for converting 5-fluoro-cytosine into 5-fluorouracil having an antitumor activity, and which specifically accumulates and grows in solid cancer. This time, the present inventors found that various diseases can be treated by locally expressing and secreting an antibody peptide specifically recognizing a target cell and a heterologous polypeptide in a bacterium of the genus Bifidobacterium. Based on the finding, they tried to identify a secretory signal peptide which enables expression and secretion of a heterologous polypeptide more efficiently than a secretory signal peptide known in the art and which is applicable to a bacterium of the genus Bifidobacterium. As a result, they found a plurality of secretory signal peptides including a secretory signal peptide designated as SP7. In addition, they found that Bifidobacterium longum transformed with a vector, in which an expression cassette comprising a promoter DNA functioning in a bacterium of the genus Bifidobacterium; a DNA encoding the secretory signal peptide as mentioned above; a DNA encoding a linker peptide; a DNA encoding a single-chain antibody(scFv antibody) having an antitumor activity; and a terminator DNA functioning in the bacterium of the genus Bifidobacterium, sequentially in this order, is integrated, secretes the scFv antibody outside the bacterial cell with high efficiency. They further found that the scFv antibody secreted outside the bacterial cell varies in the secretion amount outside the bacterial cell, binding ability thereof to an antigen and competitive binding inhibitory activity, depending upon the type of secretory signal peptide sequence as mentioned above and the number of amino acids of a linker peptide sequence located downstream thereof. Based on these findings, the present invention was accomplished.

The present invention is more specifically as follows.

[1] An expression cassette expressed in a bacterium of the genus Bifidobacterium and sequentially comprising the following DNAs (1) to (4).

(1) a promoter DNA functioning in the bacterium of the genus Bifidobacterium;

(2) a DNA encoding a secretory signal peptide consisting of an amino acid sequence represented by the following a) or b);

a) an amino acid sequence represented by any one of SEQ ID Nos: 6, 7, 8, 9, 10, 11, 12, 13, 14, 15 and 16; and b) an amino acid sequence obtained by deletion, replacement or addition of one or several amino acids in an amino acid sequence represented by any one of SEQ ID Nos: 6, 7, 8, 9, 10, 11, 12, 13, 14, 15 and 16, wherein a peptide consisting of the amino acid sequence functions as a secretory signal peptide in the bacterium of the genus *Bifidobacterium;*

(3) a DNA encoding a heterologous polypeptide; and (4) a terminator DNA functioning in the bacterium of the genus *Bifidobacterium.*

[2] The expression cassette according to [1], wherein a DNA encoding a linker peptide is linked downstream of a DNA encoding a secretory signal peptide.

[3] The expression cassette according to [2], wherein the linker peptide consists of each amino acid sequence obtained by deletion of 0 to 29 amino acid residues from the C terminal of the amino acid sequence represented by any one of SEQ ID Nos: 25, 26, 27, 28, 29, 30, 31, 32, 33, 34 and 35.

[4] The expression cassette according to [2], wherein the linker peptide consists of each amino acid sequence obtained by deletion of 10 to 29 amino acid residues from the C terminal of the amino acid sequence represented by any one of SEQ ID Nos: 25, 26, 27, 28, 29, 30, 31, 32, 33, 34 and 35.

[5] The expression cassette according to any one of [1] to [4], wherein the heterologous polypeptide is a single-chain antibody.

[6] The expression cassette according to [5], wherein the single-chain antibody is an anti-PD-1 antibody.

[7] The expression cassette according to [5], wherein the single-chain antibody is an anti-CTLA-4 antibody.

[8] A vector comprising the expression cassette according to any one of [1] to [7].

[9] A bacterium of the genus *Bifidobacterium* transformed with the vector according to [8].

[10] The bacterium of the genus *Bifidobacterium* according to [9], which is *Bifidobacterium longum.*

[11] A pharmaceutical composition comprising the bacterium of the genus *Bifidobacterium* according to [9] or [10].

[12] A secretory signal peptide consisting of the amino acid sequence represented by any one of SEQ ID Nos: 6, 7, 8, 9, 10, 11, 12, 13, 14, 15 and 16.

[13] A DNA encoding the secretory signal peptide according to [12].

[14] A secretory signal peptide-linker conjugate consisting of each amino acid sequence obtained by deletion of 0 to 29 amino acid residues from the C terminal of the amino acid sequence represented by any one of SEQ ID Nos: 105, 106, 107, 108, 109, 110, 111, 112, 113, 114 and 115.

[15] The secretory signal peptide-linker conjugate according to [14], consisting of each amino acid sequence obtained by deletion of 10 to 29 amino acid residues from the C terminal of the amino acid sequence represented by any one of SEQ ID Nos: 105, 106, 107, 108, 109, 110, 111, 112, 113, 114 and 115.

[16] A DNA encoding the secretory signal peptide-linker conjugate according to [14] or [15].

As the other aspects except those mentioned above, a therapeutic method comprising administering an effective amount of bacterium of the genus *Bifidobacterium* according to [9] or [10]; use of the bacterium of the genus *Bifidobacterium* according to [9] or [10] for preparing a therapeutic agent; and the bacterium of the genus *Bifidobacterium* according to [9] or [10] for use in treating a disease can be mentioned.

Effect of Invention

According to the present invention, it is possible to provide a bacterium of the genus *Bifidobacterium* capable of secreting a heterologous polypeptide outside the bacterial cell with high efficiency by using an expression cassette excellent in secretion of the heterologous polypeptide. If the heterologous polypeptide is an antibody having an anti-cancer effect, such as PD-1 and CTLA-4, the bacterium of the genus *Bifidobacterium* is extremely useful as an anti-cancer agent.

BRIEF DESCRIPTION OF DRAWINGS

FIG. 1 is a schematic view of expression cassettes of the present invention; (a) shows an expression cassette using an anti-PD-1 antibody as a scFv antibody; and (b) shows an expression cassette using an anti-CTLA-4 antibody as a scFv antibody.

FIG. 2 schematically shows how to prepare an anti-PD-1 or anti-CTLA-4 scFv antibody secretory plasmid: pHuSP3L22-scFv-PD-1-1, pHuSP7L20-scFv-PD-1-1, pHuSP23L27-scFv-PD-1-1, pHuSP7L20-scFv-PD-1-2, pHuSP7L20-scFv-PD-1-3, pHuSP7L20-scFv-CTLA-4-1 or pHuSP7L20-scFv-CTLA-4-2.

FIG. 3 schematically shows how to prepare an anti-PD-1-1 scFv antibody secretory plasmid using various signal peptide-linker conjugates.

FIG. 4 shows the results of Western analysis of an anti-PD-1-1 scFv antibody secreted in the culture supernatant of a bacterium of the genus *Bifidobacterium* transformed with a vector obtained by inserting an expression cassette comprising various signal peptide-linker peptide conjugates and an anti-PD-1-1 scFv antibody.

FIG. 5 shows the results of Western analysis of an anti-PD-1-1 scFv antibody secreted in the culture supernatant of a bacterium of the genus *Bifidobacterium* transformed with a vector obtained by inserting an expression cassette comprising various signal sequences and an anti-PD-1-1 scFv antibody.

FIG. 6 shows the results of Western analysis of antibodies each secreted in the culture supernatant of a bacterium of the genus *Bifidobacterium.*

FIG. 7 is a graph showing the results of the presence or absence of binding of an anti-PD-1-2 scFv antibody, an anti-CTLA-4-1 scFv antibody and an anti-CTLA-4-2 scFv antibody secreted from a bacterium of the genus *Bifidobacterium* to human PD-1 immobilized on a plate.

FIG. 8 is a graph showing the results of the presence or absence of binding of an anti-PD-1-2 scFv antibody, an anti-CTLA-4-1 scFv antibody and an anti-CTLA-4-2 scFv antibody secreted from a bacterium of the genus *Bifidobacterium* to human CTLA-4 immobilized on a plate.

FIG. 9 is a graph showing the results of the presence or absence of binding of an anti-PD-1-2 scFv antibody, an anti-PD-1-3 scFv antibody and an anti-CTLA-4-2 scFv antibody secreted from a bacterium of the genus *Bifidobacterium* to mouse PD-1 immobilized on a plate.

FIG. 10 is a graph showing the results of the presence or absence of binding of an anti-PD-1-2 scFv antibody, an anti-PD-1-3 scFv antibody and an anti-CTLA-4-2 scFv antibody secreted from a bacterium of the genus *Bifidobacterium* to human CTLA-4 immobilized on a plate.

FIG. 11 is a graph obtained by flow cytometry and showing the binding of an anti-PD-1-2 scFv antibody secreted from a bacterium of the genus *Bifidobacterium* to a Jurkat cell expressing human PD-1.

FIG. 12 is a graph obtained by flow cytometry and showing the binding of an anti-PD-1-2 scFv antibody secreted from a bacterium of the genus *Bifidobacterium* to a HEK293T cell expressing human PD-1.

FIG. 13 is a graph showing an inhibition rate of human CD80 against the binding of an anti-CTLA-4-1 scFv antibody and an anti-CTLA-4-2 scFv antibody to human CTLA-4.

FIG. 14 is a graph showing an inhibition rate of human CD86 against the binding of an anti-CTLA-4-1 scFv antibody and an anti-CTLA-4-2 scFv antibody to human CTLA-4.

FIG. 15 is a graph showing the competitive inhibition activity of an anti-mouse PD-1 scFv antibody against the binding reaction between mouse PD-1 and mouse PD-L1, where the vertical axis shows inhibitory activity and the horizontal axis shows antibody concentration.

FIG. 16 shows graphs obtained by flow cytometry. Of the graphs showing expression induction of mPD-1 into a CD4-positive T cell by stimulation with CD3/CD28, graph A shows the case where an anti-mouse PD-1 antibody was reacted with a non-stimulated CD4-positive cell and detected by FITC, and graph B shows the case where an anti-mouse PD-1 antibody was reacted with a CD3/CD28-stimulated CD-positive cell and detected by FITC. Of the graphs showing binding of the anti-mouse PD-1 scFv antibody to CD3 and CD28-stimulated CD4 positive cell (obtained by flow cytometry), graph C shows the case where an anti-mouse PD-1 scFv antibody was reacted with a non-stimulated CD4-positive cell and then an Alexa 488-anti-His-tag antibody was reacted with His thereof and detection was made; and graph D shows the case where an anti-mouse PD-1 scFv antibody was reacted with a CD3/CD28-stimulated CD-positive cell and then an Alexa 488-anti-His-tag antibody was reacted with His thereof and detection was made.

FIG. 17(A) shows immunohistochemical staining of a tumor tissue of an anti-mouse PD-1 scFv antibody-secreting bacterium of the genus *Bifidobacterium* administered mouse; and FIG. 17(B) shows immunohistochemical staining of a tumor tissue of a not administered mouse.

FIG. 18 is a graph showing a change of CT26 tumor volume in a single agent administration group and a non-administration group.

FIG. 19 is a graph showing a change of CT26 tumor volume in a single agent administration group, a combined administration group of two agents and non-administration group.

FIG. 20 is a graph showing a change of CT26 tumor volume in a single agent administration group and a combined administration group of two agents.

FIG. 21 shows the presence or absence of antibody secretion in each of *Bifidobacterium longum* 105-A/pHuSP69Ly-hPD-1scFv03 strains.

FIG. 22 is a graph showing the binding amount of *Bifidobacterium longum* 105-A/pHuSP69L5-hPD-1scFv03 strain and *Bifidobacterium longum* 105-A/pHuSP69L20-hPD-1scFv03 strain by ELISA.

FIG. 23 shows the binding amount of PD-L1 not competitively inhibited by each of scFv secreted from *Bifidobacterium longum* 105-A/pHuSP69L5-hPD-1scFv03 strain and *Bifidobacterium longum* 105-A/pHuSP69L20-hPD-1scFv03 strain, by ELISA.

FIG. 24 FIGS. 24(a) and 24(b) show the presence or absence of antibody secretion from each of *Bifidobacterium longum* 105-A/pHuSPxL20-hPD-1scFv03 strains.

FIG. 25 FIGS. 25(a) to 25(d) show the presence or absence of antibody secretion from each of *Bifidobacterium longum* 105-A/pHuSPxLy-hPD-1scFv03 strains (note that, y=5, 10, 15, 20).

FIG. 26 FIGS. 26(a) to 26(c) show the presence or absence of antibody secretion from each of *Bifidobacterium longum* 105-A/pHuSPxLy-hPD-1scFv03 strains.

FIG. 27 shows the presence or absence of antibody secretion from each of *Bifidobacterium longum* 105-A/pHuSPxLy-hPD-1scFv03 strains.

FIG. 28 shows the presence or absence of antibody secretion from each of *Bifidobacterium longum* 105-A/pP30SPxL20-hCTLA-4scFv02 strains.

FIG. 29 FIGS. 29(a) to 29(c) shows the presence or absence of antibody secretion from each of *Bifidobacterium longum* 105-A/pP30SPxLy-hCTLA-4scFv02 strains.

MODE OF CARRYING OUT THE INVENTION

The expression cassette of the present invention is not particularly limited as long as it is an expression cassette sequentially comprising (1) a promoter DNA functioning in a bacterium of the genus *Bifidobacterium*, (2) a DNA encoding a secretory signal peptide, (3) a DNA encoding a linker peptide, (4) a DNA encoding a heterologous polypeptide, and (5) a terminator DNA functioning in a bacterium of the genus *Bifidobacterium*, in which the secretory signal peptide consists of a) an amino acid sequence represented by any one of SEQ ID Nos: 6, 7, 8, 9, 10, 11, 12, 13, 14, 15 and 16, or b) an amino acid sequence obtained by deletion, replacement or addition of one or several of amino acids in the amino acid sequence represented by any one of SEQ ID Nos: 6, 7, 8, 9, 10, 11, 12, 13, 14, 15 and 16; and constituting a peptide functioning as a secretory signal peptide in the bacterium of the genus *Bifidobacterium*; and used for expressing the heterologous polypeptide in a bacterium of the genus *Bifidobacterium*. In the DNA fragments as mentioned above, the 3' end of one DNA fragment and the 5' end of another DNA fragment located downstream of the former DNA fragment may not be directly linked as long as the effect of the invention is obtained; however it is preferable that the ends are directly linked.

The promoter DNA is not particularly limited as long as it is a promoter DNA functioning in a bacterium of the genus *Bifidobacterium*. Examples thereof include Hu promoter DNA, which is a promoter involved in expression of a gene encoding histone-like DNA binding protein derived from *Bifidobacterium longum*; a promoter DNA for Gap gene derived from *Bifidobacterium breve* (Biotechnol. Lett. 2008 30: 1983-1988); a promoter DNA for AmyB gene derived from *Bifidobacterium longum* (Biotechnol. Lett. 2006 28: 163-168); 16S rRNA Promoter DNA (Biotechnol. Lett. 2008 30: 165-172), a promoter DNA for GAPDH (pr-BL1363) gene (Appl Environ Microbiol. 2006 72(11): 7401-7405); $P_R P_L$ promoter DNA (Cancer Gene Ther. 2007 14: 151-157); a promoter DNA for p572 (3-glycosidase from *B. animalis* subsp *lactis*) gene (J Microbiol Biotechnol. 2012 December; 22(12): 1714-23), p919 (rp1M promoter) DNA (J Microbiol. 2012 August; 50(4): 638-43); and p895 (rp1R promoter) DNA (J Microbiol. 2012 August; 50(4): 638-43).

Examples of the secretory signal peptide include a) a peptide consisting of an amino acid sequence represented by any one of SEQ ID Nos. 6, 7, 8, 9, 10, 11, 12, 13, 14, 15 and 16; namely, SP7, SP45, SP50, SP52, SP55, SP58, SP64, SP66, SP67, SP68, SP69 respectively, and b) a peptide consisting of an amino acid sequence obtained by deletion, replacement or addition of one or several of amino acids in the amino acid sequence represented by any one of SEQ ID Nos. 6, 7, 8, 9, 10, 11, 12, 13, 14, 15 and 16 and functioning as a secretory signal peptide in a bacterium of the genus *Bifidobacterium* (mutated secretory signal peptide). The "an amino acid sequence obtained by deletion, replacement or addition of one or several of amino acids" refers to an amino acid sequence obtained by deletion, replacement or addition of e.g., 1 to 5, preferably 1 to 3, more preferably 1 to 2 and further preferably a single amino acid. The amino acid sequence of the mutated secretory signal peptide has a sequence identity of preferably 90% or more with any of the amino acid sequence represented by SEQ ID Nos: 6, 7, 8, 9, 10, 11, 12, 13, 14, 15 and 16, more preferably 95% or more and further preferably, 98% or more.

DNA encoding a secretory signal peptide consisting of the amino acid sequence described in a) above is not particularly limited as long as it is DNA having a nucleotide sequence corresponding to the amino acid sequence described in a). Accordingly, examples of DNA include, although different DNAs due to codon degeneracy are included, DNA consisting of a nucleotide sequence represented by any one of SEQ ID Nos: 116, 117, 118, 119, 120, 121, 122, 123, 124, 125 and 126. These DNAs can be prepared by a method known to those skilled in the art, such as chemical synthesis and genetic engineering procedure.

DNA encoding a secretory signal peptide consisting of the amino acid sequence described in b) above is not particularly limited as long as it is DNA having a nucleotide sequence corresponding to the amino acid sequence described in b). Accordingly, different DNAs due to codon degeneracy are included. These DNAs molecules can be also prepared by a method known to those skilled in the art such as chemical synthesis, genetic engineering procedure and mutation induction. For example, mutated DNAs can be obtained by introducing a mutation into these DNAs, by a method of bringing a mutagenic drug into contact with DNA consisting of a nucleotide sequence represented by any of SEQ ID Nos: 116, 117, 118, 119, 120, 121, 122, 123, 124, 125 and 126; a UV irradiation method; and/or genetic engineering techniques. One of the genetic engineering procedures, i.e., site-specific mutagenesis, is useful since a specific mutation can be introduced into a specific site, and carried out in accordance with the method described in e.g., Molecular Cloning: A laboratory Manual, 2nd Ed., Cold Spring Harbor Laboratory, Cold Spring Harbor, N.Y., 1989, Current Protocols in Molecular Biology, Supplement 1 to 38, John Wiley & Sons (1987-1997).

The secretory signal peptide is preferably used in conjunction with a linker peptide in the form of a signal peptide-linker conjugate, in view of expression/secretion efficiency of a heterologous polypeptide. The linker peptide to be used herein is not particularly limited as long as it is a peptide that can be conjugated to the C terminal of a secretory signal peptide as mentioned above and successfully enhance expression/secretion efficiency of a heterologous polypeptide. As an example, a peptide consisting of an amino acid sequence having 1 to 30 amino acid residues can be mentioned. More specifically, in each of the following 11 types of amino acid sequences positioned downstream of the individual secretory signal peptides and identified in *Bifidobacterium longum* 105-A strain, a linker peptide consisting of amino acid sequence having any number of amino acids within the range of the 1st to 30th amino acid, such as a linker peptide consisting of the 1st to 5th, 1st to 10th, 1st to 15th or 1st to 20th, is mentioned.

1) Linker peptide sequence represented by SEQ ID No: 25 (downstream of SP7);
2) Linker peptide sequence represented by SEQ ID No: 26 (downstream of SP45);
3) Linker peptide sequence represented by SEQ ID No: 27 (downstream of SP50);
4) Linker peptide sequence represented by SEQ ID No: 28 (downstream of SP52);
5) Linker peptide sequence represented by SEQ ID No: 29 (downstream of SP55);
6) Linker peptide sequence represented by SEQ ID No: 30 (downstream of SP58);
7) Linker peptide sequence represented by SEQ ID No: 31 (downstream of SP64);
8) Linker peptide sequence represented by SEQ ID No: 32 (downstream of SP66);
9) Linker peptide sequence represented by SEQ ID No: 33 (downstream of SP67);
10) Linker peptide sequence represented by SEQ ID No: 34 (downstream of SP68);
11) Linker peptide sequence represented by SEQ ID No: 35 (downstream of SP69).

DNA encoding the secretory signal peptide-linker conjugate of the present invention refers to a DNA region from the 5' end of the DNA (2) encoding a secretory signal peptide to the 3' end of the DNA (3) encoding a linker peptide. Since the 3' end of DNA (2) encoding a secretory signal peptide is connected to the 5' end of DNA (3) encoding a linker peptide, the secretory signal peptide-linker conjugate is hereinafter sometimes referred to as SPxLy (where x represents the number of a secretory signal peptide designated in the specification; and y represents the number of amino acid residues of a linker peptide). As the secretory signal peptide-linker conjugate, the following 11 types can be specifically mentioned.

1) Secretory signal peptide-linker conjugate (SP7L30) represented by SEQ ID No: 105;
2) Secretory signal peptide-linker conjugate (SP45L30) represented by SEQ ID No: 106;
3) Secretory signal peptide-linker conjugate (SP50L30) represented by SEQ ID No: 107;
4) Secretory signal peptide-linker conjugate (SP52L30) represented by SEQ ID No: 108;
5) Secretory signal peptide-linker conjugate (SP55L30) represented by SEQ ID No: 109;
6) Secretory signal peptide-linker conjugate (SP58L30) represented by SEQ ID No: 110;
7) Secretory signal peptide-linker conjugate (SP64L30) represented by SEQ ID No: 111;
8) Secretory signal peptide-linker conjugate (SP66L30) represented by SEQ ID No: 112;
9) Secretory signal peptide-linker conjugate (SP67L30) represented by SEQ ID No: 113;
10) Secretory signal peptide-linker conjugate (SP68L30) represented by SEQ ID No: 114;
11) Secretory signal peptide-linker conjugate (SP69L30) represented by SEQ ID No: 115.

For example, the 5' end of DNA encoding a linker peptide, which is obtained by deletion of amino acid residues of 0 to 29 (e.g., 10 to 29, 15 to 29, 20 to 29, or 25 to 29) from the C terminal of a linker peptide consisting of the amino acid sequence represented by SEQ ID No: 25, is connected to the 3' end of DNA encoding a secretory signal peptide consisting of the amino acid sequence represented by SEQ ID No: 6. Similarly, the 5' end of DNA encoding a linker peptide, which is obtained by deletion of amino acid residues of 0 to 29 (e.g., 10 to 29, 15 to 29, 20 to 29, or 25 to 29) from the C terminal of a linker peptide consisting of the amino acid sequence represented by any one of SEQ ID Nos: 26 to 35 is correspondingly connected to the 3' end of DNA encoding a secretory signal peptide consisting of the amino acid sequence represented by any of SEQ ID Nos: 7 to 16.

Such DNA encoding the secretory signal peptide-linker conjugate can be prepared by a method known to those skilled in the art such as chemical synthesis and genetic engineering procedure based on the nucleotide sequence information represented by any of, for example, SEQ ID No: 116+SEQ ID No: 127 (SP7L30), SEQ ID No: 117+SEQ ID No: 128 (SP45L30), SEQ ID No: 118+SEQ ID No: 129 (SP50L30), SEQ ID No: 119+SEQ ID No: 130 (SP52L30), SEQ ID No: 120+SEQ ID No: 131 (SP55L30), SEQ ID No: 121+SEQ ID No: 132 (SP58L30), SEQ ID No: 122+SEQ ID No: 133 (SP64L30), SEQ ID No: 123+SEQ ID No: 134 (SP66L30), SEQ ID No: 124+SEQ ID No: 135 (SP67L30), SEQ ID No: 125+SEQ ID No: 136 (SP68L30) and SEQ ID No: 126+SEQ ID No: 137 (SP69L30).

In the expression cassette of the present invention, more specifically, in a linker peptide consisting of each amino acid sequence obtained by deletion of 0 to 29 amino acid residues from the C terminal of the amino acid sequence represented by any of SEQ ID Nos: 25, 26, 27, 28, 29, 30, 31, 32, 33, 34 and 35, reference symbol "y" of "Ly" mentioned above can be represented by any of 30, 29, 28, 27, 26, 25, 24, 23, 22, 21, 20, 19, 18, 17, 16, 15, 14, 13, 12, 11, 10, 9, 8, 7, 6, 5, 4, 3, 2 and 1.

Examples of the secretory signal peptide-linker conjugate (SPxLy) of the present invention include SP7Ly (y=any of integers of 1 to 30 (hereinafter, the same is applied), for example, y=1 to 20, y=1 to 15, y=1 to 10, y=1 to 5); SP45Ly (y=1 to 30, for example, y=1 to 20, y=1 to 15, y=1 to 10, y=1 to 5); SP50Ly (y=1 to 30, for example, y=1 to 20, y=1 to 15, y=1 to 10, y=1 to 5); SP52Ly (y=1 to 30, for example, y=1 to 20, y=1 to 15, y=1 to 10, y=1 to 5); SP55Ly (y=1 to 30, for example, y=1 to 20, y=1 to 15, y=1 to 10, y=1 to 5); SP58Ly (y=1 to 30, for example, y=1 to 20, y=1 to 15, y=1 to 10, y=1 to 5); SP64Ly (y=1 to 30, for example, y=1 to 20, y=1 to 15, y=1 to 10, y=1 to 5); SP66Ly (y=1 to 30, for example, y=1 to 20, y=1 to 15, y=1 to 10, y=1 to 5); SP67Ly (y=1 to 30, for example, y=1 to 20, y=1 to 15, y=1 to 10, y=1 to 5); SP68Ly (y=1 to 30, for example, y=1 to 20, y=1 to 15, y=1 to 10, y=1 to 5); and SP69Ly (y=1 to 30, for example, y=1 to 20, y=1 to 15, y=1 to 10, y=1 to 5).

In *Bifidobacterium longum* 105-A strain, which is transformed with a vector containing an expression cassette having anti-hPD-1scFv03 integrated downstream of a secretory signal peptide or a secretory signal peptide-linker conjugate according to the present invention, specific examples of the secretory signal peptide-linker conjugates by which successful secretion of anti-hPD-1scFv03 was observed, include SP69L1, SP69L2, SP69L3, SP69L4, SP69L5, SP69L6, SP69L7, SP69L8, SP69L9, SP69L10, SP69L15, SP69L20; SP7L20, SP45L20, SP50L20, SP52L20, SP55L20, SP58L20, SP64L20, SP66L20, SP67L20, SP68L20; SP7L5, SP7L10, SP7L15, SP45L5, SP45L10, SP45L15, SP50L5, SP50L10, SP50L15, SP52L5, SP52L10, SP52L15, SP55L5, SP55L10, SP55L15, SP58L15, SP64L5, SP64L10, SP64L15, SP66L5, SP66L10, SP66L15, SP67L5, SP67L10, SP67L15, SP68L5, SP68L10, SP68L15, SP69L5, SP69L10, SP69L15; SP45L0, SP45L1, SP45L2, SP45L3, SP50L0, SP50L1, SP50L2, SP50L3, SP50L4, SP64L0, SP64L1, SP64L2, SP64L3, SP64L4, SP68L0, SP68L1, SP68L2, SP68L3, SP68L4; and SP67L10 and SP69L7. Among them, SPSP50L0, SP50L1, SP50L2, SP50L3, SP50L4, SP50L5, SP50L10, SP50L15, SP50L20, SP64L0, SP64L1, SP64L2, SP64L3, SP64L4, SP64L5, SP64L10, SP64L15, SP64L20, SP68L1, SP68L2, SP68L3, SP68L4, SP68L5, SP68L10, SP68L15, SP68L20, SP69L7, SP69L8, SP69L9, SP69L10, SP69L15 and SP69L20, which secreted a large amount of anti-hPD-1scFv03, can be preferably mentioned.

In *Bifidobacterium longum* 105-A strains similarly transformed, when anti-hPD-1scFv03 was secreted and found to have binding ability to PD-1, specific examples of the secretory signal peptide-linker conjugate used there include SP7L5, SP7L20, SP68L5, SP68L20, SP69L5, SP69L20, SP45L20, SP50L20, SP52L20, SP55L20, SP58L20, SP64L20, SP66L20 and SP67L20. Of them, SP7L5, SP68L5 and SP69L5 secreting anti-hPD-1scFv03 binding to PD-1 in a larger amount can be preferably mentioned.

In *Bifidobacterium longum* 105-A strain similarly transformed, when anti-hPD-1scFv03 was secreted and found to inhibit the binding between hPD-1 and PD-L1, specific examples of the secretory signal peptide-linker conjugate used there include SP69L5, SP69L20, SP50L5, SP64L5, SP67L10, SP68L1, SP68L5, SP69L1 and SP69L7. SP50L5, SP68L1 and SP69L1 are preferable. Among them, SP50L5 inhibits 50% of binding between hPD-1 and PD-L1 at a low concentration (antibody concentration (IC50) is low) is particularly preferable.

In *Bifidobacterium longum* 105-A strain transformed with a vector containing an expression cassette in which anti-hCTLA-4scFv02 is integrated downstream of a secretory signal peptide or a secretory signal peptide-linker conjugate according to the present invention, when anti-hCTLA-4scFv02 was secreted, specific examples of the secretory signal peptide-linker conjugate used there include SP7L20, SP45L20, SP50L20, SP52L20, SP55L20, SP58L20, SP64L20, SP66L20, SP67L20, SP68L20, SP69L20, SP45L0, SP45L1, SP45L2, SP45L3, SP45L4, SP45L5, SP50L0, SP50L1, SP50L2, SP50L3, SP50L4, SP50L5, SP64L0, SP64L1, SP64L2, SP64L3, SP64L4, SP64L5, SP68L1, SP68L2, SP68L3, SP68L4, SP68L5, SP69L0, SP69L1, SP69L2, SP69L3, SP69L4, SP69L5, SP69L6, SP69L7, SP69L8, SP69L9 and SP69L10.

The DNA encoding a heterologous polypeptide as mentioned above is not particularly limited as long as it can be expressed in the expression cassette of the present invention and is not derived from a bacterium of the genus *Bifidobacterium*. Examples thereof include DNAs encoding a cytokines such as interferon (IFN)-α, β, γ, granulocyte-macrophage colony-stimulating factor (GM-CSF), interleukins (IL)-1α, IL-1β, IL-2, IL-3, IL-4, IL-6, IL-7, IL-10, IL-12, IL-13, IL-15, IL-18, IL-27, tumor necrosis factor (TNF)-α, lymphotoxin (LT)-β, granulocyte colony-stimulating factor (G-CSF), macrophage colony-stimulating factor (M-CSF), macrophage migration inhibitory factor (MIF); and DNAs encoding an angiogenesis-inhibiting substance such as endostatin and angiostatin. Besides, DNA encoding a cytosine deaminase, which is an enzyme of converting a prodrug of 5-fluorouracil, i.e., 5-fluoro-cytosine, to 5-fluorouracil, can be preferably mentioned. In addition, DNA encoding an antibody polypeptide can be used. To such DNA encoding a heterologous polypeptide, DNA encoding an affinity tag such as a histidine tag can be appropriately added for the convenience of isolating the polypeptide.

Examples of the antibody include an antibody targeting an interleukin-6 (IL-6) receptor for use in an antirheumatic drug and an antibody targeting α4-integrin for use in a multiple sclerosis therapeutic agent and antibodies targeting CD20, CD33, PD-1, CTLA-4, CD80 or CD86 and having an anti-cancer effect.

Of them, the anti-PD-1 antibody can be preferably mentioned as an example, since the anti-PD-1 antibody binds to a PD-1 receptor expressed on an activated lymphocyte (T cell, B cell) to inhibit binding of PD-L1 or PD-L2 expressed by a cancer cell to the PD-1 receptor, with the result that an immune reaction with a tumor cell is augmented. Also, the anti-CTLA-4 antibody can be preferably mentioned as an example, since the anti-CTLA-4 antibody suppresses the function of CTLA-4, known as a molecule suppressing an autoimmune function to augment an anti-tumor immune response and inhibit the binding of CTLA-4 to CD80 and CD86 expressed on an antigen-presenting cell, with the result that negative downregulation of immune response induced by interaction of these molecules is conceivably inhibited.

Examples of the DNA encoding the antibody polypeptide include DNA encoding a chimera antibody, a humanized antibody, Fab, Fab', F (ab')$_2$ and a scFv antibody; however, DNA encoding a scFv antibody is preferable, since it can recognize and bind to a target substance by itself; it is not excessively large in view of molecular weight and it can be expressed even if it is introduced into a bacterium of the genus *Bifidobacterium* cell. DNA encoding a heterologous polypeptide including these antibodies can be prepared by a method known in the art such as chemical synthesis and genetic engineering procedure based on its sequence information appropriately obtained from documents publicly known and database such as GenBank.

The terminator DNA is not particularly limited as long as it is terminator DNA functioning in a bacterium of the genus *Bifidobacterium*. Specific examples thereof include Hu terminator and T572 terminator derived from *Bifidobacterium longum* (J Microbiol Biotechnol. 2012 December; 22 (12): 1714-23).

A method for preparing an expression cassette of the present invention, preferably an expression cassette comprising DNA encoding a linker peptide sequentially comprises (1) a promoter DNA functioning in a bacterium of the genus *Bifidobacterium*;

(2) a DNA encoding a secretory signal peptide consisting of an amino acid sequence represented by the following a) or b);

a) an amino acid sequence represented by any of SEQ ID Nos: 6, 7, 8, 9, 10, 11, 12, 13, 14, 15 and 16;

b) an amino acid sequence obtained by deletion, replacement or addition of one or several of amino acids in the amino acid sequence represented by any of SEQ ID Nos: 6, 7, 8, 9, 10, 11, 12, 13, 14, 15 and 16 and constituting a peptide functioning as a signal peptide in the bacterium of the genus *Bifidobacterium*;

(3) a DNA encoding a linker peptide;

(4) a DNA encoding a heterologous polypeptide; and (5) a terminator DNA functioning in the bacterium of the genus *Bifidobacterium*;

in this order from upstream to downstream.

The expression cassette of the present invention can be prepared in accordance with a method described in a commercially available experimental certificate, for example, Gene Manual (Kodansha Ltd.), Gene Manipulation Experimental Technique edited by Yasutaka Takagi, (Kodansha Ltd.), Molecular Cloning [Cold Spring Harbor Laboratory (1982)], Molecular Cloning, second edition [Cold Spring Harbor Laboratory (1989)], Methods in Enzymology 194 (1991) and Gene Experimental Technique by Yeast, Experimental Medicine, Supplementary Volume, Yodosha (1994).

The vector of the present invention is not particularly limited, as long as it is a vector which allows to express a heterologous polypeptide when the expression cassette of the present invention is inserted in the vector and a bacterium of the genus *Bifidobacterium* is transformed with the vector. One or more expression cassette of the present invention can be inserted into the vector. A plasmid replication unit functioning in a bacterium of the genus *Bifidobacterium* is included in the vector of the present invention. Examples thereof include replication units such as pTB6 (Biosci Biotechnol Biochem. 2005 February; 69(2): 422-5); pMB1 (Lett Appl Microbiol. 1990 October; 11(4): 220-3); pTB4 (Structural Analysis and Application of *Bifidobacterium longum*-derived Plasmid pTB4, General Lecture, Poster Display program-Molecular Biology Society of Japan, 1994); pFI2576 (J Microbiol Biotechnol. 2009 April; 19(4): 403-8); pCIBAO (Appl Environ Microbiol. 2007 December; 73(24): 7858-66); pBC1 (Plasmid. 2007 March; 57(2): 165-74); pDOJH10S (Appl Environ Microbiol. 2006 January; 72(1): 527-35); and PKJ50 (Microbiology 1999 March; 145(Pt): 585-92). A pTB6 replication unit consisting of a pTB6 derived OriV region and RepB gene can be preferably mentioned. A marker gene such as an antibiotic resistant gene can be added to the above vector.

Examples of the marker gene include spectinomycin, chloramphenicol, erythromycin and ampicillin.

As a method for introducing the vector of the present invention into a bacterium of the genus *Bifidobacterium*, electroporation can be mentioned.

Examples of a bacterium of the genus *Bifidobacterium* according to the present invention include *Bifidobacterium longum*, *Bifidobacterium breve* (*B. breve*), *Bifidobacterium adolescentis* (*B. adolescentis*), *Bifidobacterium bifidum* (*B. bifidum*), *Bifidobacterium pseudolongum* (*B. pseudolongum*), *Bifidobacterium thermophirum* (*B. thermophirum*), *Bifidobacterium infantis* (*B. infantis*), *Bifidobacterium animalis* (*B. animalis*), *Bifidobacterium angulatum* (*B. angulatum*), *Bifidobacterium asteroides* (*B. asteroides*), *Bifidobacterium boum* (*B. boum*), *Bifidobacterium catenulatum* (*B. catenulatum*), *Bifidobacterium choerinum* (*B. choerinum*), *Bifidobacterium coryneforme* (*B. coryneforme*), *Bifidobacterium cuniculi* (*B. cuniculi*), *Bifidobacterium denticolens* (*B. denticolens*), *Bifidobacterium dentium* (*B. dentium*), *Bifidobacterium gallicum* (*B. gallicum*), *Bifidobacterium gallinarum* (*B. gallinarum*), *Bifidobacterium globosum* (*B. globosum*), *Bifidobacterium indicum* (*B. indicum*), *Bifidobacterium inopinatum* (*B. inopinatum*), *Bifidobacterium lactis* (*B. lactis*), *Bifidobacterium lactentis* (*B. lactentis*), *Bifidobacterium magnum* (*B. magnum*), *Bifidobacterium merycicum* (*B. merycicum*), *Bifidobacterium minimum* (*B. minimum*), *Bifidobacterium Mongolia Enns* (*B. Mongolia Enns*), *Bifidobacterium parvulorum* (*B. parvulorum*), *Bifidobacterium pseudocatenulatum* (*B. pseudocatenulatum*), *Bifidobacterium psychraerophilum* (*B. psychraerophilum*), *Bifidobacterium pullorum* (*B. pullorum*), *Bifidobacterium ruminale* (*B. ruminale*), *Bifidobacterium ruminantium* (*B. ruminantium*), *Bifidobacterium saeculare* (*B. saeculare*), *Bifidobacterium scardovii* (*B. scardovii*), *Bifidobacterium subtile* (*B. subtile*), *Bifidobacterium suis* (*B. suis*) and *Bifidobacterium thermacidophilum* (*B. thermacidophilum*). Of them, *Bifidobacterium longum*, *Bifidobacterium breve*, *Bifidobacterium adolescentis*, *Bifidobacterium*

*bifidum* and *Bifidobacterium infantis* are preferably used as a host cell since they are known to be endemic bacteria in the intestines of humans regardless of age, and *Bifidobacterium longum* is more preferably used. These bacteria are all commercially available or can be easily obtained from depositories.

The strain of each bacterium is not particularly limited. Examples of the strain of *Bifidobacterium longum* include *Bifidobacterium longum* 105-A strain, *Bifidobacterium longum* aE-194b strain, *Bifidobacterium longum* bs-601 strain, *Bifidobacterium longum* M101-2 strain and *Bifidobacterium longum* ATCC-15707 strain. Of them, *Bifidobacterium longum* 105-A strain is preferable. Examples of the strain of *B. breve* include *B. breve* standard strain (JCM1192), *B. breve* aS-1 strain and *B. breve* I-53-8W strain. Of them, *B. breve* standard strain and *B. breve* aS-1 strain are preferable. Examples of the strain of *B. infantis* include *B. infantis* standard strain (JCM1222) and *B. infantis* I-10-5 strain. Examples of the strain of *B. lactentis* include *B. lactentis* standard strain (JCM1210). Examples of the strain of *Bifidobacterium bifidum* include *Bifidobacterium bifidum* ATCC-11863 strain.

The vectors, transformed bacterium of the genus *Bifidobacterium*, etc. of the present invention can be prepared in accordance with a method described in a commercially available experimental certificate, for example, Gene Manual (Kodansha Ltd.), Gene Manipulation Experimental Technique edited by Yasutaka Takagi (Kodansha Ltd.), Molecular Cloning [Cold Spring Harbor Laboratory (1982)], Molecular Cloning, second edition [Cold Spring Harbor Laboratory (1989)], Methods in Enzymology 194 (1991) and Gene Experimental Technique by Yeast, Experimental Medicine, Supplementary Volume, Yodosha (1994).

A transformed bacterium of the genus *Bifidobacterium* as mentioned above does not proliferate in normal tissues but proliferates only in tumor tissues under an anaerobic environment and can express a polypeptide useful for therapy within tumor tissues. Accordingly, such a transformed bacterium of the genus *Bifidobacterium* brings about a tumor growth suppression effect and a tumor volume suppression effect, preferably a complete regression action (effect) against a tumor under an anaerobic environment, and thus can be used as a pharmaceutical composition effective for treating a solid tumor, particularly as an anti-cancer agent. Accordingly, the pharmaceutical composition of the present invention is not particularly limited as long as it contains a bacterium of the genus *Bifidobacterium* of the present invention as mentioned above capable of secreting a heterologous polypeptide, preferably an antibody having an anti-cancer effect, as active ingredient, and can contain optional ingredients such as a pharmacologically acceptable carrier, an excipient and a diluent, as long as the optional ingredients do not suppress the function and effect of the polypeptide to be secreted.

If the pharmaceutical composition of the present invention is an anti-cancer agent, examples of the applicable cancer include colorectal cancer, head and neck cancer, breast cancer, lung cancer, esophageal cancer, stomach cancer, liver cancer, gallbladder cancer, bile duct cancer, pancreatic cancer, pancreatic islet cell carcinoma, choriocarcinoma, colon cancer, renal cell cancer, adrenal cortical cancer, bladder cancer, testis cancer, prostate cancer, testicular cancer, ovarian cancer, uterine cancer, choriocarcinoma, thyroid cancer, squamous cell cancer, skin cancer, brain tumor, malignant carcinoid tumor, osteosarcoma, soft tissue sarcoma, neuroblastoma, Wilms' tumor, retinoblastoma and melanoma.

As the dosage form of the pharmaceutical composition of the present invention, a liquid preparation or solid preparation is mentioned. The liquid preparation can be produced by purifying the culture of the bacterium of the genus *Bifidobacterium* of the present invention, optionally adding appropriate saline, a replacement fluid or pharmaceutical additive(s), and charging ampoules or vials with the resultant suspension. The solid preparation can be produced by adding a suitable protective agent to a liquid preparation and charging ampoules or vials with the resultant solution, and subjecting them to lyophilization or by adding a suitable protective agent to a liquid preparation, subjecting lyophilization and thereafter charging ampoules or vials with the resultant material. As a method for administering the pharmaceutical composition of the present invention, both oral administration and parenteral administration can be employed; however, parenteral administration is preferable. Examples thereof include intravenous administration and local administration.

The dosage amount of a pharmaceutical composition of the present invention is not particularly limited as long as it is sufficient for the bacterium of the genus *Bifidobacterium* of the present invention to grow at a site of disease and express an effective therapeutic amount of active antibody. The dosage can be appropriately selected depending upon the extent of the disease and the weight, age and gender of a patient; and can be appropriately increased or decreased depending upon the degree of improvement. However, the dosage amount is preferably as low as possible within the range where a requisite therapeutic effect can be obtained, from an economic point of view and in order to avoid a side effect as much as possible.

For example, in the case of intravenous administration, it is required to reduce a risk such as embolus due to bacterial mass. Because of this, it is preferable that an injectable preparation having a lowest possible concentration is injected in a plurality of divided doses or diluted with an appropriate replacement fluid and continuously injected. For example, in the case of an adult, bacterial cells of the bacterium of the genus *Bifidobacterium* of the present invention, $10^4$ to $10^{12}$ cfu of the bacterial cells per body weight (1 kg), is administered once or in a plurality of divided doses per day for one to several days, continuously or at appropriate intervals. More specifically, a preparation containing the bacterial cells of bacterium of the genus *Bifidobacterium* of the present invention in an amount of $10^4$ to $10^{10}$ cfu/mL is administered directly in a dose of 1 to 1000 mL per adult or diluted with an appropriate replacement fluid and administered once or in a plurality of divided portions per day continuously for one to several days.

For example, in the case of local administration directly to a diseased tissue, bacterial cells are required to be colonized in the whole diseased tissue as much as possible and proliferate there. Because of this, a highly concentrated injection is desirably injected to a plurality of sites in the diseased tissue. For example, in the case of an adult, bacterial cells of the bacterium of the genus *Bifidobacterium* of the present invention, $10^4$ to $10^{12}$ cfu of the bacterial cells per body weight (1 kg) is administered once or in a plurality of divided doses per day, if necessary, for one to several days, continuously or at appropriate intervals. More specifically, a preparation containing the bacterial cells of the bacterium of the genus *Bifidobacterium* of the present invention in an amount of $10^4$ to $10^{10}$ cfu/mL is administered directly in a dose of 0.1 to 100 mL per adult in several divided portions per day, if necessary, continuously for one to a plurality of days.

Now the present invention will be more specifically described below by way of Examples; however the technical range of the present invention is not limited by these Examples.

EXAMPLES

Example 1

[Preparation of pHuSP3L22-scFv-PD-1-1, pHuSP7L20-scFv-PD-1-1 and pHuSP23L27-scFv-PD-1-1]

Anti-PD-1-1 scFv antibody secretory plasmids were prepared by using secretory signal peptides known in the art and a novel secretory signal peptide.

The details of the primers used in Examples 1 and 5 to 8 are shown in Table 1 and Table 2 below.

TABLE 1

PCR primers used in insert and vector amplification

| Insert | Forward primer | Reverse primer | PCR product (bp) |
| --- | --- | --- | --- |
| PD-1-1 | Ins_PD-1-1_F1 | Ins_PD-1-1_R1 | 747 |
| PD-1-2 | Ins_PD-1-2_F1 | Ins_PD-1-2_R1 | 759 |
| PD-1-3 | Ins_PD-1-3_F1 | Ins_PD-1-3_R1 | 771 |
| CTLA-4-1 | Ins_CTLA-4-1_F1 | Ins_CTLA-4-1_R1 | 774 |
| CTLA-4-2 | Ins_CTLA-4-1_F1 | Ins_CTLA-4-2_R1 | 756 |

| Vector | Forward primer | Reverse primer | PCR product (bp) |
| --- | --- | --- | --- |
| Vec-SP3L20 | TGA_Hu_Terminator_F | vec-SP3L20-PD-1-1_R1 | 4019 |
| Vec-SP7L20-1 | TGA_Hu_Terminator_F | vec-SP7L20-PD-1-1_R1 | 4019 |
| Vec-SP23L20 | TGA_Hu_Terminator_F | vec-SP23L20-PD-1-1_R1 | 4019 |
| Vec-SP7L20-2 | TGA_Hu_Terminator_F | vec-SP7L20-PD-1-2_R1 | 4019 |
| Vec-SP7L20-3 | TGA_Hu_Terminator_F | vec-SP7L20-PD-1-3_R1 | 4019 |
| SP3L22 | Ins_PD-1-1_F1 (5'-phosphorylated) | SP3L22_R1 (5'-phosphorylated) | 4742 |
| SP23L27 | Ins_PD-1-1_F1 (5'-phosphorylated) | SP23L27_R1 (5'-phosphorylated) | 4757 |

TABLE 2

Primer sequence in insert and vector amplification

| Primer name | Sequence (5→3) |
| --- | --- |
| Ins_PD-1-1_F1 | CAGGTCCAGCTGGTCCAGAGCGGCAGCGAA (SEQ ID No: 36) |
| Ins_PD-1-2_F1 | CAGGTCCAGCTGCAGGAATCGGGCCCGGGC (SEQ ID No: 37) |
| Ins_PD-1-3_F1 | GAAGTGCGTCTGCTGGAATCGGGCGGCGGC (SEQ ID No: 38) |
| Ins_CTLA-4-1_F1 | CAGGTCCAGCTGGTCGAATCGGGCGGCGGC (SEQ ID No: 39) |
| Ins_PD-1-1_R1 | ACGAGCAGAAGGTCAGTGGTGGTGATGATGGTGCTT (SEQ ID No: 40) |
| vec-SP3L20-PD-1-131 | GACCAGCTGGACCTGGGTCAGCTTGCCCGGCTTGTA (SEQ ID NO: 41) |
| vec-SP7L20-PD-1-1_R1 | GACCAGCTGGACCTGCACCGAACTCGCCTTCGGGAA (SEQ ID NO: 42) |
| vec-SP23L20-PD-1-1_R1 | GACCAGCTGGACCTGACGAATCTTCTTCTCCTGCGC (SEQ ID NO: 43) |
| Ins_PD-1-2_R1 | ACGAGCAGAAGGTCAGTGATGATGATGGTGGTGACG (SEQ ID NO: 44) |
| vec-SP7L20-PD-1-2_R1 | CTGCAGCTGGACCTGCACCGAACTCGCCTTCGGGAA (SEQ ID NO: 45) |
| Ins_PD-1-3_R1 | ACGAGCAGAAGGTCAGTGATGATGGTGGTGATGGCC (SEQ ID NO: 46) |
| vec-SP7L20-PD-1-3_R1 | CAGCAGACGCACTTCCACCGAACTCGCCTTCGGGAA (SEQ ID NO: 47) |
| Ins_CTLA-4-1_R1 | ACGAGCAGAAGGTCAGTGATGATGGTGATGATGCTT (SEQ ID NO: 48) |
| Ins_CTLA-4-2_R1 | ACGAGCAGAAGGTCAGTGATGATGATGATGATGCTT (SEQ ID NO: 49) |
| SP3L22_R1 | GGCGATGGTCAGCTTGCCCGGCTTGTACGT (SEQ ID NO: 50) |

TABLE 2-continued

Primer sequence in insert and vector amplification

| Primer name | Sequence (5→3) |
|---|---|
| SP23L27_R1 | GATCGTCTTGAGAATCTTCAGACGAATCTTCTTCTCCTGCGC (SEQ ID NO: 51) |
| TGA_Hu_Terminator_F | TGACCTTCTGCTCGTAGCGATTAC (SEQ ID NO: 52) |

[Expression Cassette for Anti-PD-1 scFv Antibody]

An expression cassette for an anti-PD-1 scFv antibody was, as shown in FIG. 1(a), constituted of Hu promoter DNA (derived from *Bifidobacterium longum*), a DNA encoding a secretory signal peptide, a DNA encoding a linker peptide following the secretory signal peptide, a DNA encoding an anti-PD-1 scFv antibody (containing a heavy chain sequence, a linker ((GGGGS)$_3$), a light chain sequence), a His tag sequence and a Hu terminator (derived from *Bifidobacterium longum*). As the anti-PD-1 scFv antibodies (containing nucleotide sequences containing a heavy chain sequence, a linker ((GGGGS)$_3$) and a light chain sequence) in individual expression cassettes, two anti-human PD-1 scFv antibodies and a single anti-mouse PD-1 scFv antibody were used, with reference to the documents shown in Table 3 below.

TABLE 3

| Antibody | Sequence | Reference document |
|---|---|---|
| scFv-PD-1-1 (Anti-human PD-1 antibody) | SEQ ID No: 1 (738 nucleotides) SEQ ID No: 138 (245 amino acids) Heavy chain sequence(1-354 nucleotides) (GGGGS)$_3$linker (355-399 nucleotides) Light chain sequence (400-717 nucleotides) Histidine tag (718-735 nucleotides) | U.S. Pat. No. 7,332,582B2 |
| scFv-PD-1-2 (Anti-human PD-1 antibody) | SEQ ID No: 2 (750 nucleotides) SEQ ID No: 139 (249 amino acids) Heavy chain sequence(1-360 nucleotides) (GGGGS)$_3$linker (361-405 nucleotides) Light chain sequence (406-729 nucleotides) Histidine tag (730-747 nucleotides) | Japanese Patent No. 4532409 |
| scFv-PD-1-3 (Anti-mouse PD-1 antibody) | SEQ ID No: 3 (762 nucleotides sequence) SEQ ID No: 140 (253 amino acids) Heavy chain sequence(1-366 nucleotides) (GGGGS)$_3$ linker (367-411 nucleotides) Light chain sequence (412-741 nucleotides) Histidine tag (742-759 nucleotides) | Japanese Patent No. 4249013 |

The genes of the anti-PD-1 scFv antibodies, namely scFv-PD-1-1, scFv-PD-1-2 and scFv-PD-1-3, were separately subcloned in a plasmid for *E. coli*, i.e., pUC57 by GenScript Japan Inc. and provided as artificially synthesized plasmids, namely, pUC57-scFv-PD-1-1, pUC57-scFv-PD-1-2 and pUC57-scFv-PD-1-3, respectively.

As the secretory signal peptide sequence, secretory signal peptide-linker conjugates, namely SP3L22, SP7L20 and SP23L27, were used.

As SP3L22 mentioned above, a known sequence represented by SEQ ID No: 8 described in International Publication No. WO2011/093467 was used. As SP23L27, a known sequence represented by SEQ ID No: 25 described in International Publication No. WO2011/093467 was used. As SP7L20, a nucleotide sequence, which was prepared by adding a 66-nucleotide: ATGGCGTTGATGATGAGCGTTAAGACTATTATTTCCACATCAGTGGCGATTATCGCCA CGGGTGCC (starting with ATG) to the upstream of the 5' side of a nucleotide sequence represented by SEQ ID No: 12 described in International Publication No. WO2011/093467 (used as a basic sequence), and represented by SEQ ID No: 81, was used. Such a nucleotide sequence was added because the SP7 was estimated to have a secretory signal peptide sequence at the N terminal of a protein when SP7 was analyzed by a signal sequence estimation program, Signal P 4.1 server (http://www.cbs.dtu.dk/services/SignalP/), which is a program of estimating the presence or absence of a secretory signal. In this case, the linker peptide sequence following SP7 was 20 amino acid residues at the C terminal side of SP7.

How to prepare an anti-PD-1 scFv antibody secretory plasmid is schematically shown in FIG. 2. On the left side in FIG. 2, scFv-gene is PD-1. In preparation of pHuSP7L20-scFv-PD-1-1, x=7 and n=1; in the preparation of pHuSP7L20-scFv-PD-1-2, x=7 and n=2; and in preparation of pHuSP7L20-scFv-PD-1-3, x=7 and n=3. On the right side of FIG. 2, in the preparation of pHuSP3L22-scFv-PD-1-1, x=3 and y=22; and in the preparation of pHuSP23L27-scFv-PD-1-1, x=23 and y=27. A construction method will be more specifically described below.

[Preparation of Plasmid, pHuSP3L22-scFv-PD-1-1]

In preparing a plasmid, pHuSP3L22-scFv-PD-1-1, first, a plasmid, pHuSP3L20-scFv-PD-1-1 was prepared.

[Preparation of Plasmid, pHuSP3L20-scFv-PD-1-1]

(Preparation of Anti-PD-1-1 scFv Antibody Insert)

PCR amplification was performed by using a plasmid, pUC57-scFv-PD-1-1 (500 pg) as a template and a primer set consisting of Ins_PD-1-1_F1 primer and Ins_PD-1-1_R1 primer listed in Table 1 and Table 2. The primer sequences were designed such that an insert fragment and a vector fragment were mutually overlapped at the end of 15 bp. The PCR amplification was performed by setting each primer concentration at 0.2 μM and the reaction volume at 30 μL and using PrimeSTAR HS (Premix) kit (manufactured by Takara Bio Inc.). As an amplification program, a cycle consisting of a reaction at 98° C. for 10 seconds, a reaction at 55° C. for 5 seconds and a reaction at 72° C. for seconds was repeated 30 times. The PCR product obtained by the amplification was subjected to electrophoresis on 2% agarose gel and purified by QIAquick Gel Extraction Kit (manufactured by QIAGEN) to prepare an anti-PD-1 scFv antibody insert.

(Preparation of Vector Fragment)

PCR amplification was performed by using a linearized vector fragment (500 pg) represented by SEQ ID No: 20 as a template and a primer set consisting of TGA_Hu_Terminator_F primer and vec-SP3L20-PD-1-1_R1 primer listed in Table 1 and Table 2 above, setting each primer concentration at 0.2 μM and the reaction volume at 30 μL and using PrimeSTAR HS (Premix) kit. As an amplification program, a cycle consisting of a reaction at 98° C. for 10 seconds, a reaction at 55° C. for 5 seconds and a reaction at 72° C. for 5 minutes was repeated 30 times. The PCR product obtained by the amplification was subjected to electrophoresis on 0.8% agarose gel and purified by QIAquick Gel Extraction Kit (manufactured by QIAGEN) to prepare 5'-Hu terminator-pTB6rep unit-SPCMr-pUCori-Hu promoter-SP3L20-3' vector fragment.

The linearized vector fragment is the nucleotide sequence consisting of the 4th nucleotide to the 3845th nucleotide of the nucleotide sequence represented by SEQ ID No: 20 and constituted of:

Hu terminator: the nucleotide sequence consisting of the 4th nucleotide to the 117th nucleotide of the nucleotide sequence represented by SEQ ID No: 20;

Origin of replication pTB6 rep unit of bacterium of the genus *Bifidobacterium*: the nucleotide sequence consisting of the 124th nucleotide to the 1719th nucleotide of the nucleotide sequence represented by SEQ ID No: 20;

Spectinomycin resistant gene, SPCMr: the nucleotide sequence consisting of the 1726th nucleotide to the 2804th nucleotide of the nucleotide sequence represented by SEQ ID No: 20;

Origin of replication of *E. coli*, pUCori: the nucleotide sequence consisting of the 2811st nucleotide to the 3478th nucleotide of the nucleotide sequence represented by SEQ ID No: 20; and Hu promoter: the nucleotide sequence consisting of the 3485th nucleotide to the 3845th nucleotide of the nucleotide sequence represented by SEQ ID No: 20.

(Infusion Reaction)

The vector fragment and an anti-PD-1-1 scFv antibody insert prepared above were ligated by use of In-Fusion (registered trademark) HD Cloning Kit (manufactured by Takara Bio Inc.). More specifically, in a microtube, the vector and the insert were added at a molar ratio of 1:5 and thereafter 2 μL of 5× In-Fusion HD Enzyme premix was added. The volume of the reaction solution was adjusted to be 10 μL. The reaction solution was kept at 50° C. for 15 minutes. The procedure described in the instruction of the kit except the aforementioned procedure was performed to prepare an infusion reaction solution.

(Transformation of *E. coli* and Sequencing of Plasmid DNA)

Using the infusion reaction solution (5 μL), *E. coli* HST08 competent cell (manufactured by Takara Bio Inc.) was transformed in accordance with the instruction thereof. After transformation, the bacterial suspension was spread onto a 75 pg/mL spectinomycin-containing LB agar medium and subjected to static culture at 37° C. overnight. *E. coli* colonies formed on the agar medium were cultured in a 75 pg/mL spectinomycin-containing LB liquid medium at 30° C. overnight. From the cultured medium, a plasmid was extracted by use of QIAprep Spin Miniprep Kit (manufactured by QIAGEN). An anti-PD-1-1 scFv antibody expression cassette (containing Hu promoter to Hu terminator) of the plasmid extracted was subjected to a sequencing reaction by BigDye (registered trademark) Terminator v3.1 Cycle Sequencing Kit (manufactured by Applied Biosystems) for determining the sequence thereof. The extracted plasmid was designated as pHuSP3L20-scFv-PD-1-1.

[Preparation of pHuSP3L22-scFv-PD-1-1]

(Preparation of Phosphorylated Primer)

Each of Ins_PD-1-1_F1 primer and SP3L22_R1 primer listed in Table 1 and Table 2 was phosphorylated with T4 polynucleotide kinase (manufactured by Takara Bio Inc.) in accordance with the instruction. Ins_PD-1-1_F1 phosphorylated primer and SP3L22_R1 phosphorylated primer each were adjusted so as to have a final concentration of 20 μM with 0.1×TE buffer (1 mM Tris-HCl, 0.1 mM EDTA, pH7.5).

(Preparation of Linearized Fragment of pHuSP3L22-scFv-PD-1-1 Vector)

PCR amplification was performed by using a plasmid, pHuSP3L20-scFv-PD-1-1 (500 pg) obtained above as a template and a primer set consisting of Ins_PD-1-1_F1 phosphorylated primer and SP3L22_R1 phosphorylated primer, setting each primer concentration at 0.2 μM and the reaction volume at 30 μL and using PrimeSTAR HS (Premix) kit. As an amplification program, a cycle consisting of a reaction at 98° C. for 10 seconds, a reaction at 55° C. for 5 seconds and a reaction at 72° C. for 5 minutes was repeated 30 times. The PCR product obtained by amplification was subjected to electrophoresis on 0.8% agarose gel, purified by QIAquick Gel Extraction Kit to prepare a linearized fragment pHuSP3L22-scFv-PD-1-1 vector.

(Ligation Reaction)

The linearized vector fragment obtained above was subjected to a ligation reaction using T4 DNA Ligase (manufactured by Thermo Fisher Scientific Inc.) in accordance with the instruction. The accompanying 10×buffer (2 μL) for T4 DNA ligase was added and the volume of a reaction solution was set to be 20 μL. This was subjected to a ligation reaction at 22° C. for 10 minutes to prepare a ligation reaction solution.

(Transformation of *E. coli* and Sequencing of Plasmid DNA)

Using the ligation reaction solution (10 μL) obtained above, *E. coli* HST08 competent cell was transformed. After transformation, a bacterial suspension was spread onto a 75 μg/mL spectinomycin-containing LB agar medium and subjected to static culture at 37° C. overnight. Transformation was carried out in accordance with the conditions described in the instruction for *E. coli* HST08 competent cell as outlined below. *E. coli* colonies formed on the agar medium were cultured in a 75 μg/mL spectinomycin-containing LB liquid medium at 30° C. overnight. From this, a plasmid was extracted by use of QIAprep Spin Miniprep Kit. The anti-PD-1-1 scFv antibody expression cassette (containing Hu promoter to Hu terminator) of the extracted plasmid was subjected to a sequencing reaction by use of BigDye (registered trademark) Terminator v3.1 Cycle Sequencing Kit for determining the sequence thereof. The extracted plasmid was designated as pHuSP3L22-scFv-PD-1-1.

(Transformation of Bacterium of the Genus *Bifidobacterium*)

Using the plasmid, pHuSP3L22-scFv-PD-1-1 (1000 ng) extracted from *E. coli* transformed above, *Bifidobacterium longum* 105-A strain was transformed by the electroporation system (Gene Pulser II, manufactured by Bio-Rad Laboratories, Inc.). Immediately after application of electric shock (2 kV, 25 μF, 200Ω), a solution mixture of IMR liquid medium (800 μL) and a vitamin C-added solution (50 μL) was poured in a cuvette (2 mm gap) and this was collected to a 2 mL-microtube sterilized. Individual tubes (2 mL) were prepared in the same manner and placed in an airtight container together with a de-oxygen and carbon dioxide gas generating agent (AnaeroPack (registered trademark) Kenki, manufactured by Mitsubishi Gas Chemical Company, Inc.) with the lids opened and kept warm in an incubator set at 37° C. for 3 hours.

Each of the resultant bacterium suspensions kept warm was spread onto a 75 μg/mL spectinomycin-containing IMR agar medium. These plates were placed in an airtight container together with a de-oxygen and carbon dioxide gas generating agent as mentioned above, and cultured in an incubator set at 37° C. for 2 days.

A part of the colonies formed on the spectinomycin-containing IMR agar medium was picked up, streaked on a 75 μg/mL spectinomycin-containing BL-bS agar medium (BL agar medium containing no equine defibrinated blood), placed in an airtight container together with a de-oxygen and carbon dioxide gas generating agent and cultured in an incubator set at 37° C. for one day to obtain *Bifidobacterium longum* 105-A/pHuSP3L22-scFv-PD-1-1 strain.

[Preparation of pHuSP7L20-scFv-PD-1-1]

(Preparation of Anti-PD-1-1 scFv Antibody Insert)

An anti-PD-1-1 scFv antibody insert was prepared in the same procedure as in the above section: [Preparation of plasmid, pHuSP3L20-scFv-PD-1-1], (Preparation of anti-PD-1-1 scFv antibody insert).

(Preparation of Vector Fragment)

PCR amplification was performed by using a linearized vector fragment (500 μg) represented by SEQ ID No: 21 as a template and a primer set consisting of TGA_Hu_Terminator_F primer and vec-SP7L20-PD-1-1_R1 primer described in Table 1 and Table 2 above, setting each primer concentration at 0.2 μM and the reaction volume at 30 μL and using PrimeSTAR HS (Premix) kit. As an amplification program, a cycle consisting of a reaction at 98° C. for 10 seconds, a reaction at 55° C. for 5 seconds and a reaction at 72° C. for 5 minutes was repeated 30 times. The PCR product obtained by the amplification was subjected to electrophoresis on 0.8% agarose gel and purified by QIAquick Gel Extraction Kit to prepare a 5'-Hu terminator-pTB6rep unit-SPCMr-pUCori-Hu promoter-SP7L20-3' vector fragment (1).

The linearized vector fragment is the nucleotide sequence consisting of the 4th nucleotide to the 3845th nucleotide of the nucleotide sequence represented by SEQ ID No: 21 and constituted of:

Hu terminator: the nucleotide sequence consisting of the 4th nucleotide to the 117th nucleotide of the nucleotide sequence represented by SEQ ID No: 21;

Origin of replication pTB6 rep unit of bacterium of the genus *Bifidobacterium*: the nucleotide sequence consisting of the 124th nucleotide to the 1719th nucleotide of the nucleotide sequence represented by SEQ ID No: 21;

Spectinomycin resistant gene, SPCMr: the nucleotide sequence consisting of the 1726th nucleotide to the 2804th nucleotide of the nucleotide sequence represented by SEQ ID No: 21;

Origin of replication of *E. coli*, pUCori: the nucleotide sequence consisting of the 2811st nucleotide to the 3478th nucleotide of the nucleotide sequence represented by SEQ ID No: 21; and Hu promoter: the nucleotide sequence consisting of the 3485th nucleotide to the 3845th nucleotide of the nucleotide sequence represented by SEQ ID No: 21.

(Infusion Reaction)

An infusion reaction solution was prepared in the same procedure as in the infusion reaction in the above section: [Preparation of plasmid, pHuSP3L20-scFv-PD-1-1] except that the vector fragment and the anti-PD-1-1 scFv antibody insert prepared above were used.

(Transformation of *E. coli* and Sequencing of Plasmid DNA)

*E. coli* HST08 competent cell was transformed and the anti-PD-1-1 scFv antibody expression cassette (containing Hu promoter to Hu terminator) of the extracted plasmid was subjected to a sequencing reaction in the same procedure as in the above section: [Preparation of plasmid, pHuSP3L20-scFv-PD-1-1], (Transformation of *E. coli* and sequencing of plasmid DNA) except that the infusion reaction solution (5 μL) prepared above was used. The extracted plasmid was designated as pHuSP7L20-scFv-PD-1-1.

(Transformation of Bacterium of the Genus *Bifidobacterium*)

*Bifidobacterium longum* 105-A strain was transformed in the same procedure in the above section: [Preparation of pHuSP3L22-scFv-PD-1-1], (Transformation of bacterium of the genus *Bifidobacterium*) except that DNA of a plasmid, pHuSP7L20-scFv-PD-1-1 (1000 ng) extracted from *E. coli* transformed above was used to obtain *Bifidobacterium longum* 105-A/pHuSP7L20-scFv-PD-1-1 strain.

[Preparation pHuSP23L27-scFv-PD-1-1]

For preparing a plasmid, pHuSP23L27-scFv-PD-1-1, first, a plasmid, pHuSP23L20-scFv-PD-1-1 was prepared.

[Preparation of Plasmid, pHuSP23L20-scFv-PD-1-1]

(Preparation of Anti-PD-1-1 scFv Antibody Insert)

An anti-PD-1-1 scFv antibody insert was prepared in the same procedure as in the above section: [Preparation of plasmid, pHuSP3L20-scFv-PD-1-1], (Preparation of an anti-PD-1-1 scFv antibody insert).

(Preparation of Vector Fragment)

PCR amplification was performed by using the linearized vector fragment (500 μg) represented by SEQ ID No: 22 as a template and a primer set consisting of TGA_Hu_Terminator_F primer and vec-SP23L20-PD-1-1_R1 primer listed in Table 1 and Table 2 above, setting each primer concentration at 0.2 μM and the reaction volume at 30 μL and using PrimeSTAR HS (Premix) kit. As an amplification program, a cycle consisting of a reaction at 98° C. for 10 seconds, a reaction at 55° C. for 5 seconds and a reaction at 72° C. for 5 minutes was repeated 30 times. The PCR product obtained by the amplification was subjected to electrophoresis on 0.8% agarose gel and purified by QIAquick Gel Extraction Kit to prepare a 5'-Hu terminator-pTB6rep unit-SPCMr-pUCori-Hu promoter-SP23L20-3' vector fragment.

The linearized vector fragment is the nucleotide sequence consisting of the 4th nucleotide to the 3845th nucleotide of the nucleotide sequence represented by SEQ ID No: 22 and constituted of:

Hu terminator: the nucleotide sequence consisting of the 4th nucleotide to the 117th nucleotide of the nucleotide sequence represented by SEQ ID No: 22;

Origin of replication pTB6 rep unit of bacterium of the genus *Bifidobacterium*: the nucleotide sequence from the 124th nucleotide to the 1719th nucleotide of the nucleotide sequence represented by SEQ ID No: 22;

Spectinomycin resistant gene, SPCMr: the nucleotide sequence consisting of the 1726th nucleotide to the 2804th nucleotide of the nucleotide sequence represented by SEQ ID No: 22;

Origin of replication of *E. coli*, pUCori: the nucleotide sequence consisting of the 2811st nucleotide to the 3478th nucleotide of the nucleotide sequence represented by SEQ ID No: 22; and Hu promoter: the nucleotide sequence consisting of the 3485th nucleotide to the 3845th nucleotide of the nucleotide sequence represented by SEQ ID No: 22.

(Infusion Reaction)

An infusion reaction solution was prepared in the same procedure as in the infusion reaction in the above section: [Preparation of plasmid, pHuSP3L20-scFv-PD-1-1] except that the vector fragment and the anti-PD-1-1 scFv antibody insert prepared above were used.

(Transformation of *E. coli* and Sequencing of Plasmid DNA)

*E. coli* HST08 competent cell was transformed and the anti-PD-1-1 scFv antibody expression cassette (containing Hu promoter to Hu terminator) of the extracted plasmid was subjected to a sequencing reaction (for determining the sequence) in the same procedure as in the above section: [Preparation of plasmid, pHuSP3L20-scFv-PD-1-1], (Transformation of E. coli and sequencing of plasmid DNA) except that the infusion reaction solution (5 μL) prepared above was used. The extracted plasmid was designated as pHuSP23L20-scFv-PD-1-1.

[Preparation of Plasmid, pHuSP23L27-scFv-PD-1-1]

(Preparation of Phosphorylated Primer)

Each of Ins_PD-1-1_F1 primer and SP23L27_R1 primer listed in Table 1 and Table 2 was phosphorylated by using T4 polynucleotide kinase in accordance with the instruction. Ins_PD-1-1_F1 phosphorylated primer and SP23L27_R1 phosphorylated primer each were adjusted so as to have a final concentration of 20 μM, with 0.1×TE buffer (1 mM Tris-HCl, 0.1 mM EDTA, pH7.5).

(Preparation of Linearized Fragment of pHuSP23L27-scFv-PD-1-1 Vector)

PCR amplification was performed by using a plasmid, pHuSP23L20-scFv-PD-1-1 (500 μg) obtained above as a template, a primer set consisting of Ins_PD-1-1_F1 phosphorylated primer and SP23L27_R1 phosphorylated primer, setting a final concentration at 0.2 μM and the reaction volume at 30 μL, and using PrimeSTAR HS (Premix) kit. As an amplification program, a cycle consisting of a reaction at 98° C. for 10 seconds, a reaction at 55° C. for 5 seconds and a reaction at 72° C. for 5 minutes was repeated 30 times. The PCR product obtained by the amplification was subjected to electrophoresis on 0.8% agarose gel and purified by QIAquick Gel Extraction Kit to prepare a linearized fragment of pHuSP23L27-scFv-PD-1-1 vector.

(Ligation Reaction)

The vector fragment obtained above was subjected to a ligation reaction to prepare a ligation reaction solution in the same procedure as in the above section: [Preparation of plasmid, pHuSP3L22-scFv-PD-1-1], (Ligation reaction).

(Transformation of E. coli and Sequencing of Plasmid DNA)

E. coli HST08 competent cell was transformed by using the above ligation reaction solution (10 μL) and subjected to a sequencing reaction in the same manner as in the above section: [Preparation of plasmid, pHuSP3L22-scFv-PD-1-1], (Transformation of E. coli and sequencing of plasmid DNA). The extracted plasmid was designated as pHuSP23L27-scFv-PD-1-1.

(Transformation of Bacterium of the Genus Bifidobacterium)

Using 1000 ng of DNA of plasmid, pHuSP23L27-scFv-PD-1-1 extracted from E. coli transformed above, Bifidobacterium longum 105-A strain was transformed in the same procedure as in the above section: [Preparation of plasmid, pHuSP3L22-scFv-PD-1-1], (Transformation of bacterium of the genus Bifidobacterium) to obtain Bifidobacterium longum 105-A/pHuSP23L27-scFv-PD-1-1 strain.

Example 2

(First Investigation of the Presence or Absence of Secretion of scFv Antibody in Recombinant Bacterium of the Genus Bifidobacterium)

Whether three types of recombinant bacterium of the genus Bifidobacterium (Bifidobacterium longum 105-A/pHuSP3L22-scFv-PD-1-1 strain, Bifidobacterium longum 105-A/pHuSP7L20-scFv-PD-1-1 strain, Bifidobacterium longum 105-A/pHuSP23L27-scFv-PD-1-1 strain) transformed respectively with three types of anti-PD-1-1 scFv antibody secretory plasmids prepared in Example 1 secret anti-PD-1-scFv antibody was checked by Western Analysis, as follows.

A streak culture of each of the recombinant bacterium of the genus Bifidobacterium strains on a 75 μg/mL spectinomycin-containing BL-bS agar medium was inoculated in MRS (manufactured by Becton, Dickinson and Company) liquid medium (10 mL) supplemented with spectinomycin (a final concentration of 75 μg/mL), 100 μL of a vitamin C-added solution (a solution (100 mL) containing ascorbic acid (35 g), L-cysteine hydrochloride monohydrate (2 g) and sodium carbonate (11 g)), and anaerobically cultured at 37° C. for 24 hours to obtain an activated culture solution. Subsequently, to a medium (20 mL) containing DMEM (Cat No. 11885-084: manufactured by Life Technologies) and MRS in a ratio of 9:1, a vitamin C-added solution (100 μL) and spectinomycin (75 μg/mL) were added. The activated culture solution (100 μL) was inoculated to the medium. This medium was anaerobically cultured at 37° C. for 18 hours.

After completion of the anaerobic culture, the activated culture solution was centrifuged and the culture supernatant was collected. Protein in the culture supernatant was allowed to precipitate with trichloroacetic acid (TCA, manufactured by Wako Pure Chemical Industries Ltd.), washed with acetone, dissolved in SDS-PAGE buffer and subjected to a heat treatment at 95° C. for 3 minutes to obtain a culture supernatant concentrate. Bifidobacterium longum 105-A/pBEshuttle strain was subjected to the same operation and used as a negative control.

The culture supernatant concentrate (corresponding to 1 mL of culture solution) was subjected to electrophoresis by Mini-PROTEAN (registered trademark) TGX™ gel (4 to 20%) (manufactured by Bio-Rad). The gel was transferred onto a PVDF membrane (iBlot Transfer Stacks, manufactured by Life Technologies) by use of an iBlot transfer device (manufactured by Life Technologies). After completion of blotting, the membrane was subjected to blocking (2% ECL Prime Blocking agent (manufactured by GE Healthcare Japan) in TTBS), and then to a reaction with a mouse histidine tag antibody (THE HIS Tag Antibody, mAb, Mouse, manufactured by GenScript Japan Inc.) used as a primary antibody and an ECL-peroxidase-labeled anti-mouse antibody (manufactured by GE Healthcare Japan) used as a secondary antibody, and allowed to emit light by use of Western Lightning Ultra (manufactured by PerkinElmer Co., Ltd.). The light-emission was analyzed by an imaging analyzer (Fluor SMax, manufactured by Bio-Rad). The results are shown in FIG. 4. Lane M shows a marker; lane 1 shows a negative control; lane 2 shows an antibody secreted from a bacterium of the genus Bifidobacterium transformed with pHuSP3L22-scFv-PD-1-1 in lane 2; lane 3 shows an antibody secreted from a bacterium of the genus Bifidobacterium transformed with pHuSP7L20-scFv-PD-1-1; and lane 4 shows an antibody secreted from a bacterium of the genus Bifidobacterium transformed with pHuSP23L27-scFv-PD-1-1.

(Results)

As is apparent from FIG. 4, in the bacterium of the genus Bifidobacterium transformed with pHuSP7L20-scFv-PD-1-1, (which has an insert of a novel secretory signal peptide-linker conjugate, SP7L20, consisting of a secretory signal peptide sequence SP7 and a subsequent sequence of 20 amino acids), secretion of an anti-PD-1-1 scFv antibody was observed. In contrast, in the bacterium of the genus Bifido-

*bacterium* transformed with pHuSP3L22-scFv-PD-1-1 or pHuSP23L27-scFv-PD-1-1, no secretion of the anti-PD-1-1 scFv antibody was observed.

Example 3

[Investigation on 33 Types of Secretory Signal Peptide-Linker Conjugate]

In the above pHuSP7L20-scFv-PD-1-1, secretory signal peptide-linker conjugate SP7L20 was replaced with each of types of secretory signal peptide-linker conjugates (SP42L20 to SP46L20, SP48L20 to SP75L20). In this manner, 33 types of anti-PD-1-1 scFv antibody secretory plasmids were constructed. How to construct the plasmid is schematically shown in FIG. 3. The primers used herein are more specifically shown in Table 4 and Table 5 below.

TABLE 4

| Insert | Forward primer | Reverse primer | PCR product (bp) |
|---|---|---|---|
| SP42L20 | SP42-ins_F1 | SP42-ins_R1 | 177 |
| SP45L20 | SP45-ins_F1 | SP45-ins_R1 | 192 |
| SP48L20 | SP48-ins_F1 | SP48-ins_R1 | 168 |
| SP50L20 | SP50-ins_F1 | SP50-ins_R1 | 258 |
| SP52L20 | SP52-ins_F1 | SP52-ins_R1 | 195 |
| SP55L20 | SP55-ins_F1 | SP55-ins_R1 | 234 |
| SP58L20 | SP58-ins_F1 | SP58-ins_R1 | 186 |
| SP62L20 | SP62-ins_F1 | SP62-ins_R1 | 222 |
| SP64L20 | SP64-ins_F1 | SP64-ins_R1 | 183 |
| SP66L20 | SP66-ins_F1 | SP66-ins_R1 | 168 |
| SP67L20 | SP67-ins_F1 | SP67-ins_R1 | 189 |
| SP68L20 | SP68-ins_F1 | SP68-ins_R1 | 219 |
| SP69L20 | SP69-ins_F1 | SP69-ins_R1 | 180 |

TABLE 5

| Primer Name | Sequence (5→3) |
|---|---|
| PD-1-scFv_vec_F1 | CAGGTCCAGCTGGTCCAGAG (SEQ ID NO: 53) |
| Hu_Vec_R1 | AAAGCATCCTTCTTGGGTCAGG (SEQ ID NO: 54) |
| SP42-ins_F1 | caagaaggatgctttGTGCCCGTGACTACGCG (SEQ ID NO: 55) |
| SP42-ins_R1 | gaccagctggacctgTGCCAGCAAGGTGCAGAG (SEQ ID NO: 56) |
| SP45-ins_F1 | caagaaggatgctttATGAAGCACCTCTCCCACCG (SEQ ID NO: 57) |
| SP45-ins_R1 | gaccagctggacctgATCGCCGTCGCTTCCCT (SEQ ID NO: 58) |
| SP48-ins_F1 | caagaaggatgctttGTGCTGATTCTCATCGTTCTCG (SEQ ID NO: 59) |
| SP48-ins_R1 | gaccagctggacctgGAGCGCGTTCAAAGTGTCG (SEQ ID NO: 60) |
| SP50-ins_F1 | caagaaggatgctttATGATCGTGGCCTACCCG (SEQ ID NO: 61) |
| SP50-ins_R1 | gaccagctggacctgTTCCATATCGTTGTATGGAAACGC (SEQ ID NO: 62) |
| SP52-ins_F1 | caagaaggatgctttATGAGTTTCCATGTATCCGCG (SEQ ID NO: 63) |
| SP52-ins_R1 | gaccagctggacctgCAGTTCGTTATACGCGTGACCG (SEQ ID NO: 64) |
| SP55-ins_F1 | caagaaggatgctttATGGTTGGTCGCGCCCA (SEQ ID NO: 65) |
| SP55-ins_R1 | gaccagctggacctgCCAGGTGGCGTAGTCAACG (SEQ ID NO: 66) |
| SP58-ins_F1 | caagaaggatgctttATGGCAATGGCACGGC (SEQ ID NO: 67) |
| SP58-ins_R1 | gaccagctggacctgGGTGGTTTGCCCGTTGATG (SEQ ID NO: 68) |
| SP62-ins_F1 | caagaaggatgctttATGACTCGTTCGGACGACGT (SEQ ID NO: 69) |
| SP62-ins_R1 | gaccagctggacctgCATGTTGAACATCGAACGTTTGG (SEQ ID NO: 70) |
| SP64-ins_F1 | caagaaggatgctttATGAAGTCACTAATCAGGAATGTAGCG (SEQ ID NO: 71) |
| SP64-ins_R1 | gaccagctggacctgCTTCTTGCCGTTGAACGCG (SEQ ID NO: 72) |
| SP66-ins_F1 | caagaaggatgctttGTGAAGCATTGGAAGAAGATGGC (SEQ ID NO: 73) |
| SP66-ins_R1 | gaccagctggacctgCTTAGTAGTCTGCACTGTCGCGG (SEQ ID NO: 74) |
| SP67-ins_F1 | caagaaggatgctttATGAAGATAAACAATAAGGGCAAGG (SEQ ID NO: 75) |
| SP67-ins_R1 | gaccagctggacctgGGCCTGGAACTTGGTGTATGTC (SEQ ID NO: 76) |
| SP68-ins_F1 | caagaaggatgattATGGTTTATAACATTCACATATTGCAAAC (SEQ ID NO: 77) |
| SP68-ins_R1 | gaccagctggacctgCTTCCAACCATTAAGATCGTCTTCG (SEQ ID NO: 78) |
| SP69-ins_F1 | caagaaggatgattATGAATTATTTACGACAAAAAATTTCGG (SEQ ID NO: 79) |
| SP69-ins_R1 | gaccagctggacctgACCGCTATCAGTCGTGGTGTAAC (SEQ ID NO: 80) |

[Selection of Secretory Signal Peptide Sequence and Subsequent Linker Peptide Sequence]

The whole amino acid sequence of a protein derived from *Bifidobacterium longum* NCC2705 strain registered on the NCBI genomic database (http://www.ncbi.nlm.nih.gov/genome/) was analyzed by signal sequence estimation program Signal P 4.1 server (http://www.cbs.dtu.dk/services/SignalP/) for use in estimating the presence or absence of a secretory signal. As a result of the analysis, proteins estimated to have a secretory signal peptide sequence at the N terminal were selected and a part of the amino acid sequences of the proteins was subjected to a topology analysis using program TMHMM Server v. 2.0 (http://www.cbs.dtu.dk/services/TMHMM-2.0/) estimating a transmembrane region (TM). As a result of the topology analysis, 33 types of proteins were selected as the proteins estimated to have TM at the N terminal. These 33 types of proteins were selected as secretory signal peptides derived from *Bifidobacterium longum* NCC2705 strain and estimated to have TM. In the amino acid sequences of *Bifidobacterium longum* 105A strain corresponding to the amino acid sequences of the 33 types of peptides selected, the sequence from the N terminal of each of the amino acid sequences (of the proteins) up to the amino acid which is estimated as a protease cleavage putative site by Signal P analysis was determined as a secretory signal peptide sequence. Furthermore, 20 amino acid residues following from the C terminal of each of the signal sequences was specified as the linker peptide sequence.

[Preparation of Plasmid, pHuSPxL20-scFv-PD-1-1]

(Preparation of SPxL20 Insert)

PCR amplification was performed by using *Bifidobacterium longum* 105-A strain (120 μg) as a template and each of the primer sets listed in Table 4 and Table 5. Individual primer sequences were designed such that an insert fragment and a vector fragment were overlapped at the end of 15 bp. The PCR amplification was performed by setting a primer concentration at 0.2 μM and the reaction volume at 20 μL and using PrimeSTAR HS (Premix) kit. As an amplification program, a cycle consisting of a reaction at 98° C. for 10 seconds, a reaction at 65° C. for 5 seconds and a reaction at 72° C. for 20 seconds was repeated 30 times, followed by an elongation reaction at 72° C. for 30 seconds. In this manner, inserts consisting of 33 types of secretory signal peptide-linker conjugates were obtained by amplification.

(Preparation of Vector)

PCR amplification was performed by using pHuSP7L20-scFv-PD-1-1 (2.5 ng) mentioned above as a template, and a primer set consisting of PD-1-scFv_vec_F1 primer and Hu_Vec_R1 primer listed in Table 4 and Table 5 above, setting a final concentration at 0.2 μM and the reaction volume at 50 μL, and using PrimeSTAR HS (Premix) kit. As an amplification program, a cycle consisting of a reaction at 98° C. for 10 seconds, a reaction at 65° C. for 5 seconds and a reaction at 72° C. for 4 minutes and 45 seconds was repeated 30 times followed by an elongation reaction at 72° C. for 30 seconds. In this manner, a vector fragment, 5'-scFv-PD-1-1-Hu terminator-pTB6rep unit-SPCMr-pUCori-Hu promoter-3', was prepared.

(Infusion Reaction)

The vector fragment prepared in the above and each of 33 types secretory signal peptide-linker conjugate inserts were ligated by use of In-Fusion (registered trademark) HD Cloning Kit. More specifically, in a microtube, the vector and an insert were added at a molar ratio of 1:2, and 5× In-Fusion HD Enzyme premix (2 μL) provided in the kit was added. The volume of the mixture was adjusted with 0.1×TE buffer (1 mM Tris-HCl, 0.1 mM EDTA, pH7.5) so as to be 10 μL. This solution was kept warm at 37° C. for 15 minutes and further kept warm at 50° C. for 15 minutes. The procedure as described in the instruction of the kit except the aforementioned procedure was performed to prepare 33 types of infusion reaction solutions.

(Transformation of *E. coli* and Sequencing of Plasmid DNA)

Using 33 types of infusion reaction solutions (0.8 μL) mentioned above, *E. coli* HST16CR competent cells (manufactured by Takara Bio Inc.) were separately transformed. After transformation, each of the bacterial suspensions was spread onto a 75 μg/mL spectinomycin-containing LB agar medium and subjected to static culture at 37° C. overnight. The transformation was performed in accordance with the conditions described in the instruction of *E. coli* HST16CR competent cell as outlined below. *E. coli* colonies formed on the agar medium were cultured in a 75 μg/mL spectinomycin-containing LB liquid medium at 37° C. overnight. From the culture medium, a plasmid was extracted by use of QIAprep Spin Miniprep Kit. The anti-PD-1-1 scFv antibody expression cassette (containing Hu promoter to Hu terminator) of the extracted plasmid was subjected to a sequencing reaction by BigDye (registered trademark) Terminator v3.1 Cycle Sequencing Kit for determining the sequence thereof. The extracted plasmid was designated as pHuSPxL20-scFv-PD-1-1 (where x=42 to 46, 48 to 75).

(Transformation of Bacterium of the Genus *Bifidobacterium*)

Using DNA (500 ng) of each of the plasmids represented by pHuSPxL20-scFv-PD-1-1 (where x=42 to 46, 48 to 75) extracted from the *E. coli* transformed above, *Bifidobacterium longum* 105-A strain was transformed in the same manner as in the above section: [Preparation of plasmid, pHuSP3L22-scFv-PD-1-1], (Transformation of bacterium of the genus *Bifidobacterium*) to obtain *Bifidobacterium longum* 105-A/pHuSPxL20-scFv-PD-1-1 (where x=42 to 46, 48 to 75) strain.

Example 4

(Second Investigation of the Presence or Absence of Secretion of scFv Antibody in Recombinant Bacterium of the Genus *Bifidobacterium*)

Whether each of the recombinant *Bifidobacterium* bacterial strains obtained in Example 3, and represented by *Bifidobacterium longum* 105-A/pHuSPxL20-scFv-PD-1-1 (where x=42 to 46, 48 to 75) secrets anti-PD-1-1 scFv antibody was checked by Western Analysis in the same manner as in the above (First investigation of the presence or absence of secretion of scFv antibody in recombinant bacterium of the genus *Bifidobacterium*). The results are shown in FIG. 5.

As is apparent from FIG. 5, secretion was observed in *Bifidobacterium longum* 105-A strains transformed with anti-PD-1-1 scFv antibody secretory plasmids in which 11 types of secretory signal peptide-linker conjugates (SP7L20, SP45L20, SP50L20, SP52L20, SP55L20, SP58L20, SP64L20, SP66L20, SP67L20, SP68L20, SP69L20) were respectively inserted. In contrast, secretion of an anti-PD-1-1 scFv antibody was not observed in bacterium of the genus *Bifidobacterium* transformed with plasmids in which secretory signal peptide-linker conjugates (SP42L20, SP48L20, SP62L20, (which respectively consist of secretory signal peptide sequences (SP42, SP48, SP62) and subsequent linker peptide sequences of 20 amino acid residues) were inserted.

29

From the above investigation, it was found that the bacteria of the genus *Bifidobacterium* that can secrete an scFv antibody were only those transformed by using the expression cassettes containing SP45L20, SP50L20, SP52L20, SP55L20, SP58L20, SP64L20, SP66L20, SP67L20, SP68L20 and SP69L20, and that secretion was not observed or insufficient in the other cases (23 types of sequences). Examples of secretory signal peptide-linker conjugates as to which secretion was not observed or insufficient are SP42L20, SP48L20 and SP62L20 and the sequences of them are represented by SEQ ID Nos: 17, 18 and 19.

Example 5

[Preparation of pHuSP7L20-scFv-PD-1-2]

Using the anti-PD-1-2 scFv antibody as a heterologous peptide, an anti-PD-1-2 scFv antibody secretory plasmid, pHuSP7L20-scFv-PD-1-2 having a secretory signal peptide-linker conjugate, SP7L20, was constructed. The details of the construction are as follows.

(Preparation of Anti-PD-1-2 scFv Antibody Insert)

PCR amplification was performed by using the artificial plasmid, pUC57-scFv-PD-1-2 (500 µg) synthesized above as a template and a primer set consisting of Ins_PD-1-2_F1 primer and Ins_PD-1-2_R1 primer listed in Table 1 and Table 2 above. The primer sequences were designed such that an insert fragment and a vector fragment were mutually overlapped at the end of 15 bp. The PCR reaction solution used herein was prepared so as to contain a primer in a concentration of 0.2 µM in a reaction volume of 30 µL by using PrimeSTAR HS (Premix) kit. As an amplification program, a cycle consisting of a reaction at 98° C. for 10 seconds, a reaction at 55° C. for 5 seconds and a reaction at 72° C. for 60 seconds was repeated 30 times. The PCR product obtained by the amplification was subjected to electrophoresis on 2% agarose gel and purified by QIAquick Gel Extraction Kit to prepare an anti-PD-1-2 scFv antibody insert.

(Preparation of Vector Fragment)

PCR amplification was performed by using a linearized vector fragment (500 µg) represented by SEQ ID No: 23 as a template and a primer set consisting of TGA_Hu_Terminator_F primer and vec-SP7L20-PD-1-2_R1 primer listed in Table 1 and Table 2 above, setting a final concentration at 0.2 µM and the reaction volume at 30 µL and using PrimeSTAR HS (Premix) kit. As an amplification program, a cycle consisting of a reaction at 98° C. for 10 seconds, a reaction at 55° C. for 5 seconds and a reaction at 72° C. for 5 minutes was repeated 30 times. The PCR product obtained by the amplification was subjected to electrophoresis on 0.8% agarose gel and purified by QIAquick Gel Extraction Kit to prepare a 5'-Hu terminator-pTB6rep unit-SPCMr-pUCori-Hu promoter-SP7L20-3' vector fragment (2).

The linearized vector fragment is the nucleotide sequence consisting of the 4th nucleotide to the 3845th nucleotide of the nucleotide sequence represented by SEQ ID No: 23 and constituted of:

Hu terminator: the nucleotide sequence consisting of the 4th nucleotide to the 117th nucleotide of the nucleotide sequence represented by SEQ ID No: 23;

Origin of replication of pTB6 rep unit of bacterium of the genus *Bifidobacterium*: the nucleotide sequence consisting of the 124th nucleotide to the 1719th nucleotide of the nucleotide sequence represented by SEQ ID No: 23;

30

Spectinomycin resistant gene, SPCMr: the nucleotide sequence consisting of the 1726th nucleotide to the 2804th nucleotide of the nucleotide sequence represented by SEQ ID No: 23;

Origin of replication of *E. coli*, pUCori: the nucleotide sequence consisting of the 2811st nucleotide to the 3478th nucleotide of the nucleotide sequence represented by SEQ ID No: 23; and Hu promoter: the nucleotide sequence consisting of the 3485th nucleotide to the 3845th nucleotide of the nucleotide sequence represented by SEQ ID No: 23.

(Infusion Reaction)

An infusion reaction solution was prepared in the same procedure as in the infusion reaction in the above section: [Preparation of plasmid, pHuSP3L20-scFv-PD-1-1] except that the vector fragment and anti-PD-1-2 scFv antibody insert prepared above were used.

(Transformation of *E. coli* and Sequencing of Plasmid DNA)

*E. coli* HST08 competent cell was transformed in the same procedure as in Example 1, [Preparation of plasmid, pHuSP3L20-scFv-PD-1-1], (Transformation of *E. coli* and sequencing of plasmid DNA) except that the infusion reaction solution (5 µL) prepared above was used. The anti-PD-1-2 scFv antibody expression cassette (containing Hu promoter to Hu terminator) of the plasmid extracted was subjected to a sequencing reaction for determining the sequence thereof. The extracted plasmid was designated as pHuSP7L20-scFv-PD-1-2.

(Transformation of Bacterium of the Genus *Bifidobacterium*)

Using DNA of a plasmid, pHuSP7L20-scFv-PD-1-2 (1000 ng) extracted from *E. coli* transformed above, *Bifidobacterium longum* 105-A strain was transformed in the same procedure as in the above section: [Preparation of plasmid, pHuSP3L22-scFv-PD-1-1], (Transformation of bacterium of the genus *Bifidobacterium*) to obtain *Bifidobacterium longum* 105-A/pHuSP7L20-scFv-PD-1-2 strain.

Example 6

[Preparation of pHuSP7L20-scFv-PD-1-3]

An anti-PD-1-3 scFv antibody was selected as a heterologous peptide and an anti-PD-1-3 scFv antibody secretory plasmid, pHuSP7L20-scFv-PD-1-3 having a secretory signal peptide-linker conjugate, SP7L20 was constructed. The details of the construction are as follows.

(Preparation of Anti-PD-1-3 scFv Antibody Insert)

An anti-PD-1-3 scFv antibody insert was prepared in the same procedure as in the above section: [Preparation of pHuSP7L20-scFv-PD-1-2], (Preparation of an anti-PD-1-2 scFv antibody insert) except that the artificial plasmid, pUC57-scFv-PD-1-3 (500 µg) synthesized above was used as a template and a primer set consisting of Ins_PD-1-3_F1 primer and Ins_PD-1-3_R1 primer listed in Table 1 and Table 2 was used.

(Preparation of Vector Fragment)

A 5'-Hu terminator-pTB6rep unit-SPCMr-pUCori-Hu promoter-SP7L20-3' vector fragment (3) was prepared in the same procedure in [Preparation of pHuSP7L20-scFv-PD-1-2], (Preparation of vector fragment) except that the linearized vector fragment (500 µg) represented by SEQ ID No: 24 was used as a template and a primer set consisting of TGA_Hu_Terminator_F primer and vec-SP7L20-PD-1-3_R1 primer listed in Table 1 and Table 2 above was used.

The linearized vector fragment is the nucleotide sequence consisting of the 4th nucleotide to the 3845th nucleotide of the nucleotide sequence represented by SEQ ID No: 24 and constituted of:

Hu terminator: the nucleotide sequence consisting of the 4th nucleotide to the 117th nucleotide of the nucleotide sequence represented by SEQ ID No: 24;

Origin of replication pTB6 rep unit of bacterium of the genus *Bifidobacterium*: the nucleotide sequence consisting of the 124th nucleotide to the 1719th nucleotide of the nucleotide sequence represented by SEQ ID No: 24;

Spectinomycin resistant gene, SPCMr: the nucleotide sequence consisting of the 1726th nucleotide to the 2804th nucleotide of the nucleotide sequence represented by SEQ ID No: 24;

Origin of replication of *E. coli*, pUCori: the nucleotide sequence consisting of the 2811st nucleotide to the 3478th nucleotide of the nucleotide sequence represented by SEQ ID No: 24; and Hu promoter: the nucleotide sequence consisting of the 3485th nucleotide to the 3845th nucleotide of the nucleotide sequence represented by SEQ ID No: 24.

(Infusion Reaction)

An infusion reaction solution was prepared in the same procedure as in the infusion reaction in the above section: [Preparation of plasmid, pHuSP3L20-scFv-PD-1-1] except that the vector fragment and the anti-PD-1-3 scFv antibody insert prepared above were used.

(Transformation of *E. coli* and Sequencing of Plasmid DNA)

*E. coli* HST08 competent cell was transformed in the same procedure as in Example 1, [Preparation of plasmid, pHuSP3L20-scFv-PD-1-1], (Transformation of *E. coli* and sequencing of plasmid DNA) except that the infusion reaction solution (5 µL) prepared above was used. The anti-PD-1-3 scFv antibody expression cassette (containing Hu promoter to Hu terminator) of the plasmid extracted was subjected to a sequencing reaction for determining the sequence thereof. The extracted plasmid was designated as pHuSP7L20-scFv-PD-1-3.

(Transformation of Bacterium of the Genus *Bifidobacterium*)

Using DNA of a plasmid, pHuSP7L20-scFv-PD-1-3 (1000 ng) extracted from *E. coli* transformed above, *Bifidobacterium longum* 105-A strain was transformed in the same procedure as in the above section: [Preparation of plasmid, pHuSP3L22-scFv-PD-1-1], (Transformation of bacterium of the genus *Bifidobacterium*) to obtain *Bifidobacterium longum* 105-A/pHuSP7L20-scFv-PD-1-3 strain.

Example 7

[Preparation of pHuSP7L20-scFv-CTLA-4-1]

An anti-CTLA-4-1 scFv antibody secretory plasmid, pHuSP7L20-scFv-CTLA-4-1, having a secretory signal peptide-linker conjugate, SP7L20, was constructed.

How to prepare the anti-CTLA-4 scFv antibody secretory plasmid is schematically shown in FIG. 2. On the left side of FIG. 2, scFv-gene is CTLA-4. In preparation of pHuSP7L20-scFv-CTLA-4-1, x=7 and m=1 and in the preparation of pHuSP7L20-scFv-CTLA-4-2, x=7 and m=2. The details of the construction are as follows.

[Expression Cassette for Anti-CTLA-4 scFv Antibody]

An Expression cassette for anti-CTLA-4 scFv antibody is, as shown in FIG. 1(*b*), constituted of Hu promoter DNA (derived from *Bifidobacterium longum*), a DNA encoding a secretory signal peptide, a DNA encoding a linker peptide following the secretory signal peptide, a DNA encoding an anti-CTLA-4 scFv antibody (containing a heavy chain sequence, linker ((GGGGS)$_3$) and a light chain sequence), a His tag sequence and a Hu terminator (derived from *Bifidobacterium longum*). As the anti-CTLA-4 scFv antibody (containing nucleotide sequence containing a heavy chain sequence, a linker ((GGGGS)$_3$) and a light chain sequence) in each of individual expression cassettes, two types of anti-human CTLA-4 scFv antibodies as shown below was used, with reference to the document listed in Table 6 below.

TABLE 6

| Antibody | | Reference document |
|---|---|---|
| scFv-CTLA-4-1 | SEQ ID No: 4 (765 nucleotide sequence) SEQ ID No: 141 (254 amino acids) Heavy chain sequence (1-378 nucleotides) (GGGGS)$_3$ linker (379-423 nucleotides) Light chain sequence (424-744 nucleotides) Histidine tag (745-762 nucleotides) | Japanese Patent No. 3793693 |
| scFv-CTLA-4-2 | SEQ ID No: 5 (747 nucleotide sequence) SEQ ID No: 142 (248 amino acids) Heavy chain sequence (1-357 nucleotides) (GGGGS)$_3$ linker (358-402 nucleotides) Light chain sequence (403-726 nucleotides) Histidine tag (727-744 nucleotides) | Japanese Patent No. 4093757 |

The scFv antibody genes, namely, scFv-CTLA-4-1 represented by SEQ ID No: 4 and scFv-CTLA-4-2 represented by SEQ ID No: 5, were separately subcloned in plasmids for *E. coli* pUC57 by GenScript Japan Inc. In this manner, artificial plasmids pUC57-scFv-CTLA-4-1 and pUC57-scFv-CTLA-4-2 were obtained by gene synthesis.

(Preparation of Anti-CTLA-4-1 scFv Antibody Insert)

PCR amplification was performed by using the plasmid, pUC57-scFv-CTLA-4-1 (500 µg) as a template, and a primer set consisting of Ins CTLA-4-1_F1 primer and Ins CTLA-4-1_R1 primer listed in Table 1 and Table 2 above. The primer sequences were designed such that an insert fragment and a vector fragment were mutually overlapped at the end of 15 bp. The amplification was performed by PrimeSTAR HS (Premix) (manufactured by Takara Bio Inc.) kit using a PCR reaction solution, which was prepared so as to satisfy a primer concentration of 0.2 µM and a reaction volume of 30 µL. As an amplification program, a cycle consisting of a reaction at 98° C. for 10 seconds, a reaction at 55° C. for 5 seconds and a reaction at 72° C. for 60 seconds was repeated 30 times. The insert PCR product obtained by the amplification was subjected to electrophoresis on 2% agarose gel and purified by QIAquick Gel Extraction Kit to prepare an anti-CTLA-4-1 scFv antibody insert.

(Preparation of Vector Fragment)

A 5'-Hu terminator-pTB6rep unit-SPCMr-pUCori-Hu promoter-SP7L20-3' vector fragment (1) was prepared in the same procedure as in the above section: [Preparation of pHuSP7L20-scFv-PD-1-1], (Preparation of vector fragment).

(Infusion Reaction)

An infusion reaction solution was prepared in the same procedure as in the infusion reaction in the above section: [Preparation of plasmid, pHuSP3L20-scFv-PD-1-1] except that the vector fragment and anti-CTLA-4-1 scFv antibody insert prepared above were used.

(Transformation of E. coli and Sequencing of Plasmid DNA)

E. coli HST08 competent cell was transformed in the same procedure as in the above section: [Preparation of plasmid, pHuSP3L20-scFv-PD-1-1], (Transformation of E. coli and sequencing of plasmid DNA) except that the infusion reaction solution (5 µL) prepared above was used. The anti-CTLA-4-1 scFv antibody expression cassette (containing Hu promoter to Hu terminator) of the plasmid extracted was subjected to a sequencing reaction for determining the sequence thereof. The extracted plasmid was designated as pHuSP7L20-scFv-CTLA-4-1.

(Transformation of Bacterium of the Genus *Bifidobacterium*)

*Bifidobacterium longum* 105-A strain was transformed in the same procedure as in the above section: [Preparation of pHuSP3L22-scFv-PD-1-1], (Transformation of bacterium of the genus *Bifidobacterium*) except that DNA of a plasmid, pHuSP7L20-scFv-CTLA-4-1 (1000 ng), extracted from *E. coli* transformed above was used to obtain *Bifidobacterium longum* 105-A/pHuSP7L20-scFv-CTLA-4-1 strain.

Example 8

[Preparation of pHuSP7L20-scFv-CTLA-4-2]

An anti-CTLA-4-2 scFv antibody secretory plasmid, pHuSP7L20-scFv-CTLA-4-2, having a secretory signal peptide-linker conjugate (SP7L20) was constructed. The details of the construction are as follows.

(Preparation of Anti-CTLA-4-2 scFv Antibody Insert)

An anti-CTLA-4-2 scFv antibody insert was purified in the same procedure as in the above section: (Preparation of anti-CTLA-4-1 scFv antibody insert) except that the plasmid, pUC57-scFv-CTLA-4-2 obtained above was used as a template and a primer set consisting of Ins CTLA-4-1_F1 primer and Ins CTLA-4-2_R1 primer set listed in Table 1 and Table 2 above was used.

(Preparation of Vector)

A 5'-Hu terminator-pTB6rep unit-SPCMr-pUCori-Hu promoter-SP7L20-3' vector fragment (1) was prepared in the same procedure as in the above section: [Preparation of pHuSP7L20-scFv-PD-1-1], (Preparation of vector fragment).

(Infusion Reaction)

An infusion reaction solution was prepared in the same procedure as in the infusion reaction in the above section: [Preparation of plasmid, pHuSP3L20-scFv-PD-1-1] except that the vector fragment and the anti-CTLA-4-2 scFv antibody insert prepared above were used.

(Transformation of E. coli and Sequencing of Plasmid DNA)

E. coli HST08 competent cell was transformed in the same procedure as in Example 1, [Preparation of plasmid, pHuSP3L20-scFv-PD-1-1], (Transformation of *E. coli* and sequencing of plasmid DNA) except that the infusion reaction solution (5 µL) prepared above was used. The anti-CTLA-4-2 scFv antibody expression cassette (containing Hu promoter to Hu terminator) of the plasmid extracted was subjected to a sequencing reaction for determining the sequence thereof. The extracted plasmid was designated as pHuSP7L20-scFv-CTLA-4-2.

(Transformation of Bacterium of the Genus *Bifidobacterium*)

*Bifidobacterium longum* 105-A strain was transformed in the same procedure as in the above section: [Preparation of pHuSP3L22-scFv-PD-1-1], (Transformation of bacterium of the genus *Bifidobacterium*) except that a plasmid, pHuSP7L20-scFv-CTLA-4-2 (1000 ng) extracted from *E. coli* transformed above was used to obtain *Bifidobacterium longum* 105-A/pHuSP7L20-scFv-CTLA-4-2 strain.

Example 9

(Third Investigation of the Presence or Absence of Secretion of scFv Antibody in Recombinant Bacterium of the Genus *Bifidobacterium*)

Whether the recombinant *Bifidobacterium* bacteria transformed with an anti-PD-1 scFv antibody secretory plasmid and an anti-CTLA-4 scFv antibody secretory plasmid, namely *Bifidobacterium longum* 105-A/pHuSP7L20-scFv-PD-1-1 strain, *Bifidobacterium longum* 105-A/pHuSP7L20-scFv-PD-1-2 strain, *Bifidobacterium longum* 105-A/pHuSP7L20-scFv-PD-1-3 strain, *Bifidobacterium longum* 105-A/pHuSP7L20-scFv-CTLA-4-1 strain and *Bifidobacterium longum* and 105-A/pHuSP7L20-scFv-CTLA-4-2 strain, secrete anti-PD-1 scFv antibody and anti-CTLA-4 scFv antibody was checked by Western Analysis in the same manner as in the above (First investigation of the presence or absence of secretion of scFv antibody in recombinant bacterium of the genus *Bifidobacterium*). Note that culture time was set at 15 hours. The results are shown in FIG. 6.

(Results)

As is apparent from FIG. 6, an anti-PD-1-1 scFv antibody was secreted in the culture supernatant of *Bifidobacterium longum* 105-A/pHuSP7L20-scFv-PD-1-1 strain; an anti-PD-1-2 scFv antibody was secreted in the culture supernatant of *Bifidobacterium longum* 105-A/pHuSP7L20-scFv-PD-1-2 strain; an anti-PD-1-3 scFv antibody was secreted in the culture supernatant of *Bifidobacterium longum* 105-A/pHuSP7L20-scFv-PD-1-3 strain; anti-CTLA-4-1 scFv antibody was secreted in the culture supernatant of *Bifidobacterium longum* 105-A/pHuSP7L20-scFv-CTLA-4-1 strain; and anti-CTLA-4-2 scFv antibody was secreted in the culture supernatant of *Bifidobacterium longum* 105-A/pHuSP7L20-scFv-CTLA-4-2 strain.

Example 10

[Purification of Anti-PD-1 Antibody and Anti-CTLA-4 scFv Antibody from Recombinant Bacterium of the Genus *Bifidobacterium* Strain]

A scFv antibody was purified from each of *Bifidobacterium longum* 105-A/pHuSP7L20-scFv-PD-1-1 strain, *Bifidobacterium longum* 105-A/pHuSP7L20-scFv-PD-1-2 strain, *Bifidobacterium longum* 105-A/pHuSP7L20-scFv-PD-1-3 strain, *Bifidobacterium longum* 105-A/pHuSP7L20-scFv-CTLA-4-1 strain and *Bifidobacterium longum* 105-A/pHuSP7L20-scFv-CTLA-4-2 strain, by the method shown below.

Each of the recombinant bacterium of the genus *Bifidobacterium* strains was inoculated in MRS culture medium (10 mL) supplemented with spectinomycin (a final concentration of 75 µg/mL) and a vitamin C-added solution (100 µL) and anaerobically cultured at 37° C. for 24 hours. A culture medium containing DMEM:MRS (9:1) was prepared by adding spectinomycin (a final concentration of 75 µg/mL) and a vitamin C-added solution (500 µL per culture medium 100 mL). To this medium, the culture solution obtained above (0.5% of the amount of the medium) was inoculated and anaerobically cultured at 37° C. for 18 hours.

After the anaerobic culture, the culture supernatant was obtained by centrifugation. To the culture supernatant, ammonium sulfate was added little by little while stirring the culture supernatant so as to obtain a saturation of 80%. The solution obtained was stirred at 4° C. overnight to perform salting out. The solution was centrifuged and the precipitate was recovered. A histidine tag fused protein was purified by a purification kit for a histidine tagged protein (TALON resin, manufactured by Takara Bio Inc.). The solution of the purified protein was concentrated by ultrapurification (Amicon Ultra-0.5, manufactured by Merck Millipore Corporation). The concentration of the purified protein was measured by the Bradford method (Coomassie Plus Protein Assay manufactured by Thermo Scientific). The purified scFv antibody was aliquoted, subjected to SDS-PAGE and then stained with Coomassie brilliant blue (SimplyBlue (registered trademark) Safe Stain, manufactured by Life Technologies). As a result, it was verified that each of the scFv antibodies, namely, scFv-PD-1-1, scFv-PD-1-2, scFv-PD-1-3, scFv-CTLA4-1 and scFv-CTLA4-2, is purified with a purity of about 90%.

Example 11

[Verification of the Presence or Absence of Binding Between Human PD-1 and Anti-PD-1 scFv Antibody or Anti-CTLA-4 scFv Antibody]

Whether the anti-PD-1-2 scFv antibody, which was purified from the culture supernatant of *Bifidobacterium longum* 105-A/pHuSP7L20-scFv-PD-1-2 strain, binds to human PD-1 (hPD-1) was checked by ELISA.

To 96-well plates, 100 µL of hPD-1 (Recombinant Human PD-1 Fc Chimera, manufactured by R&D Systems, Inc.) adjusted to be 1 µg/mL with 1×PBS was dispensed and incubated at 4° C. overnight to immobilize. After the solution was removed, 350 µL of 1×PBS was dispensed and the solution was removed. This operation was repeated three times to carry out washing. In the above plates, 350 µL of a 1% BSA solution was dispensed and incubated at room temperature for 2 hours to carry out blocking. After removing the solution, 350 µL of 1×PBS was dispensed and the solution was removed. This operation was repeated three times to carry out washing.

The anti-PD-1-2 scFv antibody was adjusted so as to have a concentration of 1000 ng/mL, 100 ng/mL, 10 ng/mL and 1 ng/mL with a signal enhancing reagent (Signal Enhancer HIKARI, manufactured by Nacalai Tesque). Each solution (100 µL) was dispensed in the plates to which blocking treatment was already applied. An anti-CTLA-4-1 scFv antibody and an anti-CTLA-4-2 scFv antibody purified from a bacterium of the genus *Bifidobacterium* were subjected to the same operation as above and used as a negative control(s). To a blank well, a signal enhancing reagent (100 µL) alone was dispensed. After the plates were sealed and incubated at room temperature for 2 hours, immobilized hPD-1 was allowed to react with each of the scFv antibodies. After the solution was removed, 350 µL of 1×PBS was dispensed and the solution was removed. This operation was repeated three times to carry out washing.

A secondary antibody (The His-Tag Antibody, manufactured by GenScript) was diluted 2500 fold with a signal enhancing reagent. The dilution solution (100 µL) was dispensed in the plates. The plates were sealed and incubated at room temperature for 2 hours. After the solution was removed, 350 µL of 1×PBS was dispensed and the solution was removed. This operation was repeated three times to carry out washing.

A tertiary antibody (Biotin anti-mouse IgG, manufactured by Biolegend) was diluted 20,000 fold with a signal enhancing reagent. The dilution solution (100 µL) was dispensed in the plates. The plates were sealed and incubated at room temperature for 30 minutes. After the solution was removed, 350 µL of 1×PBS was dispensed and the solution was removed. This operation was repeated three times to carry out washing. An avidin-biotinylated enzyme complex (Vectastain ABC Kit, manufactured by Vector), more specifically, three drops of each of Solution A and Solution B, were added to a signal enhancing reagent (7.5 mL). This solution (100 µL) was dispensed in the plates and the plates were sealed and incubated at room temperature for 30 minutes. After the solution was removed, 350 µL of 1×PBS was dispensed and the solution was removed. This operation was repeated three times to carry out washing.

Color Solution A and Color Solution B (manufactured by R&D Systems) serving as a detection reagent were mixed in equal amounts. This solution (200 µL) was dispensed in the plates. The plates were sealed and incubated at room temperature for 20 minutes. Accurately 20 minutes later, 50 µL of a Stop solution (manufactured by R&D Systems) was each added to terminate a color reaction. Absorbance at 450 nm was measured, whereas absorbance at 570 nm was measured as a control. The results of the presence or absence of binding of the anti-PD-1-2 scFv antibody, anti-CTLA-4-1 scFv antibody and anti-CTLA-4-2 scFv antibody to a human PD-1 immobilized plates are shown in Table 7 below and FIG. 7.

TABLE 7

| Antibody concentration | Anti-PD-1-2 scFv antibody (scFvPD-1-2) | Anti-CTLA-4-1 scFv antibody (scFvCTLA-4-1) | Anti-CTLA-4-2 scFv antibody (scFvCTLA-4-2) |
| --- | --- | --- | --- |
| 1000 ng/mL | 2.816 | −0.038 | −0.022 |
| 100 ng/mL | 3.062 | −0.117 | −0.151 |
| 10 ng/mL | 0.912 | −0.106 | −0.153 |
| 1 ng/mL | 0.058 | −0.092 | −0.161 |

(Results)

As is apparent from Table 7 and FIG. 7, the anti-PD-1-2 scFv antibody purified from a bacterium of the genus *Bifidobacterium* bound to hPD-1 in a concentration dependent manner. In contrast, the anti-CTLA-4-1 scFv antibody and anti-CTLA-4-2 scFv antibody similarly purified from a bacterium of the genus *Bifidobacterium* did not bind to hPD-1. From the results, it was verified that the anti-PD-1-2 scFv antibody (anti-human PD-1 antibody) secreted from the bacterium of the genus *Bifidobacterium* specifically binds to hPD-1.

Example 12

[Verification of the Presence or Absence of Binding Between Human CTLA-4 and Anti-PD-1 scFv Antibody or Anti-CTLA-4 scFv Antibody]

Using the anti-PD-1-2 scFv antibody, an anti-CTLA-4-scFv antibody and an anti-CTLA-4-2 scFv antibody purified from the above culture supernatants, whether the antibodies bind to human CTLA-4 (hCTLA-4) (Recombinant Human CTLA-4-Fc Chimera, carrier-free, manufactured by BioLegend, Inc.) was checked in the same procedure as in the above section: [Verification of the presence or absence of binding between human PD-1 and anti-PD-1 scFv antibody or anti-CTLA-4 scFv antibody]. The results of the presence or absence of binding of the anti-PD-1-2 scFv antibody, anti-CTLA-4-1 scFv antibody and anti-CTLA-4-2 scFv antibody to human CTLA-4 immobilized plates are shown in Table 8 below and FIG. 8.

TABLE 8

| Antibody concentration | Anti-PD-1-2 scFv antibody (scFv PD-1-2) | Anti-CTLA-4-1 scFv antibody (scFv CTLA-4-1) | Anti-CTLA-4-2 scFv antibody (scFv CTLA-4-2) |
| --- | --- | --- | --- |
| 1000 ng/mL | 0.649 | 2.240 | 2.967 |
| 100 ng/mL | 0.085 | 1.528 | 1.643 |
| 10 ng/mL | −0.006 | 0.365 | 0.404 |
| 1 ng/mL | −0.012 | 0.059 | 0.028 |

(Results)

As is apparent from Table 8 and FIG. 8, the anti-CTLA-4-1 scFv antibody and anti-CTLA-4-2 scFv antibody bound to hCTLA-4 in a concentration dependent manner. In contrast, the anti-PD-1-2 scFv antibody similarly purified from the bacterium of the genus *Bifidobacterium* did not bind to hCTLA-4. From the results, it was verified that the anti-CTLA-4-1 scFv antibody and anti-CTLA-4-2 scFv antibody (both are anti-human CTLA-4 antibodies) secreted from a bacterium of the genus *Bifidobacterium* specifically bind to hCTLA-4.

Example 13

(First Verification of the Presence or Absence of Binding Between Mouse PD-1 and Anti-PD-1-3 scFv Antibody)

Whether the anti-PD-1-3 scFv antibody purified from the culture supernatant of the *Bifidobacterium longum* 105-A/pHuSP7L20-scFv-PD-1-3 strain binds to mouse PD-1 (mPD-1) was checked by ELISA.

To 96 well plates, 100 μL of mPD-1 (Recombinant Mouse PD-1 Fc Chimera, manufactured by R&D Systems) adjusted to be 1 μg/mL with 1×PBS was dispensed and incubated at 4° C. overnight to immobilize. After the solution was removed, 350 μL of 1×PBS was dispensed and the solution was removed. This operation was repeated three times to carry out washing. In the above plates, 350 μL of a 1% BSA solution was dispensed and incubated at room temperature for 2 hours to perform blocking. After the solution was removed, 350 μL of 1×PBS was dispensed and the solution was removed. This operation was repeated three times to carry out washing.

The anti-PD-1-3 scFv antibody purified from a bacterium of the genus *Bifidobacterium* was diluted with a signal enhancing reagent (Signal Enhancer HIKARI, manufactured by Nacalai Tesque) to prepare solutions having a concentration of 1000 ng/mL, 100 ng/mL and 10 ng/mL. Each solution (100 μL) was dispensed in the plates to which blocking treatment was already applied. An anti-PD-1-2 scFv antibody purified from a bacterium of the genus *Bifidobacterium* and anti-CTLA-4-2 scFv antibody purified from a bacterium of the genus *Bifidobacterium* were subjected to the same operation as above and used as a control. To blank wells, a signal enhancing reagent (100 μL) alone was dispensed. After the plates were sealed and incubated at room temperature for 2 hours, immobilized mPD-1 was allowed to react with the anti-PD-1-3 scFv antibody. After the solution was removed, 350 μL of 1×PBS was dispensed and the solution was removed. This operation was repeated three times to carry out washing.

A secondary antibody (Anti-His-tag mAb-Biotin, MBL) was diluted 2,000 fold with a signal enhancing reagent. The dilution solution (100 μL) was dispensed to the plates. The plates were sealed and incubated at room temperature for 2 hours. After the solution was removed, 350 μL of 1×PBS was dispensed and the solution was removed. This operation was repeated three times to carry out washing.

Using the avidin-biotinylated enzyme complex, Solution A and Solution B of a kit each (three drops) were added to a signal enhancing reagent (7.5 mL). This solution (100 μL) was dispensed in the plates. The plates were sealed and incubated at room temperature for 30 minutes. After the solution was removed, 350 μL of 1×PBS was dispensed and the solution was removed. This operation was repeated three times to carry out washing.

Color Solution A and Color Solution B (manufactured by R&D Systems) serving as a detection reagent were mixed in equal amounts. This mixture (200 μL) was dispensed in the plates. The plates were sealed and incubated at room temperature for 20 minutes. Accurately 20 minutes later, 50 μL of a Stop solution (manufactured by R&D Systems) was added to terminate a color reaction.

Absorbance at 450 nm was measured, whereas absorbance at 570 nm was measured as a control. The results of the presence or absence of binding of the anti-PD-1-2 scFv antibody, anti-PD-1-3 scFv antibody and anti-CTLA-4-2 scFv antibody to mouse PD-1 immobilized plates are shown in Table 9 and FIG. 9.

TABLE 9

| Antibody concentration | Anti-PD-1-2 scFv antibody (scFv PD-1-2) | Anti-PD-1-3 scFv antibody (scFv PD-1-3) | Anti-CTLA-4-2 scFv antibody (scFv CTLA-4-2) |
| --- | --- | --- | --- |
| 1000 ng/mL | 0.014 | 3.107 | 0.090 |
| 100 ng/mL | −0.010 | 0.561 | −0.038 |
| 10 ng/mL | 0.075 | 0.312 | −0.036 |

(Results)

The anti-PD-1-3 scFv antibody bound to mPD-1 in a concentration dependent manner. In contrast, the anti-PD-1-2 scFv antibody and anti-CTLA-4-2 scFv antibody similarly purified did not bind to mPD-1. From the results, it was verified that the anti-PD-1-3 scFv antibody (anti-mouse PD-1 antibody) secreted from the bacterium of the genus *Bifidobacterium* specifically binds to mPD-1.

Example 14

(Second Verification of the Presence or Absence of Binding Between Mouse PD-1 and Anti-PD-1-3 scFv Antibody)

Whether the anti-PD-1-3 scFv antibody purified from the culture supernatant of the *Bifidobacterium longum* 105-A/pHuSP7L20-scFv-PD-1-3 strain specifically binds to mouse PD-1 (mPD-1) was verified. The same experiment as in [Example 13] was repeated except that hCTLA-4 (Recombinant Human CTLA-4-Fc Chimera carrier-free, manufactured by BioLegend) was used as the protein to be immobilized to the plate. The results are shown in Table 10 and FIG. 10.

(Results)

As is apparent from Table 10 and FIG. 10, a positive control, i.e., anti-CTLA-4-2 scFv antibody bound to hCTLA-4 in a concentration dependent manner but the anti-PD-1-3 scFv antibody did not bind. An anti-human PD-1 antibody, i.e., anti-PD-1-2 scFv antibody, did not bind. From these results, it was also verified that the binding between mPD-1 and the anti-PD-1-3 scFv antibody found in [Example 13] is specific.

TABLE 10

| Antibody concentration | Anti-PD-1-2 scFv antibody (scFv PD-1-2) | Anti-PD-1-3 scFv antibody (scFv PD-1-3) | Anti-CTLA-4-2 scFv antibody (scFv CTLA-4-2) |
| --- | --- | --- | --- |
| 1000 ng/mL | 0.045 | 0.166 | 2.984 |
| 100 ng/mL | −0.031 | 0.030 | 1.035 |
| 10 ng/mL | −0.010 | 0.004 | 0.117 |

Example 15

(Verification of the Presence or Absence of Binding Between Anti-PD-1-2 scFv Antibody and Human PD-1 by Flow Cytometric Analysis)

Binding between an anti-PD-1-2 scFv antibody and human PD-1 over-expressing cells Experiment was conducted by using Jurkat cells and HEK293T cells (provided by Prof. Shunichiro Taniguchi, Dept. Molecular Oncology, Shinshu University) over-expressing the human PD-1. Human PD-1 over-expressing Jurkat cells were seeded in a 100-mm Petri dish (Ina-optika corporation) at a rate of $5 \times 10^6$ cells/10 mL culture medium (RPMI1640 culture medium containing inactivated 10% fetal bovine serum and 50 µM 2-mercaptoethanol and 8 mM HEPES)/dish; whereas, human PD-1 over-expressing HEK293T cells were seeded in a 100 mm-dish (manufactured by Greiner Japan) at a rate of $2 \times 10^6$ cells/10 mL culture medium (DMEM culture medium containing inactivated 10% fetal bovine serum). The following day, human PD-1 over-expressing Jurkat cells were collected in a 15-mL Falcon tube (manufactured by Becton, Dickinson and Company) and the number of cells were counted by a counting chamber. The cells were dispensed in 1.5 mL-tubes (manufactured by Ina-optika corporation) so as to contain $1 \times 10^5$ cells/mL/tube. The human PD-1 over-expressing HEK293T cells, culture supernatant was removed. Cells were washed twice with PBS ($Ca^{2+}$, $Mg^{2+}$-free phosphate buffer). 1 mL of a trypsin/EDTA solution (manufactured by Wako Pure Chemical Industries Ltd.) diluted 10 fold with PBS was added. cells were incubated at room temperature for one minute. To this, DMEM culture medium (10 mL) containing inactivated 10% fetal bovine serum, was added. Cells were transferred to a 15 mL Falcon tube, spun by a low-speed centrifuge (manufactured by TOMY SEIKO CO., LTD.) at 1000 rpm for 5 minutes. Thereafter, the supernatant was removed. To this, 1 mL of DMEM culture medium containing inactivated 10% fetal bovine serum was added and the number of cells was counted. DMEM culture medium was further added to prepare a cell suspension having $1 \times 10^5$ cells/mL and dispensed to 1.5 mL tubes (Ina-optika corporation) so as to contain $1 \times 10^5$ cells/mL/tube.

PD-1 over-expressing Jurkat cell and HEK293T cells dispensed to the 1.5 mL tubes were spun by a micro refrigerated centrifuge (manufactured by TOMY SEIKO CO., LTD.) at 5000 rpm and 4° C. for one minute. After centrifugation, the supernatants were removed. The remaining cell pellets in the tube were washed twice with 0.5 mL of PBS. An anti-PD-1-2 scFv antibody and LEAF purified anti-human PD-1 antibody (clone: EH12.2H7) (manufactured by BioLegend) serving as a positive control were respectively added in a concentration of 10 µg/mL and in an amount of 50 µL. Cells were incubated on ice for 30 minutes. FACS buffer (PBS containing 1% BSA and 0.1% $NaN_3$) was added to a 500 µL per tube and spun by a micro refrigerated centrifuge mentioned above at 5000 rpm and 4° C. for one minute. After centrifugation, the supernatants were removed. Biotinylated protein L (50 µL)(manufactured by Pierce) diluted with sterilized ultrapure water to 1 µg/mL was added to the 1.5 mL tube, stirred well by pipetting and incubated on ice for 30 minutes. Thirty minutes later, 500 µL of FACS buffer (PBS containing 1% BSA and 0.1% $NaN_3$) was added to the tube and spun by the micro refrigerated centrifuge at 5000 rpm and 4° C. for one minute. After centrifugation, the supernatants were removed. Brilliant violet 421 streptavidin (50 µL) (manufactured by BioLegend) diluted with FACS buffer to 5 µg/mL was added in a 1.5 mL tube, stirred well by pipetting and incubated on ice for 15 minutes. Fifteen minutes later, centrifugation was performed by the micro refrigerated centrifuge at 5000 rpm and 4° C. for one minute. After centrifugation, the supernatants were removed and 500 µL of FACS buffer was added. Then, the cells suspended with FACS buffer were transferred to a 5 mL polystyrene round-bottom tubes (manufactured by Becton, Dickinson and Company). A propidium iodide solution (5 µL) diluted with FACS buffer to 5 µg/mL was added, analysis was performed by BD FACS cantoII flow cytometer (manufactured by Becton, Dickinson and Company) and flow cytometric analysis software Kaluza ver 1.2 (manufactured by Beckman Coulter, Inc.). The results are shown in FIG. 11 and FIG. 12.

(Results)

As is apparent from FIG. 11, it was verified that the anti-PD-1-2 scFv antibody binds to Jurkat cells over-expressing PD-1. In contrast, binding of the anti-PD-1-2 scFv antibody to Jurkat-Mock cells not expressing PD-1 was not observed. Also, it is apparent from FIG. 12, binding of the anti-PD-1-2 scFv antibody and anti-human PD-1 antibody (clone: EH12.2H7) to HEK293T-PD-1 cells over-expressing human PD-1 was verified. In contrast, binding of the anti-PD-1-2 scFv antibody and anti-human PD-1 antibody (clone: EH12.2H7) to HEK293T-Mock cell not expressing PD-1 was not verified.

Example 16

(Verification of Competitive Inhibitory Activity of Anti-CTLA-4 scFv Antibody Against Binding of Human CTLA-4 and CD80 and CD86 by ELISA)

The anti-CTLA-4-1 scFv antibody and anti-CTLA-4-2 scFv antibody respectively secreted from recombinant bacteria of the genus *Bifidobacterium* prepared by Examples and 8 were used to check the competitive inhibitory activity of these antibodies against binding between human CD80 (hCD80) or human CD86 (hCD86) to human CTLA-4 (hCTLA-4). As a negative control, an anti-PD-1-2 scFv antibody was used.

To 96 well plates, 100 µL of hCTLA-4 (Recombinant Human CTLA-4-Fc Chimera, carrier-free, manufactured by BioLegend) adjusted to be 1 µg/mL with 1×PBS was dispensed and incubated at 4° C. overnight to immobilize. After the solution was removed, 350 µL of 1×PBS was dispensed and the solution was removed. This operation was repeated three times to carry out washing.

In the above plates, 350 µL of 1% BSA solution was dispensed. The plates were incubated at room temperature for 2 hours to carry out blocking. After the solution was removed, 350 µL of 1×PBS was dispensed and the solution was removed. This operation was repeated three times to carry out washing. The concentrations of hCD80 (Recombinant Human B7-1/CD80 Fc Chimera, manufactured by R&D Systems) and hCD86 (Recombinant Human B7-2/CD86 Fc Chimera, manufactured by R&D Systems) were adjusted with a signal enhancing reagent (Signal Enhancer HIKARI, manufactured by Nacalai Tesque) to be 2000 ng/mL.

The anti-CTLA-4-1 antibody and anti-CTLA-4-2 scFv antibody purified from bacteria of the genus *Bifidobacterium* each were adjusted with a signal enhancing reagent to have a concentration of 20000 ng/mL, 2000 ng/mL, 200 ng/mL, 20 ng/mL and 2 ng/mL and mixed with hCD80 and hCD86 (each was controlled to be 110 µL) in equal amounts. Thereafter, 100 µL of each of the solutions was dispensed to the plates to which blocking treatment was already applied. The anti-PD-1-2 scFv antibody purified from a bacterium of the genus *Bifidobacterium* and serving as a negative control was similarly adjusted as mentioned above. To blank wells, 100 µL of a signal enhancing reagent alone was dispersed. The plates were sealed, incubated at room temperature for 2 hours. With the immobilized hCTLA-4, hCD80 and hCD86 mixed with the anti-CTLA-4 scFv antibody and anti-CTLA-4-2 scFv antibody were reacted. After the solution was removed, 350 µL of 1×PBS was dispensed and the solution was removed. This operation was repeated three times to carry out washing. A secondary antibody (Human B7-1/CD80 Biotinylated Antibody, manufactured by R&D Systems) against hCD80 and a secondary antibody (Biotinylated Anti-human B7-2 Antibody, manufactured by R&D Systems) against hCD86 were adjusted to have a concentration of 2.5 µg/mL and 0.5 µg/mL with a signal enhancing reagent. This (100 µL) was dispensed. The plates were sealed and incubated at room temperature for 30 minutes. After the solution was removed, 350 µL of 1×PBS was dispensed and the solution was removed. This operation was repeated three times to carry out washing.

An avidin-biotinylated enzyme complex, more specifically, Solution A and Solution B, each (three drops) were added to a signal enhancing reagent (7.5 mL). This (100 µL) was dispensed in the plates and the plates were sealed and incubated at room temperature for 30 minutes. After the solution was removed, 350 µL of 1×PBS was dispensed and the solution was removed. This operation was repeated three times to carry out washing.

Color Solution A and Color Solution B (manufactured by R&D Systems) serving as a detection reagent were mixed in equal amounts. This mixture (200 µL) was dispensed to the plates. The plates were sealed and incubated at room temperature for 20 minutes. Accurately 20 minutes later, 50 µL of a Stop solution (manufactured by R&D Systems) was added to terminate a color reaction. Absorbance at 450 nm was measured, whereas absorbance at 570 nm was measured as a control. The measurement results are shown in Table 11 and Table 12 and the inhibitory rates are shown in FIG. 13 and FIG. 14.

TABLE 11

Competitive binding (antagonistic inhibitory rate) of anti-CTLA-4-1 scFv antibody and anti-CTLA-4-2 scFv antibody to human CTLA-4 (immobilized) with hCD80 by ELISA

| Antibody concentration | Absorbance: 450-570 nm (binding inhibition rate %) | | |
|---|---|---|---|
| | Anti-CTLA-4-1 scFv antibody (scFv CTLA4-1) | Anti-CTLA-4-2 scFv antibody (scFv CTLA4-2) | Anti-PD-1-2 scFv antibody (scFv PD1-2) |
| 0.001 µg/mL | 1.807 (10.3%) | 1.862 (7.5%) | 1.299 (35.5%) |
| 0.01 µg/mL | 1.546 (23.2%) | 2.118 (−5.2%) | 1.559 (22.6%) |
| 0.1 µg/mL | 1.682 (16.5%) | 1.116 (44.6%) | 1.343 (33.3%) |
| 1 µg/mL | 0.772 (61.7%) | 0.541 (73.1%) | 1.466 (27.2%) |
| 10 µg/mL | 0.119 (94.1%) | 0.015 (99.3%) | 1.633 (18.9%) |
| Non-scFv | | 2.014 (0%) | |

TABLE 12

Competitive binding (antagonistic inhibitory rate) of anti-CTLA-4-1 scFv antibody and anti-CTLA-4-2 scFv antibody to human CTLA-4 (immobilized) with hCD86 by ELISA

| Antibody concentration | Absorbance: 450-570 nm (binding inhibition rate %) | | |
|---|---|---|---|
| | Anti-CTLA-4-1 scFv antibody (scFv CTLA4-1) | Anti-CTLA-4-2 scFv antibody (scFv CTLA4-2) | Anti-PD-1-2 scFv antibody (scFv PD1-2) |
| 0.001 µg/mL | 1.200 (39.6%) | 1.534 (22.8%) | 1.301 (34.5%) |
| 0.01 µg/mL | 1.610 (18.9%) | 1.266 (36.3%) | 1.174 (40.9%) |
| 0.1 µg/mL | 1.293 (34.9%) | 1.136 (42.8%) | 1.206 (39.3%) |
| 1 µg/mL | 0.324 (83.7%) | 0.181 (90.9%) | 1.395 (29.8%) |
| 10 µg/mL | 0.079 (96.0%) | 0.045 (97.7%) | 1.716 (13.6%) |
| Non-scFv | | 1.986 (0%) | |

(Results)

The inhibitory rate of binding of hCD80 to hCTLA-4 was 61.7% and 73.1% in the case of 1 µg/mL anti-CTLA-4-1 scFv antibody and anti-CTLA-4-2 scFv antibody, respectively, and 94.1% and 99.3%, respectively in the case of 10 µg/mL. The inhibitory rates of binding of hCD86 to hCTLA-4 by 1 µg/mL anti-CTLA-4-1 scFv antibody and anti-CTLA-4-2 scFv antibody were 83.7% and 90.9%, respectively. The inhibitory rates thereof by 10 µg/mL of anti-CTLA-4-1 scFv antibody and anti-CTLA-4-2 scFv antibody were 96.0% and 97.7%, respectively. From the above results, it was demonstrated that the anti-CTLA-4-1 scFv antibody and anti-CTLA-4-2 scFv antibody both competitively inhibit binding of hCD80 and hCD86 (1 µg/mL) to hCTLA-4 in a concentration of 1 µg/mL or more.

Example 17

[Competitive Inhibitory Activity of Anti-Mouse PD-1 scFv Antibody to the Binding Reaction Between Mouse PD-1 and Mouse PD-L1]

Using the anti-mouse PD-1 scFv antibody secreted from the *Bifidobacterium longum* 105-A/pHuSP7L20-scFv-PD-1-strain prepared in Example 6, competitive inhibition activity to the binding between mouse PD-1 (mPD-1) and mouse PD-L1 (mPD-L1) was checked by ELISA. As a negative control, an anti-human CTLA-4-2 scFv antibody was used.

To 96 well plates, 100 µL of mPD-1 adjusted to be 1 µg/mL with 1×PBS was dispensed, incubated at 4° C. overnight so as to immobilize. After the solution was removed, 350 µL of 1×PBS was dispensed and the solution was removed. This operation was repeated three times to carry out washing. To the above plates, 350 µL of a 1% BSA solution was dispensed. The plates were incubated at room temperature for 2 hours to carry out blocking. After the solution was removed, 350 µL of 1×PBS was dispensed and the solution was removed. This operation was repeated three times to carry out washing.

The mPD-L1 (Recombinant Mouse B7-H1/PD-L1 Fc Chimera, manufactured by R&D Systems) was diluted with a signal enhancing reagent (Signal Enhancer HIKARI, manufactured by Nacalai Tesque) to prepare a solution having a concentration of 2000 ng/mL. The anti-mouse PD-1 scFv antibody purified from *Bifidobacterium longum* 105-A/pHuSP7L20-scFv-PD-1-3 strain was diluted with a signal enhancing reagent to prepare solutions having a concentration of 20000 ng/mL, 2000 ng/mL, 200 ng/mL and 20 ng/mL and mixed with the mPD-L1 in the equal amounts. The solutions each (100 µL) were dispensed to the plates to which blocking treatment was already applied. The anti-human CTLA-4-2 scFv antibody purified from a bacterium of the genus *Bifidobacterium* was similarly prepared as mentioned above as a negative control. To blank wells, 100

µL of a signal enhancing reagent alone was added. The plates were sealed and incubated at room temperature for 2 hours. With the immobilized mPD-1, mPD-L1 mixed with the anti-mouse PD-1 scFv antibody was reacted. After the solution was removed, 350 µL of 1×PBS was dispensed and the solution was removed. This operation was repeated three times to carry out washing.

A secondary antibody (Biotin anti-mouse CD274, manufactured by Biolegend) against mPD-L1 was diluted with a signal enhancing reagent to prepare a solution having a concentration of 10 ng/mL. This solution (100 µL) was dispensed. The plates were sealed and incubated at room temperature for 30 minutes. After the solution was removed, 350 µL of 1×PBS was dispensed and the solution was removed. This operation was repeated three times to carry out washing. The avidin-biotinylated enzyme complex (Vectastain ABC Kit, manufactured by Vector), more specifically, Solution A and Solution B, each (a single drop) were added to a signal enhancing reagent (2.5 mL). This solution (100 µL) was dispensed to the plates. The plates were sealed and incubated at room temperature for 30 minutes. After the solution was removed, 350 µL of 1×PBS was dispensed and the solution was removed. This operation was repeated three times to carry out washing.

Color Solution A and Color Solution B (manufactured by R&D Systems) serving as a detection reagent were mixed in equal amounts. This mixture (200 µL) was dispensed to the plates. The plates were sealed and incubated at room temperature for 20 minutes. Accurately 20 minutes later, 50 µL of a Stop solution (manufactured by R&D Systems) was added to terminate a color reaction. Absorbance at 450 nm was measured, whereas absorbance at 570 nm was measured as a control. The measurement results are shown in Table 13 below and FIG. 15.

TABLE 13

Competitive inhibitory activity of anti-mouse PD-1 scFv antibody to binding reaction between mouse PD-1 and mouse PD-L1

| | Absorbance: 450-570 nm (inhibition rate %) | |
|---|---|---|
| Antibody concentration | Anti-mouse PD-1 scFv antibody (mPD-1 scFv) | Anti-human CTLA-4-2 scFv antibody (hCTLA-4 scFv02) |
| 0.01 µg/mL | 2.104 (8.3%) | 2.100 (8.5%) |
| 0.1 µg/mL | 2.195 (4.4%) | 2.059 (10.3%) |
| 1 µg/mL | 2.152 (6.2%) | 2.124 (7.5%) |
| 10 µg/mL | 1.116 (51.4%) | 2.443 (−6.4%) |
| Non-scFv | | 2.295 (0%) |

(Results)

As is apparent from Table 13 and FIG. 15, in the case where 1 µg/mL of mPD-L1 was added to immobilized mPD-1, competitive inhibitory rate of the scFv antibody to the binding reaction thereof was 51.4% at 10 µg/mL anti-mouse PD-1 scFv antibody. In the case of the anti-human CTLA-4-scFv antibody serving as a control, competitive inhibition was not observed (−6.4%). From the above results, it was verified that the anti-mouse PD-1 scFv antibody (10 µg/mL or more) exhibits competitive (binding) inhibitory activity against mPD-L1 (1 µg/mL).

Example 18

[Verification of the Presence or Absence of Binding Between Anti-Mouse PD-1 scFv Antibody and Mouse T-Cell (CD3/CD28-Stimulated CD4 Positive Cell)]

The presence or absence of binding between anti-mouse PD-1 scFv antibody (which was purified from the culture supernatant of an anti-mouse PD-1 scFv antibody secreting bacterium of the genus *Bifidobacterium*) and mPD-expressing cell was investigated by flow cytometric analysis using a CD4 positive cell expressing mPD-1 by stimulation-induction with CD3 and CD28 (hereinafter referred to also as "CD3/CD28-stimulated CD4 positive cells").

(Preparation of CD3/CD28-Stimulated CD4 Positive Cells)

The spleen was excised out from Balb/c mouse and spleen cells were collected. Thereafter, CD4 positive cells were labeled with Biotin anti-mouse CD4 Antibody (Biolegend). After excessive antibody was washed away, Streptavidin Particles Plus-DM (manufactured by Becton, Dickinson and Company, Japan) was added and magnetic beads were allowed to bind to the CD4 positive cells. The magnetic beads were separated by a magnet and the cells attracted by the magnet were collected as CD4 positive cells and suspended in RPMI-1640 culture medium containing 10% fetal bovine serum, 8 mM HEPES and 50 µM 2-mercaptoethanol to prepare CD4 positive cells ($2 \times 10^6$ cells/mL).

A purified anti-mouse CD3s antibody (manufactured by Biolegend, hereinafter referred to also as "anti-CD3 antibody") adjusted to be 2 µg/mL was dispensed to 48-well plates at a rate of 110 µL/well and incubated at 4° C. overnight to immobilize. The CD4 positive cells prepared above were dispensed to immobilized plates at a rate of 500 µL/well. Further, Functional Grade Anti-Mouse CD28 (manufactured by eBioscience, hereinafter referred to also as "anti-CD28 antibody") adjusted to be 1 mg/mL was added at a rate of 1 µL/well to obtain a CD3/CD28 stimulated CD4 positive cells. Similarly, to wells to which the anti-CD3 antibody was not immobilized, the CD4 positive cells were dispensed to obtain a non-stimulated CD4-positive cells. The plate was cultured at 37° C. in the conditions of 5% $CO_2$ for two days.

The cell obtained by culturing for two days were removed by pipetting, transferred to a 1.5 mL tube and centrifuged at 4° C. and 5000 rpm for one minute, and then the supernatants were removed. PBS (1 mL) was added and the resultant solution was centrifuged and the supernatant was removed. After this operation was repeated twice for washing, 0.9 mL of FACS buffer (PBS containing 1% BSA) was added. The solution was centrifuged and the supernatants were removed in the same manner as above. Twenty µL of TruStain fcX (manufactured by Biolegend) diluted 50 fold with Sorting buffer (PBS containing 0.5% BSA) was added, stirred and incubated on ice for 10 minutes. To this solution, 20 µL of Alexa Fluor 647 anti-mouse CD4 Antibody (manufactured by Biolegend) diluted 200 fold with FACS buffer was added. The solution was stirred and incubated on ice for 20 minutes. FACS buffer (1 mL) was added and centrifuged and the supernatants were removed. This operation was repeated twice for washing. Subsequently, 20 µL of PE anti-mouse CD69 Antibody (manufactured by Biolegend) diluted 200 fold with FACS buffer was added. The solution was stirred and incubated on ice for 20 minutes. An operation of adding 1 mL of FACS buffer, centrifuging the solution and removing the supernatants were repeated twice for washing to obtain CD3/CD28-stimulated CD4 positive cells. The cells were divided into two portions. One of the portions was used for verification of the binding to the anti-mouse PD-1 scFv antibody and the other portion was used for verification of expression of PD-1.

(Verification of Binding of Anti-Mouse PD-1 scFv Antibody to Cells)

The binding of anti-mouse PD-1 scFv antibody to the cells was checked by using the non-stimulated CD4-positive cells obtained from the mouse spleen cell and the CD3/CD28-stimulated CD4 positive cell. The cells used herein were separately collected and 1 mL of 1×PBS buffer was added and centrifuged, and the supernatants were removed.

This operation was repeated twice to wash away the medium components. To the resultant cell, further FACS buffer was added and, centrifuged, and the supernatants were removed. To this, 20 µL of TruStain fcX (manufactured by Biolegend) diluted 50 fold with FACS buffer was added. The solution obtained was stirred well and then incubated on ice for 10 minutes. Subsequently, 20 µL of Alexa Fluor 647 anti-mouse CD4 Antibody (manufactured by Biolegend) diluted 200 fold with FACS buffer was added. The solution was stirred well and then incubated on ice for 20 minutes. After the reaction, an operation of adding 1 mL of FACS buffer, centrifuging the solution and removing the supernatant was repeated twice for washing. Next, 20 µL of PE anti-mouse CD69 Antibody (manufactured by Biolegend) diluted 200 fold with FACS buffer was added. The solution was stirred well and incubated on ice for 20 minutes. After the reaction, an operation of adding 1 mL of FACS buffer, centrifuging the solution and removing the supernatants was repeated twice for washing.

The anti-mouse PD-1 scFv antibody (20 µL) controlled to have a concentration of 10 µg/mL with FACS buffer was added. The solution was stirred and incubated on ice for 20 minutes. An operation of adding 1 mL of FACS buffer, centrifuging the solution and removing the supernatant was repeated twice for washing. Subsequently, 20 µL of Anti-His-Tag Alexa Fluor 488 Antibody (MBL) diluted 1000 fold with FACS buffer was added. The solution was incubated on ice for 20 minutes. An operation of adding 1 mL of FACS buffer, centrifuging the solution and removing the supernatant was repeated twice for washing. FACS buffer (1 mL) was added and then the cells suspended with FACS buffer were transferred to a 5 mL-polystyrene round-bottom tube (manufactured by Becton, Dickinson and Company).

(Verification of PD-1 Expression on Cells)

Whether or not PD-1 is expressed on the cell used herein was verified by using a non-stimulated CD4-positive cell obtained from a mouse spleen cell and a CD3/CD28-stimulated CD4 positive cell, in which CD4 and CD69 were labelled with a fluorescent antibody. To this cells, 20 µL of FITC anti-mouse CD279 (PD-1) antibody (manufactured by Biolegend) diluted 100 fold with FACS buffer was added. The solution obtained was incubated on ice for 20 minutes. To this, 1 mL of FACS buffer was added. The solution was centrifuged and the supernatants were removed. This operation was repeated twice for washing. FACS buffer (1 mL) was added and then the cell suspended with FACS buffer were transferred to a 5 mL-polystyrene round-bottom tube (manufactured by Becton, Dickinson and Company).

To the suspension solution of the fluorescent labeled cells, 5 µL of a propidium iodide solution diluted to a 5 µg/mL with FACS buffer was added. The obtained solution was subjected to analysis performed by BD FACS canto II flow cytometer (Becton, Dickinson and Company) and flow cytometric analysis software Kaluza ver 1.2 (manufactured by Beckman Coulter, Inc.). The forward scattering (FSC) and side scattering (SSC) of the cell suspension solution were checked by the flow cytometer and gating of a cell population was performed depending upon the size and shape of the cells. Subsequently, the cell population was subjected to gating with PI and dead cells were removed to obtain a cell population. Furthermore, CD4 positive cells were subjected to gating at a wavelength of 647 nm and whether the cells express CD69 and are stimulated with CD3/CD28 was checked by PE. Expression of mPD-1 was checked and binding of the anti-mouse PD-1 scFv antibody to mPD-1 was verified by an increase of FITC positive cells (means that mPD-1 is expressed or anti-mouse PD-1 scFv antibody is bound) in the CD4 positive cell population. The results of binding of the anti-mouse PD-1 scFv antibody (which was purified from an anti-mouse PD-1 scFv antibody-secreting bacterium of the genus Bifidobacterium) to a CD3/CD28-stimulated CD4 positive cells are shown in FIG. 16C and FIG. 16D, and mPD-1 expression on the cells is shown in FIG. 16A and FIG. 16B.

(Results)

As is apparent from FIG. 16A and FIG. 16B, the anti-mPD-1 antibody specifically binds to the CD3/CD28 stimulated CD-positive cells and expression of PD-1 on the cell surface was verified. Also, as shown in FIG. 16C and FIG. 16D, it was verified that anti-mouse PD-1 scFv antibody purified from the anti-mouse PD-1 scFv antibody-secreting bacterium of the genus Bifidobacterium specifically binds to the mPD-1 expressing cells (CD3/CD28-stimulated CD4 positive cell).

Example 19

[Colonization of Anti-Mouse PD-1 scFv Antibody-Secreting Bacterium of the Genus Bifidobacterium within Tumor of a Cancer-Bearing Mouse and Secretion of Anti-Mouse PD-1 scFv Antibody]

To a cancer-bearing mouse having a mouse large-intestine cancer cell strain CT26, Bifidobacterium longum 105-A/pHuSP7L20-scFv-PD-1-3 strain was intravenously administered and colonization of the strain in the tumor and local secretion of an anti-mouse PD-1 scFv antibody were verified by immunohistochemical staining.

Mouse large-intestine cancer cell strain CT-26 (ATCC) was cultured in RPMI1640 culture medium (manufactured by Wako Pure Chemical Industries Ltd.) containing 10% of FBS (manufactured by EQUITECH-BIO, INC.) and grafted to 6 weeks old, female BALB/c mice (manufactured by Japan SLC, Inc.) to prepare cancer-bearing mice. The cancer-bearing mice having a tumor size of 30.18 to 138.16 mm$^3$ were divided into 3 groups (Day 1, each consisting of 3 mice) as shown in the Table below. The first group and second group were used for verifying secretion of an anti-mouse PD-1 scFv antibody from a recombinant bacterium of the genus Bifidobacterium in a tumor tissue; whereas, the third group was used for verifying colonization of the recombinant bacterium of the genus Bifidobacterium in the tumor tissue. To the second group and third group, a briefly prepared frozen product of an anti-mouse PD-1 scFv antibody-secreting bacterium of the genus Bifidobacterium, namely, Bifidobacterium longum 105-A/pHuSP7L20-scFv-PD-1-3 strain, was administered in an amount of $1.0 \times 10^9$ cfu from the tail vein. Note that, 1 mL of a 10% maltose solution was administered at a frequency of two times a day for 5 days. Seven days after the administration of the bacterium of the genus Bifidobacterium, a tumor was excised out. The tumor of the third group was cryopreserved and then viable bacterial count was obtained. The tumors of the first group and second group were embedded with O.C.T. compound (manufactured by Sakura Finetek Japan Co. Ltd.) and frozen. These embedded and frozen tissues were sliced by a cryostat microtome, Leica CM1900 (manufactured by Leica) and thin-slice slide samples were prepared and subjected to histological staining.

(Viable Bacterial Count)

To the tumor tissue frozen, an anaerobic diluting solution was added and homogenized. The homogenate was appropriately diluted with the anaerobic diluting solution, spread onto BLFS agar medium (BL agar medium containing 250 µg/mL 5-fluorouracil and 30 µg/mL spectinomycin) and cultured in anaerobic conditions at 37° C. for 3 days. The number of colonies formed on the BLFS agar medium was counted and the viable bacterial count of the recombinant bacterium of the genus Bifidobacterium in the tumor was calculated. The results are shown in the Table 14 below.

TABLE 14

| Group | Administration | Evaluation method | Tumor volume (mm³) (upon excision) | Tumor weight (g) (upon excision) | Viable bacterial count (cfu/g) |
|---|---|---|---|---|---|
| 1 | Non-treatment | Immunohistochemical staining (control) | 370.60 ± 379.82 | 0.31 ± 0.36 | — |
| 2 | bacterium of the genus Bifidobacterium | Immunohistochemical staining | 202.52 ± 201.33 | 0.18 ± 0.20 | — |
| 3 | bacterium of the genus Bifidobacterium | Determination of viable bacterial count | 265.56 ± 273.73 | 0.31 ± 0.37 | 2.7E+06 ± 7.0E+05 |

(Results)

As is apparent from Table 14, vial cells of $2.7 \times 10^6$ cfu per tumor (1 g) were observed.

(Immunohistochemical Staining)

The thin-slice slides were dried in air and soaked in a 4% PFA (manufactured by Wako Pure Chemical Industries Ltd.) for 10 minutes for fixation. After fixation, the thin slice slides were washed with pure water for one minute and washed three times with 1×PBS (−) for 5 minutes. Water around the tissue was wiped out and the tissue was enclosed by a line drawn by Dako pen (manufactured by Dako) and then 3% BSA-PBS was added dropwise to the tissue and allowed to react for 60 minutes to inhibit non-specific binding. An Anti-His-tag mAb-Alexa Fluor (registered trademark) 488 (manufactured by MBL) antibody reaction solution was diluted 1000 fold with 3% BSA-PBS, added dropwise onto the tissue and allowed to react at 4° C. overnight. After the antibody reaction, the tissue was washed with 1×PBS (−) for 5 minutes three times and mounted with VECTASHIELD® Mounting Medium with DAPI. The stained slice was observed by a microscope DM5000B (Manufactured by Leica) and an image thereof was photographed. The resultant images are shown in FIG. 17.

(Results)

As is apparent from FIG. 17, in the mouse administered with an anti-mouse PD-1 scFv antibody-secreting bacterium of the genus Bifidobacterium (FIG. 17A), the tumor tissue was diffusely positive to the anti-mouse PD-1 scFv antibody (stained in green).

Example 20

[Investigation of Pharmacological (Anti-Tumor) Effect of Anti-Mouse PD-1 scFv Antibody-Secreting Bacterium of the Genus Bifidobacterium on CT26 Cancer-Bearing Model Mouse]

CT26 cancer-bearing model mice were prepared in the same manner as in Example 19. The cancer-bearing mice having a tumor size of 40.51 to 88.03 mm³ were divided into 5 groups (Day 0, each consisting of 7 mice) as shown in the Table 15 below. The first group is a non-administration control group; the second group was a single agent administration (i.v.) group with an anti-mouse PD-1 scFv antibody-secreting strain (Bifidobacterium longum 105-A/pHuSP7L20-scFv-PD-1-3 strain); the third group was a single agent administration (i.t.) group with an anti-mPD-1 antibody (manufactured by BioXcell, Clone: RPM1-14); the fourth group was a single agent administration (i.t.) group with an anti-mCTLA-4 antibody (manufactured by BioXcell, Clone: 9D9); and the fifth group was a combined administration of two agents group with the anti-mouse PD-1 scFv antibody-secreting bacterium of the genus Bifidobacterium (i.v.) and the anti-mCTLA-4 antibody (i.t.). The date of drug administration, dosage and administration route are shown in Table 15 below. Furthermore, to mice of the second group and fifth group, a 10% maltose solution (1 mL) was intraperitoneally administrated at a frequency of two times a day from Day 1 to Day 5 and Day 8 to Day 12. The diameter of tumors was periodically measured (Day 0, 3, 7, 10, 14, 17, 22) in all groups. The tumors were excised out on Day 22 and weight of the tumors was measured. A change of tumor volume is shown in Table 16 below. The results of a statistical test of tumor volumes in CT26 cancer-bearing mice are shown in Table 17, and changes in CT26 tumor volume of single agent administration groups and the non-administration group are shown in FIG. 18.

TABLE 15

| Group | Administration agent | Dosage | Administration route | Administration date | Number of mice |
|---|---|---|---|---|---|
| 1 | None | — | — | — | 7 |
| 2* | Anti-mouse PD-1 scFv antibody-secreting bacterium of the genus Bifidobacterium | $5 \times 10^8$ cfu twice a day | i.v. | Day 1, 4, 8, 11 | 7 |
| 3 | Anti-mPD-1 antibody | 100 μg once a day | i.t. | Day 1, 4, 8, 11 | 7 |
| 4 | Anti-mCTLA-4 antibody | 100 μg once a day | i.t. | Day 1, 4, 8, 11 | 7 |
| 5* | Anti-mouse PD-1 scFv antibody-secreting bacterium of the genus Bifidobacterium, Anti-mCTLA-4 antibody | $5 \times 10^8$ cfu twice a day | i.v. | Day 1, 4, 8, 11 | 7 |
|  | Anti-mCTLA-4 antibody | 100 μg once a day | i.t. | Day 1, 4, 8, 11 |  | i.v.: Intravenous administration
i.t.: Intratumoral (local) administration

TABLE 16

Mean tumor volume of CT26 cancer-bearing mice on single agent administration and combined administration of two agents

| | Tumor volume (mm³) | | | | |
|---|---|---|---|---|---|
| Day | Non-administration | Anti-mouse PD-1 scFv antibody-secreting bacterium of the genus *Bifidobacterium* | Anti-mPD-1 antibody | Anti-mCTLA-4 antibody | Anti-mouse PD-1 scFv antibody-secreting bacterium of the genus *Bifidobacterium* + Anti-mCTLA-4 antibody |
| 0 | 60.30 ± 13.46 | 60.59 ± 13.86 | 61.31 ± 13.74 | 61.08 ± 13.84 | 61.21 ± 14.94 |
| 3 | 148.48 ± 36.43 | 69.96 ± 25.13 | 78.88 ± 21.81 | 108.99 ± 30.86 | 72.87 ± 34.89 |
| 7 | 466.83 ± 167.61 | 153.42 ± 77.79 | 115.71 ± 49.80 | 175.70 ± 79.77 | 116.26 ± 67.78 |
| 10 | 902.05 ± 352.64 | 209.58 ± 119.71 | 138.55 ± 86.62 | 200.04 ± 118.46 | 88.04 ± 61.75 |
| 14 | 1571.61 ± 636.62 | 364.42 ± 246.94 | 195.31 ± 202.52 | 241.99 ± 192.36 | 78.58 ± 54.86* |
| 17 | 2506.78 ± 993.48 | 615.38 ± 380.16 | 282.07 ± 328.92 | 322.65 ± 296.33 | 98.33 ± 85.98* |
| 22 | 3718.65 ± 1064.17 | 1259.90 ± 737.04 | 556.60 ± 599.70 | 475.74 ± 516.73 | 175.93 ± 215.91* |

The mean values ± S.D. of seven mice.
*The mean values ± S.D. of six mice.

TABLE 17

Statistical test on tumor volume of CT26 cancer-bearing mice

| | T-test P (T <= f) | | | | | |
|---|---|---|---|---|---|---|
| Day | First group vs Second group | First group vs Third group | First group vs Fourth group | First group vs Fifth group | Second group vs Fifth group | Fourth group vs Fifth group |
| 3 | 0.000 ** | 0.000 ** | 0.049 * | 0.002 ** | 0.861 | 0.063 |
| 7 | 0.002 ** | 0.001 ** | 0.002 ** | 0.001 ** | 0.359 | 0.159 |
| 10 | 0.002 ** | 0.001 ** | 0.002 ** | 0.001 ** | 0.034 * | 0.047 * |
| 14 | 0.002 ** | 0.001 ** | 0.001 ** | 0.001 ** | 0.021 * | 0.069 |
| 17 | 0.002 ** | 0.001 ** | 0.001 ** | 0.001 ** | 0.010 * | 0.098 |
| 22 | 0.000 ** | 0.000 ** | 0.000 ** | 0.000 ** | 0.007 ** | 0.199 |

* P value < 0.05
** P value < 0.01
First group: Non-administration
Second group: Anti-mouse PD-1 scFv antibody-secreting bacterium of the genus *Bifidobacterium* administration group#
Third group: Anti-mPD-1 antibody administration group
Fourth group: Anti-mCTLA-4 antibody administration group
Fifth group: Two agent combined administration group: anti-mouse PD-1 scFv antibody-secreting bacterium of the genus *Bifidobacterium*# + anti-mCTLA-4 antibody
*Bifidobacterium longum* 105-A/pHuSP7L20-mPD-1scFv

TABLE 18

T/C of mean tumor volume of CT26 cancer-bearing mouse on single agent administration and combined administration of two agents

| | T/C (Ratio of administration group to non-administration group) | | | |
|---|---|---|---|---|
| Day | Anti-mouse PD-1 scFv antibody-secreting bacterium of the genus *Bifidobacterium* | Anti-mPD-1 antibody | Anti-mCTLA-4 antibody | Anti-mouse PD-1 scFv antibody-bacterium of the genus *Bifidobacterium* + Anti-mCTLA-4 antibody |
| 0 | 1.00 | 1.02 | 1.01 | 1.02 |
| 3 | 0.47 | 0.53 | 0.73 | 0.49 |
| 7 | 0.33 | 0.25 | 0.38 | 0.25 |
| 10 | 0.23 | 0.15 | 0.22 | 0.10 |
| 14 | 0.23 | 0.12 | 0.15 | 0.05 |
| 17 | 0.25 | 0.11 | 0.13 | 0.04 |
| 22 | 0.34 | 0.15 | 0.13 | 0.05 |

(Results)

As is apparent from Table 17 and FIG. 18, in the anti-mouse PD-1 scFv antibody-secreting bacterium of the genus *Bifidobacterium* administration group (second group), the volume of a tumor is lower than the non-administration group (first group) at all time points and a significant growth suppression effect was observed at all time points (Table 17). Furthermore, the tumor growth suppression expressed by the ratio of the administration group relative to the non-administration group (T/C) was 0.34 or less on and after Day 10.

In the anti-mPD-1 antibody single agent administration group (third group), a significantly high suppression effect on tumor volume was observed at all time points than in the non-administration group (first group) and the T/C ratio was 0.15 or less on and after Day 10. Note that in the anti-mCTLA-4 antibody intratumoral single agent administration group (fourth group), a significantly higher inhibitory effect on tumor volume than in the non-administration group was found at all time points and the T/C ratio was 0.22 or less on and after Day 10.

In contrast, in combined administration of two agents group (the anti-mouse PD-1 scFv antibody-secreting bacterium of the genus *Bifidobacterium* and the anti-mCTLA-antibody) (fifth group), a significantly higher inhibitory effect on tumor volume than in the non-administration group was found at all time points and the T/C ratio was 0.10 or less, which was the strongest anti-tumor effect, on and after Day 10. When the combined administration of two agents group was compared to the single agent administration groups, a significantly strong inhibitory effect was produced in each single agent administration group on Day 10; and a significantly strong inhibitory effect was produced in the group administered with the anti-mouse PD-1 scFv antibody-secreting bacterium of the genus *Bifidobacterium* on and after Day 14 (see Table 16, Table 17, Table 18, FIG. 19, FIG. 20). Note that in either case of the anti-mCTLA-4 antibody administration group and the combined administration of two agents group, complete repression of a tumor was observed in a single mouse.

The same results as in tumor volume were obtained with respect to tumor weight. A significant difference was observed in all groups compared to the non-administration group. The T/C ratios of the anti-mouse PD-1 scFv antibody-secreting bacterium of the genus *Bifidobacterium* administration group, anti-mPD-1 antibody administration group, anti-mCTLA-4 antibody administration group and combined administration of two agents group were 0.31, 0.12, 0.10 and 0.04, respectively. The tumor weight value of the combined administration of two agents group was the lowest (see Table 19 and Table 20).

TABLE 19

Anti-tumor effect of on single agent administration and combined administration of two agents on CT26 cancer-bearing mice (mean tumor weight and T/C ratio)

| Administration agent | Day 22 Tumor weight (g) | T/C ratio |
|---|---|---|
| Non-treatment (C) | 5.20 ± 2.16 | — |
| Anti-mouse PD-1 scFv antibody-secreting bacterium of the genus *Bifidobacterium*[#] | 1.62 ± 0.92 | 0.31 |
| Anti-mPD-1 antibody | 0.60 ± 0.70 | 0.12 |
| Anti-mCTLA-4 antibody | 0.54 ± 0.61 | 0.10 |
| Combined administration of two agents (Anti-mouse PD-1 scFv antibody-secreting bacterium of the genus *Bifidobacterium*[#] + Anti-mCTLA-4 antibody) | 0.21 ± 0.26* | 0.04 |

The mean values ± S.D. of seven animals.
*The mean values ± S.D. of six animals.
T/C ratios = mean tumor weight of administration group/mean tumor weight of non-administration group
—: Not determined
[#]*Bifidobacterium longum* 105A/pHuSP7L20-mPD-1scFv

TABLE 20

Statistical test on tumor weight of CT26 cancer-bearing mice

| VS | Day 22 T-test P (T <= f) |
|---|---|
| First group vs Second group | 0.004** |
| First group vs Third group | 0.001** |
| First group vs Fourth group | 0.001** |
| First group vs Fifth group | 0.001** |
| Second group vs Fifth group | 0.006** |
| Fourth group vs Fifth group | 0.231 |

**P value < 0.01
First group: Non-administration
Second group: Anti-mouse PD-1 scFv antibody-secreting bacterium of the genus *Bifidobacterium* administration group[#]
Third group: Anti-mPD-1 antibody administration group
Fourth group: Anti-mCTLA-4 antibody administration group
Fifth group: Anti-mouse PD-1 scFv antibody-secreting bacterium of the genus *Bifidobacterium*[#] + Anti-mCTLA-4 antibody combined administration group of two agents
[#]*Bifidobacterium longum* 105A/pHuSP7L20-mPD-1scFv (Results)

From the above results, it was demonstrated that the anti-mouse PD-1 scFv antibody-secreting bacterium of the genus *Bifidobacterium* colonizes within a tumor of CT-26 cancer-bearing mouse by intravenous administration (Example 19) and secrets an anti-mouse PD-1 scFv antibody to produce a tumor growth suppression effect; and that the effect is almost the same obtained when an reagent antibody, i.e., an anti-mPD-1 antibody, was directly administered into the tumor. It was also demonstrated that the anti-mouse PD-1 scFv antibody secreted from a bacterium of the genus *Bifidobacterium* has an activity of competitively inhibiting binding between mPD-1 and mPD-L1 in the in-vitro test (Example 17), and inhibits the negative signal transduction between PD-1 on a T cell and PD-L1 on a tumor cell in the same mechanism also within a tumor to activate the T cell, with the result that an anti-tumor effect is presumably produced. Furthermore, the effect of combined administration of the anti-mouse PD-1 scFv antibody-secreting bacterium of the genus *Bifidobacterium* and the anti-mCTLA-4 antibody was verified. From this, usefulness of a bacterium of the genus *Bifidobacterium* simultaneously expressing both a scFv antibody inhibiting CTLA-4 and a scFv antibody inhibiting PD-1 was suggested.

Example 21

[Preparation of Anti-Human PD-1scFv03 scFv Antibody-Secreting Bacterium of the Genus *Bifidobacterium* Having a Linker Different in Length]

(Outline)

An anti-human PD-1scFv03 secretory plasmid, pHuSP7L20-hPD-1scFv03 having a secretory signal SP7 and a subsequent linker consisting of 20 amino acid residues was constructed. The secretory signal and the subsequent linker in this plasmid were replaced respectively with SP69 and a subsequent linker consisting of 20 amino acid residues corresponding to SP69 to construct an anti-human PD-1scFv03 secretory plasmid, pHuSP69L20-hPD-1scFv03. Furthermore, plasmids were constructed in the same manner as above except that the length of the linker was changed from 20 amino acid residues to L0 to 10 and 15 amino acid residues (L0, L1, L2, L3, L4, L5, L6, L7, L8, L9, L10 and L15).

[Preparation of Plasmid, pHuSP7L20-hPD-1scFv03]

(Outline)

A plasmid, pHuSP7L20-hPD-1scFv03 containing an expression cassette (anti-human PD-1scFv03 secretion expression cassette) secreting anti-hPD-1scFv03 and serving as an *E. coli*-bacterium of the genus *Bifidobacterium* shuttle vector, was prepared. The primers used herein are shown in Table 21 below.

TABLE 21

| Primer Name | DNA Sequence (5'→3') | SEQ ID NO: |
|---|---|---|
| Ins-hPD-IscFv03-F1 | CAGGTCCAGCTGGTCGAATCGGGCGGCGGC | SEQ ID No: 82 |
| Ins-hPD-IscFv03-R1 | ACGAGCAGAAGGTCAGTGGTGGTGATGATG GTGCTT | SEQ ID No: 83 |
| TGA-Hu-Terminator-F | TGACCTTCTGCTCGTAGCGA TTAC | SEQ ID No: 84 |
| vee-SP7L20-R1 | GACCAGCTGGACCTGCACCGAACTCGCCTTCGGGAA | SEQ ID No: 85 |

(Constitution of Anti-Human PD-1scFv03 Secretion Expression Cassette)

The nucleotide sequence of DNA encoding the anti-human PD-1scFv03 secretion expression cassette, which is a cassette comprising (1) to (5) DNA: (1) Hu promoter DNA, (2) a DNA encoding a signal peptide-linker conjugate, SP7L20, (3) a DNA encoding the amino acid sequence of anti-hPD-1scFv03 (containing a heavy chain sequence, a linker (GGGGS)$_3$ and a light chain sequence), (4) a DNA encoding a His tag sequence and (5) Hu terminator DNA, sequentially in this order ((1) to (5)) from the upstream side (the 5' end) to the downstream side (the 3' end) was constructed. The nucleotide sequence of DNA encoding a heavy chain sequence, a linker (GGGGS)$_3$ and a light chain sequence in the amino acid sequence of the aforementioned anti-hPD-1scFv03) was prepared with reference to the document listed in the Table 22 below.

(Artificial Synthesis of DNA of Anti-hPD-1scFv03)

The gene of the anti-hPD-1scFv03 represented by SEQ ID No: 86 was subcloned in a plasmid for *E. coli*, i.e., pUC57 by GenScript Japan Inc. and artificially synthesized as a plasmid, namely, pUC57-hPD-1scFv03.

TABLE 22

| Document regarding anti-hPD-1scFv03 | | |
|---|---|---|
| Antibody | | Reference document |
| Anti-hPD-1scFv03 | SEQ ID No: 86 (729 nucleotides sequence) Heavy chain sequence(1-342 nucleotides) (GGGGS)$_3$ linker (343-387 nucleotides) Light chain sequence (388-708 nucleotides) Histidine tag (709-726 nucleotides) | Japanese Patent No. 5028700 |

(Preparation 1: Anti-hPD-1scFv03 Insert Fragment)

PCR amplification was performed by using the plasmid, pUC57-hPD-1scFv03 (500 µg) as a template and a primer set of Ins-hPD-1scFv03-F1 primer (forward) and Ins-hPD-1scFv03-R1 primer (reverse) listed in Table 21 above. The primer sequences were designed such that an insert fragment and a vector fragment were mutually overlapped at the end of 15 bp. The PCR amplification was performed by setting each primer concentration at 0.2 µM and the reaction volume at 30 µL and using PrimeSTAR HS (Premix) kit (manufactured by Takara Bio Inc.). As an amplification program, a cycle consisting of a reaction at 98° C. for 10 seconds, a reaction at 55° C. for 5 seconds and a reaction at 72° C. for 60 seconds was repeated 30 times. The PCR product obtained by the amplification was subjected to electrophoresis on 2% agarose gel and purified by QIAquick Gel Extraction Kit (manufactured by QIAGEN) to prepare about 0.7 kbp of anti-hPD-1scFv03 insert fragment (1).

(Preparation of Vector Fragment (1) Containing DNA Encoding the Amino Acid Sequence of SP7L20)

PCR amplification was performed by using the linearized vector fragment (500 µg) represented by SEQ ID No: 87 as a template and a primer set of TGA-Hu-Terminator-F primer (forward) and vec-SP7L20-R1 primer (reverse) listed in Table 21 above. The PCR amplification was performed by setting each primer concentration at 0.2 µM and the reaction volume at 30 µL and using PrimeSTAR HS (Premix) kit. As an amplification program, a cycle consisting of a reaction at 98° C. for 10 seconds, a reaction at 55° C. for 5 seconds and a reaction at 72° C. for 5 minutes was repeated 30 times. The PCR product obtained by the amplification was subjected to electrophoresis on 0.8% agarose gel and purified by QIAquick Gel Extraction Kit to prepare about 4.0 kbp of 5'-Hu terminator-pTB6rep unit-SPCMr-pUCori-Hu promoter-SP7L20-3' vector fragment (1).

(Infusion Reaction)

The vector fragment (1) prepared above and the anti-hPD-1scFv03 insert fragment (1) were ligated by use of In-Fusion (registered trademark) HD Cloning kit (manufactured by Takara Bio Inc.). More specifically, the above vector within the kit and the insert were added in a molar ratio of 1:5 to a microtube and then 2 µL of 5× In-Fusion (registered trademark) HD Enzyme premix (manufactured by Takara Bio Inc.) was added. The reaction solution, after the volume of the solution was adjusted to be 10 µL, was kept at 50° C. for 15 minutes. The procedure described in the instruction of the kit except the aforementioned procedure was performed to prepare an infusion reaction solution 1.

(Verification of Transformation of *E. coli* and DNA Sequence of pHuSP7L20-hPD-1scFv03)

*E. coli* HST16CR competent cell was transformed by use of the infusion reaction solution (5 µL) prepared above in accordance with the instruction. After the transformation, a bacterial suspension was spread onto a pg/mL spectinomycin-containing LB agar medium and subjected to a static culture performed at 37° C. overnight. Colonies formed on the agar medium were subjected to shaking culture performed in a 75 µg/mL spectinomycin-containing LB liquid medium at 30° C. overnight. From the culture, a plasmid was extracted by use of QIAprep Spin Miniprep Kit (manufactured by QIAGEN). In order to sequence the anti-human PD-1scFv03 secretion expression cassette (5'-Hu promoter-SP7L20-anti-hPD-1scFv03-His tag-Hu terminator-3') of the extracted plasmid, a sequencing reaction using BigDye (registered trademark) Terminator v3.1 Cycle Sequencing Kit (manufactured by Applied Biosystems) was carried out. The plasmid sequenced was designated as pHuSP7L20-hPD-1scFv03. The sequence of pHuSP7L20-hPD-1scFv03 is represented by SEQ ID No: 88.

[Preparation of Plasmid, pHuSP69L20-hPD-1scFv03]

A plasmid, pHuSP69L20-hPD-1scFv03, which is obtained by replacing the signal peptide sequence and the subsequent linker peptide sequence of an anti-human PD-1scFv03 secretory plasmid, pHuSP7L20-hPD-1scFv03 from SP7L20 to SP69L20, was constructed as follows.

(Preparation of Vector Fragment and Insert Fragment)

A vector fragment was prepared by PCR amplification using a plasmid, pHuSP7L20-hPD-1scFv03 as a template and a primer set of hPD-1scFv03 Vec F1 primer and Hu-mCCL21 Vec R1 primer listed in Table 23 (V1) and Table 24 below at a primer concentration of 0.2 µM and a reaction volume of 50 µL and using PrimeSTAR HS (Pre-mix) kit. As an amplification program, a cycle consisting of a reaction at 98° C. for 10 seconds, a reaction at 65° C. for 5 seconds and a reaction at 72° C. for 4 minutes and 45 seconds was repeated 30 times. The PCR product obtained by amplification was designated as vector fragment V1.

PCR amplification was performed by using *Bifidobacterium longum* 105-A genomic DNA (800 µg) as a template and a primer set of SP69-ins F1 primer and SP69-ins_R1_hPD1_03 primer listed in Table 23 (Ins-1) and Table 24 below. The primer sequences were designed such that an insert fragment and a vector fragment were mutually overlapped at the end of 15 bp. The PCR amplification was performed in the same manner as in the above vector. However, the elongation reaction time at 72° C. was set at 20 seconds. The PCR product obtained by amplification was designated as insert fragment Ins-1.

TABLE 23

Template and primer in PCR amplification

| PCR product | Template | Forward Primer | Reverse primer | PCR product (bp) |
|---|---|---|---|---|
| V1 | pHuSP7L20-hPD-1scFv03 | hPD-1 scFv03_Vec-F1 | Hu-mCCL21_Vec_R1 | 4568 bp |
| Ins-1 | *Bifidobacterium longum* 105-A | SP69-ins_F1 | SP69-ins_R1_hPD1_03 | 180 bp |
| Ins-L0 | pHuSP69L20-hPD-1scFv03 | SP69-ins_F1 | SP69L0-ins_R1_hPD1_03 | 120 bp |
| Ins-L1 | pHuSP69L20-hPD-1scFv03 | SP69-ins_F1 | SP69L1-ins_R1_hPD1_03 | 123 bp |
| Ins-L2 | pHuSP69L20-hPD-1scFv03 | SP69-ins_F1 | SP69L2-ins_R1_hPD1_03 | 126 bp |
| Ins-L3 | pHuSP69L20-hPD-1scFv03 | SP69-ins_F1 | SP69L3-ins_R1_hPD1_03 | 129 bp |
| Ins-L4 | pHuSP69L20-hPD-1scFv03 | SP69-ins_F1 | SP69L4-ins_R1_hPD1_03 | 132 bp |
| Ins-L5 | pHuSP69L20-hPD-1scFv03 | SP69-ins_F1 | SP69L5-ins_R1_hPD1_03 | 135 bp |
| Ins-L6 | pHuSP69L20-hPD-1scFv03 | SP69-ins_F1 | SP69L6-ins_R1_hPD1_03 | 138 bp |
| Ins-L7 | pHuSP69L20-hPD-1scFv03 | SP69-ins_F1 | SP69L7-ins_R1_hPD1_03 | 141 bp |
| Ins-L8 | pHuSP69L20-hPD-1scFv03 | SP69-ins_F1 | SP69L8-ins_R1_hPD1_03 | 144 bp |
| Ins-L9 | pHuSP69L20-hPD-1scFv03 | SP69-ins_F1 | SP69L9-ins_R1_hPD1_03 | 147 bp |
| Ins-L10 | pHuSP69L20-hPD-1scFv03 | SP69-ins_F1 | SP69L10-ins_R1_hPD1_03 | 150 bp |
| Ins-L15 | pHuSP69L20-hPD-1scFv03 | SP69-ins_F1 | SP69L15-ins_R1_hPD1_03 | 165 bp |

TABLE 24

Primer sequence in PCR amplification

| Primer Name | Sequence (5'→3') | SEQ ID NO: |
|---|---|---|
| Hu-mCCL21_Vec_R1 | AAAGCATCCTTCTTGGGTCAGG | SEQ ID No: 89 |
| hPD-1 scFv03_Vec_F1 | CAGGTCCAGCTGGTCGAATC | SEQ ID No: 90 |
| SP69-ins_F1 | CAAGAAGGATGCTTTATGAATTATTTACGACAAAAAATTTCGG | SEQ ID No: 91 |
| SP69-ins_R1_hPD1_03 | GACCAGCTGGACCTGACCGCTATCAGTCGTGGTGTAAC | SEQ ID No: 92 |
| SP69L5-ins_R1_hPD1_03 | GACCAGCTGGACCTGTGGCGTTGAATCATCCGC | SEQ ID No: 93 |
| SP69L10-ins_R1_hPD1_03 | GACCAGCTGGACCTGCGATGGCGTTGAAGATGG | SEQ ID No: 94 |
| SP69L15-ins_R1_hPD1_03 | GACCAGCTGGACCTGGGTGTAACTGCCATCCGATG | SEQ ID No: 95 |
| SP69L0-ins_R1_hPD1_03 | CTACCACTCTGGACCTGCGCAAAGACCGGCATTG | SEQ ID No: 96 |
| SP69L1-ins_R1_hPD1_03 | GACCAGCTGGACCTGATCCGCAAAGACCGGCAT | SEQ ID No: 97 |
| SP69L2-ins_R1_hPD1_03 | GACCAGCTGGACCTGATCATCCGCAAAGACCGG | SEQ ID No: 98 |
| SP69L3-ins_R1_hPD1_03 | GACCAGCTGGACCTGTGAATCATCCGCAAAGACCG | SEQ ID No: 99 |

TABLE 24-continued

Primer sequence in PCR amplification

| Primer Name | Sequence (5'→3') | SEQ ID NO: |
|---|---|---|
| SP69L4-ins_R1_hPD1_03 | GACCAGCTGGACCTGCGTTGAATCATCCGCAAAGAC | SEQ ID No: 100 |
| SP69L6-ins_R1_hPD1_03 | GACCAGCTGGACCTGAGATGGCGTTGAATCATCCG | SEQ ID No: 101 |
| SP69L7-ins_R1_hPD1_03 | GACCAGCTGGACCTGTGAAGATGGCGTTGAATCATCC | SEQ ID No: 102 |
| SP69L8-ins_R1_hPD1_03 | GACCAGCTGGACCTGCGTTGAAGATGGCCTTTGAATC | SEQ ID No: 103 |
| SP69L9-ins_R1_hPD1_03 | GACCAGCTGGACCTGTGGCGTTGAAGATGGCG | SEQ ID No: 104 |

(Infusion Reaction)

Vector fragment V1 and insert fragment Ins-1 prepared above were ligated by use of In-Fusion HD Cloning Kit. More specifically, in a microtube, the vector fragment and the insert fragment were added in a molar ratio of 1:2 and then 5× In-Fusion (registered trademark) HD Enzyme premix (2 μL) and Cloning Enhancer (1 μL) were added. The reaction solution, after the volume of the solution was adjusted to be 10 μL, was kept at 37° C. for 15 minutes and then at 50° C. for 15 minutes. The procedure described in the instruction of the kit except the aforementioned procedure was performed to prepare an infusion reaction solution.

(Transformation of E. coli and Sequencing of Plasmid DNA)

E. coli HST16CR competent cell (manufactured by Takara Bio Inc.) was transformed by using the infusion reaction solution (1 μL) in accordance with the instruction. After the transformation, a bacterial suspension was spread onto a 75 μg/mL spectinomycin-containing LB agar medium and subjected to a static culture performed at 37° C. overnight. Colonies formed on the agar medium were subjected to shaking culture performed in a 75 μg/mL spectinomycin-containing LB liquid medium at 37° C. overnight. From the culture, a plasmid was extracted by use of QIAprep Spin Miniprep Kit (manufactured by QIAGE N Genomics Inc.). In order to sequence the anti-human PD-1scFv03 expression cassette (containing Hu promoter to Hu terminator) of the extracted plasmid, a sequencing reaction using BigDye (registered trademark) Terminator v3.1 Cycle Sequencing Kit (manufactured by Applied Biosystems) was carried out. The plasmid sequenced was designated as pHuSP69L20-hPD-1scFv03.

[Preparation of pHuSP69Ly-hPD-1scFv03 (y=0 to 10 and 15)]

A plasmid prepared by shortening the linker of pHuSP69L20-hPD-1scFv03 from the 3' end thereof to prepare DNA encoding 0 to 10 and 15 amino acids, namely, pHuSP69Ly-hPD-1scFv03 (y=0, 1, 2, 3, 4, 5, 6, 7, 8, 9, 10, 15), as follows.

(Preparation of Vector Fragment and Insert Fragment)

As a vector fragment, vector fragment V1 as prepared above was used. An insert fragment was prepared in the same manner as in preparation of insert fragment Ins-1 mentioned above except that a plasmid, pHuSP69L20-hPD-1scFv03 was used as a template and a primer set listed in Table 23 (Ins-L0 to 10, Ins-L15) were used. The PCR product amplified were designated as insert fragments Ins-L0, Ins-L1, Ins-L2, Ins-L3, Ins-L4, Ins-L5, Ins-L6, Ins-L7, Ins-L8, Ins-L9, Ins-L10 and Ins-L15.

(Infusion Reaction)

Vector fragment V1 and insert fragments Ins-Ly (y=0 to 10 and 15) prepared above were ligated by an infusion reaction in the same manner as in preparing pHuSP69L20-hPD-1scFv03 as mentioned above.

(Transformation of E. coli and Sequencing of Plasmid DNA)

E. coli was transformed by using the infusion reaction solution prepared above and plasmid DNA was sequenced in the same manner as in preparing pHuSP69L20-hPD-1scFv03.

[Transformation of Bacterium of the Genus Bifidobacterium]

Using 13 types of plasmids, pHuSP69Ly-hPD-1scFv03 (L0, L1, L2, L3, L4, L5, L6, L7, L8, L9, L10, L15 and L20) prepared above, Bifidobacterium longum 105-A strain was transformed by an electroporation system (Gene Pulser II, manufactured by Bio-Rad Laboratories). After electric shock (2 kV, 25 ρF, 2005) was applied, a solution mixture of IMR liquid medium (800 μL) and a vitamin C-added solution (50 μL) was immediately added in a cuvette (2 mm gap) and this was collected in a sterilized 2 mL-microtube. Individual tubes were subjected to the same operation. These 2 mL-tubes with the cap loosen were placed in an airtight container together with a de-oxygen and carbon dioxide gas generating agent (AnaeroPack (registered trademark)-Kenki, manufactured by Mitsubishi Gas Chemical Company, Inc.) and kept in an incubator set at 37° C. for 3 hours. After keeping warm, each of the bacterial suspensions was spread onto a 75 μg/mL spectinomycin-containing IMR agar medium. These plates were placed in an airtight container together with the above de-oxygen and carbon dioxide gas generating agent and cultured in an incubator set at 37° C. for 2 days.

Colonies formed on the spectinomycin-containing IMR agar medium was picked up, streaked on a 75 μg/mL spectinomycin-containing BL-bS agar medium (BL agar medium containing no equine defibrinated blood), placed in an airtight container together with de-oxygen and carbon dioxide gas generating agent and cultured in an incubator set at 37° C. for one day to obtain Bifidobacterium longum 105-A/pHuSP69Ly-hPD-1scFv03 strains (y=0, 1, 2, 3, 4, 5, 6, 7, 8, 9, 10, 15 and 20).

Example 22

[Expression Analysis of scFv of Anti-Human PD-1scFv03 Secreting Bacterium of the Genus Bifidobacterium Different in Linker Length]

Since anti-hPD-1scFv03 secreted from Bifidobacterium longum 105-A/pHuSP69Ly-hPD-1scFv03 strain (y=0, 1, 2, 3, 4, 5, 6, 7, 8, 9, 10, 15 and 20) prepared in Example 21 had a histidine tag fused to the C terminal, scFv antibody secretion was analyzed by Western blotting using an antibody against the anti-histidine tag.

(Culture of Bacterium of the Genus *Bifidobacterium*)

A streak culture of each of the recombinant bacterium of the genus *Bifidobacterium* strains on the 75 μg/mL spectinomycin-containing BL-bS agar medium was inoculated in MRS (manufactured by Becton, Dickinson and Company) liquid medium (10 mL) supplemented with spectinomycin (a final concentration of 75 μg/mL), 100 μL of vitamin C-added solution (a solution (100 mL) containing ascorbic acid (35 g), L-cysteine hydrochloride monohydrate (2 g) and sodium carbonate (11 g)) and anaerobically cultured at 37° C. for 24 hours to obtain an activated culture solution. Next, to a culture medium (20 mL) containing DMEM (Cat No. 12320-032: manufactured by Life Technologies) and MRS in a ratio of 9:1, a vitamin C-added solution (100 μL) and spectinomycin were added so as to obtain a spectinomycin concentration of 75 μg/mL and the activated culture solution (100 μL) was added for inoculation. This was anaerobically cultured at 37° C. for 18 hours.

After the anaerobic culture, the culture solution was centrifuged and the culture supernatant was collected. Protein in the culture supernatant was allowed to precipitate with trichloroacetic acid (TCA, manufactured by Wako Pure Chemical Industries Ltd.), washed with acetone, dissolved in SDS-PAGE buffer and subjected to a heat treatment at 95° C. for 3 minutes to obtain a culture supernatant concentrate.

The culture supernatant concentrate (corresponding to 1 mL of culture solution) was subjected to electrophoresis on by Mini-PROTEAN (registered trademark) TGX™ gel (4 to 20%) (manufactured by Bio-Rad). The gel was transferred onto a PVDF membrane (iBlot Transfer Stacks, manufactured by Life Technologies) by use of Trans-Blot Turbo (manufactured by Bio-Rad). After completion of blotting, the membrane was subjected to a blocking treatment (2% ECL Prime Blocking agent (manufactured by GE Healthcare Japan) in TTBS), subjected to a reaction using a mouse histidine tag antibody (THE HIS Tag Antibody, mAb, Mouse, manufactured by GenScript Japan Inc.) as a primary antibody and an ECL-peroxidase-labeled anti-mouse antibody (manufactured by GE Healthcare Japan) as a secondary antibody and allowed to emit light by use of Western Lightning Ultra (manufactured by PerkinElmer Co., Ltd.). This was analyzed by an imaging analyzer (myECL Imager manufactured by Thermo Scientific or Fluor S Max, manufactured by Bio-Rad). The results are shown in FIG. 21.

(Results)

As is apparent from FIG. 21, anti-hPD-1scFv03 was detected in all strains except *Bifidobacterium longum* 105-A/pHuSP69L0-hPD-1scFv03 strain having a linker L0. In addition, the amount of anti-hPD-1scFv03 secretion tended to decrease as the length of a linker reduced.

Example 23

[Verification of Binding of Anti-hPD-1scFv03 Having a Linker Different in Length to Human PD-L1 by ELISA]

(Purification of anti-hPD-1scFv03) Two types of bacterium of the genus *Bifidobacterium* s different in linker length, namely, *Bifidobacterium longum* 105-A/pHuSP69L20-hPD-1scFv03 strain and *Bifidobacterium longum* 105-A/pHuSP69L5-hPD-1scFv03, were cultured in the same manner as in Example 22. Note that the scale of culture was increased to 200 mL.

After the anaerobic culture, the culture supernatant was obtained by centrifugation. To the culture supernatant, ammonium sulfate was added little by little while stirring the culture supernatant so as to obtain a saturation of 80%. The solution obtained was stirred at 4° C. overnight to perform salting out. The solution was centrifuged and the precipitate was recovered. A histidine-tag fused protein was purified by a purification kit for a histidine-tagged protein (TALON resin, manufactured by Takara Bio Inc). The solution of the purified protein was concentrated by ultrapurification (Amicon Ultra-0.5, NMWL: 10,000, manufactured by Merck Millipore Corporation). The concentration of the purified protein was measured by the Bradford method (Coomassie Plus Protein Assay manufactured by Thermo Scientific). Albumin was used as the concentration standard. The purified scFv antibody was aliquoted, subjected to SDS-PAGE and stained with Coomassie brilliant blue (SimplyBlue™ Safe Stain, Life Technologies). As a result, it was verified that each of the anti-hPD-1scFv03 scFv antibodies is purified with a purity of about 90%.

(Verification of Binding of Anti-hPD-1scFv03 to Human PD-1)

Binding of anti-hPD-1scFv03, which was derived from each of *Bifidobacterium longum* 105-A/pHuSP69L20-hPD-1scFv03 strain and *Bifidobacterium longum* 105-A/pHuSP69L5-hPD-1scFv03, to human PD-1 (hPD-1) was verified by ELISA.

To 96 well plates, 100 μL of hPD-1 (Recombinant Human PD-1 Fc Chimera, manufactured by R&D Systems, Inc.) adjusted to be 1 μg/mL with 1×PBS was dispensed and incubated at 4° C. overnight to immobilize. After the solution was removed, 350 μL of 1×PBS was dispensed and the solution was removed. This operation was repeated three times to carry out washing. To the above plates, 350 μL of a 1% BSA solution was dispensed and incubated at room temperature for 2 hours to carry out blocking. After the solution was removed, 350 μL of 1×PBS was dispensed and the solution was removed. This operation was repeated three times to carry out washing.

The anti-hPD-1scFv03 was diluted with a signal enhancing reagent (Signal Enhancer HIKARI, manufactured by Nacalai Tesque) to prepare solutions having a concentration of 5 ng/mL, 10 ng/mL, 20 ng/mL and 40 ng/mL. Each solution (100 μL) was dispensed to the plates to which blocking treatment was already applied. To blank wells, a signal enhancing reagent (100 μL) alone was added. After the plates were sealed and incubated at room temperature for 2 hours, immobilized hPD-1 was allowed to react with each of scFv antibodies. After the solution was removed, 350 μL of 1×PBS was dispensed and the solution was removed. This operation was repeated three times to carry out washing.

A secondary antibody (Anti-His-tag-Biotin, manufactured by MBL) was diluted 2000 fold with a signal enhancing reagent. The dilution solution (100 μL) was dispensed to the plates. The plates were sealed and incubated at room temperature for 30 minutes. After the solution was removed, 350 μL of 1×PBS was dispensed and the solution was removed. This operation was repeated three times to carry out washing. An avidin-biotinylated enzyme complex (Vectastain ABC Kit, manufactured by Vector), more specifically, Solution A and Solution B, each (three drops) were added to a signal enhancing reagent (7.5 mL). This solution mixture (100 μL) was dispensed to the plates and the plates were sealed and incubated at room temperature for 30 minutes. After the solution was removed, 350 μL of 1×PBS was dispensed to the plates and the solution was removed. This operation was repeated three times to carry out washing. Color Solution A and Color Solution B (manufactured by R&D Systems) serving as a detection reagent were mixed in equal amounts. This solution (200 μL) was dispensed to the plates. The plates were sealed and incubated at room temperature for 20 minutes. Accurately 20 minutes later, 50 μL of a Stop solution (manufactured by R&D Systems) was added to the plates to terminate a color reaction. Absorbance at 450 nm was measured, whereas absorbance at 570 nm was measured as a control.

(Results)

The results of ELISA on binding of anti-hPD-1scFv03 are shown in FIG. 22. Anti-hPD-1scFv03 bound to human PD-1 regardless of the length of linkers (L5 and L20), and that the binding amount varied depending upon the concentration of scFv.

Example 24

[Verification of Competitive (Binding) Inhibitory Activity of Anti-hPD-1scFv03 Different in Linker Length Against the Binding Reaction Between Human PD-1 and PD-L1]

Using anti-hPD-1scFv03 different in linker length purified in Example 23, competitive (binding) inhibitory activity against the binding of human PD-L1 to human PD-1 was verified by ELISA. As a negative control, an anti-human CTLA-4-2 scFv antibody was used.

To 96 well plates, 100 µL of hPD-1 (Recombinant Human PD-1 Fc Chimera, manufactured by R&D Systems, Inc.) adjusted to be 1 µg/mL with 1×PBS was dispensed and incubated at 4° C. overnight to immobilize. After the solution was removed, 350 µL of 1×PBS was dispensed and the solution was removed. This operation was repeated three times to carry out washing. To the above plates, 350 µL of a 1% BSA solution was dispensed and incubated at room temperature for 2 hours to carry out blocking. After the solution was removed, 350 µL of 1×PBS was dispensed and the solution was removed. This operation was repeated three times to carry out washing. The concentration of hPD-L1 (manufactured by R&D Systems, Recombinant Human B7-H1, hPDL1) was controlled to be 40 nM with a signal enhancing reagent (Signal Enhancer HIKARI, manufactured by Nacalai Tesque).

The concentrations of the anti-human PD-1 scFv antibody purified from each bacterium of the genus *Bifidobacterium* were adjusted to be 1280 nM, 640 nM, 320 nM, 160 nM, 80 nM, 40 nM, 20 nM and 10 nM with a signal enhancing reagent. Each of the solutions prepared was mixed with 40 nM hPD-L1 in equal amounts. The scFv/hPD-L1 mixed solution (100 µL) was dispensed to the plates to which blocking treatment was already applied. As a negative control, an anti-human CTLA-4-2 scFv antibody purified from a bacterium of the genus *Bifidobacterium* was used and subjected to the same operation as above. Furthermore, to a scFv-free (no competitive inhibition is shown) well, a hPD-L1 solution (100 µL) controlled to be 20 nM with a signal enhancing reagent was dispensed. To a blank well, a signal enhancing reagent (100 µL) alone was dispensed. After the plates were sealed and incubated at room temperature for 2 hours, immobilized hPD-1 was allowed to react with hPD-L1 mixed with anti-hPD-1scFv. After the solution was removed, 350 µL of 1×PBS was dispensed and the solution was removed. This operation was repeated three times to carry out washing.

A secondary antibody (Biotin-anti-human CD274, PD-L1, manufactured by Biolegend) against hPD-L1 was adjusted to be 200 ng/mL with a signal enhancing reagent. This solution (100 µL) was dispensed to the plates. The plates were sealed and incubated at room temperature for 30 minutes. After the solution was removed, 350 µL of 1×PBS was dispensed and the solution was removed. This operation was repeated three times to carry out washing. An avidin-biotinylated enzyme complex (Vectastain ABC Kit, manufactured by Vector), more specifically, Solution A and Solution B, each (four drops) were added to a signal enhancing reagent (10 mL). This solution (100 µL) was dispensed to the plates and the plates were sealed and incubated at room temperature for 30 minutes. After the solution was removed, 350 µL of 1×PBS was dispensed and the solution was removed. This operation was repeated three times to carry out washing.

Color Solution A and Color Solution B (manufactured by R&D Systems) serving as a detection reagent were mixed in equal amounts. This solution (200 µL) was dispensed to the plates. The plates were sealed and incubated at room temperature for 20 minutes. Accurately 20 minutes later, 50 µL of a Stop solution (manufactured by R&D Systems) was added to terminate a color reaction. Absorbance at 450 nm was measured, whereas absorbance at 570 nm was measured as a control. From the measured values, a regression formula was obtained by use of free software Image J and the antibody concentration (IC50) at which 50% of binding between PD-1 and PD-L1 is inhibited, was obtained. Measurement values and analysis results are shown in Table 25 below and FIG. 23.

TABLE 25

Competitive inhibitory activity of various anti-human PD-1-scFv antibodies different in linker length to the binding reaction between hPD-1 and hPD-L1

| scFv Concentration nM | SP69L5 hPD-1 scFv03 A450-570 | SP69L5 hPD-1 scFv03 Inhibition (%) | SP69L20 hPD-1 scFv03 A450-570 | SP69L20 hPD-1 scFv03 Inhibition (%) | SP69L20 hCTLA4 scFv02 A450-570 | SP69L20 hCTLA4 scFv02 Inhibition (%) |
|---|---|---|---|---|---|---|
| 0 | 2.571 | 0 | 2.249 | 0 | 2.249 | 0 |
| 5 | 2.021 | 21.4 | 2.469 | −9.8 | 2.47 | −9.8 |
| 10 | 1.857 | 27.8 | 2.398 | −6.6 | 2.579 | −14.7 |
| 20 | 1.248 | 51.5 | 2.02 | 10.2 | 2.582 | −14.8 |
| 40 | 0.697 | 72.9 | 1.492 | 33.7 | 2.558 | −13.7 |
| 80 | 0.378 | 85.3 | 0.939 | 58.2 | 2.489 | −10.7 |
| 160 | 0.183 | 92.9 | 0.587 | 73.9 | 2.375 | −5.6 |
| 320 | 0.131 | 94.9 | 0.31 | 86.2 | 2.535 | −12.7 |
| 640 | 0.079 | 96.9 | 0.211 | 90.6 | 2.469 | −9.8 |
| $IC_{50}$ | 18.7 nM | | 51.7 nM | | | |

(Results)

As is apparent from Table 25 and FIG. 23, anti-hPD-1scFv03 exhibited competitive inhibitory activity against binding of human PD-L1 to human PD-1, regardless of the length of linkers (L5 and L20). The $IC_{50}$ values of anti-hPD-1scFv03 antibodies having SP69L5 and SP69L20 were 18.7 nM and 51.7 nM, respectively. The antibody having SP69L5 having a shorter exhibited competitive inhibitory activity at a lower concentration. Note that, in the negative control, i.e., anti-human CTLA-4-2 scFv antibody, competitive inhibition was not observed.

Example 25

[Expression Analysis of scFv of Anti-Human PD-1scFv03 Secreting Bacteria of the Genus *Bifidobacterium* Having Different Signal Peptides Integrated]

Since anti-hPD-1scFv03 secreted from each of *Bifidobacterium longum* 105-A/pHuSPxL20-hPD-1-scFv03 strains (where x=7, 45, 50, 52, 55, 58, 64, 66, 67, 68 and 69) has a histidine tag fused to the C terminal, scFv antibody secretion was analyzed by Western Blotting using an anti-histidine tag attached antibody in the same manner as in

[Preparation of plasmid, pHuSP7L20-hPD-1scFv03] in Example 21. The results are shown in FIGS. 24(a) and 24(b).

As is apparent from FIGS. 24(a) and 24(b), secretion of anti-hPD-1scFv03 was verified in *Bifidobacterium longum* 105-A strains transformed with vectors containing expression cassettes in which anti-hPD-1scFv03 was integrated downstream of the following 11 types of secretory signal peptide-linker conjugates (SP7L20, SP45L20, SP50L20, SP52L20, SP55L20, SP58L20, SP64L20, SP66L20, SP67L20, SP68L20, SP69L20).

Of them, in the above *Bifidobacterium longum* 105-A strains in which secretory signal peptide-linker conjugates of SP50L20, SP64L20, SP68L20 and SP69L20 were inserted, the amount of secretion was relatively large.

Example 26

[Verification of Binding of Anti-hPD-1scFv03 to Human PD-1 by ELISA]

Binding of the anti-hPD-1-scFv03 antibody, which was purified from each of the culture supernatants of *Bifidobacterium longum* 105-A/pHuSPxL20-hPD-1-scFv03 strains, to human PD-1 was verified. Absorbance at 450 nm was measured, whereas absorbance at 570 nm was measured as a control. The ELISA results of binding of anti-hPD-1scFv03 are shown in Table 26 below.

TABLE 26

| SP/Linker | Binding by ELISA A450-570 |
|---|---|
| SP7L20 | 3.171 |
| SP45L20 | 2.605 |
| SP50L20 | 3.481 |
| SP52L20 | 2.427 |
| SP55L20 | 1.449 |
| SP58L20 | 3.017 |
| SP64L20 | 3.055 |
| SP66L20 | 1.928 |
| SP67L20 | 3.411 |
| SP68L20 | 2.187 |
| SP69L20 | 1.827 |

(Results)

As is apparent from Table 26, anti-hPD-1scFv03 antibodies bound to human PD-1 regardless of the type of signal peptide. Of them, in the cases of SP7, SP50, SP64 and SP67, the amount of binding was large.

Example 27

[Verification of Competitive Binding Inhibitory Activity of Anti-hPD-1scFv03 to Binding Reaction Between Human PD-1 and PD-L1]

Various types of anti-hPD-1scFv03 antibodies purified from the above *Bifidobacterium longum* 105-A/pHuS-PxL20-hPD-1-scFv03 strains were used. To a microplate on which human PD-1 was immobilized, a mixture of each of the various types of anti-hPD-1scFv03 antibodies (10 µg/mL) and human PD-L1 (1 µg/mL) was added and the amount of PD-L1 bound to human PD-1 was measured. The competitive inhibition rate (%) to PD-1/PD-L1 binding when anti-hPD-1scFv03 antibody was co-present, was calculated provided that PD-L1 binding inhibition rate was regarded as 0% when anti-hPD-1scFv03 antibody was not added. The results are shown in Table 27 below.

TABLE 27

| SP/Linker | Competitive inhibition rate % |
|---|---|
| SP7L20 | 75.5 |
| SP45L20 | 73.7 |
| SP50L20 | 81.4 |
| SP52L20 | 74.4 |
| SP55L20 | 64.2 |
| SP58L20 | 88.1 |
| SP64L20 | 84.9 |
| SP66L20 | 87.5 |
| SP67L20 | 88.4 |
| SP68L20 | 90.4 |
| SP69L20 | 84.6 |

(Results)

As is apparent from Table 27, the competitive inhibition rate was not greatly varied by the type of signal peptide; however, when SP55L20 was used, the competitive inhibition rate was relatively low.

Example 28

[Investigation on Linker Length]

Investigation on length (Ly) of various linkers was carried out with respect to *Bifidobacterium longum* 105-A/pHuS-PxLy-hPD-1-scFv03 strains (where x=7, 45, 50, 52, 55, 58, 64, 66, 67, 68 and 69).

Eleven types of secretory signal peptides (SP7, SP45, SP50, SP52, SP55, SP58, SP64, SP66, SP67, SP68 and SP69) were used with respect to anti-hPD-1-scFv03 antibody. Anti-hPD-1scFv03 secretory plasmids were constructed by inserting secretory signal peptide-linker conjugates different in linker length. *Bifidobacterium longum* 105-A strains transformed with these plasmids were prepared.

Whether each of the *Bifidobacterium longum* 105-A strains secrets an anti-hPD-1-scFv03 antibody was analyzed by Western Blotting using an anti-histidine tagged antibody. The analysis results of the scFv antibody secretion are shown in FIGS. 25(a) to 25(d).

(Results)

As is apparent from FIGS. 25(a) to 25(d), a scFv antibody was secreted from *Bifidobacterium longum* 105-A strains transformed with an anti-hPD-1scFv03 secretory plasmids in which secretory signal peptide-linker conjugates, namely, SP7L5, SP7L10, SP7L15, SP7L20, SP45L5, SP45L10, SP45L15, SP45L20, SP50L5, SP50L10, SP50L15, SP50L20, SP52L5, SP52L10, SP52L15, SP52L20, SP55L5, SP55L10, SP55L15, SP55L20, SP58L15, SP58L20, SP64L5, SP64L10, SP64L15, SP64L20, SP66L5, SP66L10, SP66L15, SP66L20, SP67L5, SP67L10, SP67L15, SP67L20, SP68L5, SP68L10, SP68L15, SP68L20, SP69L5, SP69L10, SP69L15, SP69L20 except SP58L5 and SP58L10, were inserted.

As the detection results, the secretion products from SP7 series had the same molecular size regardless of the linker length designed; the secretion products from SP45 series had molecular sizes in accordance with the linker length designed; and the secretion products from SP50 series had molecular sizes in accordance with the linker length designed. In SP58 series, even if the linker length designed was L20, the secretion product had a small molecular size and no product was secreted in shorter linker length of (L10, L5) (see, FIG. 25(c)). The molecular size of a scFv antibody determined by Western Analysis was not always consistent with the linker length designed.

Example 29

[Verification of Binding of Anti-hPD-1scFv03 Antibody to Human PD-1 by ELISA]

The anti-hPD-1scFv03 antibody (1 µg/mL) purified from each of the culture supernatants of *Bifidobacterium longum* 105-A/pHuSPxLy-hPD-1-scFv03 strains (where x=7, 68, 69) was added and the binding amount of the antibody to human PD-1 (hPD-1) was checked by ELISA. Absorbance at 450 nm was measured, whereas absorbance at 570 nm was measured as a control. The binding amounts of anti-hPD-1scFv03 antibodies to a human PD-1-immobilized plate by ELISA are shown in Table 28 below.

TABLE 28

| SPx | Ly | | Binding amount OD450-570 |
|---|---|---|---|
| SP7 | L20 | SP7L20-hPD-1scFv03 | 1.728 |
| SP7 | L5 | SP7L5-hPD-1scFv03 | 2.861 |
| SP68 | L20 | SP68L20-hPD-1scFv03 | 2.358 |
| SP68 | L5 | SP68L5-hPD-1scFv03 | 3.119 |
| SP69 | L20 | SP69L20-hPD-1scFv03 | 2.332 |
| SP69 | L5 | SP69L5-hPD-1scFv03 | 3.643 |

(Results)

As is apparent from Table 28, in any case of SP7, SP68 and SP69, the binding amount of anti-hPD-1scFv03 antibody to the human PD-1-immobilized plate was larger in linker length 5 (L5) than in linker length 20 (L20). From this, it was demonstrated that the binding amount of anti-hPD-1scFv03 antibody to human PD-1 can be increased by optimizing the length of the linker.

Example 30

(Investigation on Linker Length L=0 to 10)

With respect to five types of signal peptides, namely, SP45, SP50, SP64, SP68 and SP69, investigation on linker length was conducted. *Bifidobacterium longum* 105-A strains were prepared by transforming them with anti-hPD-1scFv03 secretory plasmids in which secretory signal peptide-linker conjugates represented by SPxLy (note that, if x=45, y=0, 1, 2, 3, 5; if x=50, 64, 68, y=0, 1, 2, 3, 4, 5; and if x=69, y=0, 1, 2, 3, 4, 5, 6, 7, 8, 9, 10) were inserted. Secretion of the scFv antibodies was analyzed by Western Blotting using an anti-histidine tag attached antibody. The results are shown in FIG. 26.

(Results)

As is apparent from FIG. 26, no secretion was observed in *Bifidobacterium longum* 105-A strain transformed with an anti-hPD-1scFv03 secretory plasmid in which SP69L0 secretory signal peptide-linker conjugate was inserted (see, FIG. 26(c)). Except this case, secretion was observed. In other words, secretion was observed in *Bifidobacterium longum* 105-A strains transformed with an anti-hPD-1scFv03 secretory plasmids in which secretory signal peptide-linker conjugates SP45L0, SP45L1, SP45L2, SP45L3, SP45L5, SP50L0, SP50L1, SP50L2, SP50L3, SP50L4, SP50L5, SP64L0, SP64L1, SP64L2, SP64L3, SP64L4, SP64L5, SP68L0, SP68L1, SP68L2, SP68L3, SP68L4, SP68L5, SP69L1, SP69L2, SP69L3, SP69L4, SP69L5, SP69L6, SP69L7, SP69L8, SP69L9 and SP69L10 were inserted. In the cases where SP68L0 and SP68L1 were used as a secretory signal peptide-linker conjugate, the amount of secretion was low (see, FIG. 26(b)).

Example 31

*Bifidobacterium longum* 105-A strains were prepared by transforming them with anti-hPD-1scFv03 secretory plasmids in which secretory signal peptide-linker conjugates, namely, SP50Ly (note that, y=0, 1, 5), SP64Ly (note that, y=0, 5), SP67Ly (note that, y=10), SP68Ly (note that, y=1, 5), and SP69Ly (note that, y=1, 7) were inserted. Secretion of the scFv antibodies was analyzed by Western Blotting using an anti-histidine tag attached antibody. The results are shown in FIG. 27.

(Results)

As is apparent from FIG. 27, in any one of the strains transformed with anti-hPD-1scFv03 secretory plasmids in which secretory signal peptide-linker conjugates, namely, SP50L0, SP50L1, SP50L5, SP64L0, SP64L5, SP67L10, SP68L1, SP68L5, SP69L1, SP69L7 were inserted, secretion of an anti-hPD-1-scFv03 antibody was verified.

Example 32

(Verification of Competitive (Binding) Inhibitory Activity of Anti-hPD-1scFv03 to Binding Reaction Between Human PD-1 and PD-L1)

In the same manner as in Example 24, competitive (binding) inhibitory activity of scFv antibodies purified from hPD-1scFv03 secreting bacteria of the genus *Bifidobacterium* to PD-1/PD-L1 binding was verified. Absorbance at 450 nm was measured, whereas absorbance at 570 nm was measured as a control. Provided that the binding amount of PD-L1 in the absence of scFv was regarded as 100%, scFv concentration (IC50) at which 50% of binding between PD-1 and PD-L1 was inhibited was computationally obtained. The measurement results are shown in Table 29 below.

TABLE 29

| SP/Linker | IC50* (nM) |
|---|---|
| SP50L5 | 10.9 |
| SP64L5 | 23.4 |
| SP67L10 | 26.9 |
| SP68L1 | 21.7 |
| SP68L5 | 41.1 |
| SP69L1 | 21.8 |
| SP69L7 | 28.8 |

(Results)

As is apparent from Table 29, in the case of SP50L5, the binding between PD-1 and PD-L1 was inhibited at the lowest concentration. Comparison between SP68L1 and SP68L5 and between SP69L1 and SP69L7 having the same types of signal peptides (SP) and different linkers in length demonstrated that the signal peptide (SP) having a shorter linker length (L1) inhibits binding between PD-1 and PD-L1 at a lower concentration.

Example 33

(Binding Affinity)

Binding affinity of an anti-PD-1 antibody was analyzed by Biacore analysis (Biacore AB, Uppsala, Sweden). More specifically, the binding affinity of 7 samples (No. 1 to No. 7, n=5) shown in Table 30 below was analyzed. As a ligand, human PD-1 Fc chimera (manufactured by R&D) was used and dissolved in acetate pH4.5 (manufactured by GE Healthcare) to prepare a solution having a concentration of a 5 µg/mL. The solution was applied and immobilized onto a sensor chip having a gold film-surface coated with dextran having a CM group introduced therein by a standard protein immobilization method (amine coupling method). The anti-human PD-1 scFv antibody serving as an analyte was diluted with HBS-EP buffer (manufactured by GE Healthcare) to prepare a solution having a concentration of 12.5, 25, 50, 100 or 200 nM. Measurement of kinetics was started from a low concentration and carried out at an addition time of 60 seconds and at a dissociation time at 60 seconds and a flow rate at 30 µL/minute, in accordance with a single cycle method. The dissociation conditions of samples after measurement were the addition time of Glycin 1.5 (manufactured by GE Healthcare): 60 seconds; and the flow rate: 30 µL/minutes. The running buffer in this experiment was HBS-EP buffer. The results are shown in Table 30 below.

TABLE 30

|     | Sample Name     | ka (1/Ms) | kd (1/s) | KD (M)   |
|-----|-----------------|-----------|----------|----------|
| No1 | SP50L5 PD-1 scFv  | 417037.2 | 0.002666 | 6.39E−09 |
| No2 | SP64L5 PD-1 scFv  | 274449.6 | 0.003960 | 1.44E−08 |
| No3 | SP67L10 PD-1 scFv | 359502.6 | 0.003186 | 8.86E−09 |
| No4 | SP68L1 PD-1 scFv  | 398089.3 | 0.003388 | 8.51E−09 |
| No5 | SP68L5 PD-1 scFv  | 291332.5 | 0.005457 | 1.87E−08 |
| No6 | SP69L1 PD-1 scFv  | 393708.8 | 0.003379 | 8.58E−09 |
| No7 | SP69L7 PD-1 scFv  | 238025.4 | 0.003652 | 1.53E−08 |

(Results)

As is apparent from Table 30, in view of function as the antibody, SP50L5 was the most excellent since it had strong binding force (KD value is low) and slow dissociation rate (kd value is low) and subsequently SP67L10, SP68L1, SP69L1 (Sample No. 3, 4, 6) were excellent.

Example 34

[Expression Analysis of scFv of Anti-hCTLA-4scFv02-FLAG Secretion Bacteria of the Genus *Bifidobacterium* Having Signal Peptides Inserted]

*Bifidobacterium longum* 105-A/pP30SPxL20-hCTLA-4scFv02 strains (where x=7, 45, 50, 52, 55, 58, 64, 66, 67, 68 and 69) each was cultured for 18 hours. From the culture solution, a sample was prepared. Using a culture supernatant (80 µL), scFv antibody secretion was analyzed by Western Blotting using an anti-FLAG tag antibody. The results are shown in FIG. 28.

As is apparent from FIG. 28, in *Bifidobacterium longum* 105-A strains transformed with anti-hCTLA-4scFv02 secretory plasmids in which 11 types of secretory signal peptide-linker conjugates ((SP7L20, SP45L20, SP50L20, SP52L20, SP55L20, SP58L20, SP64L20, SP66L20, SP67L20, SP68L20 and SP69L20) were inserted, secretion of antibodies was verified.

Of them, in *Bifidobacterium longum* 105-A strains transformed with anti-hCTLA-4scFv02 secretory plasmids in which 11 types of secretory signal peptide-linker conjugates (SP50L20, SP52L20, SP64L20, SP67L20, SP68L20, SP69L20) were inserted, the amounts of secretion were relatively large.

Example 35

[Verification of Binding of Anti-hCTLA-4scFv02 to Human CTLA-4 by ELISA]

Binding of anti-hCTLA-4scFv02 purified from each of the culture supernatants of *Bifidobacterium longum* 105-A/ pP30SPxL20-hCTLA-4scFv02 strains to human CTLA-4 was verified. Absorbance at 450 nm was measured, whereas absorbance at 570 nm was measured as a control. The ELISA results of binding to human CTLA-4 are shown in Table 31 below.

TABLE 31

| SP/Linker | Binding by ELISA A450-570 |
|-----------|---------------------------|
| SP7L20    | 1.281 |
| SP45L20   | 0.379 |
| SP50L20   | 0.655 |
| SP52L20   | 0.388 |
| SP55L20   | 0.402 |
| SP58L20   | 0.715 |
| SP64L20   | 0.697 |
| SP66L20   | 0.306 |
| SP67L20   | 0.981 |
| SP68L20   | 0.218 |
| SP69L20   | 0.344 |

(Results)

As is apparent from Table 31, the binding amount of scFv varied depending upon the type of SP/Linker. SP7L20 and SP67L20 showed relatively high values.

Example 36

[Verification of Competitive (Binding) Inhibitory Activity of Anti-hCTLA-4scFv02 Against Binding of Human CTLA-4/Human CD80 or Human CTLA-4/Human CD86]

To a microplate having human CTLA-4 immobilized thereto, a mixture of purified scFv (10 µg/mL) and human CD80 or human CD86 (1 µg/mL) was added. The amount of human CD80 or human CD86 bound to human CTLA-4 was measured when anti-hCTLA-4scFv02 obtained from a *Bifidobacterium longum* 105-A/pP30SPxL20-hCTLA-4scFv02 strain was used. Provided that the binding inhibition rate against human CD80 or human CD86 in the absence of anti-hCTLA-4scFv02 was regarded as 0%, the competitive inhibition rate against binding of human CTLA-4/human CD80 or binding of human CTLA-4/human CD86 in the presence of anti-hCTLA-4scFv02 was computationally obtained. The results are shown in Table 32 below.

TABLE 32

|           | Competitive inhibition rate (%) | |
|-----------|-------|-------|
| SP/Linker | hCD80 | hCD86 |
| SP7L20    | 98.0  | 94.8  |
| SP45L20   | 72.3  | 81.9  |
| SP50L20   | 80.2  | 88.5  |
| SP52L20   | 77.9  | 85.6  |
| SP55L20   | 80.8  | 88.8  |
| SP58L20   | 97.3  | 98.7  |
| SP64L20   | 97.0  | 98.8  |
| SP66L20   | 91.4  | 94.8  |
| SP67L20   | 100   | 100   |
| SP68L20   | 92.3  | 87.8  |
| SP69L20   | 97.9  | 96.2  |

(Results)

In the case where the linker length was 20, no big difference was observed between the signal peptides.

Example 37

In the case of an anti-hCTLA-4scFv02 antibody, the length of a linker to be used with each of signal peptides of SP45, SP50, SP64, SP68, SP69 was investigated. *Bifidobacterium longum* 105-A strains, which were transformed with anti-hCTLA-4scFv02 secretory plasmids in which secretory signal peptide-linker conjugates represented by SPxLy (note that, if x=45, 50, 64, 68, y=0, 1, 2, 3, 4, 5; and if x=69, y=0, 1, 2, 3, 4, 5, 6, 7, 8, 9, 10) were inserted, were prepared and cultured for 18 hours. From the culture solutions, samples were prepared. Secretion of scFv antibody was analyzed by Western Blotting using an anti-FLAG tag antibody by using the culture supernatant of 100 μL. The results are shown in FIGS. 29(a) to 29(c).

(Results)

As is apparent form FIG. 29, secretion of anti-hCTLA-4scFv02 was verified in *Bifidobacterium longum* 105-A strains transformed with vectors containing expression cassettes in which anti-hCTLA-4scFv02 was integrated downstream secretory signal peptides and secretory signal peptide-linker conjugates represented by SP45L0, SP45L1, SP45L2, SP45L3, SP45L4, SP45L5, SP50L0, SP50L1, SP50L2, SP50L3, SP50L4, SP50L5, SP64L0, SP64L1, SP64L2, SP64L3, SP64L4, SP64L5, SP68L1, SP68L2, SP68L3, SP68L4, SP68L5, SP69L0, SP69L1, SP69L2, SP69L3, SP69L4, SP69L5, SP69L6, SP69L7, SP69L8, SP69L9 and SP69L10 except S68L0.

INDUSTRIAL APPLICABILITY

The bacterium of the genus *Bifidobacterium* and pharmaceutical composition of the present invention are useful in the field of medicines.

---

The invention claimed is:

1. An expression cassette expressed in a bacterium of the genus *Bifidobacterium*, sequentially comprising the following DNAs (1) to (4):
   (1) a promoter DNA functioning in the bacterium of the genus *Bifidobacterium*;
   (2) a DNA encoding a secretory signal peptide consisting of an amino acid sequence represented by any one of SEQ ID Nos. 8, 12, 14, 15, 16, 6, 7, 9, 10, 11, and 13;
   (3) a DNA encoding a heterologous polypeptide; and
   (4) a terminator DNA functioning in the bacterium of the genus *Bifidobacterium*.

2. The expression cassette according to claim 1, wherein a DNA encoding a linker peptide is linked downstream of a DNA encoding a secretory signal peptide.

3. The expression cassette according to claim 2, wherein the linker peptide is selected from the group consisting of each amino acid sequence obtained by deletion of 0 to 29 amino acid residues from a C terminal of an amino acid sequence represented by any one of SEQ ID Nos: 27, 31, 33, 34, 35, 25, 26, 28, 29, 30, and 32, wherein
   the linker peptide obtained by the deletion from the sequence represented by SEQ ID No. 27 is linked to the C terminal of the secretory signal peptide represented by SEQ ID No. 8;
   the linker peptide obtained by the deletion from the sequence represented by SEQ ID No. 31 is linked to the C terminal of the secretory signal peptide represented by SEQ ID No. 12;
   the linker peptide obtained by the deletion from the sequence represented by SEQ ID No. 33 is linked to the C terminal of the secretory signal peptide represented by SEQ ID No. 14;
   the linker peptide obtained by the deletion from the sequence represented by SEQ ID No. 34 is linked to the C terminal of the secretory signal peptide represented by SEQ ID No. 15;
   the linker peptide obtained by the deletion from the sequence represented by SEQ ID No. 35 is linked to the C terminal of the secretory signal peptide represented by SEQ ID No. 16;
   the linker peptide obtained by the deletion from the sequence represented by SEQ ID No. 25 is linked to the C terminal of the secretory signal peptide represented by SEQ ID No. 6;
   the linker peptide obtained by the deletion from the sequence represented by SEQ ID No. 26 is linked to the C terminal of the secretory signal peptide represented by SEQ ID No. 7;
   the linker peptide obtained by the deletion from the sequence represented by SEQ ID No. 28 is linked to the C terminal of the secretory signal peptide represented by SEQ ID No. 9;
   the linker peptide obtained by the deletion from the sequence represented by SEQ ID No. 29 is linked to the C terminal of the secretory signal peptide represented by SEQ ID No. 10;
   the linker peptide obtained by the deletion from the sequence represented by SEQ ID No. 30 is linked to the C terminal of the secretory signal peptide represented by SEQ ID No. 11; and
   the linker peptide obtained by the deletion from the sequence represented by SEQ ID No. 32 is linked to the C terminal of the secretory signal peptide represented by SEQ ID No. 13.

4. The expression cassette according to claim 2, wherein the linker peptide is selected from the group consisting of each amino acid sequence obtained by deletion of 10 to 29 amino acid residues from a C terminal of an amino acid sequence represented by any one of SEQ ID Nos: 27, 31, 33, 34, 35, 25, 26, 28, 29, 30, and 32, wherein
   the linker peptide obtained by the deletion from the sequence represented by SEQ ID No. 27 is linked to the C terminal of the secretory signal peptide represented by SEQ ID No. 8;

the linker peptide obtained by the deletion from the sequence represented by SEQ ID No. 31 is linked to the C terminal of the secretory signal peptide represented by SEQ ID No. 12;

the linker peptide obtained by the deletion from the sequence represented by SEQ ID No. 33 is linked to the C terminal of the secretory signal peptide represented by SEQ ID No. 14;

the linker peptide obtained by the deletion from the sequence represented by SEQ ID No. 34 is linked to the C terminal of the secretory signal peptide represented by SEQ ID No. 15;

the linker peptide obtained by the deletion from the sequence represented by SEQ ID No. 35 is linked to the C terminal of the secretory signal peptide represented by SEQ ID No. 16;

the linker peptide obtained by the deletion from the sequence represented by SEQ ID No. 25 is linked to the C terminal of the secretory signal peptide represented by SEQ ID No. 6;

the linker peptide obtained by the deletion from the sequence represented by SEQ ID No. 26 is linked to the C terminal of the secretory signal peptide represented by SEQ ID No. 7;

the linker peptide obtained by the deletion from the sequence represented by SEQ ID No. 28 is linked to the C terminal of the secretory signal peptide represented by SEQ ID No. 9;

the linker peptide obtained by the deletion from the sequence represented by SEQ ID No. 29 is linked to the C terminal of the secretory signal peptide represented by SEQ ID No. 10;

the linker peptide obtained by the deletion from the sequence represented by SEQ ID No. 30 is linked to the C terminal of the secretory signal peptide represented by SEQ ID No. 11; and the linker peptide obtained by the deletion from the sequence represented by SEQ ID No. 32 is linked to the C terminal of the secretory signal peptide represented by SEQ ID No. 13.

5. The expression cassette according to claim 1, wherein the heterologous polypeptide is a single-chain antibody.

6. The expression cassette according to claim 5, wherein the single-chain antibody is an anti-PD-1 antibody.

7. The expression cassette according to claim 5, wherein the single-chain antibody is an anti-CTLA-4 antibody.

8. A vector comprising an expression cassette expressed in a bacterium of the genus *Bifidobacterium*, sequentially comprising the following DNAs (1) to (4):

(1) a promoter DNA functioning in the bacterium of the genus *Bifidobacterium*;
(2) a DNA encoding a secretory signal peptide consisting of an amino acid sequence represented by any one of SEQ ID Nos. 8, 12, 14, 15, 16, 6, 7, 9, 10, 11 and 13;
(3) a DNA encoding a heterologous polypeptide; and
(4) a terminator DNA functioning in the bacterium of the genus *Bifidobacterium*.

9. A bacterium of the genus *Bifidobacterium* transformed with a vector comprising an expression cassette expressed in a bacterium of the genus *Bifidobacterium*, sequentially comprising the following DNAs (1) to (4):

(1) a promoter DNA functioning in the bacterium of the genus *Bifidobacterium*;
(2) a DNA encoding a secretory signal peptide consisting of an amino acid sequence represented by any one of SEQ ID Nos. 8, 12, 14, 15, 16, 6, 7, 9, 10, 11 and 13;
(3) a DNA encoding a heterologous polypeptide; and
(4) a terminator DNA functioning in the bacterium of the genus *Bifidobacterium*.

10. The bacterium of the genus *Bifidobacterium* according to claim 9, which is *Bifidobacterium longum*.

11. The expression cassette according to claim 2, wherein the heterologous polypeptide is a single-chain antibody.

12. The expression cassette according to claim 3, wherein the heterologous polypeptide is a single-chain antibody.

13. The expression cassette according to claim 4, wherein the heterologous polypeptide is a single-chain antibody.

14. The expression cassette according to claim 11, wherein the single-chain antibody is an anti-PD-1 antibody.

15. The expression cassette according to claim 12, wherein the single-chain antibody is an anti-PD-1 antibody.

16. The expression cassette according to claim 13, wherein the single-chain antibody is an anti-PD-1 antibody.

17. The expression cassette according to claim 11, wherein the single-chain antibody is an anti-CTLA-4 antibody.

18. The expression cassette according to claim 12, wherein the single-chain antibody is an anti-CTLA-4 antibody.

19. The expression cassette according to claim 13, wherein the single-chain antibody is an anti-CTLA-4 antibody.

20. The vector according to claim 8, wherein a DNA encoding a linker peptide is linked downstream of a DNA encoding a secretory signal peptide.

* * * * *